(12) United States Patent
Papadopoulos et al.

(10) Patent No.: US 7,534,868 B1
(45) Date of Patent: May 19, 2009

(54) HUMAN ANTIBODIES TO HUMAN DELTA LIKE LIGAND 4

(75) Inventors: Nicholas J. Papadopoulos, LaGrangeville, NY (US); Joel H. Martin, Putnam Valley, NY (US); Eric Smith, New York, NY (US); Irene Noguera-Troise, Bay Shore, NY (US); Gavin Thurston, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/371,159

(22) Filed: Feb. 13, 2009

Related U.S. Application Data

(63) Continuation of application No. 12/002,245, filed on Dec. 14, 2007.

(60) Provisional application No. 60/874,922, filed on Dec. 14, 2006, provisional application No. 60/916,415, filed on May 7, 2007, provisional application No. 60/985,323, filed on Nov. 5, 2007.

(51) Int. Cl.
*C07K 16/00* (2006.01)

(52) U.S. Cl. .................. 530/387.1; 424/130.1

(58) Field of Classification Search ............... None
See application file for complete search history.

(56) References Cited

U.S. PATENT DOCUMENTS

| | | | |
|---|---|---|---|
| 6,121,045 | A | 9/2000 | McCarthy et al. |
| 6,664,098 | B1 | 12/2003 | Sakano |
| 2003/0180784 | A1 | 9/2003 | McCarthy et al. |
| 2006/0134121 | A1 | 6/2006 | Thurston et al. |
| 2007/0213266 | A1* | 9/2007 | Gill et al. ............ 514/12 |
| 2008/0014196 | A1 | 1/2008 | Yan |
| 2008/0107648 | A1 | 5/2008 | Noguera et al. |
| 2008/0175847 | A1 | 7/2008 | Yan et al. |
| 2008/0187532 | A1 | 8/2008 | Gurney et al. |

FOREIGN PATENT DOCUMENTS

| WO | WO98/45434 A1 | 10/1998 |
|---|---|---|
| WO | WO98/51799 A1 | 11/1998 |
| WO | WO2008/042236 A2 | 4/2008 |

OTHER PUBLICATIONS

Gurney et al., "Compositions and Methods for Diagnosing and Treating Cancer", U.S. Appl. No. 60/847,904, filed Sep. 29, 2006.
Gurney et al., "Compositions and Methods for Diagnosing and Treating Cancer", U.S. Appl. No. 60/886,260, filed Jan. 23, 2007.
Gurney et al., "Compositions and Methods for Diagnosing and Treating Cancer", U.S. Appl. No. 60/942,542, filed Jun. 7, 2007.
Fleming, R.J. et al., Nov. 1997, "The Notch receptor and its ligands", Trends in Cell Biology 7(11):437-441.
Dorsch, Marion et al., Sep. 15, 2002, "Ectopic expression of Delta4 impairs hematopoietic development and leads to lymphoproliferative disease", Blood 100(6):2046-2055.
Dando, Jonathan et al., Apr. 2005, "Notch/Delta4 interaction in human embryonic liver CD34+CD38- cells: Positive influence on BGU-E production and LTC-IC potential maintenance", Stem Cells 23(4):550-560.
Williams, Cassin Kimmel et al., Feb. 1, 2006, "Up-regulation of the Notch ligand Delta-like 4 inhibits VEGF-induced endothelial cell function", Blood 107(3):931-939.
Lauret, E. et al., Feb. 26, 2006, "Membrane-bound Delta-4 Notch ligand reduces the proliferative activity of primitive human hematopoietic CD34+CD38 low cells while maintaining their LTC-IC potential", Leukemia 18:788-797.
Sugimoto, Akira et al., Apr. 2006, "Delta-4 Notch ligand promotes erythroid differentiation of human umbilical cord blood CD34+ cells", Experimental Hematology 34(4):424-432.
Liu, Zhao-Jun et al., May 2006, "Inhibition of endothelial cell proliferation by Notch1 signaling is mediated by repressing MAPK and P14K/Akt pathways and required MAML1", The FASEB Journal 20:E201-E210.
Hainaud, Patricia et al., Sep. 1, 2006, "The role of the vascular endothelial growth factor-Delta-like 4 ligand/Notch4-Ephrin B2 cascade in tumor vessel remodeling and endothlial cell functions", Cancer Res 66(17):8501-8510.

* cited by examiner

*Primary Examiner*—Larry R. Helms
*Assistant Examiner*—Meera Natarajan
(74) *Attorney, Agent, or Firm*—Izumi Yokoyama, Esq.

(57) ABSTRACT

An isolated human antibody or a fragment of a human antibody which specifically binds to human delta-like ligand 4 (hDll4) and blocks hDll4 binding to a Notch receptor. The human anti-hDll4 antibody or antibody fragment binds dimeric hDll4 with an affinity of 75 pM or better, as measured by surface plasmon resonance.

6 Claims, No Drawings

SEQUENCE LISTING

<160> NUMBER OF SEQ ID NOS: 957

<210> SEQ ID NO 1
<211> LENGTH: 2058
<212> TYPE: DNA
<213> ORGANISM: Homo sapiens

<400> SEQUENCE: 1

```
atggcggcag cgtcccggag cgcctctggc tgggcgctac tgctgctggt ggcactttgg      60
cagcagcgcg cggccggctc cggcgtcttc cagctgcagc tgcaggagtt catcaacgag     120
cgcggcgtac tggccagtgg gcggccttgc gagcccggct ccggactttt cttccgcgtc     180
tgccttaagc acttccaggc ggtcgtctcg cccggaccct gccttcgg gaccgtctcc      240 acgccggtat tgggcaccaa ctccttcgct gtccgggacg acagtagcgg cggggggcgc     300
aaccctctcc aactgccctt caatttcacc tggccgggta ccttctcgct catcatcgaa     360
gcttggcacg cgccaggaga cgacctgcgg ccagaggcct gccaccaga tgcactcatc      420 agcaagatcg ccatccaggg ctccctagct gtgggtcaga actggttatt ggatgagcaa     480
accagcaccc tcacaaggct gcgctactct taccgggtca tctgcagtga caactactat     540
ggagacaact gctcccgcct gtgcaagaag cgcaatgacc acttcggcca ctatgtgtgc     600
cagccagatg gcaacttgtc ctgcctgccc ggttggactg ggaatattg caacagcct      660 atctgtcttt cgggctgtca tgaacagaat ggctactgca gcaagccagc agagtgcctc     720
tgccgcccag gctggcaggg ccggctgtgt aacgaatgca tccccacaa tggctgtcgc     780 cacggcacct gcagcactcc ctggcaatgt acttgtgatg agggctgggg aggcctgttt     840
tgtgaccaag atctcaacta ctgcacccac cactccccat gcaagaatgg ggcaacgtgc     900
tccaacagtg ggcagcgaag ctacacctgc acctgtcgcc aggctacac tggtgtggac     960 tgtgagctgg agctcagcga gtgtgacagc aaccctgtc gcaatggagg cagctgtaag    1020
gaccaggagg atggctacca ctgcctgtgt cctccgggct actatggcct gcattgtgaa    1080
cacagcacct tgagctgcgc cgactccccc tgcttcaatg ggggctcctg ccgggagcgc    1140 aaccagggg ccaactatgc ttgtgaatgt cccccaact tcaccggctc caactgcgag    1200
aagaaagtgg acaggtgcac cagcaacccc tgtgccaacg ggggacagtg cctgaaccga    1260
ggtccaagcc gcatgtgccg ctgccgtcct ggattcacgg gcacctactg tgaactccac    1320
gtcagcgact gtgcccgtaa cccttgcgcc cacggtggca cttgccatga cctggagaat    1380
gggctcatgt gcacctgccc tgccggcttc tctggccgac gctgtgaggt gcggacatcc    1440
```

-continued

```
atcgatgcct gtgcctcgag tccctgcttc aacagggcca cctgctacac cgacctctcc    1500
acagacacct ttgtgtgcaa ctgcccttat ggctttgtgg gcagccgctg cgagttcccc    1560
gtgggcttgc cgcccagctt ccctggggtg gccgtctcgc tgggtgtggg gctggcagtg    1620
ctgctggtac tgctgggcat ggtggcagtg gctgtgcggc agctgcggct cgacggccg     1680 gacgacggca gcaggaagc catgaacaac ttgtcggact tccagaagga caacctgatt    1740
cctgccgccc agcttaaaaa cacaaaccag aagaaggagc tggaagtgga ctgtggcctg    1800
gacaagtcca actgtggcaa acagcaaaac cacacattgg actataatct ggccccaggg    1860
cccctggggc gggggaccat gccaggaaag tttccccaca gtgacaagag cttaggagag    1920
aaggcgccac tgcggttaca cagtgaaaag ccagagtgtc ggatatcagc gatatgctcc    1980
cccagggact ccatgtacca gtctgtgtgt ttgatatcag aggagaggaa tgaatgtgtc    2040
attgccacgg aggtataa                                                  2058
```

<210> SEQ ID NO 2
<211> LENGTH: 685
<212> TYPE: PRT
<213> ORGANISM: Homo sapiens

<400> SEQUENCE: 2

```
Met Ala Ala Ala Ser Arg Ser Ala Ser Gly Trp Ala Leu Leu Leu
 1               5                  10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
50                  55                  60

Phe Gln Ala Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
                100                 105                 110

Gly Thr Phe Ser Leu Ile Ile Glu Ala Trp His Ala Pro Gly Asp Asp
            115                 120                 125

Leu Arg Pro Glu Ala Leu Pro Pro Asp Ala Leu Ile Ser Lys Ile Ala
        130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255
```

```
Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
            275                 280                 285

Thr His His Ser Pro Cys Lys Asn Gly Ala Thr Cys Ser Asn Ser Gly
            290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
        370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
        450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
            530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
            595                 600                 605

Gln Asn His Thr Leu Asp Tyr Asn Leu Ala Pro Gly Pro Leu Gly Arg
        610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
```

<210> SEQ ID NO 3
<211> LENGTH: 358
<212> TYPE: DNA
<213> ORGANISM: Artificial Sequence
<220> FEATURE:
<223> OTHER INFORMATION: Synthetic

<400> SEQUENCE: 3

```
gaggtgcaac tggtggagtc tgggggaggc ttggtccagc ctgggggtc cctgagactc      60
tcctgtgcag cctctggatt cacctttagt acctattgga tgaactgggt ccgccaggct   120
ccagggaagg ggctggagtg ggtggccaac ataaaccaag atggaagtga aaatactat    180
gtggactctg tgaagggccg aatcaccatc tccagagaca acgccaagaa ctcactgtat   240
ctgcaaatga acagcctgag agtcgaggac acggctgtat attactgtgc gagaaaatgg   300
aacaactgga acccggagga gaactggggc cagggaaccc tggtcaccgt ctcctcag    358
```

<210> SEQ ID NO 4
<211> LENGTH: 119
<212> TYPE: PRT
<213> ORGANISM: Artificial Sequence
<220> FEATURE:
<223> OTHER INFORMATION: Synthetic

<400> SEQUENCE: 4

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Trp Met Asn Trp Val Arg Gln Ala Pro Gly Lys Gly Leu Glu Trp Val
         35                  40                  45

Ala Asn Ile Asn Gln Asp Gly Ser Glu Lys Tyr Tyr Val Asp Ser Val
     50                  55                  60

Lys Gly Arg Ile Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Ala Arg Lys Trp Asn Asn Trp Asn Pro Glu Glu Asn Trp Gly Gln Gly
            100                 105                 110

Thr Leu Val Thr Val Ser Ser
        115
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5

```
ggattcacct ttagtaccta ttgg                                          24
```

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

-continued

```
Gly Phe Thr Phe Ser Thr Tyr Trp
 1               5
```

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
ataaaccaag atggaagtga gaaa                                          24

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

```
Ile Asn Gln Asp Gly Ser Glu Lys
 1               5
```

<210> SEQ ID NO 9
<211> LENGTH: 36
<212> TYPE: DNA
<213> ORGANISM: Artificial Sequence
<220> FEATURE:
<223> OTHER INFORMATION: Synthetic

<400> SEQUENCE: 9
gcgagaaaat ggaacaactg gaacccggag gagaac                             36

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

```
Ala Arg Lys Trp Asn Asn Trp Asn Pro Glu Glu Asn
 1               5                  10
```

<210> SEQ ID NO 11
<211> LENGTH: 337
<212> TYPE: DNA
<213> ORGANISM: Artificial Sequence
<220> FEATURE:
<223> OTHER INFORMATION: Synthetic

<400> SEQUENCE: 11
gatattgtga tgactcagtc tccactctcc ctgcccgtca cccctggaga gccggcctcc    60
atctcctgca ggtctagtca gagcctcctg cataatagtg gatacaactt tttggattgg   120
tacctgcaga agccagggca gtctccacaa ctcctgatct atttgcgttc taatcgggcc   180
tccggggtcc ctgacaggtt cagtggcagt ggatcaggca cagatttyac actgaagatc   240
agaagagtgg aggctgagga tgttggggatt tattactgca tgcaagctct acacactcct   300
tacacttttg gccaggggac caaggtggag atcaaac                            337

<210> SEQ ID NO 12
<211> LENGTH: 112

```
<212> TYPE: PRT
<213> ORGANISM: Artificial Sequence
<220> FEATURE:
<223> OTHER INFORMATION: Synthetic

<400> SEQUENCE: 12

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Asn
            20                  25                  30

Ser Gly Tyr Asn Phe Leu Asp Trp Tyr Leu Gln Lys Pro Gly Gln Ser
        35                  40                  45

Pro Gln Leu Leu Ile Tyr Leu Arg Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Ile Tyr Tyr Cys Met Gln Ala
                85                  90                  95

Leu His Thr Pro Tyr Thr Phe Gly Gln Gly Thr Lys Val Glu Ile Lys
            100                 105                 110

<210> SEQ ID NO 13
<211> LENGTH: 33
<212> TYPE: DNA
<213> ORGANISM: Artificial Sequence
<220> FEATURE:
<223> OTHER INFORMATION: Synthetic

<400> SEQUENCE: 13
cagagcctcc tgcataatag tggatacaac ttt                              33

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Gln Ser Leu Leu His Asn Ser Gly Tyr Asn Phe
 1               5                  10

<210> SEQ ID NO 15
<211> LENGTH: 9
<212> TYPE: DNA
<213> ORGANISM: Artificial Sequence
<220> FEATURE:
<223> OTHER INFORMATION: Synthetic

<400> SEQUENCE: 15 ttgcgttct                                                          9

<210> SEQ ID NO 16
<211> LENGTH: 3
<212> TYPE: PRT
<213> ORGANISM: Artificial Sequence
<220> FEATURE:
<223> OTHER INFORMATION: Synthetic

<400> SEQUENCE: 16

Leu Arg Ser
 1
```

-continued

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
atgcaagctc tacacactcc ttacact                                          27

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Met Gln Ala Leu His Thr Pro Tyr Thr
 1               5

<210> SEQ ID NO 19
<211> LENGTH: 376
<212> TYPE: DNA
<213> ORGANISM: Artificial Sequence
<220> FEATURE:
<223> OTHER INFORMATION: Synthetic

<400> SEQUENCE: 19
gaggtgcagc tggtggagtc tgggggaggc ttggtccagc ctggggggtc cctgagactc      60
tcctgtgtag cctctggatt caccttagt agctattgga tgacctgggt ccgccaggct     120
ccagggaagg ggctggagtg gtggccaac ataaaacaag atggaagtga aaatactat       180 gtggactctg tgaagggccg attcaccgtc tccagagaca cgccaagaa ctcagtgtat     240 ctgcaaatga gcagcctgag agccgaggac acggctgtgt attactgtgc gagagattgg    300
aactatggcc ccgattacta ctactaccac ggtttggacg tctggggcca agggaccacg    360
gtcaccgtct cctcag                                                    376

<210> SEQ ID NO 20
<211> LENGTH: 125
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
 1               5                   10                  15

Ser Leu Arg Leu Ser Cys Val Ala Ser Gly Phe Thr Phe Ser Ser Tyr
             20                  25                  30

Trp Met Thr Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
     50                  55                  60

Lys Gly Arg Phe Thr Val Ser Arg Asp Asn Ala Lys Asn Ser Val Tyr
 65                  70                  75                  80

Leu Gln Met Ser Ser Leu Arg Ala Glu Asp Thr Ala Val Tyr Tyr Cys
                 85                  90                  95

Ala Arg Asp Trp Asn Tyr Gly Pro Asp Tyr Tyr Tyr Tyr His Gly Leu
            100                 105                 110

Asp Val Trp Gly Gln Gly Thr Thr Val Thr Val Ser Ser
        115                 120                 125

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggattcacct ttagtagcta ttgg                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Phe Thr Phe Ser Ser Tyr Trp
 1               5

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
ataaaacaag atggaagtga gaaa                                          24

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Ile Lys Gln Asp Gly Ser Glu Lys
 1               5

<210> SEQ ID NO 25
<211> LENGTH: 54
<212> TYPE: DNA
<213> ORGANISM: Artificial Sequence
<220> FEATURE:
<223> OTHER INFORMATION: Synthetic

<400> SEQUENCE: 25
gcgagagatt ggaactatgg ccccgattac tactactacc acggtttgga cgtc          54

<210> SEQ ID NO 26
<211> LENGTH: 18
<212> TYPE: PRT
<213> ORGANISM: Artificial Sequence
<220> FEATURE:
<223> OTHER INFORMATION: Synthetic

<400> SEQUENCE: 26

Ala Arg Asp Trp Asn Tyr Gly Pro Asp Tyr Tyr Tyr Tyr His Gly Leu
 1               5                  10                  15

Asp Val

<210> SEQ ID NO 27
<211> LENGTH: 322
<212> TYPE: DNA
<213> ORGANISM: Artificial Sequence
<220> FEATURE:
<223> OTHER INFORMATION: Synthetic

<400> SEQUENCE: 27

```
gacctccaga tgacccagtc tccgtcctcc ctgtctgtat ctgtaggaga cagagtcacc      60
atcacttgcc gggcaagtca gggcattaga aatgatttag ctggtttca gcagaaacca     120
gggaaagccc ctaagcgcct gatctatgct gcatccagtt tgcaaagtgg ggtcccatca    180
aggttcagcg gcagtggatc tgggacagaa ttcactctca caatcagcag cctgctgcct    240
gaagattttg caacttatta ctgtctacag cataatactt acccgtacac ttttggccag    300
gggaccaagc tggagatcaa ac                                             322
```

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Asp Leu Gln Met Thr Gln Ser Pro Ser Ser Leu Ser Val Ser Val Gly
 1               5                  10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Leu Pro
65                  70                  75                  80

Glu Asp Phe Ala Thr Tyr Tyr Cys Leu Gln His Asn Thr Tyr Pro Tyr
                85                  90                  95

Thr Phe Gly Gln Gly Thr Lys Leu Glu Ile Lys
            100                 105

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29

```
cagggcatta gaaatgat                                                   18
```

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Gln Gly Ile Arg Asn Asp
 1               5

```
<210> SEQ ID NO 31
<211> LENGTH: 9
<212> TYPE: DNA
<213> ORGANISM: Artificial Sequence
<220> FEATURE:
<223> OTHER INFORMATION: Synthetic

<400> SEQUENCE: 31 gctgcatcc                                                              9

<210> SEQ ID NO 32
<211> LENGTH: 3
<212> TYPE: PRT
<213> ORGANISM: Artificial Sequence
<220> FEATURE:
<223> OTHER INFORMATION: Synthetic

<400> SEQUENCE: 32

Ala Ala Ser
 1

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
ctacagcata atacttaccc gtacact                                          27

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Leu Gln His Asn Thr Tyr Pro Tyr Thr
 1               5

<210> SEQ ID NO 35
<211> LENGTH: 361
<212> TYPE: DNA
<213> ORGANISM: Artificial Sequence
<220> FEATURE:
<223> OTHER INFORMATION: Synthetic

<400> SEQUENCE: 35 cagggcagt tggtggagtc tgggggaggc gtggtccagc ctgggaggtc cctgagactc        60
tcctgtgaag catctggatt cagtttcaga agttatggca tgcactgggt ccgccaggct      120
ccaggcaggg gactggagtg gatggcagtt atttggtacg atggcagtaa gacatactat      180
acagagtccg tgacgggccg attcaccatc tccagagaca attccaagaa cacgctatat      240
ctgcaaatga acagcctgag agccgaggac acggctgttt attactgtgc gagcggtttt      300
tcagtgcctg ccacgatcct tgacaactgg ggccagggaa ccctggtctc cgtctcctca      360
g                                                                     361

<210> SEQ ID NO 36
<211> LENGTH: 120
<212> TYPE: PRT
<213> ORGANISM: Artificial Sequence
```

```
<220> FEATURE:
<223> OTHER INFORMATION: Synthetic

<400> SEQUENCE: 36

Gln Gly Gln Leu Val Glu Ser Gly Gly Val Val Gln Pro Gly Arg
  1               5                  10                  15

Ser Leu Arg Leu Ser Cys Glu Ala Ser Gly Phe Ser Phe Arg Ser Tyr
             20                  25                  30

Gly Met His Trp Val Arg Gln Ala Pro Gly Arg Gly Leu Glu Trp Met
         35                  40                  45

Ala Val Ile Trp Tyr Asp Gly Ser Lys Thr Tyr Thr Glu Ser Val
     50                  55                  60

Thr Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Gly Phe Ser Val Pro Ala Thr Ile Leu Asp Asn Trp Gly Gln
            100                 105                 110

Gly Thr Leu Val Ser Val Ser Ser
        115                 120

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
ggattcagtt tcagaagtta tggc                                       24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Gly Phe Ser Phe Arg Ser Tyr Gly
  1               5

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
atttggtacg atggcagtaa gaca                                       24

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Ile Trp Tyr Asp Gly Ser Lys Thr
  1               5
```

<210> SEQ ID NO 41
<211> LENGTH: 39
<212> TYPE: DNA
<213> ORGANISM: Artificial Sequence
<220> FEATURE:
<223> OTHER INFORMATION: Synthetic

<400> SEQUENCE: 41
gcgagcggtt tttcagtgcc tgccacgatc cttgacaac    39

<210> SEQ ID NO 42
<211> LENGTH: 13
<212> TYPE: PRT
<213> ORGANISM: Artificial Sequence
<220> FEATURE:
<223> OTHER INFORMATION: Synthetic

<400> SEQUENCE: 42

Ala Ser Gly Phe Ser Val Pro Ala Thr Ile Leu Asp Asn
 1               5                  10

<210> SEQ ID NO 43
<211> LENGTH: 322
<212> TYPE: DNA
<213> ORGANISM: Artificial Sequence
<220> FEATURE:
<223> OTHER INFORMATION: Synthetic

<400> SEQUENCE: 43
gacatccaga tgacccagtc tccatcctcc ctgtctgcat ctgtaggaga cagagtcacc    60
atcacttgcc gggcaagtca gggcattaga aatgatttag ctggtttca gcagaaacca   120 gggaaagccc ctaaccgcct gatctatgga gcatccagtt tggaaggtgg ggtcccatca   180
aggttcagcg gcagtggatc tgggacagat ttcactctca caatcagcag cctgcagcca   240
gaagattttg caacttatta ctgtctacag cataattctt acccgtggac gttcggccaa   300
gggaccaagg tggaaatcaa ac                                            322

<210> SEQ ID NO 44
<211> LENGTH: 107
<212> TYPE: PRT
<213> ORGANISM: Artificial Sequence
<220> FEATURE:
<223> OTHER INFORMATION: Synthetic

<400> SEQUENCE: 44

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Asn Arg Leu Ile
        35                  40                  45

Tyr Gly Ala Ser Ser Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 45
<211> LENGTH: 18
<212> TYPE: DNA
<213> ORGANISM: Artificial Sequence
<220> FEATURE:
<223> OTHER INFORMATION: Synthetic

<400> SEQUENCE: 45
cagggcatta gaaatgat					18

<210> SEQ ID NO 46
<211> LENGTH: 6
<212> TYPE: PRT
<213> ORGANISM: Artificial Sequence
<220> FEATURE:
<223> OTHER INFORMATION: Synthetic

<400> SEQUENCE: 46

Gln Gly Ile Arg Asn Asp
 1               5

<210> SEQ ID NO 47
<211> LENGTH: 9
<212> TYPE: DNA
<213> ORGANISM: Artificial Sequence
<220> FEATURE:
<223> OTHER INFORMATION: Synthetic

<400> SEQUENCE: 47 ggagcatcc					9

<210> SEQ ID NO 48
<211> LENGTH: 3
<212> TYPE: PRT
<213> ORGANISM: Artificial Sequence
<220> FEATURE:
<223> OTHER INFORMATION: Synthetic

<400> SEQUENCE: 48

Gly Ala Ser
 1

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
ctacagcata attcttaccc gtggacg					27

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Leu Gln His Asn Ser Tyr Pro Trp Thr
 1               5

<210> SEQ ID NO 51
<211> LENGTH: 367
<212> TYPE: DNA
<213> ORGANISM: Artificial Sequence

```
<220> FEATURE:
<223> OTHER INFORMATION: Synthetic

<400> SEQUENCE: 51
caggtgcagc tggtggagtc tgggggaggc gtagtccagc ctgggaggtc cctgagactc      60
tcctgtgcag cgtctggatt caccttcagt agctatggca tgcactgggt ccgccaggct     120
ccaggcaagg gctggagtg gtggcagtt atatggtatg atggaaataa taaatactat      180
atagactccg tgaagggccg attcaccatc tccagagaca attccaagaa cacgctgtat     240
ctgcaaatga acagcctgag agccgaggac acggctgtgt attactgtgc gagagaccgt     300
ggatatagtg gctacgaggg atacttcgat ctctggggcc gtggcaccct ggtcactgtc     360
tcctcag                                                              367

<210> SEQ ID NO 52
<211> LENGTH: 122
<212> TYPE: PRT
<213> ORGANISM: Artificial Sequence
<220> FEATURE:
<223> OTHER INFORMATION: Synthetic

<400> SEQUENCE: 52

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asn Asn Lys Tyr Tyr Ile Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Ser Gly Tyr Glu Gly Tyr Phe Asp Leu Trp
            100                 105                 110

Gly Arg Gly Thr Leu Val Thr Val Ser Ser
        115                 120

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
ggattcacct tcagtagcta tggc                                            24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Gly Phe Thr Phe Ser Ser Tyr Gly
 1               5
```

<210> SEQ ID NO 55
<211> LENGTH: 24
<212> TYPE: DNA
<213> ORGANISM: Artificial Sequence
<220> FEATURE:
<223> OTHER INFORMATION: Synthetic

<400> SEQUENCE: 55
atatggtatg atggaaataa taaa                                          24

<210> SEQ ID NO 56
<211> LENGTH: 8
<212> TYPE: PRT
<213> ORGANISM: Artificial Sequence
<220> FEATURE:
<223> OTHER INFORMATION: Synthetic

<400> SEQUENCE: 56

Ile Trp Tyr Asp Gly Asn Asn Lys
 1               5

<210> SEQ ID NO 57
<211> LENGTH: 45
<212> TYPE: DNA
<213> ORGANISM: Artificial Sequence
<220> FEATURE:
<223> OTHER INFORMATION: Synthetic

<400> SEQUENCE: 57
gcgagagacc gtggatatag tggctacgag ggatacttcg atctc                   45

<210> SEQ ID NO 58
<211> LENGTH: 15
<212> TYPE: PRT
<213> ORGANISM: Artificial Sequence
<220> FEATURE:
<223> OTHER INFORMATION: Synthetic

<400> SEQUENCE: 58

Ala Arg Asp Arg Gly Tyr Ser Gly Tyr Glu Gly Tyr Phe Asp Leu
 1               5                  10                  15

<210> SEQ ID NO 59
<211> LENGTH: 337
<212> TYPE: DNA
<213> ORGANISM: Artificial Sequence
<220> FEATURE:
<223> OTHER INFORMATION: Synthetic

<400> SEQUENCE: 59
gacatcgtga tgacccagtc tccagactcc ctggctgtgt ctctgggcga gagggccacc    60
ctcaactgta agtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttatttct gtcagcaata ttatactact   300
tggacgttcg gccaagggac caaggtggaa atcaaac                            337

<210> SEQ ID NO 60
<211> LENGTH: 112
<212> TYPE: PRT
<213> ORGANISM: Artificial Sequence
<220> FEATURE:
<223> OTHER INFORMATION: Synthetic

```
<400> SEQUENCE: 60

Asp Ile Val Met Thr Gln Ser Pro Asp Ser Leu Ala Val Ser Leu Gly
 1               5                  10                  15

Glu Arg Ala Thr Leu Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Thr Thr Trp Thr Phe Gly Gln Gly Thr Lys Val Glu Ile Lys
            100                 105                 110

<210> SEQ ID NO 61
<211> LENGTH: 36
<212> TYPE: DNA
<213> ORGANISM: Artificial Sequence
<220> FEATURE:
<223> OTHER INFORMATION: Synthetic

<400> SEQUENCE: 61
cagagtgttt tatacagctc aacaataag aactac                              36

<210> SEQ ID NO 62
<211> LENGTH: 12
<212> TYPE: PRT
<213> ORGANISM: Artificial Sequence
<220> FEATURE:
<223> OTHER INFORMATION: Synthetic

<400> SEQUENCE: 62

Gln Ser Val Leu Tyr Ser Ser Asn Asn Lys Asn Tyr
 1               5                  10

<210> SEQ ID NO 63
<211> LENGTH: 9
<212> TYPE: DNA
<213> ORGANISM: Artificial Sequence
<220> FEATURE:
<223> OTHER INFORMATION: Synthetic

<400> SEQUENCE: 63 tgggcatct                                                            9

<210> SEQ ID NO 64
<211> LENGTH: 3
<212> TYPE: PRT
<213> ORGANISM: Artificial Sequence
<220> FEATURE:
<223> OTHER INFORMATION: Synthetic

<400> SEQUENCE: 64

Trp Ala Ser
 1

<210> SEQ ID NO 65
<211> LENGTH: 24
<212> TYPE: DNA
<213> ORGANISM: Artificial Sequence
<220> FEATURE:
```

<223> OTHER INFORMATION: Synthetic

<400> SEQUENCE: 65
cagcaatatt atactacttg gacg                                                  24

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Gln Gln Tyr Tyr Thr Thr Trp Thr
 1               5

<210> SEQ ID NO 67
<211> LENGTH: 385
<212> TYPE: DNA
<213> ORGANISM: Artificial Sequence
<220> FEATURE:
<223> OTHER INFORMATION: Synthetic

<400> SEQUENCE: 67
caggtgcagt tggtggagtc tgggggaggc gtggtccagc ctggagggtc cctgagactc         60
tcctgtgcag cctctgcatc caccttcagt aggcatggca tgcactgggt ccgccaggct       120
ccaggcaagg gactggagtg ggtggcagtt atatcatatg atggaaataa taaatactat       180
gtagactccg tgaagggccg attcaccatc tccagagaca attccaagaa cacgctgtat       240
ctgcaaatga atagcctgag aactgacgac acggctgtgt attattgttc gaaagagtta       300
gtaggtatta ctggaaacct ggtctactac tactactacg gaatggacgt ctggggccaa       360
gggaccacgg tcaccgtctc ctcag                                              385

<210> SEQ ID NO 68
<211> LENGTH: 128
<212> TYPE: PRT
<213> ORGANISM: Artificial Sequence
<220> FEATURE:
<223> OTHER INFORMATION: Synthetic

<400> SEQUENCE: 68

Gln Val Gln Leu Val Glu Ser Gly Gly Gly Val Val Gln Pro Gly Arg
 1               5                  10                  15

Ser Leu Arg Leu Ser Cys Ala Ala Ser Ala Ser Thr Phe Ser Arg His
             20                  25                  30

Gly Met His Trp Val Arg Gln Ala Pro Gly Lys Gly Leu Glu Trp Val
         35                  40                  45

Ala Val Ile Ser Tyr Asp Gly Asn Asn Lys Tyr Tyr Val Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Thr Asp Asp Thr Ala Val Tyr Tyr Cys
                 85                  90                  95

Ser Lys Glu Leu Val Gly Ile Thr Gly Asn Leu Val Tyr Tyr Tyr Tyr
            100                 105                 110

Tyr Gly Met Asp Val Trp Gly Gln Gly Thr Thr Val Thr Val Ser Ser
        115                 120                 125

<210> SEQ ID NO 69

-continued

```
<211> LENGTH: 24
<212> TYPE: DNA
<213> ORGANISM: Artificial Sequence
<220> FEATURE:
<223> OTHER INFORMATION: Synthetic

<400> SEQUENCE: 69
gcatccacct tcagtaggca tggc                                              24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ala Ser Thr Phe Ser Arg His Gly
 1               5

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71
atatcatatg atggaaataa taaa                                              24

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Ile Ser Tyr Asp Gly Asn Asn Lys
 1               5

<210> SEQ ID NO 73
<211> LENGTH: 63
<212> TYPE: DNA
<213> ORGANISM: Artificial Sequence
<220> FEATURE:
<223> OTHER INFORMATION: Synthetic

<400> SEQUENCE: 73
tcgaaagagt tagtaggtat tactggaaac ctggtctact actactacta cggaatggac       60
gtc                                                                     63

<210> SEQ ID NO 74
<211> LENGTH: 21
<212> TYPE: PRT
<213> ORGANISM: Artificial Sequence
<220> FEATURE:
<223> OTHER INFORMATION: Synthetic

<400> SEQUENCE: 74

Ser Lys Glu Leu Val Gly Ile Thr Gly Asn Leu Val Tyr Tyr Tyr
 1               5                  10                  15

Tyr Gly Met Asp Val
            20
```

<210> SEQ ID NO 75
<211> LENGTH: 325
<212> TYPE: DNA
<213> ORGANISM: Artificial Sequence
<220> FEATURE:
<223> OTHER INFORMATION: Synthetic

<400> SEQUENCE: 75

```
gaaattgtgt tgacgcagtc tccaggcacc ctgtctttgt ctccagggga aagagccacc        60
ctctcctgca gggccagtca gactattaac agcagctact taggctggta ccagcagaaa       120
cctggccagg ctcccagact cctcatctat ggtgcatcca acagggccac tggcatccca       180
gacagtttca gtggcagtgg gtctgggaca gacttcactc tcaccatcag cagactggag       240
cctgaagatt ttgcagtgta ttactgtcaa cattataaca actcacctta cacttttggc       300
caggggacca agctggagat caaac                                             325
```

<210> SEQ ID NO 76
<211> LENGTH: 108
<212> TYPE: PRT
<213> ORGANISM: Artificial Sequence
<220> FEATURE:
<223> OTHER INFORMATION: Synthetic

<400> SEQUENCE: 76

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Thr Ile Asn Ser Ser
             20                  25                  30

Tyr Leu Gly Trp Tyr Gln Gln Lys Pro Gly Gln Ala Pro Arg Leu Leu
         35                  40                  45

Ile Tyr Gly Ala Ser Asn Arg Ala Thr Gly Ile Pro Asp Ser Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asn Asn Ser Pro
                 85                  90                  95

Tyr Thr Phe Gly Gln Gly Thr Lys Leu Glu Ile Lys
            100                 105
```

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77

```
cagactatta acagcagcta c                                                  21
```

<210> SEQ ID NO 78
<211> LENGTH: 7
<212> TYPE: PRT
<213> ORGANISM: Artificial Sequence
<220> FEATURE:
<223> OTHER INFORMATION: Synthetic

<400> SEQUENCE: 78

```
Gln Thr Ile Asn Ser Ser Tyr
  1               5
```

<210> SEQ ID NO 79

```
<211> LENGTH: 9
<212> TYPE: DNA
<213> ORGANISM: Artificial Sequence
<220> FEATURE:
<223> OTHER INFORMATION: Synthetic

<400> SEQUENCE: 79 ggtgcatcc                                                                 9

<210> SEQ ID NO 80
<211> LENGTH: 3
<212> TYPE: PRT
<213> ORGANISM: Artificial Sequence
<220> FEATURE:
<223> OTHER INFORMATION: Synthetic

<400> SEQUENCE: 80

Gly Ala Ser
 1

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81
caacattata acaactcacc ttacact                                            27

<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

Gln His Tyr Asn Asn Ser Pro Tyr Thr
 1               5

<210> SEQ ID NO 83
<211> LENGTH: 361
<212> TYPE: DNA
<213> ORGANISM: Artificial Sequence
<220> FEATURE:
<223> OTHER INFORMATION: Synthetic

<400> SEQUENCE: 83
caggtgcagc tgcaggagtc gggcccagga ctggtgaagc cttcacagac cctgtccctc        60
acctgcactg tctctggtgg ctccataagc agtggtggtt actactggag ctggatccgc       120
cactacccag gaagggcct ggagtggatt ggctacgtcc attacagtgg gaacacccac        180
tacaatacgt ccctcaagag cgacttacc atatcaatag acacgtctaa gagccaattc        240
tccctggatc tgagctctgt gactgccgcg gacacggccg tgtattactg tgcgagagcc       300
ccccgtggat accattactt tgcctactgg ggccagggaa ccctggtcac cgtctcctca       360
g                                                                       361

<210> SEQ ID NO 84
<211> LENGTH: 120
<212> TYPE: PRT
<213> ORGANISM: Artificial Sequence
<220> FEATURE:
<223> OTHER INFORMATION: Synthetic
```

<400> SEQUENCE: 84

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg His Tyr Pro Gly Lys Gly Leu Glu
        35                  40                  45

Trp Ile Gly Tyr Val His Tyr Ser Gly Asn Thr His Tyr Asn Thr Ser
    50                  55                  60

Leu Lys Arg Arg Leu Thr Ile Ser Ile Asp Thr Ser Lys Ser Gln Phe
65                  70                  75                  80

Ser Leu Asp Leu Ser Ser Val Thr Ala Ala Asp Thr Ala Val Tyr Tyr
                85                  90                  95

Cys Ala Arg Ala Pro Arg Gly Tyr His Tyr Phe Ala Tyr Trp Gly Gln
            100                 105                 110

Gly Thr Leu Val Thr Val Ser Ser
        115                 120

<210> SEQ ID NO 85
<211> LENGTH: 30
<212> TYPE: DNA
<213> ORGANISM: Artificial Sequence
<220> FEATURE:
<223> OTHER INFORMATION: Synthetic

<400> SEQUENCE: 85
ggtggctcca taagcagtgg tggttactac                                          30

<210> SEQ ID NO 86
<211> LENGTH: 10
<212> TYPE: PRT
<213> ORGANISM: Artificial Sequence
<220> FEATURE:
<223> OTHER INFORMATION: Synthetic

<400> SEQUENCE: 86

Gly Gly Ser Ile Ser Ser Gly Gly Tyr Tyr
1               5                   10

<210> SEQ ID NO 87
<211> LENGTH: 21
<212> TYPE: DNA
<213> ORGANISM: Artificial Sequence
<220> FEATURE:
<223> OTHER INFORMATION: Synthetic

<400> SEQUENCE: 87
gtccattaca gtgggaacac c                                                   21

<210> SEQ ID NO 88
<211> LENGTH: 7
<212> TYPE: PRT
<213> ORGANISM: Artificial Sequence
<220> FEATURE:
<223> OTHER INFORMATION: Synthetic

<400> SEQUENCE: 88

Val His Tyr Ser Gly Asn Thr
1               5

<210> SEQ ID NO 89

```
<211> LENGTH: 36
<212> TYPE: DNA
<213> ORGANISM: Artificial Sequence
<220> FEATURE:
<223> OTHER INFORMATION: Synthetic

<400> SEQUENCE: 89
gcgagagccc cccgtggata ccattacttt gcctac                                    36

<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

Ala Arg Ala Pro Arg Gly Tyr His Tyr Phe Ala Tyr
  1               5                  10

<210> SEQ ID NO 91
<211> LENGTH: 325
<212> TYPE: DNA
<213> ORGANISM: Artificial Sequence
<220> FEATURE:
<223> OTHER INFORMATION: Synthetic

<400> SEQUENCE: 91
gaaattgggt tgacgcagtc tccaggcacc ctgtctttgt ctccagggga aagagccacc           60
ctctcctgca gggccagtca gagtattagc agcaggtact tagcctggta ccagcagaaa          120
cctggccagg ctcccaggct cctcatcttt ggtgcatcca gcagggccac tggcatacca          180
gacaggttca gtggcagtgg gtctgggaca gacttcactc tcaccatcag cagactggag          240
cctgaagatt ttgcagtgta ttactgtcag cagtatggta gctcaccgct cactttcggc          300
ggagggacca aggtggagat caaac                                                325

<210> SEQ ID NO 92
<211> LENGTH: 108
<212> TYPE: PRT
<213> ORGANISM: Artificial Sequence
<220> FEATURE:
<223> OTHER INFORMATION: Synthetic

<400> SEQUENCE: 92

Glu Ile Gly Leu Thr Gln Ser Pro Gly Thr Leu Ser Leu Ser Pro Gly
  1               5                  10                  15

Glu Arg Ala Thr Leu Ser Cys Arg Ala Ser Gln Ser Ile Ser Ser Arg
                 20                  25                  30

Tyr Leu Ala Trp Tyr Gln Gln Lys Pro Gly Gln Ala Pro Arg Leu Leu
             35                  40                  45

Ile Phe Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
            100                 105

<210> SEQ ID NO 93
<211> LENGTH: 21
```

-continued

<212> TYPE: DNA
<213> ORGANISM: Artificial Sequence
<220> FEATURE:
<223> OTHER INFORMATION: Synthetic

<400> SEQUENCE: 93
cagagtatta gcagcaggta c                                            21

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

Gln Ser Ile Ser Ser Arg Tyr
 1               5

<210> SEQ ID NO 95
<211> LENGTH: 9
<212> TYPE: DNA
<213> ORGANISM: Artificial Sequence
<220> FEATURE:
<223> OTHER INFORMATION: Synthetic

<400> SEQUENCE: 95 ggtgcatcc                                                           9

<210> SEQ ID NO 96
<211> LENGTH: 3
<212> TYPE: PRT
<213> ORGANISM: Artificial Sequence
<220> FEATURE:
<223> OTHER INFORMATION: Synthetic

<400> SEQUENCE: 96

Gly Ala Ser
 1

<210> SEQ ID NO 97
<211> LENGTH: 27
<212> TYPE: DNA
<213> ORGANISM: Artificial Sequence
<220> FEATURE:
<223> OTHER INFORMATION: Synthetic

<400> SEQUENCE: 97
cagcagtatg gtagctcacc gctcact                                      27

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Gln Gln Tyr Gly Ser Ser Pro Leu Thr
 1               5

<210> SEQ ID NO 99
<211> LENGTH: 361
<212> TYPE: DNA
<213> ORGANISM: Artificial Sequence
<220> FEATURE:
<223> OTHER INFORMATION: Synthetic

<400> SEQUENCE: 99

| | | | | | |
|---|---|---|---|---|---|
| caggtgcagc | tgcaggagtc | gggcccagga | ctggtgaagc | cttcacagac | cctgtccctc | 60
| acctgcactg | tctctggtgg | ctccatcagc | agtagtggtt | actactggag | ttggatccgc | 120
| cagcacccag | ggaagggcct | ggagtggatt | gggtacgtcc | attacagtgg | aaacacccac | 180
| tacagcccgt | ccctcaagag | tcgacttacc | atatcagttg | acacgtctaa | gaaccagttc | 240
| tccctgaagc | tgagctctgt | gactgccgcg | gacacggccg | tgtattactg | tgcgagagcc | 300
| ccccgtggat | accattactt | tgcctactgg | ggccagggaa | ccctggtcac | cgtctcctca | 360
| g | | | | | | 361

<210> SEQ ID NO 100
<211> LENGTH: 120
<212> TYPE: PRT
<213> ORGANISM: Artificial Sequence
<220> FEATURE:
<223> OTHER INFORMATION: Synthetic

<400> SEQUENCE: 100

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Gly Tyr Tyr Trp Ser Trp Ile Arg Gln His Pro Gly Lys Gly Leu Glu
        35                  40                  45

Trp Ile Gly Tyr Val His Tyr Ser Gly Asn Thr His Tyr Ser Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Pro Arg Gly Tyr His Tyr Phe Ala Tyr Trp Gly Gln
            100                 105                 110

Gly Thr Leu Val Thr Val Ser Ser
        115                 120

<210> SEQ ID NO 101
<211> LENGTH: 30
<212> TYPE: DNA
<213> ORGANISM: Artificial Sequence
<220> FEATURE:
<223> OTHER INFORMATION: Synthetic

<400> SEQUENCE: 101
ggtggctcca tcagcagtag tggttactac                                    30

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Gly Gly Ser Ile Ser Ser Ser Gly Tyr Tyr
1               5                   10

<210> SEQ ID NO 103
<211> LENGTH: 21

```
<210> SEQ ID NO 103
<211> LENGTH: 21
<212> TYPE: DNA
<213> ORGANISM: Artificial Sequence
<220> FEATURE:
<223> OTHER INFORMATION: Synthetic

<400> SEQUENCE: 103
gtccattaca gtgggaacac c                                              21

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Val His Tyr Ser Gly Asn Thr
 1               5

<210> SEQ ID NO 105
<211> LENGTH: 36
<212> TYPE: DNA
<213> ORGANISM: Artificial Sequence
<220> FEATURE:
<223> OTHER INFORMATION: Synthetic

<400> SEQUENCE: 105
gcgagagccc cccgtggata ccattacttt gcctac                              36

<210> SEQ ID NO 106
<211> LENGTH: 12
<212> TYPE: PRT
<213> ORGANISM: Artificial Sequence
<220> FEATURE:
<223> OTHER INFORMATION: Synthetic

<400> SEQUENCE: 106

Ala Arg Ala Pro Arg Gly Tyr His Tyr Phe Ala Tyr
 1               5                  10

<210> SEQ ID NO 107
<211> LENGTH: 325
<212> TYPE: DNA
<213> ORGANISM: Artificial Sequence
<220> FEATURE:
<223> OTHER INFORMATION: Synthetic

<400> SEQUENCE: 107
aaaattgtgt tgacgcagtc tccaggcacc ctgtctttgt ctccagggga gagagccacc    60
ctctcctgca gggccagtca gagtattagc agcagctact tagcctggta ccagcagaaa   120
cctggccagg ctcccaggct cctcatcttt ggtgcatcca gcagggccac tggcatccca   180
gacaggttca gtggcagtgg gtctgggcca gacttcactc tcaccattag agactggag    240 cctgaagatt ttgcggtgta ttactgtcag cagtatggta gttcaccgct cactttcggc   300
ggagggacca aggtggagat caaac                                         325

<210> SEQ ID NO 108
<211> LENGTH: 108
<212> TYPE: PRT
<213> ORGANISM: Artificial Sequence
<220> FEATURE:
<223> OTHER INFORMATION: Synthetic

<400> SEQUENCE: 108
```

-continued

```
Lys Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
 50                  55                  60

Gly Ser Gly Ser Gly Pro Asp Phe Thr Leu Thr Ile Arg Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```

<210> SEQ ID NO 109
<211> LENGTH: 21
<212> TYPE: DNA
<213> ORGANISM: Artificial Sequence
<220> FEATURE:
<223> OTHER INFORMATION: Synthetic

<400> SEQUENCE: 109
cagagtatta gcagcagcta c                                          21

<210> SEQ ID NO 110
<211> LENGTH: 7
<212> TYPE: PRT
<213> ORGANISM: Artificial Sequence
<220> FEATURE:
<223> OTHER INFORMATION: Synthetic

<400> SEQUENCE: 110

```
Gln Ser Ile Ser Ser Ser Tyr
 1               5
```

<210> SEQ ID NO 111
<211> LENGTH: 9
<212> TYPE: DNA
<213> ORGANISM: Artificial Sequence
<220> FEATURE:
<223> OTHER INFORMATION: Synthetic

<400> SEQUENCE: 111 ggtgcatcc                                                         9

<210> SEQ ID NO 112
<211> LENGTH: 3
<212> TYPE: PRT
<213> ORGANISM: Artificial Sequence
<220> FEATURE:
<223> OTHER INFORMATION: Synthetic

<400> SEQUENCE: 112

```
Gly Ala Ser
 1
```

<210> SEQ ID NO 113
<211> LENGTH: 27
<212> TYPE: DNA
<213> ORGANISM: Artificial Sequence
<220> FEATURE:
<223> OTHER INFORMATION: Synthetic

<400> SEQUENCE: 113
cagcagtatg gtagttcacc gctcact                                                                27

<210> SEQ ID NO 114
<211> LENGTH: 9
<212> TYPE: PRT
<213> ORGANISM: Artificial Sequence
<220> FEATURE:
<223> OTHER INFORMATION: Synthetic

<400> SEQUENCE: 114

Gln Gln Tyr Gly Ser Ser Pro Leu Thr
1               5

<210> SEQ ID NO 115
<211> LENGTH: 358
<212> TYPE: DNA
<213> ORGANISM: Artificial Sequence
<220> FEATURE:
<223> OTHER INFORMATION: Synthetic

<400> SEQUENCE: 115
caggttcagt tggtgcagtc tggagctgag gtgaagaagc ctggggcctc agtgaaggtc        60
tcctgcaagg cttctggtta caccttttcc acctatggta tcagctgggt gcgacaggcc       120
cctggacaag gcttgagtg gatgggatgg atcagcgctt acgacaataa cgcggactat        180
gcacagaact tccaggccag agtcaccatg accacagaca catccacgac cacagcctac       240
atggagctga ggagcctgag atctgacgac acggccgtgt attactgtgc gaggtatagc       300
tggaactttc actggttcga cccctggggc cagggaaccc tggtcaccgt ctcctcag        358

<210> SEQ ID NO 116
<211> LENGTH: 119
<212> TYPE: PRT
<213> ORGANISM: Artificial Sequence
<220> FEATURE:
<223> OTHER INFORMATION: Synthetic

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Asn Asn Ala Asp Tyr Ala Gln Asn Phe
    50                  55                  60

Gln Ala Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ser Trp Asn Phe His Trp Phe Asp Pro Trp Gly Gln Gly
            100                 105                 110

Thr Leu Val Thr Val Ser Ser
        115

<210> SEQ ID NO 117
<211> LENGTH: 24
<212> TYPE: DNA
<213> ORGANISM: Artificial Sequence
<220> FEATURE:

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
ggttacacct tttccaccta tggt                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Gly Tyr Thr Phe Ser Thr Tyr Gly
  1               5

<210> SEQ ID NO 119
<211> LENGTH: 24
<212> TYPE: DNA
<213> ORGANISM: Artificial Sequence
<220> FEATURE:
<223> OTHER INFORMATION: Synthetic

<400> SEQUENCE: 119
atcagcgctt acgacaataa cgcg                                          24

<210> SEQ ID NO 120
<211> LENGTH: 8
<212> TYPE: PRT
<213> ORGANISM: Artificial Sequence
<220> FEATURE:
<223> OTHER INFORMATION: Synthetic

<400> SEQUENCE: 120

Ile Ser Ala Tyr Asp Asn Asn Ala
  1               5

<210> SEQ ID NO 121
<211> LENGTH: 36
<212> TYPE: DNA
<213> ORGANISM: Artificial Sequence
<220> FEATURE:
<223> OTHER INFORMATION: Synthetic

<400> SEQUENCE: 121
gcgaggtata gctggaactt tcactggttc gacccc                             36

<210> SEQ ID NO 122
<211> LENGTH: 12
<212> TYPE: PRT
<213> ORGANISM: Artificial Sequence
<220> FEATURE:
<223> OTHER INFORMATION: Synthetic

<400> SEQUENCE: 122

Ala Arg Tyr Ser Trp Asn Phe His Trp Phe Asp Pro
  1               5                  10

<210> SEQ ID NO 123
<211> LENGTH: 325
<212> TYPE: DNA
<213> ORGANISM: Artificial Sequence
<220> FEATURE:
<223> OTHER INFORMATION: Synthetic

<400> SEQUENCE: 123

```
gaaattgtgt tgacgcagtc tccaggcacc ctgtctttgt ctccagggga aagagccacc    60
ctctcctgca gggccagtca gagtgttagc agtacctact tagcctggta ccagcagcaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta actcaccgtg gacgttcggc   300
caagggacca aggtggaaat caaac                                         325
```

<210> SEQ ID NO 124
<211> LENGTH: 108
<212> TYPE: PRT
<213> ORGANISM: Artificial Sequence
<220> FEATURE:
<223> OTHER INFORMATION: Synthetic

<400> SEQUENCE: 124

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
            20                  25                  30

Tyr Leu Ala Trp Tyr Gln Gln Gln Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Trp Thr Phe Gly Gln Gly Thr Lys Val Glu Ile Lys
            100                 105
```

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125

```
cagagtgtta gcagtaccta c                                              21
```

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

```
Gln Ser Val Ser Ser Thr Tyr
 1               5
```

<210> SEQ ID NO 127
<211> LENGTH: 9
<212> TYPE: DNA
<213> ORGANISM: Artificial Sequence
<220> FEATURE:
<223> OTHER INFORMATION: Synthetic

<400> SEQUENCE: 127

```
ggtgcatcc                                                             9
```

<210> SEQ ID NO 128
<211> LENGTH: 3
<212> TYPE: PRT
<213> ORGANISM: Artificial Sequence
<220> FEATURE:
<223> OTHER INFORMATION: Synthetic

<400> SEQUENCE: 128

Gly Ala Ser
 1

<210> SEQ ID NO 129
<211> LENGTH: 27
<212> TYPE: DNA
<213> ORGANISM: Artificial Sequence
<220> FEATURE:
<223> OTHER INFORMATION: Synthetic

<400> SEQUENCE: 129
cagcagtatg gtaactcacc gtggacg                                       27

<210> SEQ ID NO 130
<211> LENGTH: 9
<212> TYPE: PRT
<213> ORGANISM: Artificial Sequence
<220> FEATURE:
<223> OTHER INFORMATION: Synthetic

<400> SEQUENCE: 130

Gln Gln Tyr Gly Asn Ser Pro Trp Thr
 1               5

<210> SEQ ID NO 131
<211> LENGTH: 358
<212> TYPE: DNA
<213> ORGANISM: Artificial Sequence
<220> FEATURE:
<223> OTHER INFORMATION: Synthetic

<400> SEQUENCE: 131
caggttcacc tggtgcagtc tggagctgag gtgaagaagc ctggggcctc agtgaaggtc    60
tcctgcaggg cttctggtta cacctttacc aactatggta tcacctgggt gcgacaggcc   120
cctggacaag gcttgagtg atgggatgg atcagcgctt acagtggtaa cacagactat    180
gcacagaagt tccaggccag aatcaccatg accacagaca catccacgac cacagcctac   240
atggaactga ggagcctgac atctgacgac acggccgtgt attactgtgc gaggtatagc   300
tggaactttc actggttcga cccctggggc cagggaaccc tggtcaccgt ctcctcag    358

<210> SEQ ID NO 132
<211> LENGTH: 119
<212> TYPE: PRT
<213> ORGANISM: Artificial Sequence
<220> FEATURE:
<223> OTHER INFORMATION: Synthetic

<400> SEQUENCE: 132

Gln Val His Leu Val Gln Ser Gly Ala Glu Val Lys Lys Pro Gly Ala
 1               5                  10                  15

Ser Val Lys Val Ser Cys Arg Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Ala Tyr Ser Gly Asn Thr Asp Tyr Ala Gln Lys Phe
        50                  55                  60

Gln Ala Arg Ile Thr Met Thr Thr Asp Thr Ser Thr Thr Thr Ala Tyr
65                  70                  75                  80

Met Glu Leu Arg Ser Leu Thr Ser Asp Thr Ala Val Tyr Tyr Cys
                85                  90                  95

Ala Arg Tyr Ser Trp Asn Phe His Trp Phe Asp Pro Trp Gly Gln Gly
            100                 105                 110

Thr Leu Val Thr Val Ser Ser
        115

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
ggttacacct ttaccaacta tggt                                      24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Gly Tyr Thr Phe Thr Asn Tyr Gly
1               5

<210> SEQ ID NO 135
<211> LENGTH: 24
<212> TYPE: DNA
<213> ORGANISM: Artificial Sequence
<220> FEATURE:
<223> OTHER INFORMATION: Synthetic

<400> SEQUENCE: 135
atcagcgctt acagtggtaa caca                                      24

<210> SEQ ID NO 136
<211> LENGTH: 8
<212> TYPE: PRT
<213> ORGANISM: Artificial Sequence
<220> FEATURE:
<223> OTHER INFORMATION: Synthetic

<400> SEQUENCE: 136

Ile Ser Ala Tyr Ser Gly Asn Thr
1               5

<210> SEQ ID NO 137
<211> LENGTH: 36
<212> TYPE: DNA
<213> ORGANISM: Artificial Sequence
<220> FEATURE:
<223> OTHER INFORMATION: Synthetic

<400> SEQUENCE: 137
gcgaggtata gctggaactt tcactggttc gacccc                         36

<210> SEQ ID NO 138
<211> LENGTH: 12
<212> TYPE: PRT
<213> ORGANISM: Artificial Sequence
<220> FEATURE:
<223> OTHER INFORMATION: Synthetic

<400> SEQUENCE: 138

Ala Arg Tyr Ser Trp Asn Phe His Trp Phe Asp Pro
 1               5                  10

<210> SEQ ID NO 139
<211> LENGTH: 325
<212> TYPE: DNA
<213> ORGANISM: Artificial Sequence
<220> FEATURE:
<223> OTHER INFORMATION: Synthetic

<400> SEQUENCE: 139

```
gaaattgtgt tgacgcagtc tccaggcacc ctgtctttgt ctccagggga cagagtcacc      60
ctctcctgca gggccagtca gagtgttagt agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagtctggag     240
cctgaagatt ttgcagtgta ttactgtcag cagtgtggtg gctcaccgtg gacgttcggc     300
caagggacca gggtggagat caaac                                            325
```

<210> SEQ ID NO 140
<211> LENGTH: 108
<212> TYPE: PRT
<213> ORGANISM: Artificial Sequence
<220> FEATURE:
<223> OTHER INFORMATION: Synthetic

<400> SEQUENCE: 140

Glu Ile Val Leu Thr Gln Ser Pro Gly Thr Leu Ser Leu Ser Pro Gly
 1               5                  10                  15

Asp Arg Val Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Cys Gly Gly Ser Pro
                85                  90                  95

Trp Thr Phe Gly Gln Gly Thr Arg Val Glu Ile Lys
                100                 105

<210> SEQ ID NO 141
<211> LENGTH: 21
<212> TYPE: DNA
<213> ORGANISM: Artificial Sequence
<220> FEATURE:
<223> OTHER INFORMATION: Synthetic

<400> SEQUENCE: 141

```
cagagtgtta gtagcagcta c                                                21
```

<210> SEQ ID NO 142

```
<211> LENGTH: 7
<212> TYPE: PRT
<213> ORGANISM: Artificial Sequence
<220> FEATURE:
<223> OTHER INFORMATION: Synthetic

<400> SEQUENCE: 142

Gln Ser Val Ser Ser Ser Tyr
 1               5

<210> SEQ ID NO 143
<211> LENGTH: 9
<212> TYPE: DNA
<213> ORGANISM: Artificial Sequence
<220> FEATURE:
<223> OTHER INFORMATION: Synthetic

<400> SEQUENCE: 143 ggtgcatcc                                                                  9

<210> SEQ ID NO 144
<211> LENGTH: 3
<212> TYPE: PRT
<213> ORGANISM: Artificial Sequence
<220> FEATURE:
<223> OTHER INFORMATION: Synthetic

<400> SEQUENCE: 144

Gly Ala Ser
 1

<210> SEQ ID NO 145
<211> LENGTH: 27
<212> TYPE: DNA
<213> ORGANISM: Artificial Sequence
<220> FEATURE:
<223> OTHER INFORMATION: Synthetic

<400> SEQUENCE: 145
cagcagtgtg gtggctcacc gtggacg                                             27

<210> SEQ ID NO 146
<211> LENGTH: 9
<212> TYPE: PRT
<213> ORGANISM: Artificial Sequence
<220> FEATURE:
<223> OTHER INFORMATION: Synthetic

<400> SEQUENCE: 146

Gln Gln Cys Gly Gly Ser Pro Trp Thr
 1               5

<210> SEQ ID NO 147
<211> LENGTH: 358
<212> TYPE: DNA
<213> ORGANISM: Artificial Sequence
<220> FEATURE:
<223> OTHER INFORMATION: Synthetic

<400> SEQUENCE: 147
caggttcaac tggtgcagtc tgggcctgag gtgaagaagc ctggggcctc agtgaaggtc          60
gcctgcaagg cttctggtta cacctttacc cactatggtt tcacctgggt gcgacaggcc        120
cctggacaag ggcttgagtg gatgggatgg atcagcgctt acagtggtca tacagactat        180
gcacggaagt tccaggccag agtcaccatg accacagaca cattcacgac cacagcctac        240
```

```
atggaactga ggagcctgag atctgacgac acggccgttt attactgtgc gagttatagc    300
tggaactttc actggttcga ccctggggc agggaaccc tggtcaccgt ctcctcag        358
```

<210> SEQ ID NO 148
<211> LENGTH: 119
<212> TYPE: PRT
<213> ORGANISM: Artificial Sequence
<220> FEATURE:
<223> OTHER INFORMATION: Synthetic

<400> SEQUENCE: 148

```
Gln Val Gln Leu Val Gln Ser Gly Pro Glu Val Lys Lys Pro Gly Ala
 1               5                  10                  15

Ser Val Lys Val Ala Cys Lys Ala Ser Gly Tyr Thr Phe Thr His Tyr
            20                  25                  30

Gly Phe Thr Trp Val Arg Gln Ala Pro Gly Gln Gly Leu Glu Trp Met
        35                  40                  45

Gly Trp Ile Ser Ala Tyr Ser Gly His Thr Asp Tyr Ala Arg Lys Phe
    50                  55                  60

Gln Ala Arg Val Thr Met Thr Thr Asp Thr Phe Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Ser Tyr Ser Trp Asn Phe His Trp Phe Asp Pro Trp Gly Gln Gly
            100                 105                 110

Thr Leu Val Thr Val Ser Ser
        115
```

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149

```
ggttacacct ttacccacta tggt                                            24
```

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

```
Gly Tyr Thr Phe Thr His Tyr Gly
 1               5
```

<210> SEQ ID NO 151
<211> LENGTH: 24
<212> TYPE: DNA
<213> ORGANISM: Artificial Sequence
<220> FEATURE:
<223> OTHER INFORMATION: Synthetic

<400> SEQUENCE: 151

```
atcagcgctt acagtggtca taca                                            24
```

<210> SEQ ID NO 152
<211> LENGTH: 8
<212> TYPE: PRT

```
<213> ORGANISM: Artificial Sequence
<220> FEATURE:
<223> OTHER INFORMATION: Synthetic

<400> SEQUENCE: 152

Ile Ser Ala Tyr Ser Gly His Thr
1               5

<210> SEQ ID NO 153
<211> LENGTH: 36
<212> TYPE: DNA
<213> ORGANISM: Artificial Sequence
<220> FEATURE:
<223> OTHER INFORMATION: Synthetic

<400> SEQUENCE: 153
gcgagttata gctggaactt tcactggttc gacccc                                    36

<210> SEQ ID NO 154
<211> LENGTH: 12
<212> TYPE: PRT
<213> ORGANISM: Artificial Sequence
<220> FEATURE:
<223> OTHER INFORMATION: Synthetic

<400> SEQUENCE: 154

Ala Ser Tyr Ser Trp Asn Phe His Trp Phe Asp Pro
1               5                   10

<210> SEQ ID NO 155
<211> LENGTH: 325
<212> TYPE: DNA
<213> ORGANISM: Artificial Sequence
<220> FEATURE:
<223> OTHER INFORMATION: Synthetic

<400> SEQUENCE: 155
caaattgtgt tgacgcagtc tccaggcacc ctgtctttgt ctccagggga aagagccacc          60
ctctcctgca gggccagtca gagtgttagt accacctact tagcctggta ccagcagaaa         120
cctggccagg ctcccagtct cctcatctat ggtacatcca ccagggccac tggcatccca         180
gacaggttca gtggcagtgg gtctgggact gacttcactc tcaccatcag cagactggag         240
cctgaagatt ttgcagtgta ttactgtcag cagtgtggtg gctcaccgtg gacgttcggc         300
caagggacca aggtgaaaat caaac                                              325

<210> SEQ ID NO 156
<211> LENGTH: 108
<212> TYPE: PRT
<213> ORGANISM: Artificial Sequence
<220> FEATURE:
<223> OTHER INFORMATION: Synthetic

<400> SEQUENCE: 156

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr Thr
            20                  25                  30

Tyr Leu Ala Trp Tyr Gln Gln Lys Pro Gly Gln Ala Pro Ser Leu Leu
        35                  40                  45

Ile Tyr Gly Thr Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
```

```
            65                  70                  75                  80
Pro Glu Asp Phe Ala Val Tyr Tyr Cys Gln Gln Cys Gly Gly Ser Pro
                85                  90                  95
Trp Thr Phe Gly Gln Gly Thr Lys Val Lys Ile Lys
            100                 105
```

<210> SEQ ID NO 157
<211> LENGTH: 21
<212> TYPE: DNA
<213> ORGANISM: Artificial Sequence
<220> FEATURE:
<223> OTHER INFORMATION: Synthetic

<400> SEQUENCE: 157
cagagtgtta gtaccaccta c                                          21

<210> SEQ ID NO 158
<211> LENGTH: 7
<212> TYPE: PRT
<213> ORGANISM: Artificial Sequence
<220> FEATURE:
<223> OTHER INFORMATION: Synthetic

<400> SEQUENCE: 158

Gln Ser Val Ser Thr Thr Tyr
 1               5

<210> SEQ ID NO 159
<211> LENGTH: 9
<212> TYPE: DNA
<213> ORGANISM: Artificial Sequence
<220> FEATURE:
<223> OTHER INFORMATION: Synthetic

<400> SEQUENCE: 159 ggtacatcc                                                         9

<210> SEQ ID NO 160
<211> LENGTH: 3
<212> TYPE: PRT
<213> ORGANISM: Artificial Sequence
<220> FEATURE:
<223> OTHER INFORMATION: Synthetic

<400> SEQUENCE: 160

Gly Thr Ser
 1

<210> SEQ ID NO 161
<211> LENGTH: 27
<212> TYPE: DNA
<213> ORGANISM: Artificial Sequence
<220> FEATURE:
<223> OTHER INFORMATION: Synthetic

<400> SEQUENCE: 161
cagcagtgtg gtggctcacc gtggacg                                    27

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Gln Gln Cys Gly Gly Ser Pro Trp Thr
 1               5

<210> SEQ ID NO 163
<211> LENGTH: 367
<212> TYPE: DNA
<213> ORGANISM: Artificial Sequence
<220> FEATURE:
<223> OTHER INFORMATION: Synthetic

<400> SEQUENCE: 163

```
caggtgcagt tggtgcagtc tggggctgag gtgaagaagc ctggggccgc tgtgaaggtc      60
tcctgcaagg cttctggata cacgttcacc agttatgata tcaactgggt gcgacaggcc     120
actggacaag gcttgagtg gatgggatgg ataaacccta acagtggtaa cacaggctat      180
gcacagaagt tcagggcag agtcaccttg accaggaaca cctccataag cacagcctac     240
atggaactga gcagcctgag atctgaggac acggccgttt attactgtgc gagagaggga     300
tattgtggtg gtgattgcta tgcttttgat atctggggcc aagggacaat ggtcaccgtc     360
tcttcag                                                               367
```

<210> SEQ ID NO 164
<211> LENGTH: 122
<212> TYPE: PRT
<213> ORGANISM: Artificial Sequence
<220> FEATURE:
<223> OTHER INFORMATION: Synthetic

<400> SEQUENCE: 164

Gln Val Gln Leu Val Gln Ser Gly Ala Glu Val Lys Lys Pro Gly Ala
 1               5                  10                  15

Ala Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Ile Asn Pro Asn Ser Gly Asn Thr Gly Tyr Ala Gln Lys Phe
        50                  55                  60

Gln Gly Arg Val Thr Leu Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Cys Gly Gly Asp Cys Tyr Ala Phe Asp Ile Trp
            100                 105                 110

Gly Gln Gly Thr Met Val Thr Val Ser Ser
        115                 120

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
ggatacacgt tcaccagtta tgat                                             24

<210> SEQ ID NO 166
<211> LENGTH: 8
<212> TYPE: PRT
<213> ORGANISM: Artificial Sequence

```
<220> FEATURE:
<223> OTHER INFORMATION: Synthetic

<400> SEQUENCE: 166

Gly Tyr Thr Phe Thr Ser Tyr Asp
  1               5

<210> SEQ ID NO 167
<211> LENGTH: 24
<212> TYPE: DNA
<213> ORGANISM: Artificial Sequence
<220> FEATURE:
<223> OTHER INFORMATION: Synthetic

<400> SEQUENCE: 167
ataaacccta acagtggtaa caca                                          24

<210> SEQ ID NO 168
<211> LENGTH: 8
<212> TYPE: PRT
<213> ORGANISM: Artificial Sequence
<220> FEATURE:
<223> OTHER INFORMATION: Synthetic

<400> SEQUENCE: 168

Ile Asn Pro Asn Ser Gly Asn Thr
  1               5

<210> SEQ ID NO 169
<211> LENGTH: 45
<212> TYPE: DNA
<213> ORGANISM: Artificial Sequence
<220> FEATURE:
<223> OTHER INFORMATION: Synthetic

<400> SEQUENCE: 169
gcgagagagg gatattgtgg tggtgattgc tatgcttttg atatc                   45

<210> SEQ ID NO 170
<211> LENGTH: 15
<212> TYPE: PRT
<213> ORGANISM: Artificial Sequence
<220> FEATURE:
<223> OTHER INFORMATION: Synthetic

<400> SEQUENCE: 170

Ala Arg Glu Gly Tyr Cys Gly Gly Asp Cys Tyr Ala Phe Asp Ile
  1               5                  10                  15

<210> SEQ ID NO 171
<211> LENGTH: 325
<212> TYPE: DNA
<213> ORGANISM: Artificial Sequence
<220> FEATURE:
<223> OTHER INFORMATION: Synthetic

<400> SEQUENCE: 171
gaaattgtgt tgacacaatc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatcttt ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccgct cactttcggc  300
ggagggacca aggtggagat caaac                                        325
```

<210> SEQ ID NO 172
<211> LENGTH: 108
<212> TYPE: PRT
<213> ORGANISM: Artificial Sequence
<220> FEATURE:
<223> OTHER INFORMATION: Synthetic

<400> SEQUENCE: 172

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
         35                  40                  45
Ile Phe Gly Ala Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Leu Thr Phe Gly Gly Gly Thr Lys Val Glu Ile Lys
            100                 105
```

<210> SEQ ID NO 173
<211> LENGTH: 21
<212> TYPE: DNA
<213> ORGANISM: Artificial Sequence
<220> FEATURE:
<223> OTHER INFORMATION: Synthetic

<400> SEQUENCE: 173
cagagtgtta gcagcagcta c                                           21

<210> SEQ ID NO 174
<211> LENGTH: 7
<212> TYPE: PRT
<213> ORGANISM: Artificial Sequence
<220> FEATURE:
<223> OTHER INFORMATION: Synthetic

<400> SEQUENCE: 174

```
Gln Ser Val Ser Ser Ser Tyr
 1               5
```

<210> SEQ ID NO 175
<211> LENGTH: 9
<212> TYPE: DNA
<213> ORGANISM: Artificial Sequence
<220> FEATURE:
<223> OTHER INFORMATION: Synthetic

<400> SEQUENCE: 175 ggtgcatcc                                                          9

<210> SEQ ID NO 176
<211> LENGTH: 3
<212> TYPE: PRT
<213> ORGANISM: Artificial Sequence
<220> FEATURE:
<223> OTHER INFORMATION: Synthetic

<400> SEQUENCE: 176

Gly Ala Ser
 1

<210> SEQ ID NO 177
<211> LENGTH: 27
<212> TYPE: DNA
<213> ORGANISM: Artificial Sequence
<220> FEATURE:
<223> OTHER INFORMATION: Synthetic

<400> SEQUENCE: 177
cagcagtatg gtagctcacc gctcact                                          27

<210> SEQ ID NO 178
<211> LENGTH: 9
<212> TYPE: PRT
<213> ORGANISM: Artificial Sequence
<220> FEATURE:
<223> OTHER INFORMATION: Synthetic

<400> SEQUENCE: 178

Gln Gln Tyr Gly Ser Ser Pro Leu Thr
 1               5

<210> SEQ ID NO 179
<211> LENGTH: 361
<212> TYPE: DNA
<213> ORGANISM: Artificial Sequence
<220> FEATURE:
<223> OTHER INFORMATION: Synthetic

<400> SEQUENCE: 179
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa gaaccagttc     240
tccctgaagc tgagctctgt gaccgccgca gacacggctg tgtattactg tgcggcaaac     300
tgggacgacg ccttcttctt tgactactgg ggccagggaa ccctggtcac cgtctcctca     360
g                                                                     361

<210> SEQ ID NO 180
<211> LENGTH: 120
<212> TYPE: PRT
<213> ORGANISM: Artificial Sequence
<220> FEATURE:
<223> OTHER INFORMATION: Synthetic

<400> SEQUENCE: 180

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ala Asn Trp Asp Asp Ala Phe Phe Phe Asp Tyr Trp Gly Gln
            100                 105                 110

Gly Thr Leu Val Thr Val Ser Ser
        115                 120

<210> SEQ ID NO 181
<211> LENGTH: 30
<212> TYPE: DNA
<213> ORGANISM: Artificial Sequence
<220> FEATURE:
<223> OTHER INFORMATION: Synthetic

<400> SEQUENCE: 181
ggtggctcca tcagcagtag tagttactac                                           30

<210> SEQ ID NO 182
<211> LENGTH: 10
<212> TYPE: PRT
<213> ORGANISM: Artificial Sequence
<220> FEATURE:
<223> OTHER INFORMATION: Synthetic

<400> SEQUENCE: 182

Gly Gly Ser Ile Ser Ser Ser Ser Tyr Tyr
1               5                   10

<210> SEQ ID NO 183
<211> LENGTH: 21
<212> TYPE: DNA
<213> ORGANISM: Artificial Sequence
<220> FEATURE:
<223> OTHER INFORMATION: Synthetic

<400> SEQUENCE: 183
atctattata gtgggagcac c                                                    21

<210> SEQ ID NO 184
<211> LENGTH: 7
<212> TYPE: PRT
<213> ORGANISM: Artificial Sequence
<220> FEATURE:
<223> OTHER INFORMATION: Synthetic

<400> SEQUENCE: 184

Ile Tyr Tyr Ser Gly Ser Thr
1               5

<210> SEQ ID NO 185
<211> LENGTH: 36
<212> TYPE: DNA
<213> ORGANISM: Artificial Sequence
<220> FEATURE:
<223> OTHER INFORMATION: Synthetic

<400> SEQUENCE: 185
gcggcaaact gggacgacgc cttcttcttt gactac                                    36

<210> SEQ ID NO 186
<211> LENGTH: 12
<212> TYPE: PRT
<213> ORGANISM: Artificial Sequence
<220> FEATURE:
<223> OTHER INFORMATION: Synthetic

<400> SEQUENCE: 186

Ala Ala Asn Trp Asp Asp Ala Phe Phe Phe Asp Tyr
1               5                   10

<210> SEQ ID NO 187
<211> LENGTH: 322
<212> TYPE: DNA
<213> ORGANISM: Artificial Sequence
<220> FEATURE:
<223> OTHER INFORMATION: Synthetic

<400> SEQUENCE: 187
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attcgtacac ttttggccag     300
gggaccaagc tggagatcaa ac                                              322

<210> SEQ ID NO 188
<211> LENGTH: 107
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 189
<211> LENGTH: 18
<212> TYPE: DNA
<213> ORGANISM: Artificial Sequence
<220> FEATURE:
<223> OTHER INFORMATION: Synthetic

<400> SEQUENCE: 189
cagagtatta gtagctgg                                                    18

<210> SEQ ID NO 190
<211> LENGTH: 6
<212> TYPE: PRT
<213> ORGANISM: Artificial Sequence
<220> FEATURE:
<223> OTHER INFORMATION: Synthetic

<400> SEQUENCE: 190

Gln Ser Ile Ser Ser Trp
1               5

<210> SEQ ID NO 191
<211> LENGTH: 9
<212> TYPE: DNA
<213> ORGANISM: Artificial Sequence
<220> FEATURE:
<223> OTHER INFORMATION: Synthetic

<400> SEQUENCE: 191 aaggcgtct                                                                9

<210> SEQ ID NO 192
<211> LENGTH: 3
<212> TYPE: PRT
<213> ORGANISM: Artificial Sequence
<220> FEATURE:
<223> OTHER INFORMATION: Synthetic

<400> SEQUENCE: 192

Lys Ala Ser
 1

<210> SEQ ID NO 193
<211> LENGTH: 27
<212> TYPE: DNA
<213> ORGANISM: Artificial Sequence
<220> FEATURE:
<223> OTHER INFORMATION: Synthetic

<400> SEQUENCE: 193
caacagtata atagttattc gtacact                                           27

<210> SEQ ID NO 194
<211> LENGTH: 9
<212> TYPE: PRT
<213> ORGANISM: Artificial Sequence
<220> FEATURE:
<223> OTHER INFORMATION: Synthetic

<400> SEQUENCE: 194

Gln Gln Tyr Asn Ser Tyr Ser Tyr Thr
 1               5

<210> SEQ ID NO 195
<211> LENGTH: 352
<212> TYPE: DNA
<213> ORGANISM: Artificial Sequence
<220> FEATURE:
<223> OTHER INFORMATION: Synthetic

<400> SEQUENCE: 195
caggtgcagc tggtgcagtc tggggctgag gtgaagaagc ctggggcctc agtgaaggtc        60
tcctgcaagg cttctggata caccttcacc ggctactata ttcactgggt acgacaggcc       120
cctggacaag gccttgagtg gatgggatgg atcaacccta acagtggtgg cacaaactat       180
gcacagaagt ttcagggcag ggtcaccatg accagggaca cgtccatcac cacagcctac       240
atggagctga gcaggctgat atctgacgac acggccgtgt attactgtgc gagaggaccc       300
tgggatttct ttgactactg gggccaggga accctggtca ccgtctcctc ag              352

<210> SEQ ID NO 196
<211> LENGTH: 117
<212> TYPE: PRT
<213> ORGANISM: Artificial Sequence

```
<220> FEATURE:
<223> OTHER INFORMATION: Synthetic

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Thr Thr Ala Tyr
65                  70                  75                  80

Met Glu Leu Ser Arg Leu Ile Ser Asp Asp Thr Ala Val Tyr Tyr Cys
                85                  90                  95

Ala Arg Gly Pro Trp Asp Phe Phe Asp Tyr Trp Gly Gln Gly Thr Leu
            100                 105                 110

Val Thr Val Ser Ser
        115

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
ggatacacct tcaccggcta ctat                                              24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Gly Tyr Thr Phe Thr Gly Tyr Tyr
1               5

<210> SEQ ID NO 199
<211> LENGTH: 24
<212> TYPE: DNA
<213> ORGANISM: Artificial Sequence
<220> FEATURE:
<223> OTHER INFORMATION: Synthetic

<400> SEQUENCE: 199
atcaacccta acagtggtgg caca                                              24

<210> SEQ ID NO 200
<211> LENGTH: 8
<212> TYPE: PRT
<213> ORGANISM: Artificial Sequence
<220> FEATURE:
<223> OTHER INFORMATION: Synthetic

<400> SEQUENCE: 200

Ile Asn Pro Asn Ser Gly Gly Thr
1               5
```

<210> SEQ ID NO 201
<211> LENGTH: 30
<212> TYPE: DNA
<213> ORGANISM: Artificial Sequence
<220> FEATURE:
<223> OTHER INFORMATION: Synthetic

<400> SEQUENCE: 201
gcgagaggac cctgggattt ctttgactac                                        30

<210> SEQ ID NO 202
<211> LENGTH: 10
<212> TYPE: PRT
<213> ORGANISM: Artificial Sequence
<220> FEATURE:
<223> OTHER INFORMATION: Synthetic

<400> SEQUENCE: 202

Ala Arg Gly Pro Trp Asp Phe Phe Asp Tyr
 1               5                  10

<210> SEQ ID NO 203
<211> LENGTH: 340
<212> TYPE: DNA
<213> ORGANISM: Artificial Sequence
<220> FEATURE:
<223> OTHER INFORMATION: Synthetic

<400> SEQUENCE: 203
gacatcgtga tgacccagtc tccagactcc ctggctgtgt ctctgggcga gagggccacc        60
atcaactgca gtccagcca gagtgtttta tacagctcca acaataagaa ctacttagct       120
tggtaccagc agaaaccagg acagcctcct aagctgctca tttactgggc atctacccgg       180
gaatccgggg tccctgaccg attcagtggc agcgggtctg ggacagattt cactctcacc       240
atcagcagcc tgcaggctga agatgtggca gtttattact gtcagcaata ttatagtact       300
ccgtacactt ttggccaggg gaccaagctg gagatcaaac                             340

<210> SEQ ID NO 204
<211> LENGTH: 113
<212> TYPE: PRT
<213> ORGANISM: Artificial Sequence
<220> FEATURE:
<223> OTHER INFORMATION: Synthetic

<400> SEQUENCE: 204

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 205
<211> LENGTH: 36
<212> TYPE: DNA
<213> ORGANISM: Artificial Sequence
<220> FEATURE:
<223> OTHER INFORMATION: Synthetic

<400> SEQUENCE: 205
cagagtgttt tatacagctc caacaataag aactac        36

<210> SEQ ID NO 206
<211> LENGTH: 12
<212> TYPE: PRT
<213> ORGANISM: Artificial Sequence
<220> FEATURE:
<223> OTHER INFORMATION: Synthetic

<400> SEQUENCE: 206

Gln Ser Val Leu Tyr Ser Ser Asn Asn Lys Asn Tyr
 1               5                  10

<210> SEQ ID NO 207
<211> LENGTH: 9
<212> TYPE: DNA
<213> ORGANISM: Artificial Sequence
<220> FEATURE:
<223> OTHER INFORMATION: Synthetic

<400> SEQUENCE: 207 tgggcatct        9

<210> SEQ ID NO 208
<211> LENGTH: 3
<212> TYPE: PRT
<213> ORGANISM: Artificial Sequence
<220> FEATURE:
<223> OTHER INFORMATION: Synthetic

<400> SEQUENCE: 208

Trp Ala Ser
 1

<210> SEQ ID NO 209
<211> LENGTH: 27
<212> TYPE: DNA
<213> ORGANISM: Artificial Sequence
<220> FEATURE:
<223> OTHER INFORMATION: Synthetic

<400> SEQUENCE: 209
cagcaatatt atagtactcc gtacact        27

<210> SEQ ID NO 210
<211> LENGTH: 9
<212> TYPE: PRT
<213> ORGANISM: Artificial Sequence
<220> FEATURE:
<223> OTHER INFORMATION: Synthetic

<400> SEQUENCE: 210

Gln Gln Tyr Tyr Ser Thr Pro Tyr Thr
 1               5

<210> SEQ ID NO 211
<211> LENGTH: 352

<212> TYPE: DNA
<213> ORGANISM: Artificial Sequence
<220> FEATURE:
<223> OTHER INFORMATION: Synthetic

<400> SEQUENCE: 211

```
caggtgcagc tggtgcagtc tggggctgag gtgaagaagc ctggggcctc agtgaaggtc      60
tcctgcaagg cttctggata caccttcacc ggctactata ttcactgggt acgacaggcc     120
cctggacaag gccttgagtg gatgggatgg atcaaccctaa acagtggtgg cacaaactat    180
gcacagaagt tcagggcag gtcaccatg accaggaca cgtccatcag cacagcctac        240
atggagctga gcaggctgag atctgacgac acggccgtgt attactgtgc gagaggaccc    300
tgggatttct ttgactactg gggccaggga accctggtca ccgtctcctc ag            352
```

<210> SEQ ID NO 212
<211> LENGTH: 117
<212> TYPE: PRT
<213> ORGANISM: Artificial Sequence
<220> FEATURE:
<223> OTHER INFORMATION: Synthetic

<400> SEQUENCE: 212

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Ile His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Pro Trp Asp Phe Phe Asp Tyr Trp Gly Gln Gly Thr Leu
            100                 105                 110

Val Thr Val Ser Ser
        115
```

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213

```
ggatacacct tcaccggcta ctat                                             24
```

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

```
Gly Tyr Thr Phe Thr Gly Tyr Tyr
  1               5
```

<210> SEQ ID NO 215
<211> LENGTH: 24
<212> TYPE: DNA
<213> ORGANISM: Artificial Sequence
<220> FEATURE:
<223> OTHER INFORMATION: Synthetic

<400> SEQUENCE: 215 atcaaccctaacagtggtggcaca                                                     24

<210> SEQ ID NO 216
<211> LENGTH: 8
<212> TYPE: PRT
<213> ORGANISM: Artificial Sequence
<220> FEATURE:
<223> OTHER INFORMATION: Synthetic

<400> SEQUENCE: 216

Ile Asn Pro Asn Ser Gly Gly Thr
 1               5

<210> SEQ ID NO 217
<211> LENGTH: 30
<212> TYPE: DNA
<213> ORGANISM: Artificial Sequence
<220> FEATURE:
<223> OTHER INFORMATION: Synthetic

<400> SEQUENCE: 217
gcgagaggac cctgggattt ctttgactac                                             30

<210> SEQ ID NO 218
<211> LENGTH: 10
<212> TYPE: PRT
<213> ORGANISM: Artificial Sequence
<220> FEATURE:
<223> OTHER INFORMATION: Synthetic

<400> SEQUENCE: 218

Ala Arg Gly Pro Trp Asp Phe Phe Asp Tyr
 1               5                  10

<210> SEQ ID NO 219
<211> LENGTH: 340
<212> TYPE: DNA
<213> ORGANISM: Artificial Sequence
<220> FEATURE:
<223> OTHER INFORMATION: Synthetic

<400> SEQUENCE: 219
gacatcgtga tgacccagtc tccagactcc ctggctgtgt ctctgggcga gagggccacc            60
atcaactgca agtccagcca gagtgtttta tacagctcca acaataagaa ctacttagct           120
tggtaccagc agaaaccagg acagcctcct aagctgctca tttactgggc atctacccgg           180
gaatccgggg tccctgaccg attcagtggc agcgggtctg ggacagattt cactctcacc           240
atcagcagcc tgcaggctga agatgtggca gtttattact gtcagcaata ttatagtact           300
ccgtacactt ttggccaggg gaccaagctg gagatcaaac                                 340

<210> SEQ ID NO 220
<211> LENGTH: 113
<212> TYPE: PRT
<213> ORGANISM: Artificial Sequence
<220> FEATURE:
<223> OTHER INFORMATION: Synthetic -continued

```
<400> SEQUENCE: 220

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 221
<211> LENGTH: 36
<212> TYPE: DNA
<213> ORGANISM: Artificial Sequence
<220> FEATURE:
<223> OTHER INFORMATION: Synthetic

<400> SEQUENCE: 221
cagagtgttt tatacagctc caacaataag aactac                              36

<210> SEQ ID NO 222
<211> LENGTH: 12
<212> TYPE: PRT
<213> ORGANISM: Artificial Sequence
<220> FEATURE:
<223> OTHER INFORMATION: Synthetic

<400> SEQUENCE: 222

Gln Ser Val Leu Tyr Ser Ser Asn Asn Lys Asn Tyr
1               5                   10

<210> SEQ ID NO 223
<211> LENGTH: 9
<212> TYPE: DNA
<213> ORGANISM: Artificial Sequence
<220> FEATURE:
<223> OTHER INFORMATION: Synthetic

<400> SEQUENCE: 223 tgggcatct                                                             9

<210> SEQ ID NO 224
<211> LENGTH: 3
<212> TYPE: PRT
<213> ORGANISM: Artificial Sequence
<220> FEATURE:
<223> OTHER INFORMATION: Synthetic

<400> SEQUENCE: 224

Trp Ala Ser
1

<210> SEQ ID NO 225
<211> LENGTH: 27
<212> TYPE: DNA
```

<213> ORGANISM: Artificial Sequence
<220> FEATURE:
<223> OTHER INFORMATION: Synthetic

<400> SEQUENCE: 225
cagcaatatt atagtactcc gtacact                                        27

<210> SEQ ID NO 226
<211> LENGTH: 9
<212> TYPE: PRT
<213> ORGANISM: Artificial Sequence
<220> FEATURE:
<223> OTHER INFORMATION: Synthetic

<400> SEQUENCE: 226

Gln Gln Tyr Tyr Ser Thr Pro Tyr Thr
 1               5

<210> SEQ ID NO 227
<211> LENGTH: 361
<212> TYPE: DNA
<213> ORGANISM: Artificial Sequence
<220> FEATURE:
<223> OTHER INFORMATION: Synthetic

<400> SEQUENCE: 227
caggtgcagt tgcaggagtc gggcccagga ctggtgaagc cttcacagac cctgtccctc     60
acctgcactg tctctggtgg ctccatcggc agtggtggtt actactggag ctggatccgc    120
cagcacccag ggaagggcct ggagtggatt gggtacgtcc attacagtgg aacaccac     180 tacaacccgt ccctcaagag tcgactttcc atatcaatag acacgtctaa gatccagttc    240
tccctgaagc tgagctctgt gactgccgcg gacacggccg tgtattactg tgcgagagcc    300
ccccgtggat accattactt tgcctactgg ggccagggaa ccctggtcac cgtctcctca    360
g                                                                    361

<210> SEQ ID NO 228
<211> LENGTH: 120
<212> TYPE: PRT
<213> ORGANISM: Artificial Sequence
<220> FEATURE:
<223> OTHER INFORMATION: Synthetic

<400> SEQUENCE: 228

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Gly Ser Gly
             20                  25                  30

Gly Tyr Tyr Trp Ser Trp Ile Arg Gln His Pro Gly Lys Gly Leu Glu
         35                  40                  45

Trp Ile Gly Tyr Val His Tyr Ser Gly Asn Thr His Tyr Asn Pro Ser
     50                  55                  60

Leu Lys Ser Arg Leu Ser Ile Ser Ile Asp Thr Ser Lys Ile Gln Phe
65                  70                  75                  80

Ser Leu Lys Leu Ser Ser Val Thr Ala Ala Asp Thr Ala Val Tyr Tyr
                 85                  90                  95

Cys Ala Arg Ala Pro Arg Gly Tyr His Tyr Phe Ala Tyr Trp Gly Gln
            100                 105                 110

Gly Thr Leu Val Thr Val Ser Ser
        115                 120

<210> SEQ ID NO 229
<211> LENGTH: 30
<212> TYPE: DNA
<213> ORGANISM: Artificial Sequence
<220> FEATURE:
<223> OTHER INFORMATION: Synthetic

<400> SEQUENCE: 229
ggtggctcca tcggcagtgg tggttactac                                    30

<210> SEQ ID NO 230
<211> LENGTH: 10
<212> TYPE: PRT
<213> ORGANISM: Artificial Sequence
<220> FEATURE:
<223> OTHER INFORMATION: Synthetic

<400> SEQUENCE: 230

Gly Gly Ser Ile Gly Ser Gly Gly Tyr Tyr
 1               5                  10

<210> SEQ ID NO 231
<211> LENGTH: 21
<212> TYPE: DNA
<213> ORGANISM: Artificial Sequence
<220> FEATURE:
<223> OTHER INFORMATION: Synthetic

<400> SEQUENCE: 231
gtccattaca gtgggaacac c                                             21

<210> SEQ ID NO 232
<211> LENGTH: 7
<212> TYPE: PRT
<213> ORGANISM: Artificial Sequence
<220> FEATURE:
<223> OTHER INFORMATION: Synthetic

<400> SEQUENCE: 232

Val His Tyr Ser Gly Asn Thr
 1               5

<210> SEQ ID NO 233
<211> LENGTH: 36
<212> TYPE: DNA
<213> ORGANISM: Artificial Sequence
<220> FEATURE:
<223> OTHER INFORMATION: Synthetic

<400> SEQUENCE: 233
gcgagagccc cccgtggata ccattacttt gcctac                             36

<210> SEQ ID NO 234
<211> LENGTH: 12
<212> TYPE: PRT
<213> ORGANISM: Artificial Sequence
<220> FEATURE:
<223> OTHER INFORMATION: Synthetic

<400> SEQUENCE: 234

Ala Arg Ala Pro Arg Gly Tyr His Tyr Phe Ala Tyr
 1               5                  10

<210> SEQ ID NO 235
<211> LENGTH: 325
<212> TYPE: DNA

<213> ORGANISM: Artificial Sequence
<220> FEATURE:
<223> OTHER INFORMATION: Synthetic

<400> SEQUENCE: 235

```
gaaattgtgt tgacacaatc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatcttt ggtgcatccc gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgct cactttcggc     300
ggagggacca aggtggagat caaac                                           325
```

<210> SEQ ID NO 236
<211> LENGTH: 108
<212> TYPE: PRT
<213> ORGANISM: Artificial Sequence
<220> FEATURE:
<223> OTHER INFORMATION: Synthetic

<400> SEQUENCE: 236

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Phe Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Leu Thr Phe Gly Gly Gly Thr Lys Val Glu Ile Lys
            100                 105
```

<210> SEQ ID NO 237
<211> LENGTH: 21
<212> TYPE: DNA
<213> ORGANISM: Artificial Sequence
<220> FEATURE:
<223> OTHER INFORMATION: Synthetic

<400> SEQUENCE: 237

```
cagagtgtta gcagcagcta c                                                21
```

<210> SEQ ID NO 238
<211> LENGTH: 7
<212> TYPE: PRT
<213> ORGANISM: Artificial Sequence
<220> FEATURE:
<223> OTHER INFORMATION: Synthetic

<400> SEQUENCE: 238

```
Gln Ser Val Ser Ser Ser Tyr
1               5
```

<210> SEQ ID NO 239
<211> LENGTH: 9
<212> TYPE: DNA
<213> ORGANISM: Artificial Sequence
<220> FEATURE:
<223> OTHER INFORMATION: Synthetic

<400> SEQUENCE: 239 ggtgcatcc    9

<210> SEQ ID NO 240
<211> LENGTH: 3
<212> TYPE: PRT
<213> ORGANISM: Artificial Sequence
<220> FEATURE:
<223> OTHER INFORMATION: Synthetic

<400> SEQUENCE: 240

Gly Ala Ser
 1

<210> SEQ ID NO 241
<211> LENGTH: 27
<212> TYPE: DNA
<213> ORGANISM: Artificial Sequence
<220> FEATURE:
<223> OTHER INFORMATION: Synthetic

<400> SEQUENCE: 241
cagcagtatg gtagctcacc gctcact    27

<210> SEQ ID NO 242
<211> LENGTH: 9
<212> TYPE: PRT
<213> ORGANISM: Artificial Sequence
<220> FEATURE:
<223> OTHER INFORMATION: Synthetic

<400> SEQUENCE: 242

Gln Gln Tyr Gly Ser Ser Pro Leu Thr
 1               5

<210> SEQ ID NO 243
<211> LENGTH: 361
<212> TYPE: DNA
<213> ORGANISM: Artificial Sequence
<220> FEATURE:
<223> OTHER INFORMATION: Synthetic

<400> SEQUENCE: 243
caggtgcagc tgcaggagtc gggcccagga ctggtgaagc cttcacagac cctgtccctc    60
acctgcactg tctctggtgg ctccatcagc agtggtggtt actactggag ctggatccgc    120
cagtacccag ggaagggcct ggagtggatt ggttacgtcc attacagtgg gagcacccac    180
tacaacccgt ccctcaagag tcgacttacc atatcaatag acacgtctaa gagccagttc    240
tccctgaagc tgagctctgt gactgccgcg gacacggccg tgtattactg tgcgagagcc    300
ccccgtggat accattactt tgcctactgg ggccagggaa ccctggtcac cgtctcctca    360
g    361

<210> SEQ ID NO 244
<211> LENGTH: 120
<212> TYPE: PRT
<213> ORGANISM: Artificial Sequence
<220> FEATURE:
<223> OTHER INFORMATION: Synthetic

<400> SEQUENCE: 244

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Tyr Tyr Trp Ser Trp Ile Arg Gln Tyr Pro Gly Lys Gly Leu Glu
        35                  40                  45

Trp Ile Gly Tyr Val His Tyr Ser Gly Ser Thr His Tyr Asn Pro Ser
50                  55                  60

Leu Lys Ser Arg Leu Thr Ile Ser Ile Asp Thr Ser Lys Ser Gln Phe
65                  70                  75                  80

Ser Leu Lys Leu Ser Ser Val Thr Ala Ala Asp Thr Ala Val Tyr Tyr
                85                  90                  95

Cys Ala Arg Ala Pro Arg Gly Tyr His Tyr Phe Ala Tyr Trp Gly Gln
            100                 105                 110

Gly Thr Leu Val Thr Val Ser Ser
        115                 120

<210> SEQ ID NO 245
<211> LENGTH: 30
<212> TYPE: DNA
<213> ORGANISM: Artificial Sequence
<220> FEATURE:
<223> OTHER INFORMATION: Synthetic

<400> SEQUENCE: 245
ggtggctcca tcagcagtgg tggttactac                                    30

<210> SEQ ID NO 246
<211> LENGTH: 10
<212> TYPE: PRT
<213> ORGANISM: Artificial Sequence
<220> FEATURE:
<223> OTHER INFORMATION: Synthetic

<400> SEQUENCE: 246

Gly Gly Ser Ile Ser Ser Gly Gly Tyr Tyr
1               5                   10

<210> SEQ ID NO 247
<211> LENGTH: 21
<212> TYPE: DNA
<213> ORGANISM: Artificial Sequence
<220> FEATURE:
<223> OTHER INFORMATION: Synthetic

<400> SEQUENCE: 247
gtccattaca gtgggagcac c                                             21

<210> SEQ ID NO 248
<211> LENGTH: 7
<212> TYPE: PRT
<213> ORGANISM: Artificial Sequence
<220> FEATURE:
<223> OTHER INFORMATION: Synthetic

<400> SEQUENCE: 248

Val His Tyr Ser Gly Ser Thr
1               5

<210> SEQ ID NO 249
<211> LENGTH: 36
<212> TYPE: DNA
<213> ORGANISM: Artificial Sequence
<220> FEATURE:
<223> OTHER INFORMATION: Synthetic

<400> SEQUENCE: 249
gcgagagccc cccgtggata ccattacttt gcctac    36

<210> SEQ ID NO 250
<211> LENGTH: 12
<212> TYPE: PRT
<213> ORGANISM: Artificial Sequence
<220> FEATURE:
<223> OTHER INFORMATION: Synthetic

<400> SEQUENCE: 250

Ala Arg Ala Pro Arg Gly Tyr His Tyr Phe Ala Tyr
 1               5                  10

<210> SEQ ID NO 251
<211> LENGTH: 325
<212> TYPE: DNA
<213> ORGANISM: Artificial Sequence
<220> FEATURE:
<223> OTHER INFORMATION: Synthetic

<400> SEQUENCE: 251
gaaattgtgt tgacgcagtc tccaggcacc ctgtctttgt ctccagggga aagagccacc    60
ctctcctgca gggccagtca gagtgttagc agcaggtact tagcctggta ccagcagaaa   120
cctggccagg ctcccaggct cctcatcttt ggtgcatcca gcagggccac tggcatacca   180
gacaggttca gtggcagtgg gtctgggaca gacttcactc tcaccatcag cagactggag   240
cctgaagatt ttgcagtgta ttactgtcag cagtatggta gctcaccgct cactttcggc   300
ggagggacca aggtggagat caaac                                         325

<210> SEQ ID NO 252
<211> LENGTH: 108
<212> TYPE: PRT
<213> ORGANISM: Artificial Sequence
<220> FEATURE:
<223> OTHER INFORMATION: Synthetic

<400> SEQUENCE: 252

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Arg
             20                  25                  30

Tyr Leu Ala Trp Tyr Gln Gln Lys Pro Gly Gln Ala Pro Arg Leu Leu
         35                  40                  45

Ile Phe Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
            100                 105

<210> SEQ ID NO 253
<211> LENGTH: 21
<212> TYPE: DNA
<213> ORGANISM: Artificial Sequence
<220> FEATURE:

<223> OTHER INFORMATION: Synthetic

<400> SEQUENCE: 253
cagagtgtta gcagcaggta c                                             21

<210> SEQ ID NO 254
<211> LENGTH: 7
<212> TYPE: PRT
<213> ORGANISM: Artificial Sequence
<220> FEATURE:
<223> OTHER INFORMATION: Synthetic

<400> SEQUENCE: 254

Gln Ser Val Ser Ser Arg Tyr
1               5

<210> SEQ ID NO 255
<211> LENGTH: 9
<212> TYPE: DNA
<213> ORGANISM: Artificial Sequence
<220> FEATURE:
<223> OTHER INFORMATION: Synthetic

<400> SEQUENCE: 255 ggtgcatcc                                                            9

<210> SEQ ID NO 256
<211> LENGTH: 3
<212> TYPE: PRT
<213> ORGANISM: Artificial Sequence
<220> FEATURE:
<223> OTHER INFORMATION: Synthetic

<400> SEQUENCE: 256

Gly Ala Ser
1

<210> SEQ ID NO 257
<211> LENGTH: 27
<212> TYPE: DNA
<213> ORGANISM: Artificial Sequence
<220> FEATURE:
<223> OTHER INFORMATION: Synthetic

<400> SEQUENCE: 257
cagcagtatg gtagctcacc gctcact                                       27

<210> SEQ ID NO 258
<211> LENGTH: 9
<212> TYPE: PRT
<213> ORGANISM: Artificial Sequence
<220> FEATURE:
<223> OTHER INFORMATION: Synthetic

<400> SEQUENCE: 258

Gln Gln Tyr Gly Ser Ser Pro Leu Thr
1               5

<210> SEQ ID NO 259
<211> LENGTH: 355
<212> TYPE: DNA
<213> ORGANISM: Artificial Sequence
<220> FEATURE:
<223> OTHER INFORMATION: Synthetic

<400> SEQUENCE: 259

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct attacagtgg gagcacctac   180
tacaacccgt ccctcaagag tcgaattatc atatcagtag acacgtctaa gaaccagttc   240
tccctgaagc tgagctctgt gactgccgcg gacacggccg tgtattactg tgcgagagaa   300
ggggctatgg tttttgacta ctggggccag ggaaccctgg tcaccgtctc ctcag        355
```

<210> SEQ ID NO 260
<211> LENGTH: 118
<212> TYPE: PRT
<213> ORGANISM: Artificial Sequence
<220> FEATURE:
<223> OTHER INFORMATION: Synthetic

<400> SEQUENCE: 260

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Ile Ile Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ala Met Val Phe Asp Tyr Trp Gly Gln Gly Thr
            100                 105                 110

Leu Val Thr Val Ser Ser
        115
```

<210> SEQ ID NO 261
<211> LENGTH: 30
<212> TYPE: DNA
<213> ORGANISM: Artificial Sequence
<220> FEATURE:
<223> OTHER INFORMATION: Synthetic

<400> SEQUENCE: 261

```
ggtggctcca tcagcagtgg tggttactac                                     30
```

<210> SEQ ID NO 262
<211> LENGTH: 10
<212> TYPE: PRT
<213> ORGANISM: Artificial Sequence
<220> FEATURE:
<223> OTHER INFORMATION: Synthetic

<400> SEQUENCE: 262

```
Gly Gly Ser Ile Ser Ser Gly Gly Tyr Tyr
 1               5                  10
```

<210> SEQ ID NO 263
<211> LENGTH: 21
<212> TYPE: DNA
<213> ORGANISM: Artificial Sequence
<220> FEATURE:
<223> OTHER INFORMATION: Synthetic

<400> SEQUENCE: 263
atctattaca gtgggagcac c					21

<210> SEQ ID NO 264
<211> LENGTH: 7
<212> TYPE: PRT
<213> ORGANISM: Artificial Sequence
<220> FEATURE:
<223> OTHER INFORMATION: Synthetic

<400> SEQUENCE: 264

Ile Tyr Tyr Ser Gly Ser Thr
1               5

<210> SEQ ID NO 265
<211> LENGTH: 30
<212> TYPE: DNA
<213> ORGANISM: Artificial Sequence
<220> FEATURE:
<223> OTHER INFORMATION: Synthetic

<400> SEQUENCE: 265
gcgagagaag gggctatggt ttttgactac			30

<210> SEQ ID NO 266
<211> LENGTH: 10
<212> TYPE: PRT
<213> ORGANISM: Artificial Sequence
<220> FEATURE:
<223> OTHER INFORMATION: Synthetic

<400> SEQUENCE: 266

Ala Arg Glu Gly Ala Met Val Phe Asp Tyr
1               5                   10

<210> SEQ ID NO 267
<211> LENGTH: 322
<212> TYPE: DNA
<213> ORGANISM: Artificial Sequence
<220> FEATURE:
<223> OTHER INFORMATION: Synthetic

<400> SEQUENCE: 267
gacatccagt tgacccagtc tccatccttc ctgtctgcat ctgtaggaga cagagtcacc		60 atcacttgct gggccagtca gggcattagc agttatttag cctggtatca gcaaaaacca		120 gggaaagccc ctaaactcct gatttatgct gcatccgctt tgcaaagtgg ggtcccatca		180 aggttcagcg gcagtggatc tgggacagaa ttcactctca ccatcagcag cctgcagcct		240 gaagattttg caacttatta ctgtcaacag cttaatagtt acccgttcac ttttggccag		300 gggaccaagc tggagatcaa ac						322

<210> SEQ ID NO 268
<211> LENGTH: 107
<212> TYPE: PRT
<213> ORGANISM: Artificial Sequence
<220> FEATURE:
<223> OTHER INFORMATION: Synthetic

<400> SEQUENCE: 268

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

-continued

```
Leu Ala Trp Tyr Gln Gln Lys Pro Gly Lys Ala Pro Lys Leu Leu Ile
             35                  40                  45

Tyr Ala Ala Ser Ala Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Phe
                 85                  90                  95

Thr Phe Gly Gln Gly Thr Lys Leu Glu Ile Lys
            100                 105

<210> SEQ ID NO 269
<211> LENGTH: 18
<212> TYPE: DNA
<213> ORGANISM: Artificial Sequence
<220> FEATURE:
<223> OTHER INFORMATION: Synthetic

<400> SEQUENCE: 269
cagggcatta gcagttat                                                     18

<210> SEQ ID NO 270
<211> LENGTH: 6
<212> TYPE: PRT
<213> ORGANISM: Artificial Sequence
<220> FEATURE:
<223> OTHER INFORMATION: Synthetic

<400> SEQUENCE: 270

Gln Gly Ile Ser Ser Tyr
 1               5

<210> SEQ ID NO 271
<211> LENGTH: 9
<212> TYPE: DNA
<213> ORGANISM: Artificial Sequence
<220> FEATURE:
<223> OTHER INFORMATION: Synthetic

<400> SEQUENCE: 271 gctgcatcc                                                                9

<210> SEQ ID NO 272
<211> LENGTH: 3
<212> TYPE: PRT
<213> ORGANISM: Artificial Sequence
<220> FEATURE:
<223> OTHER INFORMATION: Synthetic

<400> SEQUENCE: 272

Ala Ala Ser
 1

<210> SEQ ID NO 273
<211> LENGTH: 27
<212> TYPE: DNA
<213> ORGANISM: Artificial Sequence
<220> FEATURE:
<223> OTHER INFORMATION: Synthetic

<400> SEQUENCE: 273
caacagctta atagttaccc gttcact                                           27
```

<210> SEQ ID NO 274
<211> LENGTH: 9
<212> TYPE: PRT
<213> ORGANISM: Artificial Sequence
<220> FEATURE:
<223> OTHER INFORMATION: Synthetic

<400> SEQUENCE: 274

Gln Gln Leu Asn Ser Tyr Pro Phe Thr
1               5

<210> SEQ ID NO 275
<211> LENGTH: 355
<212> TYPE: DNA
<213> ORGANISM: Artificial Sequence
<220> FEATURE:
<223> OTHER INFORMATION: Synthetic

<400> SEQUENCE: 275
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgaattatc atatcagtag acacgtctaa gaaccagttc     240
tccctgaagc tgagctctgt gactgccgcg gacacggccg tgtattactg tgcgagagaa     300
ggggctatgg ttttgacta ctggggccag ggaaccctgg tcaccgtctc ctcag           355

<210> SEQ ID NO 276
<211> LENGTH: 118
<212> TYPE: PRT
<213> ORGANISM: Artificial Sequence
<220> FEATURE:
<223> OTHER INFORMATION: Synthetic

<400> SEQUENCE: 276

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Ile Ile Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ala Met Val Phe Asp Tyr Trp Gly Gln Gly Thr
            100                 105                 110

Leu Val Thr Val Ser Ser
        115

<210> SEQ ID NO 277
<211> LENGTH: 30
<212> TYPE: DNA
<213> ORGANISM: Artificial Sequence
<220> FEATURE:
<223> OTHER INFORMATION: Synthetic

<400> SEQUENCE: 277
ggtggctcca tcagcagtgg tggttactac                                      30

<210> SEQ ID NO 278
<211> LENGTH: 10
<212> TYPE: PRT
<213> ORGANISM: Artificial Sequence
<220> FEATURE:
<223> OTHER INFORMATION: Synthetic

<400> SEQUENCE: 278

Gly Gly Ser Ile Ser Ser Gly Gly Tyr Tyr
 1               5                  10

<210> SEQ ID NO 279
<211> LENGTH: 21
<212> TYPE: DNA
<213> ORGANISM: Artificial Sequence
<220> FEATURE:
<223> OTHER INFORMATION: Synthetic

<400> SEQUENCE: 279
atctattaca gtgggagcac c                                          21

<210> SEQ ID NO 280
<211> LENGTH: 7
<212> TYPE: PRT
<213> ORGANISM: Artificial Sequence
<220> FEATURE:
<223> OTHER INFORMATION: Synthetic

<400> SEQUENCE: 280

Ile Tyr Tyr Ser Gly Ser Thr
 1               5

<210> SEQ ID NO 281
<211> LENGTH: 30
<212> TYPE: DNA
<213> ORGANISM: Artificial Sequence
<220> FEATURE:
<223> OTHER INFORMATION: Synthetic

<400> SEQUENCE: 281
gcgagagaag gggctatggt ttttgactac                                 30

<210> SEQ ID NO 282
<211> LENGTH: 10
<212> TYPE: PRT
<213> ORGANISM: Artificial Sequence
<220> FEATURE:
<223> OTHER INFORMATION: Synthetic

<400> SEQUENCE: 282

Ala Arg Glu Gly Ala Met Val Phe Asp Tyr
 1               5                  10

<210> SEQ ID NO 283
<211> LENGTH: 322
<212> TYPE: DNA
<213> ORGANISM: Artificial Sequence
<220> FEATURE:
<223> OTHER INFORMATION: Synthetic

<400> SEQUENCE: 283
gacatccagt tgacccagtc tccatccttc ctgtctgcat ctgtaggaga cagagtcacc      60
atcacttgct gggccagtca gggcattagc agttatttag cctggtatca gcaaaaacca     120
gggaaagccc ctaaactcct gatttatgct gcatccgctt tgcaaagtgg ggtcccatca     180

-continued

```
aggttcagcg gcagtggatc tgggacagaa ttcactctca ccatcagcag cctgcagcct      240
gaagattttg caacttatta ctgtcaacag cttaatagtt acccgttcac ttttggccag      300
gggaccaagc tggagatcaa ac                                               322
```

<210> SEQ ID NO 284
<211> LENGTH: 107
<212> TYPE: PRT
<213> ORGANISM: Artificial Sequence
<220> FEATURE:
<223> OTHER INFORMATION: Synthetic

<400> SEQUENCE: 284

```
Asp Ile Gln Leu Thr Gln Ser Pro Ser Phe Leu Ser Ala Ser Val Gly
 1               5                  10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Phe
                85                  90                  95

Thr Phe Gly Gln Gly Thr Lys Leu Glu Ile Lys
           100                 105
```

<210> SEQ ID NO 285
<211> LENGTH: 18
<212> TYPE: DNA
<213> ORGANISM: Artificial Sequence
<220> FEATURE:
<223> OTHER INFORMATION: Synthetic

<400> SEQUENCE: 285

```
cagggcatta gcagttat                                                    18
```

<210> SEQ ID NO 286
<211> LENGTH: 6
<212> TYPE: PRT
<213> ORGANISM: Artificial Sequence
<220> FEATURE:
<223> OTHER INFORMATION: Synthetic

<400> SEQUENCE: 286

```
Gln Gly Ile Ser Ser Tyr
 1               5
```

<210> SEQ ID NO 287
<211> LENGTH: 9
<212> TYPE: DNA
<213> ORGANISM: Artificial Sequence
<220> FEATURE:
<223> OTHER INFORMATION: Synthetic

<400> SEQUENCE: 287

```
gctgcatcc                                                               9
```

<210> SEQ ID NO 288
<211> LENGTH: 3
<212> TYPE: PRT

-continued

<210> ORGANISM: Artificial Sequence
<220> FEATURE:
<223> OTHER INFORMATION: Synthetic

<400> SEQUENCE: 288

Ala Ala Ser
 1

<210> SEQ ID NO 289
<211> LENGTH: 27
<212> TYPE: DNA
<213> ORGANISM: Artificial Sequence
<220> FEATURE:
<223> OTHER INFORMATION: Synthetic

<400> SEQUENCE: 289
caacagctta atagttaccc gttcact                                        27

<210> SEQ ID NO 290
<211> LENGTH: 9
<212> TYPE: PRT
<213> ORGANISM: Artificial Sequence
<220> FEATURE:
<223> OTHER INFORMATION: Synthetic

<400> SEQUENCE: 290

Gln Gln Leu Asn Ser Tyr Pro Phe Thr
 1               5

<210> SEQ ID NO 291
<211> LENGTH: 355
<212> TYPE: DNA
<213> ORGANISM: Artificial Sequence
<220> FEATURE:
<223> OTHER INFORMATION: Synthetic

<400> SEQUENCE: 291
caggtgcagc tgcaggagtc gggcccagga ctggtgaagc cttcacagac cctgtccctc      60
acctgcactg tctctggtgg ctccatcagc agtggtggtt actactggac ctggatccgc     120
cagcacccag ggaagggcct ggagtggatt gggtacatct attacagtgg gagcacctac     180
tacaacccgt ccctcaagag tcgagttatc atatcagtag acacgtctaa gaaccagttc     240
tccctgaagc tgagctctgt gactgccgcg gacacggccg tgtattactg tgcgagagaa     300
ggggctatgg ttttgacta ctggggccag ggaaccctgg tcaccgtctc ctcag           355

<210> SEQ ID NO 292
<211> LENGTH: 118
<212> TYPE: PRT
<213> ORGANISM: Artificial Sequence
<220> FEATURE:
<223> OTHER INFORMATION: Synthetic

<400> SEQUENCE: 292

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Thr Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Ile Ile Ser Val Asp Thr Ser Lys Asn Gln Phe 65                  70                  75                  80
Ser Leu Lys Leu Ser Ser Val Thr Ala Ala Asp Thr Ala Val Tyr Tyr
                    85                  90                  95

Cys Ala Arg Glu Gly Ala Met Val Phe Asp Tyr Trp Gly Gln Gly Thr
                100                 105                 110

Leu Val Thr Val Ser Ser
        115

<210> SEQ ID NO 293
<211> LENGTH: 30
<212> TYPE: DNA
<213> ORGANISM: Artificial Sequence
<220> FEATURE:
<223> OTHER INFORMATION: Synthetic

<400> SEQUENCE: 293
ggtggctcca tcagcagtgg tggttactac                                            30

<210> SEQ ID NO 294
<211> LENGTH: 10
<212> TYPE: PRT
<213> ORGANISM: Artificial Sequence
<220> FEATURE:
<223> OTHER INFORMATION: Synthetic

<400> SEQUENCE: 294

Gly Gly Ser Ile Ser Ser Gly Gly Tyr Tyr
1               5                   10

<210> SEQ ID NO 295
<211> LENGTH: 21
<212> TYPE: DNA
<213> ORGANISM: Artificial Sequence
<220> FEATURE:
<223> OTHER INFORMATION: Synthetic

<400> SEQUENCE: 295
atctattaca gtgggagcac c                                                     21

<210> SEQ ID NO 296
<211> LENGTH: 7
<212> TYPE: PRT
<213> ORGANISM: Artificial Sequence
<220> FEATURE:
<223> OTHER INFORMATION: Synthetic

<400> SEQUENCE: 296

Ile Tyr Tyr Ser Gly Ser Thr
1               5

<210> SEQ ID NO 297
<211> LENGTH: 30
<212> TYPE: DNA
<213> ORGANISM: Artificial Sequence
<220> FEATURE:
<223> OTHER INFORMATION: Synthetic

<400> SEQUENCE: 297
gcgagagaag gggctatggt ttttgactac                                            30

<210> SEQ ID NO 298
<211> LENGTH: 10
<212> TYPE: PRT
<213> ORGANISM: Artificial Sequence
<220> FEATURE:

<223> OTHER INFORMATION: Synthetic

<400> SEQUENCE: 298

Ala Arg Glu Gly Ala Met Val Phe Asp Tyr
1               5                   10

<210> SEQ ID NO 299
<211> LENGTH: 322
<212> TYPE: DNA
<213> ORGANISM: Artificial Sequence
<220> FEATURE:
<223> OTHER INFORMATION: Synthetic

<400> SEQUENCE: 299
gacatccagt tgacccagtc tccatccttc ctgtctgcat ctgtaggaga cagagtcacc      60
atcacttgct gggccagtca gggcattagc agttatttag cctggtatca gcaaaaacca     120
gggaaagccc ctaagctcct gatctatgct gcatccgctt tgcaaagtgg ggtcccatca     180
aggttcagcg gcagtggatc tgggacagaa ttcactctca caatcagcag cctgcagcct     240
gaagattttg caacttatta ctgtcaacag cttaatagtt acccgttcac ttttggccag     300
gggaccaagc tggagatcaa ac                                              322

<210> SEQ ID NO 300
<211> LENGTH: 107
<212> TYPE: PRT
<213> ORGANISM: Artificial Sequence
<220> FEATURE:
<223> OTHER INFORMATION: Synthetic

<400> SEQUENCE: 300

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Gln Gly Thr Lys Leu Glu Ile Lys
            100                 105

<210> SEQ ID NO 301
<211> LENGTH: 18
<212> TYPE: DNA
<213> ORGANISM: Artificial Sequence
<220> FEATURE:
<223> OTHER INFORMATION: Synthetic

<400> SEQUENCE: 301
cagggcatta gcagttat                                                    18

<210> SEQ ID NO 302
<211> LENGTH: 6
<212> TYPE: PRT
<213> ORGANISM: Artificial Sequence
<220> FEATURE:
<223> OTHER INFORMATION: Synthetic

```
<400> SEQUENCE: 302

Gln Gly Ile Ser Ser Tyr
  1               5

<210> SEQ ID NO 303
<211> LENGTH: 9
<212> TYPE: DNA
<213> ORGANISM: Artificial Sequence
<220> FEATURE:
<223> OTHER INFORMATION: Synthetic

<400> SEQUENCE: 303 gctgcatcc                                                                    9

<210> SEQ ID NO 304
<211> LENGTH: 3
<212> TYPE: PRT
<213> ORGANISM: Artificial Sequence
<220> FEATURE:
<223> OTHER INFORMATION: Synthetic

<400> SEQUENCE: 304

Ala Ala Ser
  1

<210> SEQ ID NO 305
<211> LENGTH: 27
<212> TYPE: DNA
<213> ORGANISM: Artificial Sequence
<220> FEATURE:
<223> OTHER INFORMATION: Synthetic

<400> SEQUENCE: 305
caacagctta atagttaccc gttcact                                               27

<210> SEQ ID NO 306
<211> LENGTH: 9
<212> TYPE: PRT
<213> ORGANISM: Artificial Sequence
<220> FEATURE:
<223> OTHER INFORMATION: Synthetic

<400> SEQUENCE: 306

Gln Gln Leu Asn Ser Tyr Pro Phe Thr
  1               5

<210> SEQ ID NO 307
<211> LENGTH: 355
<212> TYPE: DNA
<213> ORGANISM: Artificial Sequence
<220> FEATURE:
<223> OTHER INFORMATION: Synthetic

<400> SEQUENCE: 307
caggtgcagc tgcaggagtc gggcccagga ctggtgaagc cttcacagac cctgtccctc           60
acctgcactg tctctggtgg ctccatcagc agtggtggtt actactggac ctggatccgc          120
cagtacccag ggaagggcct ggagtggatt gggtacatct attacagtgg gagcacctac          180
tacaacccgt ccctcaagag tcgagttatc atatcagtag acacgtctaa gaaccagttc          240
tccctgaggc tgagctctgt gactgccgcg gacacggccg tgtattactg tgcgagagaa          300
ggggctatgg ttttttgacta ctggggccag ggaaccctgg tcaccgtctc ctcag              355
```

<210> SEQ ID NO 308
<211> LENGTH: 118
<212> TYPE: PRT
<213> ORGANISM: Artificial Sequence
<220> FEATURE:
<223> OTHER INFORMATION: Synthetic

<400> SEQUENCE: 308

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Thr Trp Ile Arg Gln Tyr Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Ile Ile Ser Val Asp Thr Ser Lys Asn Gln Phe
 65                  70                  75                  80

Ser Leu Arg Leu Ser Ser Val Thr Ala Ala Asp Thr Ala Val Tyr Tyr
                 85                  90                  95

Cys Ala Arg Glu Gly Ala Met Val Phe Asp Tyr Trp Gly Gln Gly Thr
            100                 105                 110

Leu Val Thr Val Ser Ser
        115
```

<210> SEQ ID NO 309
<211> LENGTH: 30
<212> TYPE: DNA
<213> ORGANISM: Artificial Sequence
<220> FEATURE:
<223> OTHER INFORMATION: Synthetic

<400> SEQUENCE: 309
ggtggctcca tcagcagtgg tggttactac                                          30

<210> SEQ ID NO 310
<211> LENGTH: 10
<212> TYPE: PRT
<213> ORGANISM: Artificial Sequence
<220> FEATURE:
<223> OTHER INFORMATION: Synthetic

<400> SEQUENCE: 310

```
Gly Gly Ser Ile Ser Ser Gly Gly Tyr Tyr
 1               5                  10
```

<210> SEQ ID NO 311
<211> LENGTH: 21
<212> TYPE: DNA
<213> ORGANISM: Artificial Sequence
<220> FEATURE:
<223> OTHER INFORMATION: Synthetic

<400> SEQUENCE: 311
atctattaca gtgggagcac c                                                   21

<210> SEQ ID NO 312
<211> LENGTH: 7
<212> TYPE: PRT
<213> ORGANISM: Artificial Sequence
<220> FEATURE:
<223> OTHER INFORMATION: Synthetic

<400> SEQUENCE: 312

```
Ile Tyr Tyr Ser Gly Ser Thr
 1               5
```

<210> SEQ ID NO 313
<211> LENGTH: 30
<212> TYPE: DNA
<213> ORGANISM: Artificial Sequence
<220> FEATURE:
<223> OTHER INFORMATION: Synthetic

<400> SEQUENCE: 313

```
gcgagagaag gggctatggt ttttgactac                                       30
```

<210> SEQ ID NO 314
<211> LENGTH: 10
<212> TYPE: PRT
<213> ORGANISM: Artificial Sequence
<220> FEATURE:
<223> OTHER INFORMATION: Synthetic

<400> SEQUENCE: 314

```
Ala Arg Glu Gly Ala Met Val Phe Asp Tyr
 1               5                  10
```

<210> SEQ ID NO 315
<211> LENGTH: 322
<212> TYPE: DNA
<213> ORGANISM: Artificial Sequence
<220> FEATURE:
<223> OTHER INFORMATION: Synthetic

<400> SEQUENCE: 315

```
gacatccagt tgacccagtc tccatccttc ctgtctgcat ctgtaggaga cagagtcacc      60
atcacttgct gggccagtca gggcattagc agttatttag cctggtatca gcaaaaacca    120
gggaaagccc ctaagctcct gatctatgct gcatccgctt tgcaaagtgg ggtcccatca    180
aggttcagcg gcagtggatc tgggacagaa ttcactctca caatcagcag cctgcagcct    240
gaagattttg caacttatta ctgtcaacag cttaatagtt acccgttcac ttttggccag    300
gggaccaagc tggagatcaa ac                                             322
```

<210> SEQ ID NO 316
<211> LENGTH: 107
<212> TYPE: PRT
<213> ORGANISM: Artificial Sequence
<220> FEATURE:
<223> OTHER INFORMATION: Synthetic

<400> SEQUENCE: 316

```
Asp Ile Gln Leu Thr Gln Ser Pro Ser Phe Leu Ser Ala Ser Val Gly
 1               5                  10                  15
Asp Arg Val Thr Ile Thr Cys Trp Ala Ser Gln Gly Ile Ser Ser Tyr
                20                  25                  30
Leu Ala Trp Tyr Gln Gln Lys Pro Gly Lys Ala Pro Lys Leu Leu Ile
            35                  40                  45
Tyr Ala Ala Ser Ala Leu Gln Ser Gly Val Pro Ser Arg Phe Ser Gly
        50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Leu Asn Ser Tyr Pro Phe
                85                  90                  95
```

Thr Phe Gly Gln Gly Thr Lys Leu Glu Ile Lys
            100             105

<210> SEQ ID NO 317
<211> LENGTH: 18
<212> TYPE: DNA
<213> ORGANISM: Artificial Sequence
<220> FEATURE:
<223> OTHER INFORMATION: Synthetic

<400> SEQUENCE: 317
cagggcatta gcagttat                                                     18

<210> SEQ ID NO 318
<211> LENGTH: 6
<212> TYPE: PRT
<213> ORGANISM: Artificial Sequence
<220> FEATURE:
<223> OTHER INFORMATION: Synthetic

<400> SEQUENCE: 318

Gln Gly Ile Ser Ser Tyr
 1               5

<210> SEQ ID NO 319
<211> LENGTH: 9
<212> TYPE: DNA
<213> ORGANISM: Artificial Sequence
<220> FEATURE:
<223> OTHER INFORMATION: Synthetic

<400> SEQUENCE: 319 gctgcatcc                                                                9

<210> SEQ ID NO 320
<211> LENGTH: 3
<212> TYPE: PRT
<213> ORGANISM: Artificial Sequence
<220> FEATURE:
<223> OTHER INFORMATION: Synthetic

<400> SEQUENCE: 320

Ala Ala Ser
 1

<210> SEQ ID NO 321
<211> LENGTH: 27
<212> TYPE: DNA
<213> ORGANISM: Artificial Sequence
<220> FEATURE:
<223> OTHER INFORMATION: Synthetic

<400> SEQUENCE: 321
caacagctta atagttaccc gttcact                                           27

<210> SEQ ID NO 322
<211> LENGTH: 9
<212> TYPE: PRT
<213> ORGANISM: Artificial Sequence
<220> FEATURE:
<223> OTHER INFORMATION: Synthetic

<400> SEQUENCE: 322

Gln Gln Leu Asn Ser Tyr Pro Phe Thr
 1               5

<210> SEQ ID NO 323
<211> LENGTH: 358
<212> TYPE: DNA
<213> ORGANISM: Artificial Sequence
<220> FEATURE:
<223> OTHER INFORMATION: Synthetic

<400> SEQUENCE: 323

```
caggttcacc tggtgcagtc tggagctgag gtgaagaagc ctggggcctc agtgaaggtc      60
tcctgcaggg cttctggtta cacctttacc aactatggta tcacctgggt gcgacaggcc     120
cctggacaag gcttgagtg gatgggatgg atcagcgcta acagtggtaa cacagactct      180
gcacagaagt tccaggccag agtcaccatg accacagaca catccacgac cacagcctac     240
atggaactga ggagcctgag atctgacgac acggccgtgt attattgtgc gacgtatagt     300
tggaactttc actggttcga ccctggggc cagggaaccc tggtcaccgt ctcctcag       358
```

<210> SEQ ID NO 324
<211> LENGTH: 119
<212> TYPE: PRT
<213> ORGANISM: Artificial Sequence
<220> FEATURE:
<223> OTHER INFORMATION: Synthetic

<400> SEQUENCE: 324

Gln Val His Leu Val Gln Ser Gly Ala Glu Val Lys Lys Pro Gly Ala
1               5                   10                  15
Ser Val Lys Val Ser Cys Arg Ala Ser Gly Tyr Thr Phe Thr Asn Tyr
            20                  25                  30
Gly Ile Thr Trp Val Arg Gln Ala Pro Gly Gln Gly Leu Glu Trp Met
        35                  40                  45
Gly Trp Ile Ser Ala Asn Ser Gly Asn Thr Asp Ser Ala Gln Lys Phe
    50                  55                  60
Gln Ala Arg Val Thr Met Thr Thr Asp Thr Ser Thr Thr Thr Ala Tyr
65                  70                  75                  80
Met Glu Leu Arg Ser Leu Arg Ser Asp Asp Thr Ala Val Tyr Tyr Cys
                85                  90                  95
Ala Thr Tyr Ser Trp Asn Phe His Trp Phe Asp Pro Trp Gly Gln Gly
            100                 105                 110
Thr Leu Val Thr Val Ser Ser
        115

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325

```
ggttacacct ttaccaacta tggt                                              24
```

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Gly Tyr Thr Phe Thr Asn Tyr Gly
1               5

<210> SEQ ID NO 327
<211> LENGTH: 24
<212> TYPE: DNA
<213> ORGANISM: Artificial Sequence
<220> FEATURE:
<223> OTHER INFORMATION: Synthetic

<400> SEQUENCE: 327
atcagcgcta acagtggtaa caca                                          24

<210> SEQ ID NO 328
<211> LENGTH: 8
<212> TYPE: PRT
<213> ORGANISM: Artificial Sequence
<220> FEATURE:
<223> OTHER INFORMATION: Synthetic

<400> SEQUENCE: 328

Ile Ser Ala Asn Ser Gly Asn Thr
 1               5

<210> SEQ ID NO 329
<211> LENGTH: 36
<212> TYPE: DNA
<213> ORGANISM: Artificial Sequence
<220> FEATURE:
<223> OTHER INFORMATION: Synthetic

<400> SEQUENCE: 329
gcgacgtata gttggaactt tcactggttc gacccc                             36

<210> SEQ ID NO 330
<211> LENGTH: 12
<212> TYPE: PRT
<213> ORGANISM: Artificial Sequence
<220> FEATURE:
<223> OTHER INFORMATION: Synthetic

<400> SEQUENCE: 330

Ala Thr Tyr Ser Trp Asn Phe His Trp Phe Asp Pro
 1               5                  10

<210> SEQ ID NO 331
<211> LENGTH: 325
<212> TYPE: DNA
<213> ORGANISM: Artificial Sequence
<220> FEATURE:
<223> OTHER INFORMATION: Synthetic

<400> SEQUENCE: 331
gaaattgtgt tgacgcagtc tccaggcact ctgtctttgt ctccagggga aagagtcacc    60
ctctcctgca gggccagtca gagtgtcagt accaactact taacctggta ccagcagaaa   120
cctggccagg ctcccaggct cctcatctat ggtgcatcca gcagggccac tggcatccca   180
gacaggttca gtggcagtgg gtctgggaca gacttcattc tcaccatcag aagtctggag   240
cctgaagatt ttgcagtgta ttactgtcag cagtgtggtg gctcaccgtg gacgttcggc   300
caagggacca gggtggaaat caaac                                        325

<210> SEQ ID NO 332
<211> LENGTH: 108
<212> TYPE: PRT
<213> ORGANISM: Artificial Sequence
<220> FEATURE:

<223> OTHER INFORMATION: Synthetic

<400> SEQUENCE: 332

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Val | Thr | Leu | Ser | Cys | Arg | Ala | Ser | Gln | Ser | Val | Ser | Thr | Asn |
|---|---|---|---|---|---|---|---|---|---|---|---|---|---|---|---|
| | | | 20 | | | | | 25 | | | | | 30 | | |

| Tyr | Leu | Thr | Trp | Tyr | Gln | Gln | Lys | Pro | Gly | Gln | Ala | Pro | Arg | Leu | Leu |
|---|---|---|---|---|---|---|---|---|---|---|---|---|---|---|---|
| | | 35 | | | | | 40 | | | | | 45 | | | |

| Ile | Tyr | Gly | Ala | Ser | Ser | Arg | Ala | Thr | Gly | Ile | Pro | Asp | Arg | Phe | Ser |
|---|---|---|---|---|---|---|---|---|---|---|---|---|---|---|---|
| | 50 | | | | | 55 | | | | | 60 | | | | |

| Gly | Ser | Gly | Ser | Gly | Thr | Asp | Phe | Ile | Leu | Thr | Ile | Arg | Ser | Leu | Glu |
|---|---|---|---|---|---|---|---|---|---|---|---|---|---|---|---|
| 65 | | | | | 70 | | | | | 75 | | | | | 80 |

| Pro | Glu | Asp | Phe | Ala | Val | Tyr | Tyr | Cys | Gln | Gln | Cys | Gly | Gly | Ser | Pro |
|---|---|---|---|---|---|---|---|---|---|---|---|---|---|---|---|
| | | | | 85 | | | | | 90 | | | | | 95 | |

| Trp | Thr | Phe | Gly | Gln | Gly | Thr | Arg | Val | Glu | Ile | Lys |
|---|---|---|---|---|---|---|---|---|---|---|---|
| | | | 100 | | | | | 105 | | | |

<210> SEQ ID NO 333
<211> LENGTH: 21
<212> TYPE: DNA
<213> ORGANISM: Artificial Sequence
<220> FEATURE:
<223> OTHER INFORMATION: Synthetic

<400> SEQUENCE: 333
cagagtgtca gtaccaacta c                                          21

<210> SEQ ID NO 334
<211> LENGTH: 7
<212> TYPE: PRT
<213> ORGANISM: Artificial Sequence
<220> FEATURE:
<223> OTHER INFORMATION: Synthetic

<400> SEQUENCE: 334

Gln Ser Val Ser Thr Asn Tyr
1               5

<210> SEQ ID NO 335
<211> LENGTH: 9
<212> TYPE: DNA
<213> ORGANISM: Artificial Sequence
<220> FEATURE:
<223> OTHER INFORMATION: Synthetic

<400> SEQUENCE: 335 ggtgcatcc                                                         9

<210> SEQ ID NO 336
<211> LENGTH: 3
<212> TYPE: PRT
<213> ORGANISM: Artificial Sequence
<220> FEATURE:
<223> OTHER INFORMATION: Synthetic

<400> SEQUENCE: 336

Gly Ala Ser
1

<210> SEQ ID NO 337
<211> LENGTH: 27
<212> TYPE: DNA

<213> ORGANISM: Artificial Sequence
<220> FEATURE:
<223> OTHER INFORMATION: Synthetic

<400> SEQUENCE: 337
cagcagtgtg gtggctcacc gtggacg           27

<210> SEQ ID NO 338
<211> LENGTH: 9
<212> TYPE: PRT
<213> ORGANISM: Artificial Sequence
<220> FEATURE:
<223> OTHER INFORMATION: Synthetic

<400> SEQUENCE: 338

Gln Gln Cys Gly Gly Ser Pro Trp Thr
 1               5

<210> SEQ ID NO 339
<211> LENGTH: 355
<212> TYPE: DNA
<213> ORGANISM: Artificial Sequence
<220> FEATURE:
<223> OTHER INFORMATION: Synthetic

<400> SEQUENCE: 339
caggtgcagc tggtggagtc tgggggaggc gtggtccagc ctggaggtc tctgagactc     60 tcctgtgcag cgtctggatt caccttcagt agctatggca tgcactgggt ccgccaggct    120
ccaggcaagg gactggagtg gtggcagtt atatggtatg atggaagtaa taaatattat    180
ggagactccg tgaagggccg attcaccatc tccagagaca attccaagaa cacgctgtat    240
ctgcaaatga acagcctgag agccgaggac acggctgtat attactgtgc gagagatgga    300
gtagacggtg cttttgatat ttggggccaa gggacaacgg tcaccgtctc ttcag         355

<210> SEQ ID NO 340
<211> LENGTH: 118
<212> TYPE: PRT
<213> ORGANISM: Artificial Sequence
<220> FEATURE:
<223> OTHER INFORMATION: Synthetic

<400> SEQUENCE: 340

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Gly Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Asp Gly Val Asp Gly Ala Phe Asp Ile Trp Gly Gln Gly Thr
            100                 105                 110

Thr Val Thr Val Ser Ser
        115

<210> SEQ ID NO 341

```
<211> LENGTH: 24
<212> TYPE: DNA
<213> ORGANISM: Artificial Sequence
<220> FEATURE:
<223> OTHER INFORMATION: Synthetic

<400> SEQUENCE: 341
ggattcacct tcagtagcta tggc                                        24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Gly Phe Thr Phe Ser Ser Tyr Gly
1               5

<210> SEQ ID NO 343
<211> LENGTH: 24
<212> TYPE: DNA
<213> ORGANISM: Artificial Sequence
<220> FEATURE:
<223> OTHER INFORMATION: Synthetic

<400> SEQUENCE: 343
atatggtatg atggaagtaa taaa                                        24

<210> SEQ ID NO 344
<211> LENGTH: 8
<212> TYPE: PRT
<213> ORGANISM: Artificial Sequence
<220> FEATURE:
<223> OTHER INFORMATION: Synthetic

<400> SEQUENCE: 344

Ile Trp Tyr Asp Gly Ser Asn Lys
1               5

<210> SEQ ID NO 345
<211> LENGTH: 33
<212> TYPE: DNA
<213> ORGANISM: Artificial Sequence
<220> FEATURE:
<223> OTHER INFORMATION: Synthetic

<400> SEQUENCE: 345
gcgagagatg gagtagacgg tgctttgat att                               33

<210> SEQ ID NO 346
<211> LENGTH: 11
<212> TYPE: PRT
<213> ORGANISM: Artificial Sequence
<220> FEATURE:
<223> OTHER INFORMATION: Synthetic

<400> SEQUENCE: 346

Ala Arg Asp Gly Val Asp Gly Ala Phe Asp Ile
1               5                   10

<210> SEQ ID NO 347
<211> LENGTH: 322
<212> TYPE: DNA
<213> ORGANISM: Artificial Sequence
<220> FEATURE:
```

<223> OTHER INFORMATION: Synthetic

<400> SEQUENCE: 347

```
gccatccaga tgacccagtc tccatcctcc ctgtctgcat ctgtaggaga cagagtcacc    60
atcacttgcc gggcaagtca ggacattaga aatgatttag ctggtatca gcagaaacca   120
gggaaagccc ctaaactcct gatctatgct gcatccagtt tacaaagtgg ggtcccatca   180
aggttcagcg gcagtggatc tggcacagat ttcactctca ccatcagcag actgcagcct   240
gaagattttg caacttatta ctgtcaacaa gattacaatt acctgtatac ttttggccag   300
gggaccaacc tggagatcaa ac                                            322
```

<210> SEQ ID NO 348
<211> LENGTH: 107
<212> TYPE: PRT
<213> ORGANISM: Artificial Sequence
<220> FEATURE:
<223> OTHER INFORMATION: Synthetic

<400> SEQUENCE: 348

```
Ala Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Arg Leu Gln Pro
 65                  70                  75                  80

Glu Asp Phe Ala Thr Tyr Tyr Cys Gln Gln Asp Tyr Asn Tyr Leu Tyr
                 85                  90                  95

Thr Phe Gly Gln Gly Thr Asn Leu Glu Ile Lys
            100                 105
```

<210> SEQ ID NO 349
<211> LENGTH: 18
<212> TYPE: DNA
<213> ORGANISM: Artificial Sequence
<220> FEATURE:
<223> OTHER INFORMATION: Synthetic

<400> SEQUENCE: 349

```
caggacatta gaaatgat                                                  18
```

<210> SEQ ID NO 350
<211> LENGTH: 6
<212> TYPE: PRT
<213> ORGANISM: Artificial Sequence
<220> FEATURE:
<223> OTHER INFORMATION: Synthetic

<400> SEQUENCE: 350

```
Gln Asp Ile Arg Asn Asp
  1               5
```

<210> SEQ ID NO 351
<211> LENGTH: 9
<212> TYPE: DNA
<213> ORGANISM: Artificial Sequence
<220> FEATURE:
<223> OTHER INFORMATION: Synthetic

<210> SEQ ID NO 351

<400> SEQUENCE: 351 gctgcatcc                                                                 9

<210> SEQ ID NO 352
<211> LENGTH: 3
<212> TYPE: PRT
<213> ORGANISM: Artificial Sequence
<220> FEATURE:
<223> OTHER INFORMATION: Synthetic

<400> SEQUENCE: 352

Ala Ala Ser
 1

<210> SEQ ID NO 353
<211> LENGTH: 27
<212> TYPE: DNA
<213> ORGANISM: Artificial Sequence
<220> FEATURE:
<223> OTHER INFORMATION: Synthetic

<400> SEQUENCE: 353
caacaagatt acaattacct gtatact                                            27

<210> SEQ ID NO 354
<211> LENGTH: 9
<212> TYPE: PRT
<213> ORGANISM: Artificial Sequence
<220> FEATURE:
<223> OTHER INFORMATION: Synthetic

<400> SEQUENCE: 354

Gln Gln Asp Tyr Asn Tyr Leu Tyr Thr
 1               5

<210> SEQ ID NO 355
<211> LENGTH: 364
<212> TYPE: DNA
<213> ORGANISM: Artificial Sequence
<220> FEATURE:
<223> OTHER INFORMATION: Synthetic

<400> SEQUENCE: 355
gaggtgcagt tggtggagtc ggggggaggc ttggtccagc ctgggggtc cctgagactc         60 tcctgtgaag cctctggatt caccttttgat aactattata tgacctgggt ccgccagact      120
ccagggaagg ggctggagtg ggtggccaac ataaaggaag atggaaatga tagatactat      180
gtggactctg tgaagggccg cttcaccatc tccagagaca acgccaagca gtcactgttt      240
ctacaaatga acagtctgag agccgaggac acggctgttt attactgtgc gagagaattt      300
tggagtggcc ctcactacgg tttggacgtc tggggccaag ggaccacggt caccgtctcc      360
tcag                                                                   364

<210> SEQ ID NO 356
<211> LENGTH: 121
<212> TYPE: PRT
<213> ORGANISM: Artificial Sequence
<220> FEATURE:
<223> OTHER INFORMATION: Synthetic

<400> SEQUENCE: 356

Glu Val Gln Leu Val Glu Ser Gly Gly Gly Leu Val Gln Pro Gly Gly
 1               5                  10                  15

```
Ser Leu Arg Leu Ser Cys Glu Ala Ser Gly Phe Thr Phe Asp Asn Tyr
        20                  25                  30

Tyr Met Thr Trp Val Arg Gln Thr Pro Gly Lys Gly Leu Glu Trp Val
        35                  40                  45

Ala Asn Ile Lys Glu Asp Gly Asn Asp Arg Tyr Tyr Val Asp Ser Val
    50                  55                  60

Lys Gly Arg Phe Thr Ile Ser Arg Asp Asn Ala Lys Gln Ser Leu Phe
65                  70                  75                  80

Leu Gln Met Asn Ser Leu Arg Ala Glu Asp Thr Ala Val Tyr Tyr Cys
                85                  90                  95

Ala Arg Glu Phe Trp Ser Gly Pro His Tyr Gly Leu Asp Val Trp Gly
            100                 105                 110

Gln Gly Thr Thr Val Thr Val Ser Ser
        115                 120
```

```
<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
ggattcacct tgataacta ttat                                          24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

Gly Phe Thr Phe Asp Asn Tyr Tyr
1               5

<210> SEQ ID NO 359
<211> LENGTH: 24
<212> TYPE: DNA
<213> ORGANISM: Artificial Sequence
<220> FEATURE:
<223> OTHER INFORMATION: Synthetic

<400> SEQUENCE: 359
ataaaggaag atggaaatga taga                                         24

<210> SEQ ID NO 360
<211> LENGTH: 8
<212> TYPE: PRT
<213> ORGANISM: Artificial Sequence
<220> FEATURE:
<223> OTHER INFORMATION: Synthetic

<400> SEQUENCE: 360

Ile Lys Glu Asp Gly Asn Asp Arg
1               5

<210> SEQ ID NO 361
<211> LENGTH: 42
<212> TYPE: DNA
<213> ORGANISM: Artificial Sequence
<220> FEATURE:
<223> OTHER INFORMATION: Synthetic
```

<400> SEQUENCE: 361
gcgagagaat tttggagtgg ccctcactac ggtttggacg tc        42

<210> SEQ ID NO 362
<211> LENGTH: 14
<212> TYPE: PRT
<213> ORGANISM: Artificial Sequence
<220> FEATURE:
<223> OTHER INFORMATION: Synthetic

<400> SEQUENCE: 362

Ala Arg Glu Phe Trp Ser Gly Pro His Tyr Gly Leu Asp Val
 1               5                  10

<210> SEQ ID NO 363
<211> LENGTH: 322
<212> TYPE: DNA
<213> ORGANISM: Artificial Sequence
<220> FEATURE:
<223> OTHER INFORMATION: Synthetic

<400> SEQUENCE: 363
gccctccaga tgacccagtc tccatcctcc ctgtctgcac ctgtaggcga cagagtcacc        60
atcacttgcc gggcaagtca ggacgttaga ataaatttag ctggtatca gcagaaacca       120 gggaatgccc ctaaattcct gatctatgct gcatccagtt tacaaagtgg aatcccatca       180
aggttcagcg gcagtggatc tggctcagat ttcactctca ccatcagcag cctgcagcct       240
gaagattttg caacttatta ctgtctacaa gattacaatt accctccgac gttcggccag       300
gggaccaagg tggaaatcaa gc                                                322

<210> SEQ ID NO 364
<211> LENGTH: 107
<212> TYPE: PRT
<213> ORGANISM: Artificial Sequence
<220> FEATURE:
<223> OTHER INFORMATION: Synthetic

<400> SEQUENCE: 364

Ala Leu Gln Met Thr Gln Ser Pro Ser Ser Leu Ser Ala Pro Val Gly
 1               5                  10                  15

Asp Arg Val Thr Ile Thr Cys Arg Ala Ser Gln Asp Val Arg Asn Asn
                20                  25                  30

Leu Gly Trp Tyr Gln Gln Lys Pro Gly Asn Ala Pro Lys Phe Leu Ile
            35                  40                  45

Tyr Ala Ala Ser Ser Leu Gln Ser Gly Ile Pro Ser Arg Phe Ser Gly
        50                  55                  60

Ser Gly Ser Gly Ser Asp Phe Thr Leu Thr Ile Ser Ser Leu Gln Pro
 65                 70                  75                  80

Glu Asp Phe Ala Thr Tyr Tyr Cys Leu Gln Asp Tyr Asn Tyr Pro Pro
                85                  90                  95

Thr Phe Gly Gln Gly Thr Lys Val Glu Ile Lys
            100                 105

<210> SEQ ID NO 365
<211> LENGTH: 18
<212> TYPE: DNA
<213> ORGANISM: Artificial Sequence
<220> FEATURE:
<223> OTHER INFORMATION: Synthetic

```
<400> SEQUENCE: 365
caggacgtta gaaataat                                                    18

<210> SEQ ID NO 366
<211> LENGTH: 6
<212> TYPE: PRT
<213> ORGANISM: Artificial Sequence
<220> FEATURE:
<223> OTHER INFORMATION: Synthetic

<400> SEQUENCE: 366

Gln Asp Val Arg Asn Asn
 1               5

<210> SEQ ID NO 367
<211> LENGTH: 9
<212> TYPE: DNA
<213> ORGANISM: Artificial Sequence
<220> FEATURE:
<223> OTHER INFORMATION: Synthetic

<400> SEQUENCE: 367 gctgcatcc                                                               9

<210> SEQ ID NO 368
<211> LENGTH: 3
<212> TYPE: PRT
<213> ORGANISM: Artificial Sequence
<220> FEATURE:
<223> OTHER INFORMATION: Synthetic

<400> SEQUENCE: 368

Ala Ala Ser
 1

<210> SEQ ID NO 369
<211> LENGTH: 27
<212> TYPE: DNA
<213> ORGANISM: Artificial Sequence
<220> FEATURE:
<223> OTHER INFORMATION: Synthetic

<400> SEQUENCE: 369
ctacaagatt acaattaccc tccgacg                                          27

<210> SEQ ID NO 370
<211> LENGTH: 9
<212> TYPE: PRT
<213> ORGANISM: Artificial Sequence
<220> FEATURE:
<223> OTHER INFORMATION: Synthetic

<400> SEQUENCE: 370

Leu Gln Asp Tyr Asn Tyr Pro Pro Thr
 1               5

<210> SEQ ID NO 371
<211> LENGTH: 370
<212> TYPE: DNA
<213> ORGANISM: Artificial Sequence
<220> FEATURE:
<223> OTHER INFORMATION: Synthetic

<400> SEQUENCE: 371
caggtgcagc tggtggagtc tgggggaggc gtggtccagc ctggagggtc cctgagactc      60
```

-continued

```
tcctgtgcag cgtctggatt caccttcagt agttatggca tgcactgggt ccgccaggct      120
ccaggcaagg ggctggagtg ggtggcagtt ttatggtatg atggaagtaa taaaaactat      180
gtagactccg tgaagggccg attcaccatc tcaagagaca attccaagaa cacgctgtat      240
ctgcaaatga acagcctgag agccgaggac acggctgtgt attactgtgc gagagatcac      300
gattttagga gtggttatga ggggtggttc gaccccctggg gccagggaac cttggtcacc      360
gtctcctcag                                                             370
```

<210> SEQ ID NO 372
<211> LENGTH: 123
<212> TYPE: PRT
<213> ORGANISM: Artificial Sequence
<220> FEATURE:
<223> OTHER INFORMATION: Synthetic

<400> SEQUENCE: 372

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Leu Trp Tyr Asp Gly Ser Asn Lys Asn Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120
```

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373

```
ggattcacct tcagtagtta tggc                                              24
```

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

```
Gly Phe Thr Phe Ser Ser Tyr Gly
 1               5
```

<210> SEQ ID NO 375
<211> LENGTH: 24
<212> TYPE: DNA
<213> ORGANISM: Artificial Sequence
<220> FEATURE:
<223> OTHER INFORMATION: Synthetic

<400> SEQUENCE: 375
ttatggtatg atggaagtaa taaa   24

<210> SEQ ID NO 376
<211> LENGTH: 8
<212> TYPE: PRT
<213> ORGANISM: Artificial Sequence
<220> FEATURE:
<223> OTHER INFORMATION: Synthetic

<400> SEQUENCE: 376

Leu Trp Tyr Asp Gly Ser Asn Lys
1               5

<210> SEQ ID NO 377
<211> LENGTH: 48
<212> TYPE: DNA
<213> ORGANISM: Artificial Sequence
<220> FEATURE:
<223> OTHER INFORMATION: Synthetic

<400> SEQUENCE: 377
gcgagagatc acgattttag gagtggttat gagggggtggt tcgacccc   48

<210> SEQ ID NO 378
<211> LENGTH: 16
<212> TYPE: PRT
<213> ORGANISM: Artificial Sequence
<220> FEATURE:
<223> OTHER INFORMATION: Synthetic

<400> SEQUENCE: 378

Ala Arg Asp His Asp Phe Arg Ser Gly Tyr Glu Gly Trp Phe Asp Pro
1               5                   10                  15

<210> SEQ ID NO 379
<211> LENGTH: 322
<212> TYPE: DNA
<213> ORGANISM: Artificial Sequence
<220> FEATURE:
<223> OTHER INFORMATION: Synthetic

<400> SEQUENCE: 379
gaaattgtgt tgacacagtc tccagccacc ctgtctttgt ctccagggga aagagccacc   60
ctctcctgca gggccagtca gagtgttcgc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcac cgtagcaact ggcctccac tttcggcgga  300 gggaccgagg tggaggtcag ac                                           322

<210> SEQ ID NO 380
<211> LENGTH: 107
<212> TYPE: PRT
<213> ORGANISM: Artificial Sequence
<220> FEATURE:
<223> OTHER INFORMATION: Synthetic

<400> SEQUENCE: 380

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Gly Gly Thr Glu Val Glu Val Arg
            100                 105
```

```
<210> SEQ ID NO 381
<211> LENGTH: 18
<212> TYPE: DNA
<213> ORGANISM: Artificial Sequence
<220> FEATURE:
<223> OTHER INFORMATION: Synthetic

<400> SEQUENCE: 381
cagagtgttc gcagctac                                                  18

<210> SEQ ID NO 382
<211> LENGTH: 6
<212> TYPE: PRT
<213> ORGANISM: Artificial Sequence
<220> FEATURE:
<223> OTHER INFORMATION: Synthetic

<400> SEQUENCE: 382

Gln Ser Val Arg Ser Tyr
 1               5

<210> SEQ ID NO 383
<211> LENGTH: 9
<212> TYPE: DNA
<213> ORGANISM: Artificial Sequence
<220> FEATURE:
<223> OTHER INFORMATION: Synthetic

<400> SEQUENCE: 383 gatgcatcc                                                             9

<210> SEQ ID NO 384
<211> LENGTH: 3
<212> TYPE: PRT
<213> ORGANISM: Artificial Sequence
<220> FEATURE:
<223> OTHER INFORMATION: Synthetic

<400> SEQUENCE: 384

Asp Ala Ser
 1

<210> SEQ ID NO 385
<211> LENGTH: 27
<212> TYPE: DNA
<213> ORGANISM: Artificial Sequence
<220> FEATURE:
<223> OTHER INFORMATION: Synthetic

<400> SEQUENCE: 385
cagcaccgta gcaactggcc tcccact                                        27
```

```
<210> SEQ ID NO 386
<211> LENGTH: 9
<212> TYPE: PRT
<213> ORGANISM: Artificial Sequence
<220> FEATURE:
<223> OTHER INFORMATION: Synthetic

<400> SEQUENCE: 386

Gln His Arg Ser Asn Trp Pro Pro Thr
 1               5

<210> SEQ ID NO 387
<211> LENGTH: 16
<212> TYPE: DNA
<213> ORGANISM: Artificial Sequence
<220> FEATURE:
<223> OTHER INFORMATION: Synthetic

<400> SEQUENCE: 387
taccggctcc cgatgg                                                     16

<210> SEQ ID NO 388
<211> LENGTH: 19
<212> TYPE: DNA
<213> ORGANISM: Artificial Sequence
<220> FEATURE:
<223> OTHER INFORMATION: Synthetic

<400> SEQUENCE: 388
ggcggctaag gtgtttgga                                                  19

<210> SEQ ID NO 389
<211> LENGTH: 22
<212> TYPE: DNA
<213> ORGANISM: Artificial Sequence
<220> FEATURE:
<223> OTHER INFORMATION: Synthetic

<400> SEQUENCE: 389
ttgggaatga ggaaagcaaa ct                                              22

<210> SEQ ID NO 390
<211> LENGTH: 18
<212> TYPE: DNA
<213> ORGANISM: Artificial Sequence
<220> FEATURE:
<223> OTHER INFORMATION: Synthetic

<400> SEQUENCE: 390
ctgaagtacc ggaggaga                                                   18

<210> SEQ ID NO 391
<211> LENGTH: 20
<212> TYPE: DNA
<213> ORGANISM: Artificial Sequence
<220> FEATURE:
<223> OTHER INFORMATION: Synthetic

<400> SEQUENCE: 391
atcacgctgg tggtcctctt                                                 20

<210> SEQ ID NO 392
<211> LENGTH: 16
<212> TYPE: DNA
<213> ORGANISM: Artificial Sequence
<220> FEATURE:
<223> OTHER INFORMATION: Synthetic
```

<210> SEQ ID NO 393
<211> LENGTH: 23
<212> TYPE: DNA
<213> ORGANISM: Artificial Sequence
<220> FEATURE:
<223> OTHER INFORMATION: Synthetic

<400> SEQUENCE: 393
tggcaaatgc tggacccaac aca                                          23

<210> SEQ ID NO 394
<211> LENGTH: 19
<212> TYPE: DNA
<213> ORGANISM: Artificial Sequence
<220> FEATURE:
<223> OTHER INFORMATION: Synthetic

<400> SEQUENCE: 394
gggtcctggc atcttgtcc                                               19

<210> SEQ ID NO 395
<211> LENGTH: 22
<212> TYPE: DNA
<213> ORGANISM: Artificial Sequence
<220> FEATURE:
<223> OTHER INFORMATION: Synthetic

<400> SEQUENCE: 395
gcagatgaaa aactgggaac ca                                           22

<210> SEQ ID NO 396
<211> LENGTH: 372
<212> TYPE: DNA
<213> ORGANISM: Artificial Sequence
<220> FEATURE:
<223> OTHER INFORMATION: Synthetic

<400> SEQUENCE: 396
caggtgcagc tggtgcagtc aggtccagga ctggtgaagc cctcgcagaa cctctcactc    60
acctgtgcca tctccggaga cagtgtctct agtgatagtg ctgcttggaa ctggatcagg   120
cagtccccat cgagaggcct tgagtggctg gaaggacat actacaggtc caagtggtat   180
aatgattatg cagtatctgt gaaaagtcga ataaccttca acccagatac atccaagaac   240
cacatctccc tgcagctgaa ctctgtgact cccgaggaca cggctatcta ttactgtgca   300 agagagggg ataattggaa ttacggctgg ctcgacccct ggggccaggg aaccacggtc   360
accgtctcct ca                                                     372

<210> SEQ ID NO 397
<211> LENGTH: 124
<212> TYPE: PRT
<213> ORGANISM: Artificial Sequence
<220> FEATURE:
<223> OTHER INFORMATION: Synthetic

<400> SEQUENCE: 397

Gln Val Gln Leu Val Gln Ser Gly Pro Gly Leu Val Lys Pro Ser Gln
 1               5                  10                  15

Asn Leu Ser Leu Thr Cys Ala Ile Ser Gly Asp Ser Val Ser Ser Asp

```
                    20                  25                  30
Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Phe Asn Pro Asp Thr Ser Lys Asn
 65                  70                  75                  80

His Ile Ser Leu Gln Leu Asn Ser Val Thr Pro Glu Asp Thr Ala Ile
                85                  90                  95

Tyr Tyr Cys Ala Arg Glu Gly Asp Asn Trp Asn Tyr Gly Trp Leu Asp
            100                 105                 110

Pro Trp Gly Gln Gly Thr Thr Val Thr Val Ser Ser
        115                 120
```

<210> SEQ ID NO 398
<211> LENGTH: 30
<212> TYPE: DNA
<213> ORGANISM: Artificial Sequence
<220> FEATURE:
<223> OTHER INFORMATION: Synthetic

<400> SEQUENCE: 398
ggagacagtg tctctagtga tagtgctgct                                    30

<210> SEQ ID NO 399
<211> LENGTH: 10
<212> TYPE: PRT
<213> ORGANISM: Artificial Sequence
<220> FEATURE:
<223> OTHER INFORMATION: Synthetic

<400> SEQUENCE: 399

```
Gly Asp Ser Val Ser Ser Asp Ser Ala Ala
 1               5                  10
```

<210> SEQ ID NO 400
<211> LENGTH: 27
<212> TYPE: DNA
<213> ORGANISM: Artificial Sequence
<220> FEATURE:
<223> OTHER INFORMATION: Synthetic

<400> SEQUENCE: 400
acatactaca ggtccaagtg gtataat                                       27

<210> SEQ ID NO 401
<211> LENGTH: 9
<212> TYPE: PRT
<213> ORGANISM: Artificial Sequence
<220> FEATURE:
<223> OTHER INFORMATION: Synthetic

<400> SEQUENCE: 401

```
Thr Tyr Tyr Arg Ser Lys Trp Tyr Asn
 1               5
```

<210> SEQ ID NO 402
<211> LENGTH: 42
<212> TYPE: DNA
<213> ORGANISM: Artificial Sequence
<220> FEATURE:
<223> OTHER INFORMATION: Synthetic

<400> SEQUENCE: 402

```
gcaagagagg gggataattg gaattacggc tggctcgacc cc                    42
```

<210> SEQ ID NO 403
<211> LENGTH: 14
<212> TYPE: PRT
<213> ORGANISM: Artificial Sequence
<220> FEATURE:
<223> OTHER INFORMATION: Synthetic

<400> SEQUENCE: 403

Ala Arg Glu Gly Asp Asn Trp Asn Tyr Gly Trp Leu Asp Pro
1               5                   10

<210> SEQ ID NO 404
<211> LENGTH: 336
<212> TYPE: DNA
<213> ORGANISM: Artificial Sequence
<220> FEATURE:
<223> OTHER INFORMATION: Synthetic

<400> SEQUENCE: 404

```
gacatccagt tgacccagtc tccactctcc ctgcccgtca cccctggaga gccggcctcc    60
atctcctgca ggtctagtca gagcctcctt cttagtaatg gatacaacta tttggattgg   120
tacctgcaga agccagggca gtctccacaa ctcctgatct atttggtttc tagtcgggcc   180
tccggggtcc ctgacaggtt cagtggcagt ggatccggca cagatttttac actgaaaatc   240
agcagagtgg aggctgagga ttttggaatt tattattgta tgcaagctct acaaactccg   300
tacacttttg gccgggggac caaggtggaa atcaaa                             336
```

<210> SEQ ID NO 405
<211> LENGTH: 112
<212> TYPE: PRT
<213> ORGANISM: Artificial Sequence
<220> FEATURE:
<223> OTHER INFORMATION: Synthetic

<400> SEQUENCE: 405

Asp Ile Gln Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Leu Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Val Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Ile Tyr Tyr Cys Met Gln Ala
                85                  90                  95

Leu Gln Thr Pro Tyr Thr Phe Gly Arg Gly Thr Lys Val Glu Ile Lys
            100                 105                 110

<210> SEQ ID NO 406
<211> LENGTH: 33
<212> TYPE: DNA
<213> ORGANISM: Artificial Sequence
<220> FEATURE:
<223> OTHER INFORMATION: Synthetic

<400> SEQUENCE: 406

```
cagagcctcc ttcttagtaa tggatacaac tat                                    33

<210> SEQ ID NO 407
<211> LENGTH: 11
<212> TYPE: PRT
<213> ORGANISM: Artificial Sequence
<220> FEATURE:
<223> OTHER INFORMATION: Synthetic

<400> SEQUENCE: 407

Gln Ser Leu Leu Leu Ser Asn Gly Tyr Asn Tyr
 1               5                  10

<210> SEQ ID NO 408
<211> LENGTH: 9
<212> TYPE: DNA
<213> ORGANISM: Artificial Sequence
<220> FEATURE:
<223> OTHER INFORMATION: Synthetic

<400> SEQUENCE: 408 ttggtttct                                                                9

<210> SEQ ID NO 409
<211> LENGTH: 3
<212> TYPE: PRT
<213> ORGANISM: Artificial Sequence
<220> FEATURE:
<223> OTHER INFORMATION: Synthetic

<400> SEQUENCE: 409

Leu Val Ser
 1

<210> SEQ ID NO 410
<211> LENGTH: 27
<212> TYPE: DNA
<213> ORGANISM: Artificial Sequence
<220> FEATURE:
<223> OTHER INFORMATION: Synthetic

<400> SEQUENCE: 410
atgcaagctc tacaaactcc gtacact                                           27

<210> SEQ ID NO 411
<211> LENGTH: 9
<212> TYPE: PRT
<213> ORGANISM: Artificial Sequence
<220> FEATURE:
<223> OTHER INFORMATION: Synthetic

<400> SEQUENCE: 411

Met Gln Ala Leu Gln Thr Pro Tyr Thr
 1               5

<210> SEQ ID NO 412
<211> LENGTH: 360
<212> TYPE: DNA
<213> ORGANISM: Artificial Sequence
<220> FEATURE:
<223> OTHER INFORMATION: Synthetic

<400> SEQUENCE: 412
caggtgcagc tgcaggagtc gggcccagga ctggtgaagc cttcacagac cctgtccctc       60
acctgcactg tctctggtgg ctccgtcagc agtggtaatt actactggag ctgggtccgc      120
```

| | | |
|---|---|---|
| caacacccag ggaagggcct ggagtggttt ggttacatca aaaacagtgg gggcacctac | 180 | |
| tacaacccgt ccctcaagag tcgaattacc atatcagtag acacgtctaa gaaccacttc | 240 | |
| tccctgaggc tgagctctat gacggccgcg gacacggccg tgtattactg tgcgagagct | 300 | |
| ggttcgggga gtcactactt tgactactgg ggccaggaa ccctggtcac cgtctcctca | 360 | |

<210> SEQ ID NO 413
<211> LENGTH: 120
<212> TYPE: PRT
<213> ORGANISM: Artificial Sequence
<220> FEATURE:
<223> OTHER INFORMATION: Synthetic

<400> SEQUENCE: 413

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Ser Gly
            20                  25                  30

Asn Tyr Tyr Trp Ser Trp Val Arg Gln His Pro Gly Lys Gly Leu Glu
        35                  40                  45

Trp Phe Gly Tyr Ile Lys Asn Ser Gly Gly Thr Tyr Tyr Asn Pro Ser
    50                  55                  60

Leu Lys Ser Arg Ile Thr Ile Ser Val Asp Thr Ser Lys Asn His Phe
65                  70                  75                  80

Ser Leu Arg Leu Ser Ser Met Thr Ala Ala Asp Thr Ala Val Tyr Tyr
                85                  90                  95

Cys Ala Arg Ala Gly Ser Gly Ser His Tyr Phe Asp Tyr Trp Gly Gln
            100                 105                 110

Gly Thr Leu Val Thr Val Ser Ser
        115                 120

<210> SEQ ID NO 414
<211> LENGTH: 30
<212> TYPE: DNA
<213> ORGANISM: Artificial Sequence
<220> FEATURE:
<223> OTHER INFORMATION: Synthetic

<400> SEQUENCE: 414
ggtggctccg tcagcagtgg taattactac                                        30

<210> SEQ ID NO 415
<211> LENGTH: 10
<212> TYPE: PRT
<213> ORGANISM: Artificial Sequence
<220> FEATURE:
<223> OTHER INFORMATION: Synthetic

<400> SEQUENCE: 415

Gly Gly Ser Val Ser Ser Gly Asn Tyr Tyr
1               5                   10

<210> SEQ ID NO 416
<211> LENGTH: 21
<212> TYPE: DNA
<213> ORGANISM: Artificial Sequence
<220> FEATURE:
<223> OTHER INFORMATION: Synthetic

<400> SEQUENCE: 416
atcaaaaaca gtgggggcac c                                                 21

<210> SEQ ID NO 417
<211> LENGTH: 7
<212> TYPE: PRT
<213> ORGANISM: Artificial Sequence
<220> FEATURE:
<223> OTHER INFORMATION: Synthetic

<400> SEQUENCE: 417

Ile Lys Asn Ser Gly Gly Thr
1               5

<210> SEQ ID NO 418
<211> LENGTH: 36
<212> TYPE: DNA
<213> ORGANISM: Artificial Sequence
<220> FEATURE:
<223> OTHER INFORMATION: Synthetic

<400> SEQUENCE: 418
gcgagagctg gttcggggag tcactacttt gactac                                 36

<210> SEQ ID NO 419
<211> LENGTH: 12
<212> TYPE: PRT
<213> ORGANISM: Artificial Sequence
<220> FEATURE:
<223> OTHER INFORMATION: Synthetic

<400> SEQUENCE: 419

Ala Arg Ala Gly Ser Gly Ser His Tyr Phe Asp Tyr
1               5                   10

<210> SEQ ID NO 420
<211> LENGTH: 324
<212> TYPE: DNA
<213> ORGANISM: Artificial Sequence
<220> FEATURE:
<223> OTHER INFORMATION: Synthetic

<400> SEQUENCE: 420
gacatccagt tgacccagtc tccaggcacc ctgtctttgt ctccagggga aagagccacc        60
ctctcctgca gggccagtca gagtgttagc agcaactact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt gtgcagtgta ttactgtcag cagtacggtt actcaccgat caccttcggc       300
caagggacca agctggagat caaa                                              324

<210> SEQ ID NO 421
<211> LENGTH: 108
<212> TYPE: PRT
<213> ORGANISM: Artificial Sequence
<220> FEATURE:
<223> OTHER INFORMATION: Synthetic

<400> SEQUENCE: 421

Asp Ile Gln Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Cys Ala Val Tyr Tyr Cys Gln Gln Tyr Gly Tyr Ser Pro
                85                  90                  95

Ile Thr Phe Gly Gln Gly Thr Lys Leu Glu Ile Lys
            100                 105
```

<210> SEQ ID NO 422
<211> LENGTH: 21
<212> TYPE: DNA
<213> ORGANISM: Artificial Sequence
<220> FEATURE:
<223> OTHER INFORMATION: Synthetic

<400> SEQUENCE: 422
cagagtgtta gcagcaacta c                                          21

<210> SEQ ID NO 423
<211> LENGTH: 7
<212> TYPE: PRT
<213> ORGANISM: Artificial Sequence
<220> FEATURE:
<223> OTHER INFORMATION: Synthetic

<400> SEQUENCE: 423

```
Gln Ser Val Ser Ser Asn Tyr
 1               5
```

<210> SEQ ID NO 424
<211> LENGTH: 9
<212> TYPE: DNA
<213> ORGANISM: Artificial Sequence
<220> FEATURE:
<223> OTHER INFORMATION: Synthetic

<400> SEQUENCE: 424 ggtgcatcc                                                         9

<210> SEQ ID NO 425
<211> LENGTH: 3
<212> TYPE: PRT
<213> ORGANISM: Artificial Sequence
<220> FEATURE:
<223> OTHER INFORMATION: Synthetic

<400> SEQUENCE: 425

```
Gly Ala Ser
 1
```

<210> SEQ ID NO 426
<211> LENGTH: 27
<212> TYPE: DNA
<213> ORGANISM: Artificial Sequence
<220> FEATURE:
<223> OTHER INFORMATION: Synthetic

<400> SEQUENCE: 426
cagcagtacg gttactcacc gatcacc                                    27

<210> SEQ ID NO 427
<211> LENGTH: 9
<212> TYPE: PRT
<213> ORGANISM: Artificial Sequence

```
<220> FEATURE:
<223> OTHER INFORMATION: Synthetic

<400> SEQUENCE: 427

Gln Gln Tyr Gly Tyr Ser Pro Ile Thr
 1               5

<210> SEQ ID NO 428
<211> LENGTH: 369
<212> TYPE: DNA
<213> ORGANISM: Artificial Sequence
<220> FEATURE:
<223> OTHER INFORMATION: Synthetic

<400> SEQUENCE: 428
gaggtgcagc tggtgcagtc tggggggaggc gtggtccagc ctggggaggtc cctgagactc      60 tcctgtgcag cgtctggatt caccttcagt agttatggca tgcactgggt ccgccaggct     120
ccaggcaagg ggctggagtg ggtgtcattt ttatggtatg atggaactaa taaaaactat     180
gtagagtccg tgaagggccg attcaccatc tcaagagaca attccaagaa tatgctgtat     240
ctggaaatga acagcctgag agccgaggac acggctgtgt attactgtgc gagagatcac     300
gattttagga gtggttatga ggggtggttc gacccctggg gccagggaac cctggtcacc     360
gtctcctca                                                               369

<210> SEQ ID NO 429
<211> LENGTH: 123
<212> TYPE: PRT
<213> ORGANISM: Artificial Sequence
<220> FEATURE:
<223> OTHER INFORMATION: Synthetic

<400> SEQUENCE: 429

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Phe Leu Trp Tyr Asp Gly Thr Asn Lys Asn Tyr Val Glu Ser Val
        50                  55                  60

Lys Gly Arg Phe Thr Ile Ser Arg Asp Asn Ser Lys Asn Met Leu Tyr
 65                 70                  75                  80

Leu Glu Met Asn Ser Leu Arg Ala Glu Asp Thr Ala Val Tyr Tyr Cys
                85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120

<210> SEQ ID NO 430
<211> LENGTH: 24
<212> TYPE: DNA
<213> ORGANISM: Artificial Sequence
<220> FEATURE:
<223> OTHER INFORMATION: Synthetic

<400> SEQUENCE: 430
ggattcacct tcagtagtta tggc                                              24
```

```
<210> SEQ ID NO 431
<211> LENGTH: 8
<212> TYPE: PRT
<213> ORGANISM: Artificial Sequence
<220> FEATURE:
<223> OTHER INFORMATION: Synthetic

<400> SEQUENCE: 431

Gly Phe Thr Phe Ser Ser Tyr Gly
 1               5

<210> SEQ ID NO 432
<211> LENGTH: 24
<212> TYPE: DNA
<213> ORGANISM: Artificial Sequence
<220> FEATURE:
<223> OTHER INFORMATION: Synthetic

<400> SEQUENCE: 432
ttatggtatg atggaactaa taaa                                            24

<210> SEQ ID NO 433
<211> LENGTH: 8
<212> TYPE: PRT
<213> ORGANISM: Artificial Sequence
<220> FEATURE:
<223> OTHER INFORMATION: Synthetic

<400> SEQUENCE: 433

Leu Trp Tyr Asp Gly Thr Asn Lys
 1               5

<210> SEQ ID NO 434
<211> LENGTH: 48
<212> TYPE: DNA
<213> ORGANISM: Artificial Sequence
<220> FEATURE:
<223> OTHER INFORMATION: Synthetic

<400> SEQUENCE: 434
gcgagagatc acgattttag gagtggttat gagggggtggt tcgacccc                  48

<210> SEQ ID NO 435
<211> LENGTH: 16
<212> TYPE: PRT
<213> ORGANISM: Artificial Sequence
<220> FEATURE:
<223> OTHER INFORMATION: Synthetic

<400> SEQUENCE: 435

Ala Arg Asp His Asp Phe Arg Ser Gly Tyr Glu Gly Trp Phe Asp Pro
 1               5                  10                  15

<210> SEQ ID NO 436
<211> LENGTH: 321
<212> TYPE: DNA
<213> ORGANISM: Artificial Sequence
<220> FEATURE:
<223> OTHER INFORMATION: Synthetic

<400> SEQUENCE: 436
gaaatagtga tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
```

```
gaagattttg cagtttatta ctgtcaacac cgtagcaact ggcctcccac tttcggcgga    300
gggaccaagg tggaaatcaa a                                              321
```

<210> SEQ ID NO 437
<211> LENGTH: 107
<212> TYPE: PRT
<213> ORGANISM: Artificial Sequence
<220> FEATURE:
<223> OTHER INFORMATION: Synthetic

<400> SEQUENCE: 437

```
Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Gly Gly Thr Lys Val Glu Ile Lys
            100                 105
```

<210> SEQ ID NO 438
<211> LENGTH: 18
<212> TYPE: DNA
<213> ORGANISM: Artificial Sequence
<220> FEATURE:
<223> OTHER INFORMATION: Synthetic

<400> SEQUENCE: 438

```
cagagtgtta gcagctac                                                  18
```

<210> SEQ ID NO 439
<211> LENGTH: 6
<212> TYPE: PRT
<213> ORGANISM: Artificial Sequence
<220> FEATURE:
<223> OTHER INFORMATION: Synthetic

<400> SEQUENCE: 439

```
Gln Ser Val Ser Ser Tyr
 1               5
```

<210> SEQ ID NO 440
<211> LENGTH: 9
<212> TYPE: DNA
<213> ORGANISM: Artificial Sequence
<220> FEATURE:
<223> OTHER INFORMATION: Synthetic

<400> SEQUENCE: 440

```
gatgcatcc                                                             9
```

<210> SEQ ID NO 441
<211> LENGTH: 3
<212> TYPE: PRT
<213> ORGANISM: Artificial Sequence
<220> FEATURE:

<210> SEQ ID NO 442
<211> LENGTH: 27
<212> TYPE: DNA
<213> ORGANISM: Artificial Sequence
<220> FEATURE:
<223> OTHER INFORMATION: Synthetic

<400> SEQUENCE: 441

Asp Ala Ser
 1

<210> SEQ ID NO 442
<211> LENGTH: 27
<212> TYPE: DNA
<213> ORGANISM: Artificial Sequence
<220> FEATURE:
<223> OTHER INFORMATION: Synthetic

<400> SEQUENCE: 442
caacaccgta gcaactggcc tcccact                                          27

<210> SEQ ID NO 443
<211> LENGTH: 9
<212> TYPE: PRT
<213> ORGANISM: Artificial Sequence
<220> FEATURE:
<223> OTHER INFORMATION: Synthetic

<400> SEQUENCE: 443

Gln His Arg Ser Asn Trp Pro Pro Thr
 1               5

<210> SEQ ID NO 444
<211> LENGTH: 366
<212> TYPE: DNA
<213> ORGANISM: Artificial Sequence
<220> FEATURE:
<223> OTHER INFORMATION: Synthetic

<400> SEQUENCE: 444
caggtacagc tgcagcagtc gggtccagga ctgctgaaac cttcacagac cctgtccctc      60
acctgctctg tctctggtgg ctccatcagc agtggtaatt actactggac ctggatccgc     120
cagcacccag ggaagggcct ggagtggatt gggtacatca agaacagtgg aagcgcctac     180
tacaatccgt ccctcaagag tcgacttacc atgtcaatag acacgtctca gaaccacttc     240
tccttgattt tgacttctgt gactgccgcg gacacggcct tatattactg tgcgagagat     300
gaaaatatag cagttcgtca tgcttttgat atctggggcc aagggacatc ggtcaccgtc     360
tcctca                                                                366

<210> SEQ ID NO 445
<211> LENGTH: 122
<212> TYPE: PRT
<213> ORGANISM: Artificial Sequence
<220> FEATURE:
<223> OTHER INFORMATION: Synthetic

<400> SEQUENCE: 445

Gln Val Gln Leu Gln Gln Ser Gly Pro Gly Leu Leu Lys Pro Ser Gln
 1               5                  10                  15

Thr Leu Ser Leu Thr Cys Ser Val Ser Gly Gly Ser Ile Ser Ser Gly
             20                  25                  30

Asn Tyr Tyr Trp Thr Trp Ile Arg Gln His Pro Gly Lys Gly Leu Glu
         35                  40                  45

Trp Ile Gly Tyr Ile Lys Asn Ser Gly Ser Ala Tyr Tyr Asn Pro Ser
     50                  55                  60

Leu Lys Ser Arg Leu Thr Met Ser Ile Asp Thr Ser Gln Asn His Phe

```
                65                  70                  75                  80
Ser Leu Ile Leu Thr Ser Val Thr Ala Ala Asp Thr Ala Leu Tyr Tyr
                    85                  90                  95

Cys Ala Arg Asp Glu Asn Ile Ala Val Arg His Ala Phe Asp Ile Trp
                100                 105                 110

Gly Gln Gly Thr Ser Val Thr Val Ser Ser
        115                 120
```

<210> SEQ ID NO 446
<211> LENGTH: 30
<212> TYPE: DNA
<213> ORGANISM: Artificial Sequence
<220> FEATURE:
<223> OTHER INFORMATION: Synthetic

<400> SEQUENCE: 446
ggtggctcca tcagcagtgg taattactac                                        30

<210> SEQ ID NO 447
<211> LENGTH: 10
<212> TYPE: PRT
<213> ORGANISM: Artificial Sequence
<220> FEATURE:
<223> OTHER INFORMATION: Synthetic

<400> SEQUENCE: 447

```
Gly Gly Ser Ile Ser Ser Gly Asn Tyr Tyr
  1               5                  10
```

<210> SEQ ID NO 448
<211> LENGTH: 21
<212> TYPE: DNA
<213> ORGANISM: Artificial Sequence
<220> FEATURE:
<223> OTHER INFORMATION: Synthetic

<400> SEQUENCE: 448
atcaagaaca gtggaagcgc c                                                 21

<210> SEQ ID NO 449
<211> LENGTH: 7
<212> TYPE: PRT
<213> ORGANISM: Artificial Sequence
<220> FEATURE:
<223> OTHER INFORMATION: Synthetic

<400> SEQUENCE: 449

```
Ile Lys Asn Ser Gly Ser Ala
  1               5
```

<210> SEQ ID NO 450
<211> LENGTH: 42
<212> TYPE: DNA
<213> ORGANISM: Artificial Sequence
<220> FEATURE:
<223> OTHER INFORMATION: Synthetic

<400> SEQUENCE: 450
gcgagagatg aaaatatagc agttcgtcat gcttttgata tc                          42

<210> SEQ ID NO 451
<211> LENGTH: 14
<212> TYPE: PRT
<213> ORGANISM: Artificial Sequence
<220> FEATURE:

<223> OTHER INFORMATION: Synthetic

<400> SEQUENCE: 451

Ala Arg Asp Glu Asn Ile Ala Val Arg His Ala Phe Asp Ile
 1               5                  10

<210> SEQ ID NO 452
<211> LENGTH: 324
<212> TYPE: DNA
<213> ORGANISM: Artificial Sequence
<220> FEATURE:
<223> OTHER INFORMATION: Synthetic

<400> SEQUENCE: 452

```
gaaatagtgt tgacacagtc tccaggcgcc ctgtctttgt ctccaggaga aagagccacc      60
ctctcctgta gggccagtcg gactgttagc agcagctact tagcctggta ccaacagaaa     120
cctggccagg ctcccaggct cctcatctat ggtacatcca gccgggccac tggcatccca     180
gacaggttca gtggcagtgg gtctgggaca gacttcactc tcaccatcac cagactggag     240
cctgaagatt ttgcaatata ttactgtcag cagtctggtt actcacctct cactttcggc     300
ggagggacca aggtggaaat caaa                                            324
```

<210> SEQ ID NO 453
<211> LENGTH: 108
<212> TYPE: PRT
<213> ORGANISM: Artificial Sequence
<220> FEATURE:
<223> OTHER INFORMATION: Synthetic

<400> SEQUENCE: 453

Glu Ile Val Leu Thr Gln Ser Pro Gly Ala Leu Ser Leu Ser Pro Gly
 1               5                  10                  15

Glu Arg Ala Thr Leu Ser Cys Arg Ala Ser Arg Thr Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Thr Ser Ser Arg Ala Thr Gly Ile Pro Asp Arg Phe Ser
        50                  55                  60

Gly Ser Gly Ser Gly Thr Asp Phe Thr Leu Thr Ile Thr Arg Leu Glu
 65                  70                  75                  80

Pro Glu Asp Phe Ala Ile Tyr Tyr Cys Gln Gln Ser Gly Tyr Ser Pro
                85                  90                  95

Leu Thr Phe Gly Gly Gly Thr Lys Val Glu Ile Lys
            100                 105

<210> SEQ ID NO 454
<211> LENGTH: 21
<212> TYPE: DNA
<213> ORGANISM: Artificial Sequence
<220> FEATURE:
<223> OTHER INFORMATION: Synthetic

<400> SEQUENCE: 454
cggactgtta gcagcagcta c                                                21

<210> SEQ ID NO 455
<211> LENGTH: 7
<212> TYPE: PRT
<213> ORGANISM: Artificial Sequence
<220> FEATURE:
<223> OTHER INFORMATION: Synthetic

<400> SEQUENCE: 455

Arg Thr Val Ser Ser Ser Tyr
1               5

<210> SEQ ID NO 456
<211> LENGTH: 9
<212> TYPE: DNA
<213> ORGANISM: Artificial Sequence
<220> FEATURE:
<223> OTHER INFORMATION: Synthetic

<400> SEQUENCE: 456 ggtacatcc                                                                  9

<210> SEQ ID NO 457
<211> LENGTH: 3
<212> TYPE: PRT
<213> ORGANISM: Artificial Sequence
<220> FEATURE:
<223> OTHER INFORMATION: Synthetic

<400> SEQUENCE: 457

Gly Thr Ser
1

<210> SEQ ID NO 458
<211> LENGTH: 27
<212> TYPE: DNA
<213> ORGANISM: Artificial Sequence
<220> FEATURE:
<223> OTHER INFORMATION: Synthetic

<400> SEQUENCE: 458
cagcagtctg gttactcacc tctcact                                             27

<210> SEQ ID NO 459
<211> LENGTH: 9
<212> TYPE: PRT
<213> ORGANISM: Artificial Sequence
<220> FEATURE:
<223> OTHER INFORMATION: Synthetic

<400> SEQUENCE: 459

Gln Gln Ser Gly Tyr Ser Pro Leu Thr
1               5

<210> SEQ ID NO 460
<211> LENGTH: 357
<212> TYPE: DNA
<213> ORGANISM: Artificial Sequence
<220> FEATURE:
<223> OTHER INFORMATION: Synthetic

<400> SEQUENCE: 460
caggtgcagc tgcaggagtc gggcccagga ctggtgaagc cttcacagac cctgtccctc         60
acctgcactg tctctgatga ctccatcaac aatgttgaat cctactggac ctggatccgc        120
caacacccag ggaagggcct ggagtggatt ggatacatca atacactggg ggcatccac         180 tataaccgt ccctcaagag tcgactcgcc atatcagtgg acacgtcaaa gaaccagttc         240
tccctgaaaa tgaactctgt gactgccgcg gacacggcca atattactg tgcgagagca         300 cgtggaagtc atactttga tgtctggggc caggggacaa cggtcaccgt ctcctca            357

<210> SEQ ID NO 461
<211> LENGTH: 119
<212> TYPE: PRT
<213> ORGANISM: Artificial Sequence
<220> FEATURE:
<223> OTHER INFORMATION: Synthetic

<400> SEQUENCE: 461

```
Gln Val Gln Leu Gln Glu Ser Gly Pro Gly Leu Val Lys Pro Ser Gln
 1               5                  10                  15

Thr Leu Ser Leu Thr Cys Thr Val Ser Asp Asp Ser Ile Asn Asn Val
            20                  25                  30

Glu Ser Tyr Trp Thr Trp Ile Arg Gln His Pro Gly Lys Gly Leu Glu
        35                  40                  45

Trp Ile Gly Tyr Ile Lys Tyr Thr Gly Gly Ile His Tyr Asn Pro Ser
 50                  55                  60

Leu Lys Ser Arg Leu Ala Ile Ser Val Asp Thr Ser Lys Asn Gln Phe
 65                  70                  75                  80

Ser Leu Lys Met Asn Ser Val Thr Ala Ala Asp Thr Ala Lys Tyr Tyr
                85                  90                  95

Cys Ala Arg Ala Arg Gly Ser His Thr Phe Asp Val Trp Gly Gln Gly
            100                 105                 110

Thr Thr Val Thr Val Ser Ser
        115
```

<210> SEQ ID NO 462
<211> LENGTH: 30
<212> TYPE: DNA
<213> ORGANISM: Artificial Sequence
<220> FEATURE:
<223> OTHER INFORMATION: Synthetic

<400> SEQUENCE: 462
gatgactcca tcaacaatgt tgaatcctac                                    30

<210> SEQ ID NO 463
<211> LENGTH: 10
<212> TYPE: PRT
<213> ORGANISM: Artificial Sequence
<220> FEATURE:
<223> OTHER INFORMATION: Synthetic

<400> SEQUENCE: 463

```
Asp Asp Ser Ile Asn Asn Val Glu Ser Tyr
 1               5                  10
```

<210> SEQ ID NO 464
<211> LENGTH: 21
<212> TYPE: DNA
<213> ORGANISM: Artificial Sequence
<220> FEATURE:
<223> OTHER INFORMATION: Synthetic

<400> SEQUENCE: 464
atcaaataca ctgggggcat c                                             21

<210> SEQ ID NO 465
<211> LENGTH: 7
<212> TYPE: PRT
<213> ORGANISM: Artificial Sequence
<220> FEATURE:
<223> OTHER INFORMATION: Synthetic

<400> SEQUENCE: 465

```
Ile Lys Tyr Thr Gly Gly Ile
 1               5
```

<210> SEQ ID NO 466
<211> LENGTH: 33
<212> TYPE: DNA
<213> ORGANISM: Artificial Sequence
<220> FEATURE:
<223> OTHER INFORMATION: Synthetic

<400> SEQUENCE: 466
gcgagagcac gtggaagtca tactttgat gtc                           33

<210> SEQ ID NO 467
<211> LENGTH: 11
<212> TYPE: PRT
<213> ORGANISM: Artificial Sequence
<220> FEATURE:
<223> OTHER INFORMATION: Synthetic

<400> SEQUENCE: 467

```
Ala Arg Ala Arg Gly Ser His Thr Phe Asp Val
 1               5                  10
```

<210> SEQ ID NO 468
<211> LENGTH: 324
<212> TYPE: DNA
<213> ORGANISM: Artificial Sequence
<220> FEATURE:
<223> OTHER INFORMATION: Synthetic

<400> SEQUENCE: 468
gccatccggt tgacccagtc tccaggcacc ctgtcttggt ctccagggga aagagccacc     60
ctctcctgca gggccagtca gagtgttagc agtaactact tagcctggta ccagcagaaa    120
cctggccagg ctccccgact cctcatttat ggtgcatcca gcagggtcgc tggcatccca    180
gacaggttca gtggcagtgg gtctgggaca gacttcactc tcaccatcag cagactggag    240
cctgaagatt ttgcactgta ttattgtcag caatatagta ggtcaccgat caccttcggc    300
caagggacca agctggagat caaa                                          324

<210> SEQ ID NO 469
<211> LENGTH: 108
<212> TYPE: PRT
<213> ORGANISM: Artificial Sequence
<220> FEATURE:
<223> OTHER INFORMATION: Synthetic

<400> SEQUENCE: 469

```
Ala Ile Arg Leu Thr Gln Ser Pro Gly Thr Leu Ser Trp Ser Pro Gly
 1               5                  10                  15

Glu Arg Ala Thr Leu Ser Cys Arg Ala Ser Gln Ser Val Ser Ser Asn
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Val Ala Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Leu Tyr Tyr Cys Gln Gln Tyr Ser Arg Ser Pro
                 85                  90                  95
```

```
Ile Thr Phe Gly Gln Gly Thr Lys Leu Glu Ile Lys
        100                 105
```

<210> SEQ ID NO 470
<211> LENGTH: 21
<212> TYPE: DNA
<213> ORGANISM: Artificial Sequence
<220> FEATURE:
<223> OTHER INFORMATION: Synthetic

<400> SEQUENCE: 470
cagagtgtta gcagtaacta c       21

<210> SEQ ID NO 471
<211> LENGTH: 7
<212> TYPE: PRT
<213> ORGANISM: Artificial Sequence
<220> FEATURE:
<223> OTHER INFORMATION: Synthetic

<400> SEQUENCE: 471

```
Gln Ser Val Ser Ser Asn Tyr
1               5
```

<210> SEQ ID NO 472
<211> LENGTH: 9
<212> TYPE: DNA
<213> ORGANISM: Artificial Sequence
<220> FEATURE:
<223> OTHER INFORMATION: Synthetic

<400> SEQUENCE: 472 ggtgcatcc       9

<210> SEQ ID NO 473
<211> LENGTH: 3
<212> TYPE: PRT
<213> ORGANISM: Artificial Sequence
<220> FEATURE:
<223> OTHER INFORMATION: Synthetic

<400> SEQUENCE: 473

```
Gly Ala Ser
1
```

<210> SEQ ID NO 474
<211> LENGTH: 27
<212> TYPE: DNA
<213> ORGANISM: Artificial Sequence
<220> FEATURE:
<223> OTHER INFORMATION: Synthetic

<400> SEQUENCE: 474
cagcaatata gtaggtcacc gatcacc       27

<210> SEQ ID NO 475
<211> LENGTH: 9
<212> TYPE: PRT
<213> ORGANISM: Artificial Sequence
<220> FEATURE:
<223> OTHER INFORMATION: Synthetic

<400> SEQUENCE: 475

```
Gln Gln Tyr Ser Arg Ser Pro Ile Thr
1               5
```

<210> SEQ ID NO 476
<211> LENGTH: 357
<212> TYPE: DNA
<213> ORGANISM: Artificial Sequence
<220> FEATURE:
<223> OTHER INFORMATION: Synthetic

<400> SEQUENCE: 476

```
caggtgcagc tgcaggagtc gggcccagga ctggtgaagc cttcacagac cctgtccctc      60
acctgcactg tctctggtgg ctccatcaac agtgttactt actactggac ctggatccgc     120
cagcacccag ggaggggcct agagtggatt gggtacatca aattcagtgg gagcacctac     180
tacaacccgt ccctcaaggg tcgagtcacc atatcagtgg acacgtctaa gaaccaattc     240
tcccttaaaa ttaactctgt gactgccgcg gacacggccg tgtttactg tgcgagagct      300
tctggaagtc atactttga tatctggggc caagggacaa tggtcaccgt ctcctca         357
```

<210> SEQ ID NO 477
<211> LENGTH: 119
<212> TYPE: PRT
<213> ORGANISM: Artificial Sequence
<220> FEATURE:
<223> OTHER INFORMATION: Synthetic

<400> SEQUENCE: 477

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Asn Ser Val
             20                  25                  30

Thr Tyr Tyr Trp Thr Trp Ile Arg Gln His Pro Gly Arg Gly Leu Glu
         35                  40                  45

Trp Ile Gly Tyr Ile Lys Phe Ser Gly Ser Thr Tyr Tyr Asn Pro Ser
     50                  55                  60

Leu Lys Gly Arg Val Thr Ile Ser Val Asp Thr Ser Lys Asn Gln Phe
 65                  70                  75                  80

Ser Leu Lys Ile Asn Ser Val Thr Ala Ala Asp Thr Ala Val Phe Tyr
                 85                  90                  95

Cys Ala Arg Ala Ser Gly Ser His Thr Phe Asp Ile Trp Gly Gln Gly
            100                 105                 110

Thr Met Val Thr Val Ser Ser
        115
```

<210> SEQ ID NO 478
<211> LENGTH: 30
<212> TYPE: DNA
<213> ORGANISM: Artificial Sequence
<220> FEATURE:
<223> OTHER INFORMATION: Synthetic

<400> SEQUENCE: 478

```
ggtggctcca tcaacagtgt tacttactac                                        30
```

<210> SEQ ID NO 479
<211> LENGTH: 10
<212> TYPE: PRT
<213> ORGANISM: Artificial Sequence
<220> FEATURE:
<223> OTHER INFORMATION: Synthetic

<400> SEQUENCE: 479

```
Gly Gly Ser Ile Asn Ser Val Thr Tyr Tyr
  1               5                  10
```

<210> SEQ ID NO 480
<211> LENGTH: 21
<212> TYPE: DNA
<213> ORGANISM: Artificial Sequence
<220> FEATURE:
<223> OTHER INFORMATION: Synthetic

<400> SEQUENCE: 480
atcaaattca gtgggagcac c                                         21

<210> SEQ ID NO 481
<211> LENGTH: 7
<212> TYPE: PRT
<213> ORGANISM: Artificial Sequence
<220> FEATURE:
<223> OTHER INFORMATION: Synthetic

<400> SEQUENCE: 481

Ile Lys Phe Ser Gly Ser Thr
1               5

<210> SEQ ID NO 482
<211> LENGTH: 33
<212> TYPE: DNA
<213> ORGANISM: Artificial Sequence
<220> FEATURE:
<223> OTHER INFORMATION: Synthetic

<400> SEQUENCE: 482
gcgagagctt ctggaagtca tacttttgat atc                             33

<210> SEQ ID NO 483
<211> LENGTH: 11
<212> TYPE: PRT
<213> ORGANISM: Artificial Sequence
<220> FEATURE:
<223> OTHER INFORMATION: Synthetic

<400> SEQUENCE: 483

Ala Arg Ala Ser Gly Ser His Thr Phe Asp Ile
1               5                   10

<210> SEQ ID NO 484
<211> LENGTH: 321
<212> TYPE: DNA
<213> ORGANISM: Artificial Sequence
<220> FEATURE:
<223> OTHER INFORMATION: Synthetic

<400> SEQUENCE: 484
gccatccgga tgacccagtc tccagccacc ctgtctttgt ctccagggga aagagccacc    60
ctctcctgct gggccagtca gagtattagc ggctattttg cctggtatca acagaaacct   120
ggccaggctc ccaggctcct catctatgat acatcctaca gggccactga cgtcccagcc   180
aggttcagtg gcagtgggtc tgggacagac ttcactctca ccatcaacaa cctagagcct   240
gaagattttg cagtttatta ctgtcagcag cgtagcgact ggccgctcag cttcggcgga   300
gggaccaaac tggagatcaa a                                            321

<210> SEQ ID NO 485
<211> LENGTH: 107
<212> TYPE: PRT
<213> ORGANISM: Artificial Sequence
<220> FEATURE:

<223> OTHER INFORMATION: Synthetic

<400> SEQUENCE: 485

```
Ala Ile Arg Met Thr Gln Ser Pro Ala Thr Leu Ser Leu Ser Pro Gly
 1               5                  10                  15
Glu Arg Ala Thr Leu Ser Cys Trp Ala Ser Gln Ser Ile Ser Gly Tyr
            20                  25                  30
Phe Ala Trp Tyr Gln Gln Lys Pro Gly Gln Ala Pro Arg Leu Leu Ile
        35                  40                  45
Tyr Asp Thr Ser Tyr Arg Ala Thr Asp Val Pro Ala Arg Phe Ser Gly
 50                  55                  60
Ser Gly Ser Gly Thr Asp Phe Thr Leu Thr Ile Asn Asn Leu Glu Pro
 65                  70                  75                  80
Glu Asp Phe Ala Val Tyr Tyr Cys Gln Gln Arg Ser Asp Trp Pro Leu
                85                  90                  95
Ser Phe Gly Gly Gly Thr Lys Leu Glu Ile Lys
            100                 105
```

<210> SEQ ID NO 486
<211> LENGTH: 18
<212> TYPE: DNA
<213> ORGANISM: Artificial Sequence
<220> FEATURE:
<223> OTHER INFORMATION: Synthetic

<400> SEQUENCE: 486
cagagtatta gcggctat        18

<210> SEQ ID NO 487
<211> LENGTH: 6
<212> TYPE: PRT
<213> ORGANISM: Artificial Sequence
<220> FEATURE:
<223> OTHER INFORMATION: Synthetic

<400> SEQUENCE: 487

```
Gln Ser Ile Ser Gly Tyr
 1               5
```

<210> SEQ ID NO 488
<211> LENGTH: 9
<212> TYPE: DNA
<213> ORGANISM: Artificial Sequence
<220> FEATURE:
<223> OTHER INFORMATION: Synthetic

<400> SEQUENCE: 488 gatacatcc        9

<210> SEQ ID NO 489
<211> LENGTH: 3
<212> TYPE: PRT
<213> ORGANISM: Artificial Sequence
<220> FEATURE:
<223> OTHER INFORMATION: Synthetic

<400> SEQUENCE: 489

```
Asp Thr Ser
 1
```

<210> SEQ ID NO 490
<211> LENGTH: 27
<212> TYPE: DNA

<213> ORGANISM: Artificial Sequence
<220> FEATURE:
<223> OTHER INFORMATION: Synthetic

<400> SEQUENCE: 490

```
cagcagcgta gcgactggcc gctcagc                                          27
```

<210> SEQ ID NO 491
<211> LENGTH: 9
<212> TYPE: PRT
<213> ORGANISM: Artificial Sequence
<220> FEATURE:
<223> OTHER INFORMATION: Synthetic

<400> SEQUENCE: 491

Gln Gln Arg Ser Asp Trp Pro Leu Ser
 1               5

<210> SEQ ID NO 492
<211> LENGTH: 357
<212> TYPE: DNA
<213> ORGANISM: Artificial Sequence
<220> FEATURE:
<223> OTHER INFORMATION: Synthetic

<400> SEQUENCE: 492

```
caggtgcagc tgcaggagtc gggcccagga ctggtgaagc cttcacagac cctgtccctc      60
acctgcactg tctctggtgg ctccatcaac agtgttactt actactggac ctggatccgc     120
cagcacccag ggaggggcct agagtggatt gggtacatca aattcagtgg agcacctac      180
tacaacccgt ccctcaaggg tcgagtcacc atatcagtgg acacgtctaa gaaccaattc     240
tcccttaaaa ttaactctgt gactgccgcg gacacggccg tgttttactg tgcgagagct     300
tctggaagtc atactttga tatctggggc caagggacaa tggtcaccgt ctcctca         357
```

<210> SEQ ID NO 493
<211> LENGTH: 119
<212> TYPE: PRT
<213> ORGANISM: Artificial Sequence
<220> FEATURE:
<223> OTHER INFORMATION: Synthetic

<400> SEQUENCE: 493

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Asn Ser Val
            20                  25                  30

Thr Tyr Tyr Trp Thr Trp Ile Arg Gln His Pro Gly Arg Gly Leu Glu
        35                  40                  45

Trp Ile Gly Tyr Ile Lys Phe Ser Gly Ser Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Ile Asn Ser Val Thr Ala Ala Asp Thr Ala Val Phe Tyr
                85                  90                  95

Cys Ala Arg Ala Ser Gly Ser His Thr Phe Asp Ile Trp Gly Gln Gly
            100                 105                 110

Thr Met Val Thr Val Ser Ser
        115

<210> SEQ ID NO 494

```
<211> LENGTH: 30
<212> TYPE: DNA
<213> ORGANISM: Artificial Sequence
<220> FEATURE:
<223> OTHER INFORMATION: Synthetic

<400> SEQUENCE: 494
ggtggctcca tcaacagtgt tacttactac                                            30

<210> SEQ ID NO 495
<211> LENGTH: 10
<212> TYPE: PRT
<213> ORGANISM: Artificial Sequence
<220> FEATURE:
<223> OTHER INFORMATION: Synthetic

<400> SEQUENCE: 495

Gly Gly Ser Ile Asn Ser Val Thr Tyr Tyr
 1               5                  10

<210> SEQ ID NO 496
<211> LENGTH: 21
<212> TYPE: DNA
<213> ORGANISM: Artificial Sequence
<220> FEATURE:
<223> OTHER INFORMATION: Synthetic

<400> SEQUENCE: 496
atcaaattca gtgggagcac c                                                     21

<210> SEQ ID NO 497
<211> LENGTH: 7
<212> TYPE: PRT
<213> ORGANISM: Artificial Sequence
<220> FEATURE:
<223> OTHER INFORMATION: Synthetic

<400> SEQUENCE: 497

Ile Lys Phe Ser Gly Ser Thr
 1               5

<210> SEQ ID NO 498
<211> LENGTH: 33
<212> TYPE: DNA
<213> ORGANISM: Artificial Sequence
<220> FEATURE:
<223> OTHER INFORMATION: Synthetic

<400> SEQUENCE: 498
gcgagagctt ctggaagtca tactttttgat atc                                       33

<210> SEQ ID NO 499
<211> LENGTH: 11
<212> TYPE: PRT
<213> ORGANISM: Artificial Sequence
<220> FEATURE:
<223> OTHER INFORMATION: Synthetic

<400> SEQUENCE: 499

Ala Arg Ala Ser Gly Ser His Thr Phe Asp Ile
 1               5                  10

<210> SEQ ID NO 500
<211> LENGTH: 324
<212> TYPE: DNA
<213> ORGANISM: Artificial Sequence
<220> FEATURE:
```

-continued

<223> OTHER INFORMATION: Synthetic

<400> SEQUENCE: 500

```
gatattgtga tgacccagtc tccaggcacc ctgtctttgt ctccagggga aagagccacc    60
ctctcctgca gggccagtca gagtgttagc aacagctact tagcctggta ccagcagaaa   120
cctggccagg ctcccaggct cctcatctct ggtgcgtcca gcagggtcac tggcatccca   180
gacaggttca gtggcagtgg gtctgggaca gacttcactc tcaccatcag cagactggag   240
cctgaagatt ttggaatgta ttactgtcag cagtatagta ggtcaccgat caccttcggc   300
caagggacca aggtggaaat caaa                                          324
```

<210> SEQ ID NO 501
<211> LENGTH: 108
<212> TYPE: PRT
<213> ORGANISM: Artificial Sequence
<220> FEATURE:
<223> OTHER INFORMATION: Synthetic

<400> SEQUENCE: 501

Asp Ile Val Met Thr Gln Ser Pro Gly Thr Leu Ser Leu Ser Pro Gly
1               5                   10                  15
Glu Arg Ala Thr Leu Ser Cys Arg Ala Ser Gln Ser Val Ser Asn Ser
            20                  25                  30
Tyr Leu Ala Trp Tyr Gln Gln Lys Pro Gly Gln Ala Pro Arg Leu Leu
        35                  40                  45
Ile Ser Gly Ala Ser Ser Arg Val Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Gly Met Tyr Tyr Cys Gln Gln Tyr Ser Arg Ser Pro
                85                  90                  95
Ile Thr Phe Gly Gln Gly Thr Lys Val Glu Ile Lys
            100                 105

<210> SEQ ID NO 502
<211> LENGTH: 21
<212> TYPE: DNA
<213> ORGANISM: Artificial Sequence
<220> FEATURE:
<223> OTHER INFORMATION: Synthetic

<400> SEQUENCE: 502
cagagtgtta gcaacagcta c                                              21

<210> SEQ ID NO 503
<211> LENGTH: 7
<212> TYPE: PRT
<213> ORGANISM: Artificial Sequence
<220> FEATURE:
<223> OTHER INFORMATION: Synthetic

<400> SEQUENCE: 503

Gln Ser Val Ser Asn Ser Tyr
1               5

<210> SEQ ID NO 504
<211> LENGTH: 9
<212> TYPE: DNA
<213> ORGANISM: Artificial Sequence
<220> FEATURE:
<223> OTHER INFORMATION: Synthetic -continued

<400> SEQUENCE: 504 ggtgcgtcc						9

<210> SEQ ID NO 505
<211> LENGTH: 3
<212> TYPE: PRT
<213> ORGANISM: Artificial Sequence
<220> FEATURE:
<223> OTHER INFORMATION: Synthetic

<400> SEQUENCE: 505

Gly Ala Ser
 1

<210> SEQ ID NO 506
<211> LENGTH: 27
<212> TYPE: DNA
<213> ORGANISM: Artificial Sequence
<220> FEATURE:
<223> OTHER INFORMATION: Synthetic

<400> SEQUENCE: 506
cagcagtata gtaggtcacc gatcacc						27

<210> SEQ ID NO 507
<211> LENGTH: 9
<212> TYPE: PRT
<213> ORGANISM: Artificial Sequence
<220> FEATURE:
<223> OTHER INFORMATION: Synthetic

<400> SEQUENCE: 507

Gln Gln Tyr Ser Arg Ser Pro Ile Thr
 1               5

<210> SEQ ID NO 508
<211> LENGTH: 357
<212> TYPE: DNA
<213> ORGANISM: Artificial Sequence
<220> FEATURE:
<223> OTHER INFORMATION: Synthetic

<400> SEQUENCE: 508
gaggtgcagc tggtgcagtc tggagctgag gtgaagaagc ctggggcctc agtgaaggtc		60
tcctgcaagg cttctggtta ctcctttacc agctttggtt tcagctgggt gcgacaggcc		120
cctggacaag gacttgagtg gctgggatgg atcagcgctt acagtggtga cacagactat		180
gcacagaagt tccagggcag agtcaccctg accactgaca catccacgac cactgcctac		240
atggagctga ggagcctgag atctgacgac acggccgtct attactgtgc gcgatataac		300
tggaacctcc actggttcga ccccctgggg cagggaaccc tggtcaccgt ctcctca		357

<210> SEQ ID NO 509
<211> LENGTH: 119
<212> TYPE: PRT
<213> ORGANISM: Artificial Sequence
<220> FEATURE:
<223> OTHER INFORMATION: Synthetic

<400> SEQUENCE: 509

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Phe

```
                    20                  25                  30

Gly Phe Ser Trp Val Arg Gln Ala Pro Gly Gln Gly Leu Glu Trp Leu
            35                  40                  45

Gly Trp Ile Ser Ala Tyr Ser Gly Asp Thr Asp Tyr Ala Gln Lys Phe
        50                  55                  60

Gln Gly Arg Val Thr Leu Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Asn Trp Asn Leu His Trp Phe Asp Pro Trp Gly Gln Gly
            100                 105                 110

Thr Leu Val Thr Val Ser Ser
        115
```

<210> SEQ ID NO 510
<211> LENGTH: 24
<212> TYPE: DNA
<213> ORGANISM: Artificial Sequence
<220> FEATURE:
<223> OTHER INFORMATION: Synthetic

<400> SEQUENCE: 510
ggttactcct ttaccagctt tggt                                      24

<210> SEQ ID NO 511
<211> LENGTH: 8
<212> TYPE: PRT
<213> ORGANISM: Artificial Sequence
<220> FEATURE:
<223> OTHER INFORMATION: Synthetic

<400> SEQUENCE: 511

Gly Tyr Ser Phe Thr Ser Phe Gly
1               5

<210> SEQ ID NO 512
<211> LENGTH: 24
<212> TYPE: DNA
<213> ORGANISM: Artificial Sequence
<220> FEATURE:
<223> OTHER INFORMATION: Synthetic

<400> SEQUENCE: 512
atcagcgctt acagtggtga caca                                      24

<210> SEQ ID NO 513
<211> LENGTH: 8
<212> TYPE: PRT
<213> ORGANISM: Artificial Sequence
<220> FEATURE:
<223> OTHER INFORMATION: Synthetic

<400> SEQUENCE: 513

Ile Ser Ala Tyr Ser Gly Asp Thr
1               5

<210> SEQ ID NO 514
<211> LENGTH: 36
<212> TYPE: DNA
<213> ORGANISM: Artificial Sequence
<220> FEATURE:
<223> OTHER INFORMATION: Synthetic

<400> SEQUENCE: 514

```
gcgcgatata actggaacct ccactggttc gacccc                                    36
```

<210> SEQ ID NO 515
<211> LENGTH: 12
<212> TYPE: PRT
<213> ORGANISM: Artificial Sequence
<220> FEATURE:
<223> OTHER INFORMATION: Synthetic

<400> SEQUENCE: 515

```
Ala Arg Tyr Asn Trp Asn Leu His Trp Phe Asp Pro
 1               5                  10
```

<210> SEQ ID NO 516
<211> LENGTH: 324
<212> TYPE: DNA
<213> ORGANISM: Artificial Sequence
<220> FEATURE:
<223> OTHER INFORMATION: Synthetic

<400> SEQUENCE: 516

```
gacatccgga tgacccagtc tccaggcatc ctgtctttgt ctccagggga aagagccacc    60
ctctcctgca gggccagtca gaatattaaa agcaactact tagcctggta ccagcagaaa   120
cctggccagg ctcccaggct cctcatcttt ggtacatcca acagggccac tgccatttca   180
gacaggttca gtggcagtgg gtctgggaca gacttccttt tcaccatcag cagactggag   240
cctgaagatt ttgcagtgta ttactgtcag cagtatggta actcaccgtg gacgttcggc   300
caagggacca agtggatat caaa                                            324
```

<210> SEQ ID NO 517
<211> LENGTH: 108
<212> TYPE: PRT
<213> ORGANISM: Artificial Sequence
<220> FEATURE:
<223> OTHER INFORMATION: Synthetic

<400> SEQUENCE: 517

```
Asp Ile Arg Met Thr Gln Ser Pro Gly Ile Leu Ser Leu Ser Pro Gly
 1               5                  10                  15
Glu Arg Ala Thr Leu Ser Cys Arg Ala Ser Gln Asn Ile Lys Ser Asn
             20                  25                  30
Tyr Leu Ala Trp Tyr Gln Gln Lys Pro Gly Gln Ala Pro Arg Leu Leu
         35                  40                  45
Ile Phe Gly Thr Ser Asn Arg Ala Thr Ala Ile Ser Asp Arg Phe Ser
     50                  55                  60
Gly Ser Gly Ser Gly Thr Asp Phe Leu Phe Thr Ile Ser Arg Leu Glu
 65                  70                  75                  80
Pro Glu Asp Phe Ala Val Tyr Tyr Cys Gln Gln Tyr Gly Asn Ser Pro
             85                  90                  95
Trp Thr Phe Gly Gln Gly Thr Lys Val Asp Ile Lys
            100                 105
```

<210> SEQ ID NO 518
<211> LENGTH: 21
<212> TYPE: DNA
<213> ORGANISM: Artificial Sequence
<220> FEATURE:
<223> OTHER INFORMATION: Synthetic

<400> SEQUENCE: 518

```
cagaatatta aaagcaacta c                                              21
```

<210> SEQ ID NO 519
<211> LENGTH: 7
<212> TYPE: PRT
<213> ORGANISM: Artificial Sequence
<220> FEATURE:
<223> OTHER INFORMATION: Synthetic

<400> SEQUENCE: 519

Gln Asn Ile Lys Ser Asn Tyr
 1               5

<210> SEQ ID NO 520
<211> LENGTH: 9
<212> TYPE: DNA
<213> ORGANISM: Artificial Sequence
<220> FEATURE:
<223> OTHER INFORMATION: Synthetic

<400> SEQUENCE: 520

```
ggtacatcc                                                             9
```

<210> SEQ ID NO 521
<211> LENGTH: 3
<212> TYPE: PRT
<213> ORGANISM: Artificial Sequence
<220> FEATURE:
<223> OTHER INFORMATION: Synthetic

<400> SEQUENCE: 521

Gly Thr Ser
 1

<210> SEQ ID NO 522
<211> LENGTH: 27
<212> TYPE: DNA
<213> ORGANISM: Artificial Sequence
<220> FEATURE:
<223> OTHER INFORMATION: Synthetic

<400> SEQUENCE: 522

```
cagcagtatg gtaactcacc gtggacg                                        27
```

<210> SEQ ID NO 523
<211> LENGTH: 9
<212> TYPE: PRT
<213> ORGANISM: Artificial Sequence
<220> FEATURE:
<223> OTHER INFORMATION: Synthetic

<400> SEQUENCE: 523

Gln Gln Tyr Gly Asn Ser Pro Trp Thr
 1               5

<210> SEQ ID NO 524
<211> LENGTH: 357
<212> TYPE: DNA
<213> ORGANISM: Artificial Sequence
<220> FEATURE:
<223> OTHER INFORMATION: Synthetic

<400> SEQUENCE: 524

```
caggtgcagc tgcaggagtc gggcccagga ctggtgaagc cttcacagac cctgtccctc    60
acctgcactg tctctgatgg ctccatcaac agtgttgaat cctactggac ctggatccgc   120
```

```
cagcacccag ggaagggcct ggagtggatt ggatacatca aatacactgg gggcatccac    180
tataacccgt ccctcaagag tcgacttgcc atatcagtgg acacgtcaaa gaaccagttc    240
tccctgaaaa tgagctctgt gactgccgcg gacacggccg tgtattactg tgcgagagca    300
cgtggaagtc atactttgga tgtctggggc caggggacaa tggtcaccgt ctcttca       357
```

<210> SEQ ID NO 525
<211> LENGTH: 119
<212> TYPE: PRT
<213> ORGANISM: Artificial Sequence
<220> FEATURE:
<223> OTHER INFORMATION: Synthetic

<400> SEQUENCE: 525

```
Gln Val Gln Leu Gln Glu Ser Gly Pro Gly Leu Val Lys Pro Ser Gln
  1               5                  10                  15

Thr Leu Ser Leu Thr Cys Thr Val Ser Asp Gly Ser Ile Asn Ser Val
             20                  25                  30

Glu Ser Tyr Trp Thr Trp Ile Arg Gln His Pro Gly Lys Gly Leu Glu
         35                  40                  45

Trp Ile Gly Tyr Ile Lys Tyr Thr Gly Gly Ile His Tyr Asn Pro Ser
 50                  55                  60

Leu Lys Ser Arg Leu Ala Ile Ser Val Asp Thr Ser Lys Asn Gln Phe
 65                  70                  75                  80

Ser Leu Lys Met Ser Ser Val Thr Ala Ala Asp Thr Ala Val Tyr Tyr
             85                  90                  95

Cys Ala Arg Ala Arg Gly Ser His Thr Phe Asp Val Trp Gly Gln Gly
            100                 105                 110

Thr Met Val Thr Val Ser Ser
            115
```

<210> SEQ ID NO 526
<211> LENGTH: 30
<212> TYPE: DNA
<213> ORGANISM: Artificial Sequence
<220> FEATURE:
<223> OTHER INFORMATION: Synthetic

<400> SEQUENCE: 526

```
gatggctcca tcaacagtgt tgaatcctac                                      30
```

<210> SEQ ID NO 527
<211> LENGTH: 10
<212> TYPE: PRT
<213> ORGANISM: Artificial Sequence
<220> FEATURE:
<223> OTHER INFORMATION: Synthetic

<400> SEQUENCE: 527

```
Asp Gly Ser Ile Asn Ser Val Glu Ser Tyr
  1               5                  10
```

<210> SEQ ID NO 528
<211> LENGTH: 21
<212> TYPE: DNA
<213> ORGANISM: Artificial Sequence
<220> FEATURE:
<223> OTHER INFORMATION: Synthetic

<400> SEQUENCE: 528

```
atcaaataca ctgggggcat c                                               21
```

<210> SEQ ID NO 529
<211> LENGTH: 7
<212> TYPE: PRT
<213> ORGANISM: Artificial Sequence
<220> FEATURE:
<223> OTHER INFORMATION: Synthetic

<400> SEQUENCE: 529

Ile Lys Tyr Thr Gly Gly Ile
1               5

<210> SEQ ID NO 530
<211> LENGTH: 33
<212> TYPE: DNA
<213> ORGANISM: Artificial Sequence
<220> FEATURE:
<223> OTHER INFORMATION: Synthetic

<400> SEQUENCE: 530
gcgagagcac gtggaagtca tacttttgat gtc                              33

<210> SEQ ID NO 531
<211> LENGTH: 11
<212> TYPE: PRT
<213> ORGANISM: Artificial Sequence
<220> FEATURE:
<223> OTHER INFORMATION: Synthetic

<400> SEQUENCE: 531

Ala Arg Ala Arg Gly Ser His Thr Phe Asp Val
1               5                   10

<210> SEQ ID NO 532
<211> LENGTH: 324
<212> TYPE: DNA
<213> ORGANISM: Artificial Sequence
<220> FEATURE:
<223> OTHER INFORMATION: Synthetic

<400> SEQUENCE: 532
gaaattgtgc tgactcagtc tccaggcacc ctgtcttggt ctccagggga aagagccacc    60
ctctcctgca gggccagtca gagtattagc agtaactact tagcctggta ccagcagaaa   120
cctggccagg ctcccagact cctcatttat ggtgcatcca gcagggtcac tggcatccca   180
gacaggttca gtggcagtgg gtctgggaca gacttcactc tcaccatcag cagactggag   240
cctgaagatt ttgcactgta ttattgtcag cagtatagta ggtcaccgat caccttcggc   300
caagggacca agtggatat caaa                                            324

<210> SEQ ID NO 533
<211> LENGTH: 108
<212> TYPE: PRT
<213> ORGANISM: Artificial Sequence
<220> FEATURE:
<223> OTHER INFORMATION: Synthetic

<400> SEQUENCE: 533

Glu Ile Val Leu Thr Gln Ser Pro Gly Thr Leu Ser Trp Ser Pro Gly
1               5                   10                  15

Glu Arg Ala Thr Leu Ser Cys Arg Ala Ser Gln Ser Ile Ser Ser Asn
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Val Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Tyr Ser Arg Ser Pro
                85                  90                  95

Ile Thr Phe Gly Gln Gly Thr Lys Val Asp Ile Lys
            100                 105
```

<210> SEQ ID NO 534
<211> LENGTH: 21
<212> TYPE: DNA
<213> ORGANISM: Artificial Sequence
<220> FEATURE:
<223> OTHER INFORMATION: Synthetic

<400> SEQUENCE: 534
cagagtatta gcagtaacta c                                    21

<210> SEQ ID NO 535
<211> LENGTH: 7
<212> TYPE: PRT
<213> ORGANISM: Artificial Sequence
<220> FEATURE:
<223> OTHER INFORMATION: Synthetic

<400> SEQUENCE: 535

```
Gln Ser Ile Ser Ser Asn Tyr
 1               5
```

<210> SEQ ID NO 536
<211> LENGTH: 9
<212> TYPE: DNA
<213> ORGANISM: Artificial Sequence
<220> FEATURE:
<223> OTHER INFORMATION: Synthetic

<400> SEQUENCE: 536 ggtgcatcc                                                   9

<210> SEQ ID NO 537
<211> LENGTH: 3
<212> TYPE: PRT
<213> ORGANISM: Artificial Sequence
<220> FEATURE:
<223> OTHER INFORMATION: Synthetic

<400> SEQUENCE: 537

```
Gly Ala Ser
 1
```

<210> SEQ ID NO 538
<211> LENGTH: 27
<212> TYPE: DNA
<213> ORGANISM: Artificial Sequence
<220> FEATURE:
<223> OTHER INFORMATION: Synthetic

<400> SEQUENCE: 538
cagcagtata gtaggtcacc gatcacc                               27

<210> SEQ ID NO 539
<211> LENGTH: 9
<212> TYPE: PRT
<213> ORGANISM: Artificial Sequence -continued

```
<220> FEATURE:
<223> OTHER INFORMATION: Synthetic

<400> SEQUENCE: 539

Gln Gln Tyr Ser Arg Ser Pro Ile Thr
 1               5

<210> SEQ ID NO 540
<211> LENGTH: 360
<212> TYPE: DNA
<213> ORGANISM: Artificial Sequence
<220> FEATURE:
<223> OTHER INFORMATION: Synthetic

<400> SEQUENCE: 540
caggtgcagc tgcaggagtc gggcccagga ctggtgaagc cttcacagac cctgtccctc      60
acctgcactg tctctggtgg ctccgtcagc agtggtaatt actactggag ctggatccgc     120
cagcacccag ggaagggcct ggagtggttt gggtacatca aaaacagtgg ggcacctac     180 tacaacccgt ccctcaagag tcgaattacc atatcagtag acacgtctaa gaaccacttc     240
tccctgaggc tgagctctat gacggccgcg gacacggccg tgtattactg tgcgagagct     300
ggttcgggga gtcactactt tgactactgg ggccaggaa ccctggtcac cgtctcctca     360

<210> SEQ ID NO 541
<211> LENGTH: 120
<212> TYPE: PRT
<213> ORGANISM: Artificial Sequence
<220> FEATURE:
<223> OTHER INFORMATION: Synthetic

<400> SEQUENCE: 541

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Val Ser Ser Gly
            20                  25                  30

Asn Tyr Tyr Trp Ser Trp Ile Arg Gln His Pro Gly Lys Gly Leu Glu
        35                  40                  45

Trp Phe Gly Tyr Ile Lys Asn Ser Gly Gly Thr Tyr Tyr Asn Pro Ser
    50                  55                  60

Leu Lys Ser Arg Ile Thr Ile Ser Val Asp Thr Ser Lys Asn His Phe
65                  70                  75                  80

Ser Leu Arg Leu Ser Ser Met Thr Ala Ala Asp Thr Ala Val Tyr Tyr
                85                  90                  95

Cys Ala Arg Ala Gly Ser Gly Ser His Tyr Phe Asp Tyr Trp Gly Gln
            100                 105                 110

Gly Thr Leu Val Thr Val Ser Ser
        115                 120

<210> SEQ ID NO 542
<211> LENGTH: 30
<212> TYPE: DNA
<213> ORGANISM: Artificial Sequence
<220> FEATURE:
<223> OTHER INFORMATION: Synthetic

<400> SEQUENCE: 542
ggtggctccg tcagcagtgg taattactac                                       30

<210> SEQ ID NO 543
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 543

Gly Gly Ser Val Ser Ser Gly Asn Tyr Tyr
 1               5                  10

<210> SEQ ID NO 544
<211> LENGTH: 21
<212> TYPE: DNA
<213> ORGANISM: Artificial Sequence
<220> FEATURE:
<223> OTHER INFORMATION: Synthetic

<400> SEQUENCE: 544
atcaaaaaca gtgggggcac c                                              21

<210> SEQ ID NO 545
<211> LENGTH: 7
<212> TYPE: PRT
<213> ORGANISM: Artificial Sequence
<220> FEATURE:
<223> OTHER INFORMATION: Synthetic

<400> SEQUENCE: 545

Ile Lys Asn Ser Gly Gly Thr
 1               5

<210> SEQ ID NO 546
<211> LENGTH: 36
<212> TYPE: DNA
<213> ORGANISM: Artificial Sequence
<220> FEATURE:
<223> OTHER INFORMATION: Synthetic

<400> SEQUENCE: 546
gcgagagctg gttcggggag tcactacttt gactac                              36

<210> SEQ ID NO 547
<211> LENGTH: 12
<212> TYPE: PRT
<213> ORGANISM: Artificial Sequence
<220> FEATURE:
<223> OTHER INFORMATION: Synthetic

<400> SEQUENCE: 547

Ala Arg Ala Gly Ser Gly Ser His Tyr Phe Asp Tyr
 1               5                  10

<210> SEQ ID NO 548
<211> LENGTH: 324
<212> TYPE: DNA
<213> ORGANISM: Artificial Sequence
<220> FEATURE:
<223> OTHER INFORMATION: Synthetic

<400> SEQUENCE: 548
gaaacgacac tcacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggctca gtggcagtgg gtctgggaca gacttcactc tcaccatcag cagactggag    240
cctgaagatt gtgcagtgta ttactgtcag cagtatggtt actcaccgat caccttcggc    300
```

```
caagggacca aggtggaaat caaa                                              324
```

<210> SEQ ID NO 549
<211> LENGTH: 108
<212> TYPE: PRT
<213> ORGANISM: Artificial Sequence
<220> FEATURE:
<223> OTHER INFORMATION: Synthetic

<400> SEQUENCE: 549

```
Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Leu Ser
    50                  55                  60

Gly Ser Gly Ser Gly Thr Asp Phe Thr Leu Thr Ile Ser Arg Leu Glu
65                  70                  75                  80

Pro Glu Asp Cys Ala Val Tyr Tyr Cys Gln Gln Tyr Gly Tyr Ser Pro
                85                  90                  95

Ile Thr Phe Gly Gln Gly Thr Lys Val Glu Ile Lys
            100                 105
```

<210> SEQ ID NO 550
<211> LENGTH: 21
<212> TYPE: DNA
<213> ORGANISM: Artificial Sequence
<220> FEATURE:
<223> OTHER INFORMATION: Synthetic

<400> SEQUENCE: 550

```
cagagtgtta gcagcagcta c                                                 21
```

<210> SEQ ID NO 551
<211> LENGTH: 7
<212> TYPE: PRT
<213> ORGANISM: Artificial Sequence
<220> FEATURE:
<223> OTHER INFORMATION: Synthetic

<400> SEQUENCE: 551

```
Gln Ser Val Ser Ser Ser Tyr
 1               5
```

<210> SEQ ID NO 552
<211> LENGTH: 9
<212> TYPE: DNA
<213> ORGANISM: Artificial Sequence
<220> FEATURE:
<223> OTHER INFORMATION: Synthetic

<400> SEQUENCE: 552

```
ggtgcatcc                                                                9
```

<210> SEQ ID NO 553
<211> LENGTH: 3
<212> TYPE: PRT
<213> ORGANISM: Artificial Sequence
<220> FEATURE:
<223> OTHER INFORMATION: Synthetic

<400> SEQUENCE: 553

Gly Ala Ser
1

<210> SEQ ID NO 554
<211> LENGTH: 27
<212> TYPE: DNA
<213> ORGANISM: Artificial Sequence
<220> FEATURE:
<223> OTHER INFORMATION: Synthetic

<400> SEQUENCE: 554
cagcagtatg gttactcacc gatcacc                                           27

<210> SEQ ID NO 555
<211> LENGTH: 9
<212> TYPE: PRT
<213> ORGANISM: Artificial Sequence
<220> FEATURE:
<223> OTHER INFORMATION: Synthetic

<400> SEQUENCE: 555

Gln Gln Tyr Gly Tyr Ser Pro Ile Thr
1               5

<210> SEQ ID NO 556
<211> LENGTH: 369
<212> TYPE: DNA
<213> ORGANISM: Artificial Sequence
<220> FEATURE:
<223> OTHER INFORMATION: Synthetic

<400> SEQUENCE: 556
gaagtgcagc tggtgcagtc tgggggaggc gtggtccagc ctggggaggtc cctgagactc       60 tcctgtacag cgtctggatt caccttcagt agctatgcca tgtactgggt ccgccaggct      120
ccaggcaagg ggctggagtg ggtggcagtt atatggtatg atggaagtaa taaaaactat      180
gcagactccg tgaagggccg attcaccatc tccagagaca attccaagaa cacactgtat      240
ctgcaagtga acagcctgag agccgaggac acggctgtgt attactgtgc gagagatcac      300
gattttttga gtggttatga ggggtggttc daccccctggg gccagggaac cctggtcacc      360
gtctcctca                                                             369

<210> SEQ ID NO 557
<211> LENGTH: 123
<212> TYPE: PRT
<213> ORGANISM: Artificial Sequence
<220> FEATURE:
<223> OTHER INFORMATION: Synthetic

<400> SEQUENCE: 557

Glu Val Gln Leu Val Gln Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ala Val Ile Trp Tyr Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Val Asn Ser Leu Arg Ala Glu Asp Thr Ala Val Tyr Tyr Cys
            85                  90                  95

Ala Arg Asp His Asp Phe Leu Ser Gly Tyr Glu Gly Trp Phe Asp Pro
        100                 105                 110

Trp Gly Gln Gly Thr Leu Val Thr Val Ser Ser
        115                 120
```

<210> SEQ ID NO 558
<211> LENGTH: 24
<212> TYPE: DNA
<213> ORGANISM: Artificial Sequence
<220> FEATURE:
<223> OTHER INFORMATION: Synthetic

<400> SEQUENCE: 558
ggattcacct tcagtagcta tgcc                                         24

<210> SEQ ID NO 559
<211> LENGTH: 8
<212> TYPE: PRT
<213> ORGANISM: Artificial Sequence
<220> FEATURE:
<223> OTHER INFORMATION: Synthetic

<400> SEQUENCE: 559

```
Gly Phe Thr Phe Ser Ser Tyr Ala
 1               5
```

<210> SEQ ID NO 560
<211> LENGTH: 24
<212> TYPE: DNA
<213> ORGANISM: Artificial Sequence
<220> FEATURE:
<223> OTHER INFORMATION: Synthetic

<400> SEQUENCE: 560
atatggtatg atggaagtaa taaa                                         24

<210> SEQ ID NO 561
<211> LENGTH: 8
<212> TYPE: PRT
<213> ORGANISM: Artificial Sequence
<220> FEATURE:
<223> OTHER INFORMATION: Synthetic

<400> SEQUENCE: 561

```
Ile Trp Tyr Asp Gly Ser Asn Lys
 1               5
```

<210> SEQ ID NO 562
<211> LENGTH: 48
<212> TYPE: DNA
<213> ORGANISM: Artificial Sequence
<220> FEATURE:
<223> OTHER INFORMATION: Synthetic

<400> SEQUENCE: 562
gcgagagatc acgattttt gagtggttat gagggtggt tcgacccc                 48

<210> SEQ ID NO 563
<211> LENGTH: 16
<212> TYPE: PRT
<213> ORGANISM: Artificial Sequence
<220> FEATURE:
<223> OTHER INFORMATION: Synthetic

<400> SEQUENCE: 563

Ala Arg Asp His Asp Phe Leu Ser Gly Tyr Glu Gly Trp Phe Asp Pro
1               5                   10                  15

<210> SEQ ID NO 564
<211> LENGTH: 321
<212> TYPE: DNA
<213> ORGANISM: Artificial Sequence
<220> FEATURE:
<223> OTHER INFORMATION: Synthetic

<400> SEQUENCE: 564
gaaattgtgc tgactcagtc tccagccacc ctgtctttgt ctccagggga aagagccacc    60
ctctcctgca gggccagtca gagtgttagt agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagtag cctagagcct   240
gaagattttg cagtttatta ctgtcagcaa cgtagcaact ggcctcccac tttcggcgga   300
gggaccaaag tggatatcaa a                                              321

<210> SEQ ID NO 565
<211> LENGTH: 107
<212> TYPE: PRT
<213> ORGANISM: Artificial Sequence
<220> FEATURE:
<223> OTHER INFORMATION: Synthetic

<400> SEQUENCE: 565

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gly Gly Thr Lys Val Asp Ile Lys
            100                 105

<210> SEQ ID NO 566
<211> LENGTH: 18
<212> TYPE: DNA
<213> ORGANISM: Artificial Sequence
<220> FEATURE:
<223> OTHER INFORMATION: Synthetic

<400> SEQUENCE: 566
cagagtgtta gtagctac                                                   18

<210> SEQ ID NO 567
<211> LENGTH: 6
<212> TYPE: PRT
<213> ORGANISM: Artificial Sequence
<220> FEATURE:
<223> OTHER INFORMATION: Synthetic

<400> SEQUENCE: 567

Gln Ser Val Ser Ser Tyr
 1               5

<210> SEQ ID NO 568
<211> LENGTH: 9
<212> TYPE: DNA
<213> ORGANISM: Artificial Sequence
<220> FEATURE:
<223> OTHER INFORMATION: Synthetic

<400> SEQUENCE: 568 gatgcatcc                                                                9

<210> SEQ ID NO 569
<211> LENGTH: 3
<212> TYPE: PRT
<213> ORGANISM: Artificial Sequence
<220> FEATURE:
<223> OTHER INFORMATION: Synthetic

<400> SEQUENCE: 569

Asp Ala Ser
 1

<210> SEQ ID NO 570
<211> LENGTH: 27
<212> TYPE: DNA
<213> ORGANISM: Artificial Sequence
<220> FEATURE:
<223> OTHER INFORMATION: Synthetic

<400> SEQUENCE: 570
cagcaacgta gcaactggcc tcccact                                            27

<210> SEQ ID NO 571
<211> LENGTH: 9
<212> TYPE: PRT
<213> ORGANISM: Artificial Sequence
<220> FEATURE:
<223> OTHER INFORMATION: Synthetic

<400> SEQUENCE: 571

Gln Gln Arg Ser Asn Trp Pro Pro Thr
 1               5

<210> SEQ ID NO 572
<211> LENGTH: 375
<212> TYPE: DNA
<213> ORGANISM: Artificial Sequence
<220> FEATURE:
<223> OTHER INFORMATION: Synthetic

<400> SEQUENCE: 572
gaggtgcagc tggtgcagtc tggagctgaa gtgaagaacc ctggggcctc agttagggtc        60
tcctgcaagg cttctggtta cacctttacc acctatggta tcacctgggt gcgacagggc       120
cctggacaag gcttgagtg gatgggatgg atcagcgctt tcaatggtga cacaaacttt        180
gcacagaacc tccagaacag agtcaccctg accacagaca catccactag cacagcctat       240
atggaactga ggagcctgag atctgacgac acggccgttt attactgtgc gagaggggga       300
ggagctcgtc cggggaactt cttcttctac ggtatgacg tctggggcca ggggaccacg        360
gtcaccgtct cctca                                                        375

```
<210> SEQ ID NO 573
<211> LENGTH: 125
<212> TYPE: PRT
<213> ORGANISM: Artificial Sequence
<220> FEATURE:
<223> OTHER INFORMATION: Synthetic

<400> SEQUENCE: 573

Glu Val Gln Leu Val Gln Ser Gly Ala Glu Val Lys Asn Pro Gly Ala
  1               5                  10                  15

Ser Val Arg Val Ser Cys Lys Ala Ser Gly Tyr Thr Phe Thr Thr Tyr
             20                  25                  30

Gly Ile Thr Trp Val Arg Gln Gly Pro Gly Gln Gly Leu Glu Trp Met
         35                  40                  45

Gly Trp Ile Ser Ala Phe Asn Gly Asp Thr Asn Phe Ala Gln Asn Leu
     50                  55                  60

Gln Asn Arg Val Thr Leu Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Gly Ala Arg Pro Gly Asn Phe Phe Tyr Gly Met
             100                 105                 110

Asp Val Trp Gly Gln Gly Thr Thr Val Thr Val Ser Ser
         115                 120                 125

<210> SEQ ID NO 574
<211> LENGTH: 24
<212> TYPE: DNA
<213> ORGANISM: Artificial Sequence
<220> FEATURE:
<223> OTHER INFORMATION: Synthetic

<400> SEQUENCE: 574
ggttacacct ttaccaccta tggt                                        24

<210> SEQ ID NO 575
<211> LENGTH: 8
<212> TYPE: PRT
<213> ORGANISM: Artificial Sequence
<220> FEATURE:
<223> OTHER INFORMATION: Synthetic

<400> SEQUENCE: 575

Gly Tyr Thr Phe Thr Thr Tyr Gly
  1               5

<210> SEQ ID NO 576
<211> LENGTH: 24
<212> TYPE: DNA
<213> ORGANISM: Artificial Sequence
<220> FEATURE:
<223> OTHER INFORMATION: Synthetic

<400> SEQUENCE: 576
atcagcgctt tcaatggtga caca                                        24

<210> SEQ ID NO 577
<211> LENGTH: 8
<212> TYPE: PRT
<213> ORGANISM: Artificial Sequence
<220> FEATURE:
<223> OTHER INFORMATION: Synthetic

<400> SEQUENCE: 577
```

Ile Ser Ala Phe Asn Gly Asp Thr
  1               5

<210> SEQ ID NO 578
<211> LENGTH: 54
<212> TYPE: DNA
<213> ORGANISM: Artificial Sequence
<220> FEATURE:
<223> OTHER INFORMATION: Synthetic

<400> SEQUENCE: 578
gcgagagggg gaggagctcg tccggggaac ttcttcttct acggtatgga cgtc        54

<210> SEQ ID NO 579
<211> LENGTH: 18
<212> TYPE: PRT
<213> ORGANISM: Artificial Sequence
<220> FEATURE:
<223> OTHER INFORMATION: Synthetic

<400> SEQUENCE: 579

Ala Arg Gly Gly Gly Ala Arg Pro Gly Asn Phe Phe Phe Tyr Gly Met
  1               5                  10                  15

Asp Val

<210> SEQ ID NO 580
<211> LENGTH: 321
<212> TYPE: DNA
<213> ORGANISM: Artificial Sequence
<220> FEATURE:
<223> OTHER INFORMATION: Synthetic

<400> SEQUENCE: 580
gatgttgtga tgactcagtc tccagccacc ctgtctttgt ctccagggga aagagccacc    60
ctctcctgta gggccagtca gagttttgcc agctacttag cctggtacca acagaaacct   120
ggccaggctc ccaggctcct catctatgat acctcctaca gggccactgg cgtcccagcc   180
aggttcagtg gcagtgggtc tgggacagac ttcactctca acatcagcaa cctggagcct   240
gaagattttg cagtttatta ctgtcagcaa cgtggcaact ggccgctcac tttcggcgga   300
gggaccaagg tggaaatcaa a                                             321

<210> SEQ ID NO 581
<211> LENGTH: 107
<212> TYPE: PRT
<213> ORGANISM: Artificial Sequence
<220> FEATURE:
<223> OTHER INFORMATION: Synthetic

<400> SEQUENCE: 581

Asp Val Val Met Thr Gln Ser Pro Ala Thr Leu Ser Leu Ser Pro Gly
  1               5                  10                  15

Glu Arg Ala Thr Leu Ser Cys Arg Ala Ser Gln Ser Phe Ala Ser Tyr
                 20                  25                  30

Leu Ala Trp Tyr Gln Gln Lys Pro Gly Gln Ala Pro Arg Leu Leu Ile
             35                  40                  45

Tyr Asp Thr Ser Tyr Arg Ala Thr Gly Val Pro Ala Arg Phe Ser Gly
         50                  55                  60

Ser Gly Ser Gly Thr Asp Phe Thr Leu Asn Ile Ser Asn Leu Glu Pro
 65                  70                  75                  80

Glu Asp Phe Ala Val Tyr Tyr Cys Gln Gln Arg Gly Asn Trp Pro Leu

-continued

```
                85                  90                  95

Thr Phe Gly Gly Gly Thr Lys Val Glu Ile Lys
        100                 105

<210> SEQ ID NO 582
<211> LENGTH: 18
<212> TYPE: DNA
<213> ORGANISM: Artificial Sequence
<220> FEATURE:
<223> OTHER INFORMATION: Synthetic

<400> SEQUENCE: 582
cagagttttg ccagctac                                                 18

<210> SEQ ID NO 583
<211> LENGTH: 6
<212> TYPE: PRT
<213> ORGANISM: Artificial Sequence
<220> FEATURE:
<223> OTHER INFORMATION: Synthetic

<400> SEQUENCE: 583

Gln Ser Phe Ala Ser Tyr
1               5

<210> SEQ ID NO 584
<211> LENGTH: 9
<212> TYPE: DNA
<213> ORGANISM: Artificial Sequence
<220> FEATURE:
<223> OTHER INFORMATION: Synthetic

<400> SEQUENCE: 584 gatacctcc                                                            9

<210> SEQ ID NO 585
<211> LENGTH: 3
<212> TYPE: PRT
<213> ORGANISM: Artificial Sequence
<220> FEATURE:
<223> OTHER INFORMATION: Synthetic

<400> SEQUENCE: 585

Asp Thr Ser
1

<210> SEQ ID NO 586
<211> LENGTH: 27
<212> TYPE: DNA
<213> ORGANISM: Artificial Sequence
<220> FEATURE:
<223> OTHER INFORMATION: Synthetic

<400> SEQUENCE: 586
cagcaacgtg gcaactggcc gctcact                                       27

<210> SEQ ID NO 587
<211> LENGTH: 9
<212> TYPE: PRT
<213> ORGANISM: Artificial Sequence
<220> FEATURE:
<223> OTHER INFORMATION: Synthetic

<400> SEQUENCE: 587

Gln Gln Arg Gly Asn Trp Pro Leu Thr
1               5
```

<210> SEQ ID NO 588
<211> LENGTH: 357
<212> TYPE: DNA
<213> ORGANISM: Artificial Sequence
<220> FEATURE:
<223> OTHER INFORMATION: Synthetic

<400> SEQUENCE: 588

```
caggtgcagc tggtgcagtc tggaactgag gtgaagaagc ctggggcctc agtgaaggtc      60
tcctgcaagg cttctggtta cacctttagc tacaatggtg tcacttgggt acgacaggcc     120
cctggacaag ggcttgagtg gatgggatgg atcagcgctt acgatggtaa cacagactat    180
gcacagaagt tccaagacag aatcaccatg accacagaca catccacgag tacagcctac     240
atggaactga ggagccttag atctgacgac acggccgtct attactgtgc gaggtatagt    300
tggaacaacc actggttcga ccctgggggc cagggaaccc tggtcaccgt ctcctca       357
```

<210> SEQ ID NO 589
<211> LENGTH: 119
<212> TYPE: PRT
<213> ORGANISM: Artificial Sequence
<220> FEATURE:
<223> OTHER INFORMATION: Synthetic

<400> SEQUENCE: 589

```
Gln Val Gln Leu Val Gln Ser Gly Thr Glu Val Lys Lys Pro Gly Ala
 1               5                  10                  15
Ser Val Lys Val Ser Cys Lys Ala Ser Gly Tyr Thr Phe Ser Tyr Asn
            20                  25                  30
Gly Val Thr Trp Val Arg Gln Ala Pro Gly Gln Gly Leu Glu Trp Met
        35                  40                  45
Gly Trp Ile Ser Ala Tyr Asp Gly Asn Thr Asp Tyr Ala Gln Lys Phe
    50                  55                  60
Gln Asp Arg Ile Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Tyr Ser Trp Asn Asn His Trp Phe Asp Pro Trp Gly Gln Gly
            100                 105                 110
Thr Leu Val Thr Val Ser Ser
        115
```

<210> SEQ ID NO 590
<211> LENGTH: 24
<212> TYPE: DNA
<213> ORGANISM: Artificial Sequence
<220> FEATURE:
<223> OTHER INFORMATION: Synthetic

<400> SEQUENCE: 590

```
ggttacacct ttagctacaa tggt                                             24
```

<210> SEQ ID NO 591
<211> LENGTH: 8
<212> TYPE: PRT
<213> ORGANISM: Artificial Sequence
<220> FEATURE:
<223> OTHER INFORMATION: Synthetic

<400> SEQUENCE: 591

```
Gly Tyr Thr Phe Ser Tyr Asn Gly
1               5
```

<210> SEQ ID NO 592
<211> LENGTH: 24
<212> TYPE: DNA
<213> ORGANISM: Artificial Sequence
<220> FEATURE:
<223> OTHER INFORMATION: Synthetic

<400> SEQUENCE: 592
atcagcgctt acgatggtaa caca                                              24

<210> SEQ ID NO 593
<211> LENGTH: 8
<212> TYPE: PRT
<213> ORGANISM: Artificial Sequence
<220> FEATURE:
<223> OTHER INFORMATION: Synthetic

<400> SEQUENCE: 593

```
Ile Ser Ala Tyr Asp Gly Asn Thr
1               5
```

<210> SEQ ID NO 594
<211> LENGTH: 36
<212> TYPE: DNA
<213> ORGANISM: Artificial Sequence
<220> FEATURE:
<223> OTHER INFORMATION: Synthetic

<400> SEQUENCE: 594
gcgaggtata gttggaacaa ccactggttc gacccc                                 36

<210> SEQ ID NO 595
<211> LENGTH: 12
<212> TYPE: PRT
<213> ORGANISM: Artificial Sequence
<220> FEATURE:
<223> OTHER INFORMATION: Synthetic

<400> SEQUENCE: 595

```
Ala Arg Tyr Ser Trp Asn Asn His Trp Phe Asp Pro
1               5                   10
```

<210> SEQ ID NO 596
<211> LENGTH: 324
<212> TYPE: DNA
<213> ORGANISM: Artificial Sequence
<220> FEATURE:
<223> OTHER INFORMATION: Synthetic

<400> SEQUENCE: 596
gatattgtga tgactcagtc tccaggcacc ctgtctttgt ctccaggaga cggggccacc       60
ctctcctgca gggccagtca gagtgtttcc ggcagctact tagcctggta ccagcagaaa      120
cctggccagg ctcccaggct cctcatttat ggtgcatcca acagggccac tggcatccca      180
gacaggttca ctggcagtgg gtctgggaca gacttcactc tcaccatcag cagactggag      240
cctgaagatt ttgcagtgta tttctgtcag cagagtgctt tctcaccgtg gacgttcggc      300
caagggacca agctggagat caaa                                             324

<210> SEQ ID NO 597
<211> LENGTH: 108
<212> TYPE: PRT

```
<213> ORGANISM: Artificial Sequence
<220> FEATURE:
<223> OTHER INFORMATION: Synthetic

<400> SEQUENCE: 597

Asp Ile Val Met Thr Gln Ser Pro Gly Thr Leu Ser Leu Ser Pro Gly
 1               5                  10                  15

Asp Gly Ala Thr Leu Ser Cys Arg Ala Ser Gln Ser Val Ser Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Ser Ala Phe Ser Pro
                85                  90                  95

Trp Thr Phe Gly Gln Gly Thr Lys Leu Glu Ile Lys
            100                 105

<210> SEQ ID NO 598
<211> LENGTH: 21
<212> TYPE: DNA
<213> ORGANISM: Artificial Sequence
<220> FEATURE:
<223> OTHER INFORMATION: Synthetic

<400> SEQUENCE: 598
cagagtgttt ccggcagcta c                                          21

<210> SEQ ID NO 599
<211> LENGTH: 7
<212> TYPE: PRT
<213> ORGANISM: Artificial Sequence
<220> FEATURE:
<223> OTHER INFORMATION: Synthetic

<400> SEQUENCE: 599

Gln Ser Val Ser Gly Ser Tyr
 1               5

<210> SEQ ID NO 600
<211> LENGTH: 9
<212> TYPE: DNA
<213> ORGANISM: Artificial Sequence
<220> FEATURE:
<223> OTHER INFORMATION: Synthetic

<400> SEQUENCE: 600 ggtgcatcc                                                         9

<210> SEQ ID NO 601
<211> LENGTH: 3
<212> TYPE: PRT
<213> ORGANISM: Artificial Sequence
<220> FEATURE:
<223> OTHER INFORMATION: Synthetic

<400> SEQUENCE: 601

Gly Ala Ser
 1

<210> SEQ ID NO 602
```

<211> LENGTH: 27
<212> TYPE: DNA
<213> ORGANISM: Artificial Sequence
<220> FEATURE:
<223> OTHER INFORMATION: Synthetic

<400> SEQUENCE: 602
cagcagagtg ctttctcacc gtggacg                                              27

<210> SEQ ID NO 603
<211> LENGTH: 9
<212> TYPE: PRT
<213> ORGANISM: Artificial Sequence
<220> FEATURE:
<223> OTHER INFORMATION: Synthetic

<400> SEQUENCE: 603

Gln Gln Ser Ala Phe Ser Pro Trp Thr
 1               5

<210> SEQ ID NO 604
<211> LENGTH: 351
<212> TYPE: DNA
<213> ORGANISM: Artificial Sequence
<220> FEATURE:
<223> OTHER INFORMATION: Synthetic

<400> SEQUENCE: 604
gaagtgcagc tggtgcagtc tgggggaggc ttggtacagc ctggggggtc cctgagactc          60
tcctgtgcag cctctggatt caccttcagt atgtacgaca tgcactgggt ccgccaaact        120
ataggaaaag gtctggagtg ggtctcagca attggtactg ctggtgacac atactatcca        180
ggctccgtga agggccgatt caccatctcc agagaaaatg ccaagaactc cttgtttctt        240
caaatgaaca gcctgagagc cggggacacg gctgtttatt actgtgtaag atccgggact        300
acagagtggt tcgaccctg gggccaggga accccggtca ctgtctcctc a                  351

<210> SEQ ID NO 605
<211> LENGTH: 117
<212> TYPE: PRT
<213> ORGANISM: Artificial Sequence
<220> FEATURE:
<223> OTHER INFORMATION: Synthetic

<400> SEQUENCE: 605

Glu Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Met Tyr
             20                  25                  30

Asp Met His Trp Val Arg Gln Thr Ile Gly Lys Gly Leu Glu Trp Val
         35                  40                  45

Ser Ala Ile Gly Thr Ala Gly Asp Thr Tyr Tyr Pro Gly Ser Val Lys
     50                  55                  60

Gly Arg Phe Thr Ile Ser Arg Glu Asn Ala Lys Asn Ser Leu Phe Leu
 65                  70                  75                  80

Gln Met Asn Ser Leu Arg Ala Gly Asp Thr Ala Val Tyr Tyr Cys Val
                 85                  90                  95

Arg Ser Gly Thr Thr Glu Trp Phe Asp Pro Trp Gly Gln Gly Thr Pro
            100                 105                 110

Val Thr Val Ser Ser
        115

```
<210> SEQ ID NO 606
<211> LENGTH: 24
<212> TYPE: DNA
<213> ORGANISM: Artificial Sequence
<220> FEATURE:
<223> OTHER INFORMATION: Synthetic

<400> SEQUENCE: 606
ggattcacct tcagtatgta cgac                                              24

<210> SEQ ID NO 607
<211> LENGTH: 8
<212> TYPE: PRT
<213> ORGANISM: Artificial Sequence
<220> FEATURE:
<223> OTHER INFORMATION: Synthetic

<400> SEQUENCE: 607

Gly Phe Thr Phe Ser Met Tyr Asp
 1               5

<210> SEQ ID NO 608
<211> LENGTH: 21
<212> TYPE: DNA
<213> ORGANISM: Artificial Sequence
<220> FEATURE:
<223> OTHER INFORMATION: Synthetic

<400> SEQUENCE: 608
attggtactg ctggtgacac a                                                 21

<210> SEQ ID NO 609
<211> LENGTH: 7
<212> TYPE: PRT
<213> ORGANISM: Artificial Sequence
<220> FEATURE:
<223> OTHER INFORMATION: Synthetic

<400> SEQUENCE: 609

Ile Gly Thr Ala Gly Asp Thr
 1               5

<210> SEQ ID NO 610
<211> LENGTH: 33
<212> TYPE: DNA
<213> ORGANISM: Artificial Sequence
<220> FEATURE:
<223> OTHER INFORMATION: Synthetic

<400> SEQUENCE: 610
gtaagatccg ggactacaga gtggttcgac ccc                                    33

<210> SEQ ID NO 611
<211> LENGTH: 11
<212> TYPE: PRT
<213> ORGANISM: Artificial Sequence
<220> FEATURE:
<223> OTHER INFORMATION: Synthetic

<400> SEQUENCE: 611

Val Arg Ser Gly Thr Thr Glu Trp Phe Asp Pro
 1               5                  10

<210> SEQ ID NO 612
<211> LENGTH: 321
<212> TYPE: DNA
```

<213> ORGANISM: Artificial Sequence
<220> FEATURE:
<223> OTHER INFORMATION: Synthetic

<400> SEQUENCE: 612

```
gacatccggt tgacccagtc tccatcttcc gtgtctgcat ctgtgggaga cagagtcacc      60
atcacttgtc ggacgagtca gggtattagt agctggttag cctggtatca gcagaaacca     120
ggaaaagccc ctaacctcct gatctatgct gcatccagtt tacaaagtgg ggtcccatca     180
aggttcagcg gcagtggatc tgggacagat ttcactctca ccatcagcag cctgcagcct     240
gaagattttg caacttacta ttgtctacag gctaacagtt tcccgtacac ttttggccag     300
gggaccaagg tggagatcaa a                                                321
```

<210> SEQ ID NO 613
<211> LENGTH: 107
<212> TYPE: PRT
<213> ORGANISM: Artificial Sequence
<220> FEATURE:
<223> OTHER INFORMATION: Synthetic

<400> SEQUENCE: 613

```
Asp Ile Arg Leu Thr Gln Ser Pro Ser Ser Val Ser Ala Ser Val Gly
 1               5                  10                  15
Asp Arg Val Thr Ile Thr Cys Arg Thr Ser Gln Gly Ile Ser Ser Trp
            20                  25                  30
Leu Ala Trp Tyr Gln Gln Lys Pro Gly Lys Ala Pro Asn Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Ala Asn Ser Phe Pro Tyr
                85                  90                  95
Thr Phe Gly Gln Gly Thr Lys Val Glu Ile Lys
            100                 105
```

<210> SEQ ID NO 614
<211> LENGTH: 18
<212> TYPE: DNA
<213> ORGANISM: Artificial Sequence
<220> FEATURE:
<223> OTHER INFORMATION: Synthetic

<400> SEQUENCE: 614

```
cagggtatta gtagctgg                                                    18
```

<210> SEQ ID NO 615
<211> LENGTH: 6
<212> TYPE: PRT
<213> ORGANISM: Artificial Sequence
<220> FEATURE:
<223> OTHER INFORMATION: Synthetic

<400> SEQUENCE: 615

```
Gln Gly Ile Ser Ser Trp
 1               5
```

<210> SEQ ID NO 616
<211> LENGTH: 9
<212> TYPE: DNA
<213> ORGANISM: Artificial Sequence

```
<220> FEATURE:
<223> OTHER INFORMATION: Synthetic

<400> SEQUENCE: 616 gctgcatcc                                                                 9

<210> SEQ ID NO 617
<211> LENGTH: 3
<212> TYPE: PRT
<213> ORGANISM: Artificial Sequence
<220> FEATURE:
<223> OTHER INFORMATION: Synthetic

<400> SEQUENCE: 617

Ala Ala Ser
 1

<210> SEQ ID NO 618
<211> LENGTH: 27
<212> TYPE: DNA
<213> ORGANISM: Artificial Sequence
<220> FEATURE:
<223> OTHER INFORMATION: Synthetic

<400> SEQUENCE: 618
ctacaggcta acagtttccc gtacact                                            27

<210> SEQ ID NO 619
<211> LENGTH: 9
<212> TYPE: PRT
<213> ORGANISM: Artificial Sequence
<220> FEATURE:
<223> OTHER INFORMATION: Synthetic

<400> SEQUENCE: 619

Leu Gln Ala Asn Ser Phe Pro Tyr Thr
 1               5

<210> SEQ ID NO 620
<211> LENGTH: 369
<212> TYPE: DNA
<213> ORGANISM: Artificial Sequence
<220> FEATURE:
<223> OTHER INFORMATION: Synthetic

<400> SEQUENCE: 620
caggtccagc tggtgcagtc tgggggaggc gtggtccagc ctgggaggtc cctgagactc        60
tcctgtgcag cgtctggatt caccttcagt agttatggca tgcactgggt ccgccaggct       120
ccaggcaagg ggctggagtg ggtggcagtt ttatggtatg atggaagtaa taaaaactat       180
gtagactccg tgaagggccg attcaccatc tcaagagaca attccaagaa cacgctttat       240
ctgcaaatga acagcctgag agccgaggac acggctgtgt attattgtgc gagagatcat       300
gattttagga gtggttatga ggggtggttc gacccctggg gccagggaac cctggtcacc       360
gtctcctca                                                              369

<210> SEQ ID NO 621
<211> LENGTH: 123
<212> TYPE: PRT
<213> ORGANISM: Artificial Sequence
<220> FEATURE:
<223> OTHER INFORMATION: Synthetic

<400> SEQUENCE: 621
```

```
Gln Val Gln Leu Val Gln Ser Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Leu Trp Tyr Asp Gly Ser Asn Lys Asn Tyr Val Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120
```

```
<210> SEQ ID NO 622
<211> LENGTH: 24
<212> TYPE: DNA
<213> ORGANISM: Artificial Sequence
<220> FEATURE:
<223> OTHER INFORMATION: Synthetic

<400> SEQUENCE: 622
ggattcacct tcagtagtta tggc                                          24
```

```
<210> SEQ ID NO 623
<211> LENGTH: 8
<212> TYPE: PRT
<213> ORGANISM: Artificial Sequence
<220> FEATURE:
<223> OTHER INFORMATION: Synthetic

<400> SEQUENCE: 623

Gly Phe Thr Phe Ser Ser Tyr Gly
  1               5
```

```
<210> SEQ ID NO 624
<211> LENGTH: 24
<212> TYPE: DNA
<213> ORGANISM: Artificial Sequence
<220> FEATURE:
<223> OTHER INFORMATION: Synthetic

<400> SEQUENCE: 624
ttatggtatg atggaagtaa taaa                                          24
```

```
<210> SEQ ID NO 625
<211> LENGTH: 8
<212> TYPE: PRT
<213> ORGANISM: Artificial Sequence
<220> FEATURE:
<223> OTHER INFORMATION: Synthetic

<400> SEQUENCE: 625

Leu Trp Tyr Asp Gly Ser Asn Lys
  1               5
```

```
<210> SEQ ID NO 626
<211> LENGTH: 48
<212> TYPE: DNA
<213> ORGANISM: Artificial Sequence
```

<220> FEATURE:
<223> OTHER INFORMATION: Synthetic

<400> SEQUENCE: 626

```
gcgagagatc atgatttag gagtggttat gagggggtggt tcgacccc         48
```

<210> SEQ ID NO 627
<211> LENGTH: 16
<212> TYPE: PRT
<213> ORGANISM: Artificial Sequence
<220> FEATURE:
<223> OTHER INFORMATION: Synthetic

<400> SEQUENCE: 627

Ala Arg Asp His Asp Phe Arg Ser Gly Tyr Glu Gly Trp Phe Asp Pro
 1               5                  10                  15

<210> SEQ ID NO 628
<211> LENGTH: 321
<212> TYPE: DNA
<213> ORGANISM: Artificial Sequence
<220> FEATURE:
<223> OTHER INFORMATION: Synthetic

<400> SEQUENCE: 628

```
gaaattgtgc tgacgcagtc tccagccacc ctgtctttgt ctccagggga aagagccacc    60
ctctcctgca gggccagtca gagtgttcgc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcaacac cgtagcaact ggcctcccac tttcggcgga   300
gggaccaagg tggaaatcaa a                                             321
```

<210> SEQ ID NO 629
<211> LENGTH: 107
<212> TYPE: PRT
<213> ORGANISM: Artificial Sequence
<220> FEATURE:
<223> OTHER INFORMATION: Synthetic

<400> SEQUENCE: 629

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Gly Gly Thr Lys Val Glu Ile Lys
            100                 105

<210> SEQ ID NO 630
<211> LENGTH: 18
<212> TYPE: DNA
<213> ORGANISM: Artificial Sequence
<220> FEATURE:

<223> OTHER INFORMATION: Synthetic

<400> SEQUENCE: 630
cagagtgttc gcagctac 18

<210> SEQ ID NO 631
<211> LENGTH: 6
<212> TYPE: PRT
<213> ORGANISM: Artificial Sequence
<220> FEATURE:
<223> OTHER INFORMATION: Synthetic

<400> SEQUENCE: 631

Gln Ser Val Arg Ser Tyr
1               5

<210> SEQ ID NO 632
<211> LENGTH: 9
<212> TYPE: DNA
<213> ORGANISM: Artificial Sequence
<220> FEATURE:
<223> OTHER INFORMATION: Synthetic

<400> SEQUENCE: 632 gatgcatcc 9

<210> SEQ ID NO 633
<211> LENGTH: 3
<212> TYPE: PRT
<213> ORGANISM: Artificial Sequence
<220> FEATURE:
<223> OTHER INFORMATION: Synthetic

<400> SEQUENCE: 633

Asp Ala Ser
1

<210> SEQ ID NO 634
<211> LENGTH: 27
<212> TYPE: DNA
<213> ORGANISM: Artificial Sequence
<220> FEATURE:
<223> OTHER INFORMATION: Synthetic

<400> SEQUENCE: 634
caacaccgta gcaactggcc tcccact 27

<210> SEQ ID NO 635
<211> LENGTH: 9
<212> TYPE: PRT
<213> ORGANISM: Artificial Sequence
<220> FEATURE:
<223> OTHER INFORMATION: Synthetic

<400> SEQUENCE: 635

Gln His Arg Ser Asn Trp Pro Pro Thr
1               5

<210> SEQ ID NO 636
<211> LENGTH: 354
<212> TYPE: DNA
<213> ORGANISM: Artificial Sequence
<220> FEATURE:
<223> OTHER INFORMATION: Synthetic

<400> SEQUENCE: 636

```
caggtcacct tgaaggagtc gggcccagga ctggtgaagt cttcggagac cctgtccctc    60
acttgcactg tctctactgg ctccatcagc agtagtagtt actactgggc ctggatccgc   120
cagcccccag ggaagggact ggagtggatt gggagtatct attatagtgg gagtaaattc   180
tacagcccgt ccctcaagag tcgagtcacc atatacgttg acacgtccaa gaatcagttc   240
tccctgcaac tgagctcggt gaccgccgca gacacggctg tatattactg tgcgagacag   300
gtcggtgcaa tctttgacta ctggggccag ggaaccctgg tcaccgtctc ctca         354
```

<210> SEQ ID NO 637
<211> LENGTH: 118
<212> TYPE: PRT
<213> ORGANISM: Artificial Sequence
<220> FEATURE:
<223> OTHER INFORMATION: Synthetic

<400> SEQUENCE: 637

```
Gln Val Thr Leu Lys Glu Ser Gly Pro Gly Leu Val Lys Ser Ser Glu
  1               5                  10                  15

Thr Leu Ser Leu Thr Cys Thr Val Ser Thr Gly Ser Ile Ser Ser Ser
             20                  25                  30

Ser Tyr Tyr Trp Ala Trp Ile Arg Gln Pro Pro Gly Lys Gly Leu Glu
         35                  40                  45

Trp Ile Gly Ser Ile Tyr Tyr Ser Gly Ser Lys Phe Tyr Ser Pro Ser
     50                  55                  60

Leu Lys Ser Arg Val Thr Ile Tyr Val Asp Thr Ser Lys Asn Gln Phe
 65                  70                  75                  80

Ser Leu Gln Leu Ser Ser Val Thr Ala Ala Asp Thr Ala Val Tyr Tyr
                 85                  90                  95

Cys Ala Arg Gln Val Gly Ala Ile Phe Asp Tyr Trp Gly Gln Gly Thr
            100                 105                 110

Leu Val Thr Val Ser Ser
        115
```

<210> SEQ ID NO 638
<211> LENGTH: 30
<212> TYPE: DNA
<213> ORGANISM: Artificial Sequence
<220> FEATURE:
<223> OTHER INFORMATION: Synthetic

<400> SEQUENCE: 638

```
actggctcca tcagcagtag tagttactac                                     30
```

<210> SEQ ID NO 639
<211> LENGTH: 10
<212> TYPE: PRT
<213> ORGANISM: Artificial Sequence
<220> FEATURE:
<223> OTHER INFORMATION: Synthetic

<400> SEQUENCE: 639

```
Thr Gly Ser Ile Ser Ser Ser Ser Tyr Tyr
  1               5                  10
```

<210> SEQ ID NO 640
<211> LENGTH: 21
<212> TYPE: DNA
<213> ORGANISM: Artificial Sequence
<220> FEATURE:
<223> OTHER INFORMATION: Synthetic

```
<400> SEQUENCE: 640
atctattata gtgggagtaa a                                              21

<210> SEQ ID NO 641
<211> LENGTH: 7
<212> TYPE: PRT
<213> ORGANISM: Artificial Sequence
<220> FEATURE:
<223> OTHER INFORMATION: Synthetic

<400> SEQUENCE: 641

Ile Tyr Tyr Ser Gly Ser Lys
1               5

<210> SEQ ID NO 642
<211> LENGTH: 30
<212> TYPE: DNA
<213> ORGANISM: Artificial Sequence
<220> FEATURE:
<223> OTHER INFORMATION: Synthetic

<400> SEQUENCE: 642
gcgagacagg tcggtgcaat ctttgactac                                     30

<210> SEQ ID NO 643
<211> LENGTH: 10
<212> TYPE: PRT
<213> ORGANISM: Artificial Sequence
<220> FEATURE:
<223> OTHER INFORMATION: Synthetic

<400> SEQUENCE: 643

Ala Arg Gln Val Gly Ala Ile Phe Asp Tyr
1               5                   10

<210> SEQ ID NO 644
<211> LENGTH: 321
<212> TYPE: DNA
<213> ORGANISM: Artificial Sequence
<220> FEATURE:
<223> OTHER INFORMATION: Synthetic

<400> SEQUENCE: 644
gccatccggt tgacccagtc tccttccacc ctgtctgcat ctgtaggaga cagagtcacc     60
atctcttgcc gggccagtca gagtattagt agttggttgg cctggtatca gcacaaacca    120
gggaaagccc ctaaactcct gctctataag gcgtctagtt tagaaagtgg ggtcccatca    180
aggttcagcg gcagtggatc tgggacagag ttcactctca ccatcagcag cctgcagcct    240
gatgattttg caacttatta ctgccaacag tataatagtt attctcggac gttcggccaa    300
gggaccaagg tggagatcaa a                                             321

<210> SEQ ID NO 645
<211> LENGTH: 107
<212> TYPE: PRT
<213> ORGANISM: Artificial Sequence
<220> FEATURE:
<223> OTHER INFORMATION: Synthetic

<400> SEQUENCE: 645

Ala Ile Arg Leu Thr Gln Ser Pro Ser Thr Leu Ser Ala Ser Val Gly
1               5                   10                  15

Asp Arg Val Thr Ile Ser Cys Arg Ala Ser Gln Ser Ile Ser Ser Trp
            20                  25                  30
```

Leu Ala Trp Tyr Gln His Lys Pro Gly Lys Ala Pro Lys Leu Leu Leu
         35                  40                  45

Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Arg
                 85                  90                  95

Thr Phe Gly Gln Gly Thr Lys Val Glu Ile Lys
            100                 105

<210> SEQ ID NO 646
<211> LENGTH: 18
<212> TYPE: DNA
<213> ORGANISM: Artificial Sequence
<220> FEATURE:
<223> OTHER INFORMATION: Synthetic

<400> SEQUENCE: 646
cagagtatta gtagttgg                                                       18

<210> SEQ ID NO 647
<211> LENGTH: 6
<212> TYPE: PRT
<213> ORGANISM: Artificial Sequence
<220> FEATURE:
<223> OTHER INFORMATION: Synthetic

<400> SEQUENCE: 647

Gln Ser Ile Ser Ser Trp
 1               5

<210> SEQ ID NO 648
<211> LENGTH: 9
<212> TYPE: DNA
<213> ORGANISM: Artificial Sequence
<220> FEATURE:
<223> OTHER INFORMATION: Synthetic

<400> SEQUENCE: 648 aaggcgtct                                                                  9

<210> SEQ ID NO 649
<211> LENGTH: 3
<212> TYPE: PRT
<213> ORGANISM: Artificial Sequence
<220> FEATURE:
<223> OTHER INFORMATION: Synthetic

<400> SEQUENCE: 649

Lys Ala Ser
 1

<210> SEQ ID NO 650
<211> LENGTH: 27
<212> TYPE: DNA
<213> ORGANISM: Artificial Sequence
<220> FEATURE:
<223> OTHER INFORMATION: Synthetic

<400> SEQUENCE: 650
caacagtata atagttattc tcggacg                                             27

<210> SEQ ID NO 651
<211> LENGTH: 9
<212> TYPE: PRT
<213> ORGANISM: Artificial Sequence
<220> FEATURE:
<223> OTHER INFORMATION: Synthetic

<400> SEQUENCE: 651

Gln Gln Tyr Asn Ser Tyr Ser Arg Thr
 1               5

<210> SEQ ID NO 652
<211> LENGTH: 372
<212> TYPE: DNA
<213> ORGANISM: Artificial Sequence
<220> FEATURE:
<223> OTHER INFORMATION: Synthetic

<400> SEQUENCE: 652
gaggtgcagc tggtgcagtc tggagctgag gtgaagaagc ctggggcctc agtgaaggtc      60
tcctgcaagg cctctggtta cacctttaac atctatggta tcagctgggt acgacaggcc     120
cctggacaag gcttgagtg gatgggatgg atcagcgctt acaatggtaa cacaaactat      180
gcacagaaac tccagggcag agtcaccatg accacagaaa catccacgac acagcctac     240 atggagttga ggagcctgag atctgacgac acggccgtgt attactgtgc gagagattct     300
gattggggaa ctccctacca ctactacggt atggacgtct ggggccaagg gaccacggtc     360
accgtctcct ca                                                        372

<210> SEQ ID NO 653
<211> LENGTH: 124
<212> TYPE: PRT
<213> ORGANISM: Artificial Sequence
<220> FEATURE:
<223> OTHER INFORMATION: Synthetic

<400> SEQUENCE: 653

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Ile Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Glu Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Asp Trp Gly Thr Pro Tyr His Tyr Tyr Gly Met Asp
            100                 105                 110

Val Trp Gly Gln Gly Thr Thr Val Thr Val Ser Ser
        115                 120

<210> SEQ ID NO 654
<211> LENGTH: 24
<212> TYPE: DNA
<213> ORGANISM: Artificial Sequence
<220> FEATURE:
<223> OTHER INFORMATION: Synthetic

<400> SEQUENCE: 654

```
ggttacacct ttaacatcta tggt                                              24
```

<210> SEQ ID NO 655
<211> LENGTH: 8
<212> TYPE: PRT
<213> ORGANISM: Artificial Sequence
<220> FEATURE:
<223> OTHER INFORMATION: Synthetic

<400> SEQUENCE: 655

Gly Tyr Thr Phe Asn Ile Tyr Gly
 1               5

<210> SEQ ID NO 656
<211> LENGTH: 24
<212> TYPE: DNA
<213> ORGANISM: Artificial Sequence
<220> FEATURE:
<223> OTHER INFORMATION: Synthetic

<400> SEQUENCE: 656

```
atcagcgctt acaatggtaa caca                                              24
```

<210> SEQ ID NO 657
<211> LENGTH: 8
<212> TYPE: PRT
<213> ORGANISM: Artificial Sequence
<220> FEATURE:
<223> OTHER INFORMATION: Synthetic

<400> SEQUENCE: 657

Ile Ser Ala Tyr Asn Gly Asn Thr
 1               5

<210> SEQ ID NO 658
<211> LENGTH: 51
<212> TYPE: DNA
<213> ORGANISM: Artificial Sequence
<220> FEATURE:
<223> OTHER INFORMATION: Synthetic

<400> SEQUENCE: 658

```
gcgagagatt ctgattgggg aactccctac cactactacg gtatggacgt c               51
```

<210> SEQ ID NO 659
<211> LENGTH: 17
<212> TYPE: PRT
<213> ORGANISM: Artificial Sequence
<220> FEATURE:
<223> OTHER INFORMATION: Synthetic

<400> SEQUENCE: 659

Ala Arg Asp Ser Asp Trp Gly Thr Pro Tyr His Tyr Tyr Gly Met Asp
 1               5                  10                  15

Val

<210> SEQ ID NO 660
<211> LENGTH: 339
<212> TYPE: DNA
<213> ORGANISM: Artificial Sequence
<220> FEATURE:
<223> OTHER INFORMATION: Synthetic

<400> SEQUENCE: 660

```
gatattgtga tgacccagtc tccagactcc ctggctgtgt ctctgggcga gagggccacc      60
```

```
atcaactgca agtccagcca gaatatttta tacacctcca acaataagaa ctacttagct    120
tggtaccagc agaaaccagg acagcctcct aagctgctca tttactgggc atttacccgg    180
aaatccgggg tccctgaccg attcagtggc agcgggtctg ggacagattt cactctcacc    240
atcagcagcc tgcaggctga agatgtggca gtttattact gtcagcaata ttataatact    300
cctcggacgt tcggccaagg gaccaaagtg gatatcaaa                            339
```

<210> SEQ ID NO 661
<211> LENGTH: 113
<212> TYPE: PRT
<213> ORGANISM: Artificial Sequence
<220> FEATURE:
<223> OTHER INFORMATION: Synthetic

<400> SEQUENCE: 661

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Asn Ile Leu Tyr Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Phe Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Arg Thr Phe Gly Gln Gly Thr Lys Val Asp Ile
            100                 105                 110

Lys
```

<210> SEQ ID NO 662
<211> LENGTH: 36
<212> TYPE: DNA
<213> ORGANISM: Artificial Sequence
<220> FEATURE:
<223> OTHER INFORMATION: Synthetic

<400> SEQUENCE: 662

```
cagaatattt tatacacctc aacaataag aactac                                36
```

<210> SEQ ID NO 663
<211> LENGTH: 12
<212> TYPE: PRT
<213> ORGANISM: Artificial Sequence
<220> FEATURE:
<223> OTHER INFORMATION: Synthetic

<400> SEQUENCE: 663

```
Gln Asn Ile Leu Tyr Thr Ser Asn Asn Lys Asn Tyr
 1               5                  10
```

<210> SEQ ID NO 664
<211> LENGTH: 9
<212> TYPE: DNA
<213> ORGANISM: Artificial Sequence
<220> FEATURE:
<223> OTHER INFORMATION: Synthetic

<400> SEQUENCE: 664

-continued

```
tgggcattt                                                                9
```

<210> SEQ ID NO 665
<211> LENGTH: 3
<212> TYPE: PRT
<213> ORGANISM: Artificial Sequence
<220> FEATURE:
<223> OTHER INFORMATION: Synthetic

<400> SEQUENCE: 665

Trp Ala Phe
 1

<210> SEQ ID NO 666
<211> LENGTH: 27
<212> TYPE: DNA
<213> ORGANISM: Artificial Sequence
<220> FEATURE:
<223> OTHER INFORMATION: Synthetic

<400> SEQUENCE: 666

```
cagcaatatt ataatactcc tcggacg                                           27
```

<210> SEQ ID NO 667
<211> LENGTH: 9
<212> TYPE: PRT
<213> ORGANISM: Artificial Sequence
<220> FEATURE:
<223> OTHER INFORMATION: Synthetic

<400> SEQUENCE: 667

Gln Gln Tyr Tyr Asn Thr Pro Arg Thr
 1               5

<210> SEQ ID NO 668
<211> LENGTH: 357
<212> TYPE: DNA
<213> ORGANISM: Artificial Sequence
<220> FEATURE:
<223> OTHER INFORMATION: Synthetic

<400> SEQUENCE: 668

```
cagatcaccl tgaaggagtc gggcccagga ctggtgaagc cttcacagac cctgtccctc       60
acctgcactg tctctgatgg ctccatcaac agtggtggtt cctactggag ctggatccgc      120
cagcacccgg ggaagggcct ggagtggatt gggtacatca atacagtggg ggcgtccac       180
tataacccgt ccctcaagag tcgaatcacc atatcagtgg acacgtctaa gaaccatttc     240
tccctgaaaa tgacctctgt gactgccgcg gacacggccg tgtatttctg tgcgagagca      300
cctggaagtc acacttttga tatctggggc caggggacaa tggtcaccgt ctcttca         357
```

<210> SEQ ID NO 669
<211> LENGTH: 119
<212> TYPE: PRT
<213> ORGANISM: Artificial Sequence
<220> FEATURE:
<223> OTHER INFORMATION: Synthetic

<400> SEQUENCE: 669

Gln Ile Thr Leu Lys Glu Ser Gly Pro Gly Leu Val Lys Pro Ser Gln
 1               5                  10                  15

Thr Leu Ser Leu Thr Cys Thr Val Ser Asp Gly Ser Ile Asn Ser Gly
                20                  25                  30

Gly Ser Tyr Trp Ser Trp Ile Arg Gln His Pro Gly Lys Gly Leu Glu

```
            35                  40                  45
Trp Ile Gly Tyr Ile Lys Tyr Ser Gly Gly Val His Tyr Asn Pro Ser
     50                  55                  60

Leu Lys Ser Arg Ile Thr Ile Ser Val Asp Thr Ser Lys Asn His Phe
65                  70                  75                  80

Ser Leu Lys Met Thr Ser Val Thr Ala Ala Asp Thr Ala Val Tyr Phe
                85                  90                  95

Cys Ala Arg Ala Pro Gly Ser His Thr Phe Asp Ile Trp Gly Gln Gly
            100                 105                 110

Thr Met Val Thr Val Ser Ser
        115

<210> SEQ ID NO 670
<211> LENGTH: 30
<212> TYPE: DNA
<213> ORGANISM: Artificial Sequence
<220> FEATURE:
<223> OTHER INFORMATION: Synthetic

<400> SEQUENCE: 670
gatggctcca tcaacagtgg tggttcctac                                    30

<210> SEQ ID NO 671
<211> LENGTH: 10
<212> TYPE: PRT
<213> ORGANISM: Artificial Sequence
<220> FEATURE:
<223> OTHER INFORMATION: Synthetic

<400> SEQUENCE: 671

Asp Gly Ser Ile Asn Ser Gly Gly Ser Tyr
1               5                   10

<210> SEQ ID NO 672
<211> LENGTH: 21
<212> TYPE: DNA
<213> ORGANISM: Artificial Sequence
<220> FEATURE:
<223> OTHER INFORMATION: Synthetic

<400> SEQUENCE: 672
atcaaataca gtgggggcgt c                                             21

<210> SEQ ID NO 673
<211> LENGTH: 7
<212> TYPE: PRT
<213> ORGANISM: Artificial Sequence
<220> FEATURE:
<223> OTHER INFORMATION: Synthetic

<400> SEQUENCE: 673

Ile Lys Tyr Ser Gly Gly Val
1               5

<210> SEQ ID NO 674
<211> LENGTH: 33
<212> TYPE: DNA
<213> ORGANISM: Artificial Sequence
<220> FEATURE:
<223> OTHER INFORMATION: Synthetic

<400> SEQUENCE: 674
gcgagagcac ctggaagtca cactttgat atc                                 33
```

<210> SEQ ID NO 675
<211> LENGTH: 11
<212> TYPE: PRT
<213> ORGANISM: Artificial Sequence
<220> FEATURE:
<223> OTHER INFORMATION: Synthetic

<400> SEQUENCE: 675

Ala Arg Ala Pro Gly Ser His Thr Phe Asp Ile
1               5                   10

<210> SEQ ID NO 676
<211> LENGTH: 324
<212> TYPE: DNA
<213> ORGANISM: Artificial Sequence
<220> FEATURE:
<223> OTHER INFORMATION: Synthetic

<400> SEQUENCE: 676
gatattgtga tgactcagtc tccaggcacc ctgtctttgt ctccagggga aagagccacc       60
ctctcctgca gggccagtca gagtgttagc aacaactact tagcctggta ccagcagaaa      120
cctggccagg ctcccagact cctcatctat ggtacatcca atagggtcag tggcatccca      180
gacaggttca gtggcagtgg gtctgggaca gacttcactc tcaccatcag cagactggag      240
cctgaagatt ttgaactata ttattgtcag cagtatagta ggtcaccgat caccttcggc      300
caagggacac gactggagat taaa                                             324

<210> SEQ ID NO 677
<211> LENGTH: 108
<212> TYPE: PRT
<213> ORGANISM: Artificial Sequence
<220> FEATURE:
<223> OTHER INFORMATION: Synthetic

<400> SEQUENCE: 677

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Thr Ser Asn Arg Val Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Glu Leu Tyr Tyr Cys Gln Gln Tyr Ser Arg Ser Pro
                85                  90                  95

Ile Thr Phe Gly Gln Gly Thr Arg Leu Glu Ile Lys
            100                 105

<210> SEQ ID NO 678
<211> LENGTH: 21
<212> TYPE: DNA
<213> ORGANISM: Artificial Sequence
<220> FEATURE:
<223> OTHER INFORMATION: Synthetic

<400> SEQUENCE: 678
cagagtgtta gcaacaacta c                                                 21

```
<210> SEQ ID NO 679
<211> LENGTH: 7
<212> TYPE: PRT
<213> ORGANISM: Artificial Sequence
<220> FEATURE:
<223> OTHER INFORMATION: Synthetic

<400> SEQUENCE: 679

Gln Ser Val Ser Asn Asn Tyr
  1               5

<210> SEQ ID NO 680
<211> LENGTH: 9
<212> TYPE: DNA
<213> ORGANISM: Artificial Sequence
<220> FEATURE:
<223> OTHER INFORMATION: Synthetic

<400> SEQUENCE: 680 ggtacatcc                                                             9

<210> SEQ ID NO 681
<211> LENGTH: 3
<212> TYPE: PRT
<213> ORGANISM: Artificial Sequence
<220> FEATURE:
<223> OTHER INFORMATION: Synthetic

<400> SEQUENCE: 681

Gly Thr Ser
  1

<210> SEQ ID NO 682
<211> LENGTH: 27
<212> TYPE: DNA
<213> ORGANISM: Artificial Sequence
<220> FEATURE:
<223> OTHER INFORMATION: Synthetic

<400> SEQUENCE: 682
cagcagtata gtaggtcacc gatcacc                                         27

<210> SEQ ID NO 683
<211> LENGTH: 9
<212> TYPE: PRT
<213> ORGANISM: Artificial Sequence
<220> FEATURE:
<223> OTHER INFORMATION: Synthetic

<400> SEQUENCE: 683

Gln Gln Tyr Ser Arg Ser Pro Ile Thr
  1               5

<210> SEQ ID NO 684
<211> LENGTH: 360
<212> TYPE: DNA
<213> ORGANISM: Artificial Sequence
<220> FEATURE:
<223> OTHER INFORMATION: Synthetic

<400> SEQUENCE: 684
gaggtgcagc tggtgcagtc tgggggaggc ttggtacaac ctggggggtc cctgagactc      60
tcctgtgcag cctctggatt cacctttaac aactttgcca tgacctgggt ccgccaggct     120
ccagggaagg gcctggagtg gtctcaact attagtggta gtggcgttga cacatactgc     180
gcagactccg tgaagggccg gttcaccatc tccagagaca attccaagaa cacactgtat     240
```

```
ctgcaaatga acagcctgag agccgaggac acggccgtat attactgtgc gaaagatggc      300
gccttctata gtggctacga acactactgg ggccagggaa caatggtcac cgtctcctca      360
```

<210> SEQ ID NO 685
<211> LENGTH: 120
<212> TYPE: PRT
<213> ORGANISM: Artificial Sequence
<220> FEATURE:
<223> OTHER INFORMATION: Synthetic

<400> SEQUENCE: 685

```
Glu Val Gln Leu Val Gln Ser Gly Gly Gly Leu Val Gln Pro Gly Gly
  1               5                  10                  15

Ser Leu Arg Leu Ser Cys Ala Ala Ser Gly Phe Thr Phe Asn Asn Phe
             20                  25                  30

Ala Met Thr Trp Val Arg Gln Ala Pro Gly Lys Gly Leu Glu Trp Val
         35                  40                  45

Ser Thr Ile Ser Gly Ser Gly Val Asp Thr Tyr Cys Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Ala Phe Tyr Ser Gly Tyr Glu His Tyr Trp Gly Gln
            100                 105                 110

Gly Thr Met Val Thr Val Ser Ser
        115                 120
```

<210> SEQ ID NO 686
<211> LENGTH: 24
<212> TYPE: DNA
<213> ORGANISM: Artificial Sequence
<220> FEATURE:
<223> OTHER INFORMATION: Synthetic

<400> SEQUENCE: 686

```
ggattcacct ttaacaactt tgcc                                              24
```

<210> SEQ ID NO 687
<211> LENGTH: 8
<212> TYPE: PRT
<213> ORGANISM: Artificial Sequence
<220> FEATURE:
<223> OTHER INFORMATION: Synthetic

<400> SEQUENCE: 687

```
Gly Phe Thr Phe Asn Asn Phe Ala
  1               5
```

<210> SEQ ID NO 688
<211> LENGTH: 24
<212> TYPE: DNA
<213> ORGANISM: Artificial Sequence
<220> FEATURE:
<223> OTHER INFORMATION: Synthetic

<400> SEQUENCE: 688

```
attagtggta gtggcgttga caca                                              24
```

<210> SEQ ID NO 689
<211> LENGTH: 8

```
<212> TYPE: PRT
<213> ORGANISM: Artificial Sequence
<220> FEATURE:
<223> OTHER INFORMATION: Synthetic

<400> SEQUENCE: 689

Ile Ser Gly Ser Gly Val Asp Thr
  1               5

<210> SEQ ID NO 690
<211> LENGTH: 39
<212> TYPE: DNA
<213> ORGANISM: Artificial Sequence
<220> FEATURE:
<223> OTHER INFORMATION: Synthetic

<400> SEQUENCE: 690
gcgaaagatg gcgccttcta tagtggctac gaacactac                              39

<210> SEQ ID NO 691
<211> LENGTH: 13
<212> TYPE: PRT
<213> ORGANISM: Artificial Sequence
<220> FEATURE:
<223> OTHER INFORMATION: Synthetic

<400> SEQUENCE: 691

Ala Lys Asp Gly Ala Phe Tyr Ser Gly Tyr Glu His Tyr
  1               5                  10

<210> SEQ ID NO 692
<211> LENGTH: 324
<212> TYPE: DNA
<213> ORGANISM: Artificial Sequence
<220> FEATURE:
<223> OTHER INFORMATION: Synthetic

<400> SEQUENCE: 692
gaaacgacac tcacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtacatcca cagggcctc tggcatccca        180 gacaggctca ttggcagtgg gtctgggaca gacttcactc tcaccatcag cagactggag       240
tctgaagatt ttgcagtgta ttactgtcag cagtatggta gctcacctcg acgttcggc        300 caagggacca agtggatat caaa                                               324

<210> SEQ ID NO 693
<211> LENGTH: 108
<212> TYPE: PRT
<213> ORGANISM: Artificial Sequence
<220> FEATURE:
<223> OTHER INFORMATION: Synthetic

<400> SEQUENCE: 693

Glu Thr Thr Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Thr Ser Asn Arg Ala Ser Gly Ile Pro Asp Arg Leu Ile
         50                  55                  60
```

```
Gly Ser Gly Ser Gly Thr Asp Phe Thr Leu Thr Ile Ser Arg Leu Glu
 65                  70                  75                  80

Ser Glu Asp Phe Ala Val Tyr Tyr Cys Gln Gln Tyr Gly Ser Ser Pro
                 85                  90                  95

Arg Thr Phe Gly Gln Gly Thr Lys Val Asp Ile Lys
            100                 105
```

<210> SEQ ID NO 694
<211> LENGTH: 21
<212> TYPE: DNA
<213> ORGANISM: Artificial Sequence
<220> FEATURE:
<223> OTHER INFORMATION: Synthetic

<400> SEQUENCE: 694
cagagtgtta gcagcagcta c                                       21

<210> SEQ ID NO 695
<211> LENGTH: 7
<212> TYPE: PRT
<213> ORGANISM: Artificial Sequence
<220> FEATURE:
<223> OTHER INFORMATION: Synthetic

<400> SEQUENCE: 695

```
Gln Ser Val Ser Ser Ser Tyr
 1               5
```

<210> SEQ ID NO 696
<211> LENGTH: 9
<212> TYPE: DNA
<213> ORGANISM: Artificial Sequence
<220> FEATURE:
<223> OTHER INFORMATION: Synthetic

<400> SEQUENCE: 696 ggtacatcc                                                      9

<210> SEQ ID NO 697
<211> LENGTH: 3
<212> TYPE: PRT
<213> ORGANISM: Artificial Sequence
<220> FEATURE:
<223> OTHER INFORMATION: Synthetic

<400> SEQUENCE: 697

```
Gly Thr Ser
 1
```

<210> SEQ ID NO 698
<211> LENGTH: 27
<212> TYPE: DNA
<213> ORGANISM: Artificial Sequence
<220> FEATURE:
<223> OTHER INFORMATION: Synthetic

<400> SEQUENCE: 698
cagcagtatg gtagctcacc tcggacg                                  27

<210> SEQ ID NO 699
<211> LENGTH: 9
<212> TYPE: PRT
<213> ORGANISM: Artificial Sequence
<220> FEATURE:
<223> OTHER INFORMATION: Synthetic

<400> SEQUENCE: 699

Gln Gln Tyr Gly Ser Ser Pro Arg Thr
1               5

<210> SEQ ID NO 700
<211> LENGTH: 363
<212> TYPE: DNA
<213> ORGANISM: Artificial Sequence
<220> FEATURE:
<223> OTHER INFORMATION: Synthetic

<400> SEQUENCE: 700

```
gaggtgcagc tggtgcagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa catgctgtat     240
ctgcaaatga acagcctgag agccgaggac acggctgtgt attactgtgc ggcttacgat     300
attttgattg gttattcccc ggttgactac tggggccagg gaaccctggt caccgtctcc     360
tca                                                                  363
```

<210> SEQ ID NO 701
<211> LENGTH: 121
<212> TYPE: PRT
<213> ORGANISM: Artificial Sequence
<220> FEATURE:
<223> OTHER INFORMATION: Synthetic

<400> SEQUENCE: 701

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Ala Tyr Asp Ile Leu Ile Gly Tyr Ser Pro Val Asp Tyr Trp Gly
            100                 105                 110

Gln Gly Thr Leu Val Thr Val Ser Ser
        115                 120

<210> SEQ ID NO 702
<211> LENGTH: 24
<212> TYPE: DNA
<213> ORGANISM: Artificial Sequence
<220> FEATURE:
<223> OTHER INFORMATION: Synthetic

<400> SEQUENCE: 702

```
ggattcacct tcagtagcta tggc                                            24
```

<210> SEQ ID NO 703
<211> LENGTH: 8
<212> TYPE: PRT

<213> ORGANISM: Artificial Sequence
<220> FEATURE:
<223> OTHER INFORMATION: Synthetic

<400> SEQUENCE: 703

Gly Phe Thr Phe Ser Ser Tyr Gly
 1               5

<210> SEQ ID NO 704
<211> LENGTH: 24
<212> TYPE: DNA
<213> ORGANISM: Artificial Sequence
<220> FEATURE:
<223> OTHER INFORMATION: Synthetic

<400> SEQUENCE: 704
atatggtatg atggaagtaa taaa                                          24

<210> SEQ ID NO 705
<211> LENGTH: 8
<212> TYPE: PRT
<213> ORGANISM: Artificial Sequence
<220> FEATURE:
<223> OTHER INFORMATION: Synthetic

<400> SEQUENCE: 705

Ile Trp Tyr Asp Gly Ser Asn Lys
 1               5

<210> SEQ ID NO 706
<211> LENGTH: 42
<212> TYPE: DNA
<213> ORGANISM: Artificial Sequence
<220> FEATURE:
<223> OTHER INFORMATION: Synthetic

<400> SEQUENCE: 706
gcggcttacg atattttgat tggttattcc ccggttgact ac                       42

<210> SEQ ID NO 707
<211> LENGTH: 14
<212> TYPE: PRT
<213> ORGANISM: Artificial Sequence
<220> FEATURE:
<223> OTHER INFORMATION: Synthetic

<400> SEQUENCE: 707

Ala Ala Tyr Asp Ile Leu Ile Gly Tyr Ser Pro Val Asp Tyr
 1               5                  10

<210> SEQ ID NO 708
<211> LENGTH: 318
<212> TYPE: DNA
<213> ORGANISM: Artificial Sequence
<220> FEATURE:
<223> OTHER INFORMATION: Synthetic

<400> SEQUENCE: 708
gatattgtga tgacccagtc tccagccacc ctgtctgtgt ctccagggga aagagccacc    60
ctctcctgca gggccagtca gactgttagt agcaacttag cctggttcca gcagaaacct   120
ggccaggctc ccagactcct catctatgat gcatccacca gggccactgg tatcccagcc   180
aggttcagtg gcagtgggtc tgggacagaa ttcactctca ccatcagcag cctgcagtct   240
gaagattttg cagtttatta ctgtcagcag tataataact ggtacacttt tggccagggg   300
accaagctgg agatcaaa                                                318

<210> SEQ ID NO 709
<211> LENGTH: 106
<212> TYPE: PRT
<213> ORGANISM: Artificial Sequence
<220> FEATURE:
<223> OTHER INFORMATION: Synthetic

<400> SEQUENCE: 709

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Ser Ser Asn
            20                  25                  30

Leu Ala Trp Phe Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Tyr Thr
                85                  90                  95

Phe Gly Gln Gly Thr Lys Leu Glu Ile Lys
            100                 105

<210> SEQ ID NO 710
<211> LENGTH: 18
<212> TYPE: DNA
<213> ORGANISM: Artificial Sequence
<220> FEATURE:
<223> OTHER INFORMATION: Synthetic

<400> SEQUENCE: 710
cagactgtta gtagcaac                                                18

<210> SEQ ID NO 711
<211> LENGTH: 6
<212> TYPE: PRT
<213> ORGANISM: Artificial Sequence
<220> FEATURE:
<223> OTHER INFORMATION: Synthetic

<400> SEQUENCE: 711

Gln Thr Val Ser Ser Asn
1               5

<210> SEQ ID NO 712
<211> LENGTH: 9
<212> TYPE: DNA
<213> ORGANISM: Artificial Sequence
<220> FEATURE:
<223> OTHER INFORMATION: Synthetic

<400> SEQUENCE: 712 gatgcatcc                                                          9

<210> SEQ ID NO 713
<211> LENGTH: 3
<212> TYPE: PRT
<213> ORGANISM: Artificial Sequence
<220> FEATURE:
<223> OTHER INFORMATION: Synthetic

<400> SEQUENCE: 713

Asp Ala Ser
 1

<210> SEQ ID NO 714
<211> LENGTH: 24
<212> TYPE: DNA
<213> ORGANISM: Artificial Sequence
<220> FEATURE:
<223> OTHER INFORMATION: Synthetic

<400> SEQUENCE: 714
cagcagtata ataactggta cact                                            24

<210> SEQ ID NO 715
<211> LENGTH: 8
<212> TYPE: PRT
<213> ORGANISM: Artificial Sequence
<220> FEATURE:
<223> OTHER INFORMATION: Synthetic

<400> SEQUENCE: 715

Gln Gln Tyr Asn Asn Trp Tyr Thr
 1               5

<210> SEQ ID NO 716
<211> LENGTH: 357
<212> TYPE: DNA
<213> ORGANISM: Artificial Sequence
<220> FEATURE:
<223> OTHER INFORMATION: Synthetic

<400> SEQUENCE: 716
gaggtgcagc tggtgcagtc gggcccagga ctggtgaagc cttcacagac cctgtccctc      60
acctgcactg tctctggtgg ctccattacc agtggtggtt actactggac ctggatccgc     120
cagcacccag ggaagggcct ggaatggatt ggatacatca aatttagtgg aaacacctac     180
tacaacccgt ccctcaggag tcgagtcacc atatcacttg acacgtctaa gaatcagttc     240
tccctgaata tgacctctgt gactgccgcg gacacggccg tgtattattg cgagagca      300 cctggaagtc ataactttga catctggggc caagggacaa tggtcaccgt ctcttca       357

<210> SEQ ID NO 717
<211> LENGTH: 119
<212> TYPE: PRT
<213> ORGANISM: Artificial Sequence
<220> FEATURE:
<223> OTHER INFORMATION: Synthetic

<400> SEQUENCE: 717

Glu Val Gln Leu Val Gln Ser Gly Pro Gly Leu Val Lys Pro Ser Gln
 1               5                  10                  15

Thr Leu Ser Leu Thr Cys Thr Val Ser Gly Gly Ser Ile Thr Ser Gly
            20                  25                  30

Gly Tyr Tyr Trp Thr Trp Ile Arg Gln His Pro Gly Lys Gly Leu Glu
        35                  40                  45

Trp Ile Gly Tyr Ile Lys Phe Ser Gly Asn Thr Tyr Tyr Asn Pro Ser
    50                  55                  60

Leu Arg Ser Arg Val Thr Ile Ser Leu Asp Thr Ser Lys Asn Gln Phe
65                  70                  75                  80

Ser Leu Asn Met Thr Ser Val Thr Ala Ala Asp Thr Ala Val Tyr Tyr
                85                  90                  95

```
Cys Ala Arg Ala Pro Gly Ser His Asn Phe Asp Ile Trp Gly Gln Gly
            100                 105                 110

Thr Met Val Thr Val Ser Ser
        115

<210> SEQ ID NO 718
<211> LENGTH: 30
<212> TYPE: DNA
<213> ORGANISM: Artificial Sequence
<220> FEATURE:
<223> OTHER INFORMATION: Synthetic

<400> SEQUENCE: 718
ggtggctcca ttaccagtgg tggttactac                                      30

<210> SEQ ID NO 719
<211> LENGTH: 10
<212> TYPE: PRT
<213> ORGANISM: Artificial Sequence
<220> FEATURE:
<223> OTHER INFORMATION: Synthetic

<400> SEQUENCE: 719

Gly Gly Ser Ile Thr Ser Gly Gly Tyr Tyr
 1               5                  10

<210> SEQ ID NO 720
<211> LENGTH: 21
<212> TYPE: DNA
<213> ORGANISM: Artificial Sequence
<220> FEATURE:
<223> OTHER INFORMATION: Synthetic

<400> SEQUENCE: 720
atcaaattta gtgggaacac c                                               21

<210> SEQ ID NO 721
<211> LENGTH: 7
<212> TYPE: PRT
<213> ORGANISM: Artificial Sequence
<220> FEATURE:
<223> OTHER INFORMATION: Synthetic

<400> SEQUENCE: 721

Ile Lys Phe Ser Gly Asn Thr
 1               5

<210> SEQ ID NO 722
<211> LENGTH: 33
<212> TYPE: DNA
<213> ORGANISM: Artificial Sequence
<220> FEATURE:
<223> OTHER INFORMATION: Synthetic

<400> SEQUENCE: 722
gcgagagcac ctggaagtca taactttgac atc                                  33

<210> SEQ ID NO 723
<211> LENGTH: 11
<212> TYPE: PRT
<213> ORGANISM: Artificial Sequence
<220> FEATURE:
<223> OTHER INFORMATION: Synthetic

<400> SEQUENCE: 723

Ala Arg Ala Pro Gly Ser His Asn Phe Asp Ile
 1               5                  10
```

<210> SEQ ID NO 724
<211> LENGTH: 324
<212> TYPE: DNA
<213> ORGANISM: Artificial Sequence
<220> FEATURE:
<223> OTHER INFORMATION: Synthetic

<400> SEQUENCE: 724

```
gccatccggt tgacccagtc tccagacacc ctgtctttgt ctccagggga aagagccacc     60
ctctcctgca gggccagtgt gagtattagt aataactatt tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag aagactggag    240
tctgcagatt ttgcaccgta ttactgtcag caatatagta ggtcaccgat caccttcggc    300
caagggacac gactggagat taaa                                           324
```

<210> SEQ ID NO 725
<211> LENGTH: 108
<212> TYPE: PRT
<213> ORGANISM: Artificial Sequence
<220> FEATURE:
<223> OTHER INFORMATION: Synthetic

<400> SEQUENCE: 725

Ala Ile Arg Leu Thr Gln Ser Pro Asp Thr Leu Ser Leu Ser Pro Gly
1               5                   10                  15
Glu Arg Ala Thr Leu Ser Cys Arg Ala Ser Val Ser Ile Ser Asn Asn
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Arg Arg Leu Glu
65                  70                  75                  80
Ser Ala Asp Phe Ala Pro Tyr Tyr Cys Gln Gln Tyr Ser Arg Ser Pro
                85                  90                  95
Ile Thr Phe Gly Gln Gly Thr Arg Leu Glu Ile Lys
            100                 105

<210> SEQ ID NO 726
<211> LENGTH: 21
<212> TYPE: DNA
<213> ORGANISM: Artificial Sequence
<220> FEATURE:
<223> OTHER INFORMATION: Synthetic

<400> SEQUENCE: 726

```
gtgagtatta gtaataacta t                                               21
```

<210> SEQ ID NO 727
<211> LENGTH: 7
<212> TYPE: PRT
<213> ORGANISM: Artificial Sequence
<220> FEATURE:
<223> OTHER INFORMATION: Synthetic

<400> SEQUENCE: 727

Val Ser Ile Ser Asn Asn Tyr
1               5

<210> SEQ ID NO 728
<211> LENGTH: 9
<212> TYPE: DNA
<213> ORGANISM: Artificial Sequence
<220> FEATURE:
<223> OTHER INFORMATION: Synthetic

<400> SEQUENCE: 728 ggtgcatcc                                                                9

<210> SEQ ID NO 729
<211> LENGTH: 3
<212> TYPE: PRT
<213> ORGANISM: Artificial Sequence
<220> FEATURE:
<223> OTHER INFORMATION: Synthetic

<400> SEQUENCE: 729

Gly Ala Ser
 1

<210> SEQ ID NO 730
<211> LENGTH: 27
<212> TYPE: DNA
<213> ORGANISM: Artificial Sequence
<220> FEATURE:
<223> OTHER INFORMATION: Synthetic

<400> SEQUENCE: 730
cagcaatata gtaggtcacc gatcacc                                            27

<210> SEQ ID NO 731
<211> LENGTH: 9
<212> TYPE: PRT
<213> ORGANISM: Artificial Sequence
<220> FEATURE:
<223> OTHER INFORMATION: Synthetic

<400> SEQUENCE: 731

Gln Gln Tyr Ser Arg Ser Pro Ile Thr
 1               5

<210> SEQ ID NO 732
<211> LENGTH: 357
<212> TYPE: DNA
<213> ORGANISM: Artificial Sequence
<220> FEATURE:
<223> OTHER INFORMATION: Synthetic

<400> SEQUENCE: 732
caggtgcagc tgcaggagtc gggcccagga ctggtgaagc cttcacagac cctgtccctc         60
acctgcactg tctctggtgg ctccatcaac agtgttactt actactggac ctggatccgc        120
cagcacccag ggaggggcct agagtggatt gggtacatca aattcagtgg gagcacctac        180 acaacccgt ccctcaaggg tcgagtcacc atatcagtgg acacgtctaa gaaccaattc         240
tcccttaaaa ttaactctgt gactgccgcg gacacggccg tgttttactg tgcgagagct        300
tctggaagtc atactttga tatctggggc caagggacaa tggtcaccgt ctcctca           357

<210> SEQ ID NO 733
<211> LENGTH: 119
<212> TYPE: PRT
<213> ORGANISM: Artificial Sequence
<220> FEATURE:

<223> OTHER INFORMATION: Synthetic

<400> SEQUENCE: 733

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Val
            20                  25                  30

Thr Tyr Tyr Trp Thr Trp Ile Arg Gln His Pro Gly Arg Gly Leu Glu
        35                  40                  45

Trp Ile Gly Tyr Ile Lys Phe Ser Gly Ser Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Ile Asn Ser Val Thr Ala Ala Asp Thr Ala Val Phe Tyr
                85                  90                  95

Cys Ala Arg Ala Ser Gly Ser His Thr Phe Asp Ile Trp Gly Gln Gly
            100                 105                 110

Thr Met Val Thr Val Ser Ser
        115

<210> SEQ ID NO 734
<211> LENGTH: 30
<212> TYPE: DNA
<213> ORGANISM: Artificial Sequence
<220> FEATURE:
<223> OTHER INFORMATION: Synthetic

<400> SEQUENCE: 734
ggtggctcca tcaacagtgt tacttactac                                    30

<210> SEQ ID NO 735
<211> LENGTH: 10
<212> TYPE: PRT
<213> ORGANISM: Artificial Sequence
<220> FEATURE:
<223> OTHER INFORMATION: Synthetic

<400> SEQUENCE: 735

Gly Gly Ser Ile Asn Ser Val Thr Tyr Tyr
1               5                   10

<210> SEQ ID NO 736
<211> LENGTH: 21
<212> TYPE: DNA
<213> ORGANISM: Artificial Sequence
<220> FEATURE:
<223> OTHER INFORMATION: Synthetic

<400> SEQUENCE: 736
atcaaattca gtgggagcac c                                             21

<210> SEQ ID NO 737
<211> LENGTH: 7
<212> TYPE: PRT
<213> ORGANISM: Artificial Sequence
<220> FEATURE:
<223> OTHER INFORMATION: Synthetic

<400> SEQUENCE: 737

Ile Lys Phe Ser Gly Ser Thr
1               5

<210> SEQ ID NO 738
<211> LENGTH: 33
<212> TYPE: DNA
<213> ORGANISM: Artificial Sequence
<220> FEATURE:
<223> OTHER INFORMATION: Synthetic

<400> SEQUENCE: 738
gcgagagctt ctggaagtca tactttttgat atc    33

<210> SEQ ID NO 739
<211> LENGTH: 11
<212> TYPE: PRT
<213> ORGANISM: Artificial Sequence
<220> FEATURE:
<223> OTHER INFORMATION: Synthetic

<400> SEQUENCE: 739

Ala Arg Ala Ser Gly Ser His Thr Phe Asp Ile
1               5                   10

<210> SEQ ID NO 740
<211> LENGTH: 324
<212> TYPE: DNA
<213> ORGANISM: Artificial Sequence
<220> FEATURE:
<223> OTHER INFORMATION: Synthetic

<400> SEQUENCE: 740
gaaacgacac tcacgcagtc tccaggcacc ctgtctttgt ctccagggga aagagccacc    60
ctctcctgca gggccagtca gagtgttagc aacagctact tagcctggta ccagcagaaa   120
cctggccagg ctcccaggct cctcatctct ggtgcgtcca gcagggtcac tggcatccca   180
gacaggttca gtggcagtgg gtctgggaca gacttcactc tcaccatcag cagactggag   240
cctgaagatt ttggaatgta ttactgtcag cagtatagta ggtcaccgat caccttcggc   300
caagggacca agctggagat caaa                                          324

<210> SEQ ID NO 741
<211> LENGTH: 108
<212> TYPE: PRT
<213> ORGANISM: Artificial Sequence
<220> FEATURE:
<223> OTHER INFORMATION: Synthetic

<400> SEQUENCE: 741

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Ser Gly Ala Ser Ser Arg Val Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Gly Met Tyr Tyr Cys Gln Gln Tyr Ser Arg Ser Pro
                85                  90                  95

Ile Thr Phe Gly Gln Gly Thr Lys Leu Glu Ile Lys
            100                 105

<210> SEQ ID NO 742

```
<211> LENGTH: 21
<212> TYPE: DNA
<213> ORGANISM: Artificial Sequence
<220> FEATURE:
<223> OTHER INFORMATION: Synthetic

<400> SEQUENCE: 742
cagagtgtta gcaacagcta c                                              21

<210> SEQ ID NO 743
<211> LENGTH: 7
<212> TYPE: PRT
<213> ORGANISM: Artificial Sequence
<220> FEATURE:
<223> OTHER INFORMATION: Synthetic

<400> SEQUENCE: 743

Gln Ser Val Ser Asn Ser Tyr
 1               5

<210> SEQ ID NO 744
<211> LENGTH: 9
<212> TYPE: DNA
<213> ORGANISM: Artificial Sequence
<220> FEATURE:
<223> OTHER INFORMATION: Synthetic

<400> SEQUENCE: 744 ggtgcgtcc                                                             9

<210> SEQ ID NO 745
<211> LENGTH: 3
<212> TYPE: PRT
<213> ORGANISM: Artificial Sequence
<220> FEATURE:
<223> OTHER INFORMATION: Synthetic

<400> SEQUENCE: 745

Gly Ala Ser
 1

<210> SEQ ID NO 746
<211> LENGTH: 27
<212> TYPE: DNA
<213> ORGANISM: Artificial Sequence
<220> FEATURE:
<223> OTHER INFORMATION: Synthetic

<400> SEQUENCE: 746
cagcagtata gtaggtcacc gatcacc                                        27

<210> SEQ ID NO 747
<211> LENGTH: 9
<212> TYPE: PRT
<213> ORGANISM: Artificial Sequence
<220> FEATURE:
<223> OTHER INFORMATION: Synthetic

<400> SEQUENCE: 747

Gln Gln Tyr Ser Arg Ser Pro Ile Thr
 1               5

<210> SEQ ID NO 748
<211> LENGTH: 357
<212> TYPE: DNA
<213> ORGANISM: Artificial Sequence
<220> FEATURE:
```

-continued

```
<223> OTHER INFORMATION: Synthetic

<400> SEQUENCE: 748
gaggtgcagc tggtgcagtc tgggggaggc ttggtacagc ctggcaggtc cctgagactc        60
tcctgtgcag cctctggagt caccttggat gattatgcca tgcactgggt ccggcaagct       120
ccagggaagg gcctggagtg ggtctcaagt attagttgga atagtggtag tataggctat       180
gcggactctg tgaagggccg cttcaccatc tccagagaca acgccaagaa ctccctgtat       240
ctgcaaatga acagtctgag agctgaggac acggccttgt attactgtgc aaaagatggg       300
tggaacccgt actactttga ctattggggc caggaataa cggtcaccgt ctcctca          357

<210> SEQ ID NO 749
<211> LENGTH: 119
<212> TYPE: PRT
<213> ORGANISM: Artificial Sequence
<220> FEATURE:
<223> OTHER INFORMATION: Synthetic

<400> SEQUENCE: 749

Glu Val Gln Leu Val Gln Ser Gly Gly Gly Leu Val Gln Pro Gly Arg
 1               5                  10                  15

Ser Leu Arg Leu Ser Cys Ala Ala Ser Gly Val Thr Leu Asp Asp Tyr
            20                  25                  30

Ala Met His Trp Val Arg Gln Ala Pro Gly Lys Gly Leu Glu Trp Val
        35                  40                  45

Ser Ser Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Trp Asn Pro Tyr Tyr Phe Asp Tyr Trp Gly Gln Gly
            100                 105                 110

Ile Thr Val Thr Val Ser Ser
        115

<210> SEQ ID NO 750
<211> LENGTH: 24
<212> TYPE: DNA
<213> ORGANISM: Artificial Sequence
<220> FEATURE:
<223> OTHER INFORMATION: Synthetic

<400> SEQUENCE: 750
ggagtcacct tggatgatta tgcc                                               24

<210> SEQ ID NO 751
<211> LENGTH: 8
<212> TYPE: PRT
<213> ORGANISM: Artificial Sequence
<220> FEATURE:
<223> OTHER INFORMATION: Synthetic

<400> SEQUENCE: 751

Gly Val Thr Leu Asp Asp Tyr Ala
 1               5

<210> SEQ ID NO 752
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 752
attagttgga atagtggtag tata                                           24

<210> SEQ ID NO 753
<211> LENGTH: 8
<212> TYPE: PRT
<213> ORGANISM: Artificial Sequence
<220> FEATURE:
<223> OTHER INFORMATION: Synthetic

<400> SEQUENCE: 753

Ile Ser Trp Asn Ser Gly Ser Ile
 1               5

<210> SEQ ID NO 754
<211> LENGTH: 36
<212> TYPE: DNA
<213> ORGANISM: Artificial Sequence
<220> FEATURE:
<223> OTHER INFORMATION: Synthetic

<400> SEQUENCE: 754
gcaaaagatg ggtggaaccc gtactacttt gactat                              36

<210> SEQ ID NO 755
<211> LENGTH: 12
<212> TYPE: PRT
<213> ORGANISM: Artificial Sequence
<220> FEATURE:
<223> OTHER INFORMATION: Synthetic

<400> SEQUENCE: 755

Ala Lys Asp Gly Trp Asn Pro Tyr Tyr Phe Asp Tyr
 1               5                  10

<210> SEQ ID NO 756
<211> LENGTH: 321
<212> TYPE: DNA
<213> ORGANISM: Artificial Sequence
<220> FEATURE:
<223> OTHER INFORMATION: Synthetic

<400> SEQUENCE: 756
gacatccagt tgacccagtc tccatcctcc ctgtctgcat ctgtaggaga cagagtcacc     60
atcacttgcc gggcaagtca gggcattaga agtgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctctcac tttcggcgga    300
gggaccaagg tggaaatcaa a                                             321

<210> SEQ ID NO 757
<211> LENGTH: 107
<212> TYPE: PRT
<213> ORGANISM: Artificial Sequence
<220> FEATURE:
<223> OTHER INFORMATION: Synthetic

<400> SEQUENCE: 757

Asp Ile Gln Leu Thr Gln Ser Pro Ser Ser Leu Ser Ala Ser Val Gly
```

```
            1               5                  10                 15
Asp Arg Val Thr Ile Thr Cys Arg Ala Ser Gln Gly Ile Arg Ser Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
            85                  90                  95

Thr Phe Gly Gly Gly Thr Lys Val Glu Ile Lys
            100                 105
```

<210> SEQ ID NO 758
<211> LENGTH: 18
<212> TYPE: DNA
<213> ORGANISM: Artificial Sequence
<220> FEATURE:
<223> OTHER INFORMATION: Synthetic

<400> SEQUENCE: 758
cagggcatta gaagtgat                                              18

<210> SEQ ID NO 759
<211> LENGTH: 6
<212> TYPE: PRT
<213> ORGANISM: Artificial Sequence
<220> FEATURE:
<223> OTHER INFORMATION: Synthetic

<400> SEQUENCE: 759

Gln Gly Ile Arg Ser Asp
 1               5

<210> SEQ ID NO 760
<211> LENGTH: 9
<212> TYPE: DNA
<213> ORGANISM: Artificial Sequence
<220> FEATURE:
<223> OTHER INFORMATION: Synthetic

<400> SEQUENCE: 760 gctgcatcc                                                         9

<210> SEQ ID NO 761
<211> LENGTH: 3
<212> TYPE: PRT
<213> ORGANISM: Artificial Sequence
<220> FEATURE:
<223> OTHER INFORMATION: Synthetic

<400> SEQUENCE: 761

Ala Ala Ser
 1

<210> SEQ ID NO 762
<211> LENGTH: 27
<212> TYPE: DNA
<213> ORGANISM: Artificial Sequence
<220> FEATURE:
<223> OTHER INFORMATION: Synthetic

<400> SEQUENCE: 762

```
ctacagcata atagttaccc tctcact                                              27
```

<210> SEQ ID NO 763
<211> LENGTH: 9
<212> TYPE: PRT
<213> ORGANISM: Artificial Sequence
<220> FEATURE:
<223> OTHER INFORMATION: Synthetic

<400> SEQUENCE: 763

Leu Gln His Asn Ser Tyr Pro Leu Thr
 1               5

<210> SEQ ID NO 764
<211> LENGTH: 357
<212> TYPE: DNA
<213> ORGANISM: Artificial Sequence
<220> FEATURE:
<223> OTHER INFORMATION: Synthetic

<400> SEQUENCE: 764

```
cagatcaccT tgaaggagtc gggcccagga ctggtgaagc cttcacagac cctgtccctc    60
acctgcgccg tctctggtga ctccttcagc agtggtaatt actactggag ctggatccgc   120
caacacccag ggaagggcct ggagtggatt gggtacatca gtacactgg gagcacctac   180 tacaacccgt ccctcaagag tcgagttatt atattagtag acacgtctaa gacccagttc   240
tccctgaagc tgagctctgt gaatgccgcg gacacggccg tgtattactg tgcgagagca   300
cctggaactc atgcttttga tgtttggggc caagggacaa tggtcaccgt ctcctca     357
```

<210> SEQ ID NO 765
<211> LENGTH: 119
<212> TYPE: PRT
<213> ORGANISM: Artificial Sequence
<220> FEATURE:
<223> OTHER INFORMATION: Synthetic

<400> SEQUENCE: 765

Gln Ile Thr Leu Lys Glu Ser Gly Pro Gly Leu Val Lys Pro Ser Gln
 1               5                  10                  15

Thr Leu Ser Leu Thr Cys Ala Val Ser Gly Asp Ser Phe Ser Ser Gly
             20                  25                  30

Asn Tyr Tyr Trp Ser Trp Ile Arg Gln His Pro Gly Lys Gly Leu Glu
         35                  40                  45

Trp Ile Gly Tyr Ile Lys Tyr Thr Gly Ser Thr Tyr Tyr Asn Pro Ser
     50                  55                  60

Leu Lys Ser Arg Val Ile Ile Leu Val Asp Thr Ser Lys Thr Gln Phe
65                  70                  75                  80

Ser Leu Lys Leu Ser Ser Val Asn Ala Ala Asp Thr Ala Val Tyr Tyr
                 85                  90                  95

Cys Ala Arg Ala Pro Gly Thr His Ala Phe Asp Val Trp Gly Gln Gly
            100                 105                 110

Thr Met Val Thr Val Ser Ser
        115

<210> SEQ ID NO 766
<211> LENGTH: 30
<212> TYPE: DNA
<213> ORGANISM: Artificial Sequence
<220> FEATURE:
<223> OTHER INFORMATION: Synthetic

```
<400> SEQUENCE: 766
ggtgactcct tcagcagtgg taattactac                                          30

<210> SEQ ID NO 767
<211> LENGTH: 10
<212> TYPE: PRT
<213> ORGANISM: Artificial Sequence
<220> FEATURE:
<223> OTHER INFORMATION: Synthetic

<400> SEQUENCE: 767

Gly Asp Ser Phe Ser Ser Gly Asn Tyr Tyr
1               5                   10

<210> SEQ ID NO 768
<211> LENGTH: 21
<212> TYPE: DNA
<213> ORGANISM: Artificial Sequence
<220> FEATURE:
<223> OTHER INFORMATION: Synthetic

<400> SEQUENCE: 768
atcaagtaca ctgggagcac c                                                   21

<210> SEQ ID NO 769
<211> LENGTH: 7
<212> TYPE: PRT
<213> ORGANISM: Artificial Sequence
<220> FEATURE:
<223> OTHER INFORMATION: Synthetic

<400> SEQUENCE: 769

Ile Lys Tyr Thr Gly Ser Thr
1               5

<210> SEQ ID NO 770
<211> LENGTH: 33
<212> TYPE: DNA
<213> ORGANISM: Artificial Sequence
<220> FEATURE:
<223> OTHER INFORMATION: Synthetic

<400> SEQUENCE: 770
gcgagagcac ctggaactca tgcttttgat gtt                                      33

<210> SEQ ID NO 771
<211> LENGTH: 11
<212> TYPE: PRT
<213> ORGANISM: Artificial Sequence
<220> FEATURE:
<223> OTHER INFORMATION: Synthetic

<400> SEQUENCE: 771

Ala Arg Ala Pro Gly Thr His Ala Phe Asp Val
1               5                   10

<210> SEQ ID NO 772
<211> LENGTH: 324
<212> TYPE: DNA
<213> ORGANISM: Artificial Sequence
<220> FEATURE:
<223> OTHER INFORMATION: Synthetic

<400> SEQUENCE: 772
gaaacgacac tcacgcagtc tccaggcacc ctgtctttgt ttccagggga aagagccacc         60
```

-continued

```
ctctcctgca gggccagtca gagtgttagc agtagctact tagcctggta ccagcagaaa    120
cctggccagg ctcccaggct cctcatctat ggtgcatcca gcagggccac tggcatccca    180
gacaggttca gtggcagtgg gtctgtgaca gactccactc tcaccatcag cagcctggag    240
cctgaagatt ttgcagtgta ttactgtcag cagtatagta ggtcaccgat caccttcggc    300
caagggacca agctggagat caaa                                           324
```

<210> SEQ ID NO 773
<211> LENGTH: 108
<212> TYPE: PRT
<213> ORGANISM: Artificial Sequence
<220> FEATURE:
<223> OTHER INFORMATION: Synthetic

<400> SEQUENCE: 773

```
Glu Thr Thr Leu Thr Gln Ser Pro Gly Thr Leu Ser Leu Phe Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Val Thr Asp Ser Thr Leu Thr Ile Ser Ser Leu Glu
 65                  70                  75                  80

Pro Glu Asp Phe Ala Val Tyr Tyr Cys Gln Gln Tyr Ser Arg Ser Pro
             85                  90                  95

Ile Thr Phe Gly Gln Gly Thr Lys Leu Glu Ile Lys
        100                 105
```

<210> SEQ ID NO 774
<211> LENGTH: 21
<212> TYPE: DNA
<213> ORGANISM: Artificial Sequence
<220> FEATURE:
<223> OTHER INFORMATION: Synthetic

<400> SEQUENCE: 774

```
cagagtgtta gcagtagcta c                                               21
```

<210> SEQ ID NO 775
<211> LENGTH: 7
<212> TYPE: PRT
<213> ORGANISM: Artificial Sequence
<220> FEATURE:
<223> OTHER INFORMATION: Synthetic

<400> SEQUENCE: 775

```
Gln Ser Val Ser Ser Ser Tyr
  1               5
```

<210> SEQ ID NO 776
<211> LENGTH: 9
<212> TYPE: DNA
<213> ORGANISM: Artificial Sequence
<220> FEATURE:
<223> OTHER INFORMATION: Synthetic

<400> SEQUENCE: 776

```
ggtgcatcc                                                              9
```

<210> SEQ ID NO 777
<211> LENGTH: 3
<212> TYPE: PRT
<213> ORGANISM: Artificial Sequence
<220> FEATURE:
<223> OTHER INFORMATION: Synthetic

<400> SEQUENCE: 777

Gly Ala Ser
 1

<210> SEQ ID NO 778
<211> LENGTH: 27
<212> TYPE: DNA
<213> ORGANISM: Artificial Sequence
<220> FEATURE:
<223> OTHER INFORMATION: Synthetic

<400> SEQUENCE: 778
cagcagtata gtaggtcacc gatcacc                                              27

<210> SEQ ID NO 779
<211> LENGTH: 9
<212> TYPE: PRT
<213> ORGANISM: Artificial Sequence
<220> FEATURE:
<223> OTHER INFORMATION: Synthetic

<400> SEQUENCE: 779

Gln Gln Tyr Ser Arg Ser Pro Ile Thr
 1               5

<210> SEQ ID NO 780
<211> LENGTH: 360
<212> TYPE: DNA
<213> ORGANISM: Artificial Sequence
<220> FEATURE:
<223> OTHER INFORMATION: Synthetic

<400> SEQUENCE: 780
gaagtgcagc tggtgcagtc tgggggagcc ttggtacaac tggggggtc cctgagactc        60 tcctgtgcag cctctggatt caccttaac aactttgcca tgacctgggt ccgccaggct       120
ccagggaagg gcctggagtg gtctcaact attagtggta gtggcgttga cacatactgc       180
gcagactccg tgaagggccg gttcaccatc tccagagaca attccaagaa cacactgtat       240
ctgcaaatga acagcctgag agccgaggac acggccgtat attactgttc gaaagatggc       300
gccttctata gtggctacga aacactactgg ggccagggaa ccacggtcac cgtctcctca       360

<210> SEQ ID NO 781
<211> LENGTH: 120
<212> TYPE: PRT
<213> ORGANISM: Artificial Sequence
<220> FEATURE:
<223> OTHER INFORMATION: Synthetic

<400> SEQUENCE: 781

Glu Val Gln Leu Val Gln Ser Gly Gly Ala Leu Val Gln Pro Gly Gly
 1               5                  10                  15

Ser Leu Arg Leu Ser Cys Ala Ala Ser Gly Phe Thr Phe Asn Asn Phe
             20                  25                  30

Ala Met Thr Trp Val Arg Gln Ala Pro Gly Lys Gly Leu Glu Trp Val
         35                  40                  45

```
Ser Thr Ile Ser Gly Ser Gly Val Asp Thr Tyr Cys Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ser Lys Asp Gly Ala Phe Tyr Ser Gly Tyr Glu His Tyr Trp Gly Gln
            100                 105                 110

Gly Thr Thr Val Thr Val Ser Ser
        115                 120

<210> SEQ ID NO 782
<211> LENGTH: 24
<212> TYPE: DNA
<213> ORGANISM: Artificial Sequence
<220> FEATURE:
<223> OTHER INFORMATION: Synthetic

<400> SEQUENCE: 782
ggattcacct ttaacaactt tgcc                                          24

<210> SEQ ID NO 783
<211> LENGTH: 8
<212> TYPE: PRT
<213> ORGANISM: Artificial Sequence
<220> FEATURE:
<223> OTHER INFORMATION: Synthetic

<400> SEQUENCE: 783

Gly Phe Thr Phe Asn Asn Phe Ala
 1               5

<210> SEQ ID NO 784
<211> LENGTH: 24
<212> TYPE: DNA
<213> ORGANISM: Artificial Sequence
<220> FEATURE:
<223> OTHER INFORMATION: Synthetic

<400> SEQUENCE: 784
attagtggta gtggcgttga caca                                          24

<210> SEQ ID NO 785
<211> LENGTH: 8
<212> TYPE: PRT
<213> ORGANISM: Artificial Sequence
<220> FEATURE:
<223> OTHER INFORMATION: Synthetic

<400> SEQUENCE: 785

Ile Ser Gly Ser Gly Val Asp Thr
 1               5

<210> SEQ ID NO 786
<211> LENGTH: 39
<212> TYPE: DNA
<213> ORGANISM: Artificial Sequence
<220> FEATURE:
<223> OTHER INFORMATION: Synthetic

<400> SEQUENCE: 786
tcgaaagatg gcgccttcta tagtggctac gaacactac                          39

<210> SEQ ID NO 787
```

<211> LENGTH: 13
<212> TYPE: PRT
<213> ORGANISM: Artificial Sequence
<220> FEATURE:
<223> OTHER INFORMATION: Synthetic

<400> SEQUENCE: 787

Ser Lys Asp Gly Ala Phe Tyr Ser Gly Tyr Glu His Tyr
1               5                   10

<210> SEQ ID NO 788
<211> LENGTH: 324
<212> TYPE: DNA
<213> ORGANISM: Artificial Sequence
<220> FEATURE:
<223> OTHER INFORMATION: Synthetic

<400> SEQUENCE: 788
gaaacgacac tcacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtacatcca acagggccac tggcatccca     180
gacaggttca gtggcagtgg gtctgggaca gacttcactc tcaccatcag cagactggag     240
tctgaagatt ttgcagtgta ttactgtcag cagtatggta gctcacctcg gacgttcggc     300
caagggacca aggtggagat caaa                                            324

<210> SEQ ID NO 789
<211> LENGTH: 108
<212> TYPE: PRT
<213> ORGANISM: Artificial Sequence
<220> FEATURE:
<223> OTHER INFORMATION: Synthetic

<400> SEQUENCE: 789

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Ser Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 790
<211> LENGTH: 21
<212> TYPE: DNA
<213> ORGANISM: Artificial Sequence
<220> FEATURE:
<223> OTHER INFORMATION: Synthetic

<400> SEQUENCE: 790
cagagtgtta gcagcagcta c                                                21

<210> SEQ ID NO 791
<211> LENGTH: 7

```
<212> TYPE: PRT
<213> ORGANISM: Artificial Sequence
<220> FEATURE:
<223> OTHER INFORMATION: Synthetic

<400> SEQUENCE: 791

Gln Ser Val Ser Ser Ser Tyr
 1               5

<210> SEQ ID NO 792
<211> LENGTH: 9
<212> TYPE: DNA
<213> ORGANISM: Artificial Sequence
<220> FEATURE:
<223> OTHER INFORMATION: Synthetic

<400> SEQUENCE: 792 ggtacatcc                                                                  9

<210> SEQ ID NO 793
<211> LENGTH: 3
<212> TYPE: PRT
<213> ORGANISM: Artificial Sequence
<220> FEATURE:
<223> OTHER INFORMATION: Synthetic

<400> SEQUENCE: 793

Gly Thr Ser
 1

<210> SEQ ID NO 794
<211> LENGTH: 27
<212> TYPE: DNA
<213> ORGANISM: Artificial Sequence
<220> FEATURE:
<223> OTHER INFORMATION: Synthetic

<400> SEQUENCE: 794
cagcagtatg gtagctcacc tcggacg                                             27

<210> SEQ ID NO 795
<211> LENGTH: 9
<212> TYPE: PRT
<213> ORGANISM: Artificial Sequence
<220> FEATURE:
<223> OTHER INFORMATION: Synthetic

<400> SEQUENCE: 795

Gln Gln Tyr Gly Ser Ser Pro Arg Thr
 1               5

<210> SEQ ID NO 796
<211> LENGTH: 357
<212> TYPE: DNA
<213> ORGANISM: Artificial Sequence
<220> FEATURE:
<223> OTHER INFORMATION: Synthetic

<400> SEQUENCE: 796
gaagtgcagc tggtgcagtc tggacctgag gtgaagaagc ctggggcctc agtgaaggtc         60
tcctgcaagg cttctggtta cacctttacc tactatggta tcagttggat acgacagacc        120
cctggacaag gcttgagtg gatgggatgg atcagcgctt acgatggtaa cacagactat         180
gcacagaagt tccaagacag aatcaccatg accacagaca catcctcgac cacagcctac        240
atggaactga ggagcctgag atctgacgac acggccgtct attactgtgc gaggtatagt        300
```
tggaacaagc actggttcga ccccctgggc agggaacca tggtcaccgt ctcttca    357

<210> SEQ ID NO 797
<211> LENGTH: 119
<212> TYPE: PRT
<213> ORGANISM: Artificial Sequence
<220> FEATURE:
<223> OTHER INFORMATION: Synthetic

<400> SEQUENCE: 797

Glu Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Gly Ile Ser Trp Ile Arg Gln Thr Pro Gly Gln Gly Leu Glu Trp Met
        35                  40                  45

Gly Trp Ile Ser Ala Tyr Asp Gly Asn Thr Asp Tyr Ala Gln Lys Phe
    50                  55                  60

Gln Asp Arg Ile Thr Met Thr Thr Asp Thr Ser Ser Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ser Trp Asn Lys His Trp Phe Asp Pro Trp Gly Gln Gly
            100                 105                 110

Thr Met Val Thr Val Ser Ser
        115

<210> SEQ ID NO 798
<211> LENGTH: 24
<212> TYPE: DNA
<213> ORGANISM: Artificial Sequence
<220> FEATURE:
<223> OTHER INFORMATION: Synthetic

<400> SEQUENCE: 798
ggttacacct ttacctacta tggt                                        24

<210> SEQ ID NO 799
<211> LENGTH: 8
<212> TYPE: PRT
<213> ORGANISM: Artificial Sequence
<220> FEATURE:
<223> OTHER INFORMATION: Synthetic

<400> SEQUENCE: 799

Gly Tyr Thr Phe Thr Tyr Tyr Gly
1               5

<210> SEQ ID NO 800
<211> LENGTH: 24
<212> TYPE: DNA
<213> ORGANISM: Artificial Sequence
<220> FEATURE:
<223> OTHER INFORMATION: Synthetic

<400> SEQUENCE: 800
atcagcgctt acgatggtaa caca                                        24

<210> SEQ ID NO 801
<211> LENGTH: 8
<212> TYPE: PRT
<213> ORGANISM: Artificial Sequence
<220> FEATURE:
<223> OTHER INFORMATION: Synthetic

<400> SEQUENCE: 801

Ile Ser Ala Tyr Asp Gly Asn Thr
1               5

<210> SEQ ID NO 802
<211> LENGTH: 36
<212> TYPE: DNA
<213> ORGANISM: Artificial Sequence
<220> FEATURE:
<223> OTHER INFORMATION: Synthetic

<400> SEQUENCE: 802
gcgaggtata gttggaacaa gcactggttc gacccc                              36

<210> SEQ ID NO 803
<211> LENGTH: 12
<212> TYPE: PRT
<213> ORGANISM: Artificial Sequence
<220> FEATURE:
<223> OTHER INFORMATION: Synthetic

<400> SEQUENCE: 803

Ala Arg Tyr Ser Trp Asn Lys His Trp Phe Asp Pro
1               5                   10

<210> SEQ ID NO 804
<211> LENGTH: 324
<212> TYPE: DNA
<213> ORGANISM: Artificial Sequence
<220> FEATURE:
<223> OTHER INFORMATION: Synthetic

<400> SEQUENCE: 804
gaaattgtga tgacacagtc tccaggcacc ctgtctttgt ctccagggga cagagccacc    60
ctctcctgca gggccagtca gagtgttacc ggcagctact tagcctggta ccagcagaaa   120
cctggccagg ctcccagact cctcatctat ggtgcatcca acagggccac tggcatccca   180
gacaggttca ctggcagtgg gtctgggaca gacttcactc tcaccatcag cagactggag   240
cctgaagatt ttgcagtgta tttctgtcaa cagtctgctt tctcaccgtg gacgttcggc   300
caggggacca aggtggaaat caaa                                          324

<210> SEQ ID NO 805
<211> LENGTH: 108
<212> TYPE: PRT
<213> ORGANISM: Artificial Sequence
<220> FEATURE:
<223> OTHER INFORMATION: Synthetic

<400> SEQUENCE: 805

Glu Ile Val Met Thr Gln Ser Pro Gly Thr Leu Ser Leu Ser Pro Gly
1               5                   10                  15

Asp Arg Ala Thr Leu Ser Cys Arg Ala Ser Gln Ser Val Thr Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Thr
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Phe Cys Gln Gln Ser Ala Phe Ser Pro
             85                  90                  95

Trp Thr Phe Gly Gln Gly Thr Lys Val Glu Ile Lys
            100                 105
```

<210> SEQ ID NO 806
<211> LENGTH: 21
<212> TYPE: DNA
<213> ORGANISM: Artificial Sequence
<220> FEATURE:
<223> OTHER INFORMATION: Synthetic

<400> SEQUENCE: 806
cagagtgtta ccggcagcta c     21

<210> SEQ ID NO 807
<211> LENGTH: 7
<212> TYPE: PRT
<213> ORGANISM: Artificial Sequence
<220> FEATURE:
<223> OTHER INFORMATION: Synthetic

<400> SEQUENCE: 807

```
Gln Ser Val Thr Gly Ser Tyr
 1               5
```

<210> SEQ ID NO 808
<211> LENGTH: 9
<212> TYPE: DNA
<213> ORGANISM: Artificial Sequence
<220> FEATURE:
<223> OTHER INFORMATION: Synthetic

<400> SEQUENCE: 808 ggtgcatcc     9

<210> SEQ ID NO 809
<211> LENGTH: 3
<212> TYPE: PRT
<213> ORGANISM: Artificial Sequence
<220> FEATURE:
<223> OTHER INFORMATION: Synthetic

<400> SEQUENCE: 809

```
Gly Ala Ser
 1
```

<210> SEQ ID NO 810
<211> LENGTH: 27
<212> TYPE: DNA
<213> ORGANISM: Artificial Sequence
<220> FEATURE:
<223> OTHER INFORMATION: Synthetic

<400> SEQUENCE: 810
caacagtctg ctttctcacc gtggacg     27

<210> SEQ ID NO 811
<211> LENGTH: 9
<212> TYPE: PRT
<213> ORGANISM: Artificial Sequence
<220> FEATURE:
<223> OTHER INFORMATION: Synthetic

<400> SEQUENCE: 811

Gln Gln Ser Ala Phe Ser Pro Trp Thr
1               5

<210> SEQ ID NO 812
<211> LENGTH: 357
<212> TYPE: DNA
<213> ORGANISM: Artificial Sequence
<220> FEATURE:
<223> OTHER INFORMATION: Synthetic

<400> SEQUENCE: 812
gaggtgcagc tggtgcagtc tgggggaggc ttggtacagc ctggcaggtc cctgagactc    60
tcctgtgcag cctctggagt caccttggat gattatgcca tgcactgggt ccggcaagct   120
ccagggaagg gcctggagtg ggtctcaagt attagttgga atagtggtag tataggctat   180
gcggactctg tgaagggccg cttcaccatc tccagagaca acgccaagaa ctccctgtat   240
ctgcaaatga acagtctgag agctgaggac acggccttgt attactgtgc aaaagatggg   300
tggaacccgt actactttga ctattggggc caggaaatac cggtcaccgt ctcctca      357

<210> SEQ ID NO 813
<211> LENGTH: 119
<212> TYPE: PRT
<213> ORGANISM: Artificial Sequence
<220> FEATURE:
<223> OTHER INFORMATION: Synthetic

<400> SEQUENCE: 813

Glu Val Gln Leu Val Gln Ser Gly Gly Gly Leu Val Gln Pro Gly Arg
1               5                   10                  15

Ser Leu Arg Leu Ser Cys Ala Ala Ser Gly Val Thr Leu Asp Asp Tyr
            20                  25                  30

Ala Met His Trp Val Arg Gln Ala Pro Gly Lys Gly Leu Glu Trp Val
        35                  40                  45

Ser Ser Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Trp Asn Pro Tyr Tyr Phe Asp Tyr Trp Gly Gln Gly
            100                 105                 110

Ile Pro Val Thr Val Ser Ser
        115

<210> SEQ ID NO 814
<211> LENGTH: 24
<212> TYPE: DNA
<213> ORGANISM: Artificial Sequence
<220> FEATURE:
<223> OTHER INFORMATION: Synthetic

<400> SEQUENCE: 814
ggagtcacct tggatgatta tgcc                                           24

<210> SEQ ID NO 815
<211> LENGTH: 8
<212> TYPE: PRT
<213> ORGANISM: Artificial Sequence
<220> FEATURE:
<223> OTHER INFORMATION: Synthetic

<400> SEQUENCE: 815

Gly Val Thr Leu Asp Asp Tyr Ala
1               5

<210> SEQ ID NO 816
<211> LENGTH: 24
<212> TYPE: DNA
<213> ORGANISM: Artificial Sequence
<220> FEATURE:
<223> OTHER INFORMATION: Synthetic

<400> SEQUENCE: 816
attagttgga atagtggtag tata                                          24

<210> SEQ ID NO 817
<211> LENGTH: 8
<212> TYPE: PRT
<213> ORGANISM: Artificial Sequence
<220> FEATURE:
<223> OTHER INFORMATION: Synthetic

<400> SEQUENCE: 817

Ile Ser Trp Asn Ser Gly Ser Ile
1               5

<210> SEQ ID NO 818
<211> LENGTH: 36
<212> TYPE: DNA
<213> ORGANISM: Artificial Sequence
<220> FEATURE:
<223> OTHER INFORMATION: Synthetic

<400> SEQUENCE: 818
gcaaaagatg ggtggaaccc gtactacttt gactat                             36

<210> SEQ ID NO 819
<211> LENGTH: 12
<212> TYPE: PRT
<213> ORGANISM: Artificial Sequence
<220> FEATURE:
<223> OTHER INFORMATION: Synthetic

<400> SEQUENCE: 819

Ala Lys Asp Gly Trp Asn Pro Tyr Tyr Phe Asp Tyr
1               5                   10

<210> SEQ ID NO 820
<211> LENGTH: 321
<212> TYPE: DNA
<213> ORGANISM: Artificial Sequence
<220> FEATURE:
<223> OTHER INFORMATION: Synthetic

<400> SEQUENCE: 820
gacatccaga tgacccagtc tccatcctcc ctgtctgcat ctgtaggaga cagagtcacc    60
atcacttgcc gggcaagtca gggcattaga agtgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacctatta ctgtctacag cataatagtt accctctcac tttcggcgga   300
gggaccaagc tggagatcaa a                                            321

<210> SEQ ID NO 821

<211> LENGTH: 107
<212> TYPE: PRT
<213> ORGANISM: Artificial Sequence
<220> FEATURE:
<223> OTHER INFORMATION: Synthetic

<400> SEQUENCE: 821

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Ser Asp
            20                  25                  30
Leu Gly Trp Tyr Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Leu
                85                  90                  95
Thr Phe Gly Gly Gly Thr Lys Leu Glu Ile Lys
            100                 105

<210> SEQ ID NO 822
<211> LENGTH: 18
<212> TYPE: DNA
<213> ORGANISM: Artificial Sequence
<220> FEATURE:
<223> OTHER INFORMATION: Synthetic

<400> SEQUENCE: 822
cagggcatta gaagtgat                                                 18

<210> SEQ ID NO 823
<211> LENGTH: 6
<212> TYPE: PRT
<213> ORGANISM: Artificial Sequence
<220> FEATURE:
<223> OTHER INFORMATION: Synthetic

<400> SEQUENCE: 823

Gln Gly Ile Arg Ser Asp
1               5

<210> SEQ ID NO 824
<211> LENGTH: 9
<212> TYPE: DNA
<213> ORGANISM: Artificial Sequence
<220> FEATURE:
<223> OTHER INFORMATION: Synthetic

<400> SEQUENCE: 824 gctgcatcc                                                            9

<210> SEQ ID NO 825
<211> LENGTH: 3
<212> TYPE: PRT
<213> ORGANISM: Artificial Sequence
<220> FEATURE:
<223> OTHER INFORMATION: Synthetic

<400> SEQUENCE: 825

Ala Ala Ser
1

```
<210> SEQ ID NO 826
<211> LENGTH: 27
<212> TYPE: DNA
<213> ORGANISM: Artificial Sequence
<220> FEATURE:
<223> OTHER INFORMATION: Synthetic

<400> SEQUENCE: 826
ctacagcata atagttaccc tctcact                                               27

<210> SEQ ID NO 827
<211> LENGTH: 9
<212> TYPE: PRT
<213> ORGANISM: Artificial Sequence
<220> FEATURE:
<223> OTHER INFORMATION: Synthetic

<400> SEQUENCE: 827

Leu Gln His Asn Ser Tyr Pro Leu Thr
 1               5

<210> SEQ ID NO 828
<211> LENGTH: 357
<212> TYPE: DNA
<213> ORGANISM: Artificial Sequence
<220> FEATURE:
<223> OTHER INFORMATION: Synthetic

<400> SEQUENCE: 828
caggtacagc tgcagcagtc gggcccagga ctggtgaagc cttcacagac cctgtccctc            60
acctgcgctg tctctggtga ctccttcagc agtggtaatt actactggag ctggatccgc           120
caacacccag gaagggcct  ggagtggatt gggtacatca gtacactgg  gagcactac            180 tacaacccgt ccctcaagag tcgagttacc atattagtag acacgtctaa gacccagttc           240
tccctgaagc tgagctctgt gactgccgcg gacacggccg tgtattactg tgcgagagca           300
cctggaactc atgttttga  tgtctggggc caagggacaa tggtcaccgt ctcttca              357

<210> SEQ ID NO 829
<211> LENGTH: 119
<212> TYPE: PRT
<213> ORGANISM: Artificial Sequence
<220> FEATURE:
<223> OTHER INFORMATION: Synthetic

<400> SEQUENCE: 829

Gln Val Gln Leu Gln Gln Ser Gly Pro Gly Leu Val Lys Pro Ser Gln
 1               5                  10                  15

Thr Leu Ser Leu Thr Cys Ala Val Ser Gly Asp Ser Phe Ser Ser Gly
            20                  25                  30

Asn Tyr Tyr Trp Ser Trp Ile Arg Gln His Pro Gly Lys Gly Leu Glu
        35                  40                  45

Trp Ile Gly Tyr Ile Lys Tyr Thr Gly Ser Thr Tyr Tyr Asn Pro Ser
    50                  55                  60

Leu Lys Ser Arg Val Thr Ile Leu Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Ala Pro Gly Thr His Val Phe Asp Val Trp Gly Gln Gly
            100                 105                 110

Thr Met Val Thr Val Ser Ser
        115
```

<210> SEQ ID NO 830
<211> LENGTH: 30
<212> TYPE: DNA
<213> ORGANISM: Artificial Sequence
<220> FEATURE:
<223> OTHER INFORMATION: Synthetic

<400> SEQUENCE: 830
ggtgactcct tcagcagtgg taattactac        30

<210> SEQ ID NO 831
<211> LENGTH: 10
<212> TYPE: PRT
<213> ORGANISM: Artificial Sequence
<220> FEATURE:
<223> OTHER INFORMATION: Synthetic

<400> SEQUENCE: 831

Gly Asp Ser Phe Ser Ser Gly Asn Tyr Tyr
1               5                   10

<210> SEQ ID NO 832
<211> LENGTH: 21
<212> TYPE: DNA
<213> ORGANISM: Artificial Sequence
<220> FEATURE:
<223> OTHER INFORMATION: Synthetic

<400> SEQUENCE: 832
atcaagtaca ctgggagcac c        21

<210> SEQ ID NO 833
<211> LENGTH: 6
<212> TYPE: PRT
<213> ORGANISM: Artificial Sequence
<220> FEATURE:
<223> OTHER INFORMATION: Synthetic

<400> SEQUENCE: 833

Lys Tyr Thr Gly Ser Thr
1               5

<210> SEQ ID NO 834
<211> LENGTH: 33
<212> TYPE: DNA
<213> ORGANISM: Artificial Sequence
<220> FEATURE:
<223> OTHER INFORMATION: Synthetic

<400> SEQUENCE: 834
gcgagagcac ctggaactca tgtttttgat gtc        33

<210> SEQ ID NO 835
<211> LENGTH: 11
<212> TYPE: PRT
<213> ORGANISM: Artificial Sequence
<220> FEATURE:
<223> OTHER INFORMATION: Synthetic

<400> SEQUENCE: 835

Ala Arg Ala Pro Gly Thr His Val Phe Asp Val
1               5                   10

<210> SEQ ID NO 836

```
<211> LENGTH: 324
<212> TYPE: DNA
<213> ORGANISM: Artificial Sequence
<220> FEATURE:
<223> OTHER INFORMATION: Synthetic

<400> SEQUENCE: 836
gacatccagt tgacccagtc tccaggcacc ctgtctttgc ttccagggga aagagccacc    60
ctctcctgca gggccagtca gagtgttagc agtagctatt tagcctggta ccagcagaaa   120
cctggccagg ctcccaggct cctcatctat ggtgcatcca gcagggccac tggcatccca   180
gacaggttca gtggcagtgg gtctgtgaca gacttcactc tcaccatcag cagcctggag   240
cctgaagatt ttgcagtgta ttactgtcag cagtatagta ggtcaccgat caccttcggc   300
caagggacca aggtggagat caaa                                          324

<210> SEQ ID NO 837
<211> LENGTH: 108
<212> TYPE: PRT
<213> ORGANISM: Artificial Sequence
<220> FEATURE:
<223> OTHER INFORMATION: Synthetic

<400> SEQUENCE: 837

Asp Ile Gln Leu Thr Gln Ser Pro Gly Thr Leu Ser Leu Leu Pro Gly
 1               5                  10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Val Thr Asp Phe Thr Leu Thr Ile Ser Ser Leu Glu
65                  70                  75                  80
Pro Glu Asp Phe Ala Val Tyr Tyr Cys Gln Gln Tyr Ser Arg Ser Pro
                85                  90                  95
Ile Thr Phe Gly Gln Gly Thr Lys Val Glu Ile Lys
            100                 105

<210> SEQ ID NO 838
<211> LENGTH: 21
<212> TYPE: DNA
<213> ORGANISM: Artificial Sequence
<220> FEATURE:
<223> OTHER INFORMATION: Synthetic

<400> SEQUENCE: 838
cagagtgtta gcagtagcta t                                              21

<210> SEQ ID NO 839
<211> LENGTH: 7
<212> TYPE: PRT
<213> ORGANISM: Artificial Sequence
<220> FEATURE:
<223> OTHER INFORMATION: Synthetic

<400> SEQUENCE: 839

Gln Ser Val Ser Ser Ser Tyr
 1               5

<210> SEQ ID NO 840
<211> LENGTH: 9
```

<212> TYPE: DNA
<213> ORGANISM: Artificial Sequence
<220> FEATURE:
<223> OTHER INFORMATION: Synthetic

<400> SEQUENCE: 840 ggtgcatcc                                                                         9

<210> SEQ ID NO 841
<211> LENGTH: 3
<212> TYPE: PRT
<213> ORGANISM: Artificial Sequence
<220> FEATURE:
<223> OTHER INFORMATION: Synthetic

<400> SEQUENCE: 841

Gly Ala Ser
 1

<210> SEQ ID NO 842
<211> LENGTH: 27
<212> TYPE: DNA
<213> ORGANISM: Artificial Sequence
<220> FEATURE:
<223> OTHER INFORMATION: Synthetic

<400> SEQUENCE: 842
cagcagtata gtaggtcacc gatcacc                                                    27

<210> SEQ ID NO 843
<211> LENGTH: 9
<212> TYPE: PRT
<213> ORGANISM: Artificial Sequence
<220> FEATURE:
<223> OTHER INFORMATION: Synthetic

<400> SEQUENCE: 843

Gln Gln Tyr Ser Arg Ser Pro Ile Thr
 1               5

<210> SEQ ID NO 844
<211> LENGTH: 363
<212> TYPE: DNA
<213> ORGANISM: Artificial Sequence
<220> FEATURE:
<223> OTHER INFORMATION: Synthetic

<400> SEQUENCE: 844
caggtgcagc tgcaggagtc gggcccagga ctggtgaagc cttcacagac cctgtccctc        60
acctgcactg tctctggtgg ctccatcagc agtggtggtt actactggag ttggatccgc       120
cagcacccag ggaagggcct ggagtggatt gggtacatcc attatagtgg gaacacccac       180
tacaatccga ccctcaagag tcgaattacc atatcagtag acacgtctaa gaaccagttc       240
tcccttgagg tgaactctgt gactgccgcg gacacggccg tatactactg tgcgaggaat       300
atggttcggg gagttcactg gttcgacccc tggggccagg gaaccacggt caccgtctcc       360
tca                                                                     363

<210> SEQ ID NO 845
<211> LENGTH: 121
<212> TYPE: PRT
<213> ORGANISM: Artificial Sequence
<220> FEATURE:
<223> OTHER INFORMATION: Synthetic -continued

<400> SEQUENCE: 845

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile His Tyr Ser Gly Asn Thr His Tyr Asn Pro Thr
    50                  55                  60

Leu Lys Ser Arg Ile Thr Ile Ser Val Asp Thr Ser Lys Asn Gln Phe
65                  70                  75                  80

Ser Leu Glu Val Asn Ser Val Thr Ala Ala Asp Thr Ala Val Tyr Tyr
                85                  90                  95

Cys Ala Arg Asn Met Val Arg Gly Val His Trp Phe Asp Pro Trp Gly
            100                 105                 110

Gln Gly Thr Thr Val Thr Val Ser Ser
        115                 120

<210> SEQ ID NO 846
<211> LENGTH: 30
<212> TYPE: DNA
<213> ORGANISM: Artificial Sequence
<220> FEATURE:
<223> OTHER INFORMATION: Synthetic

<400> SEQUENCE: 846
ggtggctcca tcagcagtgg tggttactac                                    30

<210> SEQ ID NO 847
<211> LENGTH: 10
<212> TYPE: PRT
<213> ORGANISM: Artificial Sequence
<220> FEATURE:
<223> OTHER INFORMATION: Synthetic

<400> SEQUENCE: 847

Gly Gly Ser Ile Ser Ser Gly Gly Tyr Tyr
1               5                   10

<210> SEQ ID NO 848
<211> LENGTH: 21
<212> TYPE: DNA
<213> ORGANISM: Artificial Sequence
<220> FEATURE:
<223> OTHER INFORMATION: Synthetic

<400> SEQUENCE: 848
atccattata gtgggaacac c                                             21

<210> SEQ ID NO 849
<211> LENGTH: 7
<212> TYPE: PRT
<213> ORGANISM: Artificial Sequence
<220> FEATURE:
<223> OTHER INFORMATION: Synthetic

<400> SEQUENCE: 849

Ile His Tyr Ser Gly Asn Thr
1               5

<210> SEQ ID NO 850
<211> LENGTH: 39

<212> TYPE: DNA
<213> ORGANISM: Artificial Sequence
<220> FEATURE:
<223> OTHER INFORMATION: Synthetic

<400> SEQUENCE: 850
gcgaggaata tggttcgggg agttcactgg ttcgacccc                                      39

<210> SEQ ID NO 851
<211> LENGTH: 13
<212> TYPE: PRT
<213> ORGANISM: Artificial Sequence
<220> FEATURE:
<223> OTHER INFORMATION: Synthetic

<400> SEQUENCE: 851

Ala Arg Asn Met Val Arg Gly Val His Trp Phe Asp Pro
 1               5                  10

<210> SEQ ID NO 852
<211> LENGTH: 324
<212> TYPE: DNA
<213> ORGANISM: Artificial Sequence
<220> FEATURE:
<223> OTHER INFORMATION: Synthetic

<400> SEQUENCE: 852
gaaatagtgt tgacacagtc tccaggcacc ctgtctttgt ctccagggga gagagccacc       60
ctcttctgtt gggccagtcg gagtgttagc agcagctact tagcctgta ccagcagaaa       120 cctggccagg ctcccaggct cctcatctct ggtgcatcca gcagggccac tggcatccca      180
gacaggttca gtggcagtgg gtctgggaca gacttcactc tcaccatcag cagactggag      240
cctgaagatt ttgcagtata tttctgtcaa cagtatagta gttcaccgct cactttcggc      300
ggagggacca agctggagat caaa                                              324

<210> SEQ ID NO 853
<211> LENGTH: 108
<212> TYPE: PRT
<213> ORGANISM: Artificial Sequence
<220> FEATURE:
<223> OTHER INFORMATION: Synthetic

<400> SEQUENCE: 853

Glu Ile Val Leu Thr Gln Ser Pro Gly Thr Leu Ser Leu Ser Pro Gly
 1               5                  10                  15

Glu Arg Ala Thr Leu Phe Cys Trp Ala Ser Arg Ser Val Ser Ser Ser
                20                  25                  30

Tyr Leu Ala Trp Tyr Gln Gln Lys Pro Gly Gln Ala Pro Arg Leu Leu
            35                  40                  45

Ile Ser Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
    65                  70                  75                  80

Pro Glu Asp Phe Ala Val Tyr Phe Cys Gln Gln Tyr Ser Ser Ser Pro
                85                  90                  95

Leu Thr Phe Gly Gly Gly Thr Lys Leu Glu Ile Lys
            100                 105

<210> SEQ ID NO 854
<211> LENGTH: 21
<212> TYPE: DNA

```
<213> ORGANISM: Artificial Sequence
<220> FEATURE:
<223> OTHER INFORMATION: Synthetic

<400> SEQUENCE: 854
cggagtgtta gcagcagcta c                                              21

<210> SEQ ID NO 855
<211> LENGTH: 7
<212> TYPE: PRT
<213> ORGANISM: Artificial Sequence
<220> FEATURE:
<223> OTHER INFORMATION: Synthetic

<400> SEQUENCE: 855

Arg Ser Val Ser Ser Ser Tyr
 1               5

<210> SEQ ID NO 856
<211> LENGTH: 9
<212> TYPE: DNA
<213> ORGANISM: Artificial Sequence
<220> FEATURE:
<223> OTHER INFORMATION: Synthetic

<400> SEQUENCE: 856 ggtgcatcc                                                             9

<210> SEQ ID NO 857
<211> LENGTH: 3
<212> TYPE: PRT
<213> ORGANISM: Artificial Sequence
<220> FEATURE:
<223> OTHER INFORMATION: Synthetic

<400> SEQUENCE: 857

Gly Ala Ser
 1

<210> SEQ ID NO 858
<211> LENGTH: 27
<212> TYPE: DNA
<213> ORGANISM: Artificial Sequence
<220> FEATURE:
<223> OTHER INFORMATION: Synthetic

<400> SEQUENCE: 858
caacagtata gtagttcacc gctcact                                        27

<210> SEQ ID NO 859
<211> LENGTH: 9
<212> TYPE: PRT
<213> ORGANISM: Artificial Sequence
<220> FEATURE:
<223> OTHER INFORMATION: Synthetic

<400> SEQUENCE: 859

Gln Gln Tyr Ser Ser Ser Pro Leu Thr
 1               5

<210> SEQ ID NO 860
<211> LENGTH: 357
<212> TYPE: DNA
<213> ORGANISM: Artificial Sequence
<220> FEATURE:
<223> OTHER INFORMATION: Synthetic
```

-continued

<400> SEQUENCE: 860

```
caggtgcagc tgcaggagtc gggcccagga ctggtgaagc cttcacagac cctgtccctc    60
acctgcactg tctctagtga ctccatcagc agtggtaata actactggac ctggatccgc   120
cagcacccag ggaggggcct ggagtggatt gggtacatca atacactgg gagcgcccac   180
tacaacccgt ccctcaagag tcgagtcacc atgtcagtag acacgtctaa gaatcagttc   240
tccctgaaaa tgacctctgt gactgacgcg gacacggccg tgtattattg tgcgagggca   300
cctggaagcc attcttttga tatatggggc cgagggacaa tggtcaccgt ctcctca      357
```

<210> SEQ ID NO 861
<211> LENGTH: 119
<212> TYPE: PRT
<213> ORGANISM: Artificial Sequence
<220> FEATURE:
<223> OTHER INFORMATION: Synthetic

<400> SEQUENCE: 861

```
Gln Val Gln Leu Gln Glu Ser Gly Pro Gly Leu Val Lys Pro Ser Gln
 1               5                  10                  15
Thr Leu Ser Leu Thr Cys Thr Val Ser Ser Asp Ser Ile Ser Ser Gly
            20                  25                  30
Asn Asn Tyr Trp Thr Trp Ile Arg Gln His Pro Gly Arg Gly Leu Glu
        35                  40                  45
Trp Ile Gly Tyr Ile Lys Tyr Thr Gly Ser Ala His Tyr Asn Pro Ser
    50                  55                  60
Leu Lys Ser Arg Val Thr Met Ser Val Asp Thr Ser Lys Asn Gln Phe
65                  70                  75                  80
Ser Leu Lys Met Thr Ser Val Thr Asp Ala Asp Thr Ala Val Tyr Tyr
                85                  90                  95
Cys Ala Arg Ala Pro Gly Ser His Ser Phe Asp Ile Trp Gly Arg Gly
            100                 105                 110
Thr Met Val Thr Val Ser Ser
        115
```

<210> SEQ ID NO 862
<211> LENGTH: 30
<212> TYPE: DNA
<213> ORGANISM: Artificial Sequence
<220> FEATURE:
<223> OTHER INFORMATION: Synthetic

<400> SEQUENCE: 862

```
agtgactcca tcagcagtgg taataactac                                      30
```

<210> SEQ ID NO 863
<211> LENGTH: 10
<212> TYPE: PRT
<213> ORGANISM: Artificial Sequence
<220> FEATURE:
<223> OTHER INFORMATION: Synthetic

<400> SEQUENCE: 863

```
Ser Asp Ser Ile Ser Ser Gly Asn Asn Tyr
 1               5                  10
```

<210> SEQ ID NO 864
<211> LENGTH: 21
<212> TYPE: DNA
<213> ORGANISM: Artificial Sequence
<220> FEATURE:

<223> OTHER INFORMATION: Synthetic

<400> SEQUENCE: 864
atcaaataca ctgggagcgc c                                        21

<210> SEQ ID NO 865
<211> LENGTH: 7
<212> TYPE: PRT
<213> ORGANISM: Artificial Sequence
<220> FEATURE:
<223> OTHER INFORMATION: Synthetic

<400> SEQUENCE: 865

Ile Lys Tyr Thr Gly Ser Ala
 1               5

<210> SEQ ID NO 866
<211> LENGTH: 33
<212> TYPE: DNA
<213> ORGANISM: Artificial Sequence
<220> FEATURE:
<223> OTHER INFORMATION: Synthetic

<400> SEQUENCE: 866
gcgagggcac ctggaagcca ttcttttgat ata                           33

<210> SEQ ID NO 867
<211> LENGTH: 11
<212> TYPE: PRT
<213> ORGANISM: Artificial Sequence
<220> FEATURE:
<223> OTHER INFORMATION: Synthetic

<400> SEQUENCE: 867

Ala Arg Ala Pro Gly Ser His Ser Phe Asp Ile
 1               5                  10

<210> SEQ ID NO 868
<211> LENGTH: 324
<212> TYPE: DNA
<213> ORGANISM: Artificial Sequence
<220> FEATURE:
<223> OTHER INFORMATION: Synthetic

<400> SEQUENCE: 868
gatgttgtga tgacccagtc tccaggcacc ctgttttgt ctccagggga aagagccacc      60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaacatcag cagactggag    240
cctgaagatt ttgcactgta ttactgtcag cagtatagta ggtcaccgat caccttcggc    300
caagggacac gactggagat taaa                                           324

<210> SEQ ID NO 869
<211> LENGTH: 108
<212> TYPE: PRT
<213> ORGANISM: Artificial Sequence
<220> FEATURE:
<223> OTHER INFORMATION: Synthetic

<400> SEQUENCE: 869

Asp Val Val Met Thr Gln Ser Pro Gly Thr Leu Phe Leu Ser Pro Gly
 1               5                  10                  15

-continued

```
Glu Arg Ala Thr Leu Ser Cys Arg Ala Ser Gln Ser Val Ser Ser
        20                  25                  30
Tyr Leu Ala Trp Tyr Gln Gln Lys Pro Gly Gln Ala Pro Arg Leu Leu
    35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Asn Ile Ser Arg Leu Glu
65                  70                  75                  80
Pro Glu Asp Phe Ala Leu Tyr Tyr Cys Gln Gln Tyr Ser Arg Ser Pro
                85                  90                  95
Ile Thr Phe Gly Gln Gly Thr Arg Leu Glu Ile Lys
            100                 105
```

<210> SEQ ID NO 870
<211> LENGTH: 21
<212> TYPE: DNA
<213> ORGANISM: Artificial Sequence
<220> FEATURE:
<223> OTHER INFORMATION: Synthetic

<400> SEQUENCE: 870
cagagtgtta gcagcagcta c    21

<210> SEQ ID NO 871
<211> LENGTH: 7
<212> TYPE: PRT
<213> ORGANISM: Artificial Sequence
<220> FEATURE:
<223> OTHER INFORMATION: Synthetic

<400> SEQUENCE: 871

```
Gln Ser Val Ser Ser Ser Tyr
 1               5
```

<210> SEQ ID NO 872
<211> LENGTH: 9
<212> TYPE: DNA
<213> ORGANISM: Artificial Sequence
<220> FEATURE:
<223> OTHER INFORMATION: Synthetic

<400> SEQUENCE: 872 ggtgcatcc    9

<210> SEQ ID NO 873
<211> LENGTH: 3
<212> TYPE: PRT
<213> ORGANISM: Artificial Sequence
<220> FEATURE:
<223> OTHER INFORMATION: Synthetic

<400> SEQUENCE: 873

```
Gly Ala Ser
 1
```

<210> SEQ ID NO 874
<211> LENGTH: 27
<212> TYPE: DNA
<213> ORGANISM: Artificial Sequence
<220> FEATURE:
<223> OTHER INFORMATION: Synthetic

<400> SEQUENCE: 874
cagcagtata gtaggtcacc gatcacc    27

<210> SEQ ID NO 875
<211> LENGTH: 9
<212> TYPE: PRT
<213> ORGANISM: Artificial Sequence
<220> FEATURE:
<223> OTHER INFORMATION: Synthetic

<400> SEQUENCE: 875

Gln Gln Tyr Ser Arg Ser Pro Ile Thr
 1               5

<210> SEQ ID NO 876
<211> LENGTH: 360
<212> TYPE: DNA
<213> ORGANISM: Artificial Sequence
<220> FEATURE:
<223> OTHER INFORMATION: Synthetic

<400> SEQUENCE: 876
caggtgcagc tggtgcagtc tgggggaggc ttggtacaac ctggggggtc cctaagactc      60
tcctgtgcag cctctggatt cacctctaac aactttgcca tgacctgggt ccgccaggct     120
ccagggaagg gcctggagtg ggtctcaact attagtggta gtggcgttga cacatactgc     180
gcagactccg tgaagggccg gttcaccatc tccagagaca attccaagaa cacactgtat     240
ctgcaaatga acagcctgag agtcgaggac acggccgtat attactgtgc taaagatggc     300
gccttctata gtggctacga acactactgg ggccagggaa ccctggtcac cgtctcctca     360

<210> SEQ ID NO 877
<211> LENGTH: 120
<212> TYPE: PRT
<213> ORGANISM: Artificial Sequence
<220> FEATURE:
<223> OTHER INFORMATION: Synthetic

<400> SEQUENCE: 877

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Ser Asn Asn Phe
            20                  25                  30

Ala Met Thr Trp Val Arg Gln Ala Pro Gly Lys Gly Leu Glu Trp Val
        35                  40                  45

Ser Thr Ile Ser Gly Ser Gly Val Asp Thr Tyr Cys Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Gly Ala Phe Tyr Ser Gly Tyr Glu His Tyr Trp Gly Gln
            100                 105                 110

Gly Thr Leu Val Thr Val Ser Ser
        115                 120

<210> SEQ ID NO 878
<211> LENGTH: 24
<212> TYPE: DNA
<213> ORGANISM: Artificial Sequence
<220> FEATURE:
<223> OTHER INFORMATION: Synthetic

<400> SEQUENCE: 878

```
ggattcacct ctaacaactt tgcc                                            24
```

<210> SEQ ID NO 879
<211> LENGTH: 8
<212> TYPE: PRT
<213> ORGANISM: Artificial Sequence
<220> FEATURE:
<223> OTHER INFORMATION: Synthetic

<400> SEQUENCE: 879

```
Gly Phe Thr Ser Asn Asn Phe Ala
1               5
```

<210> SEQ ID NO 880
<211> LENGTH: 24
<212> TYPE: DNA
<213> ORGANISM: Artificial Sequence
<220> FEATURE:
<223> OTHER INFORMATION: Synthetic

<400> SEQUENCE: 880

```
attagtggta gtggcgttga caca                                            24
```

<210> SEQ ID NO 881
<211> LENGTH: 8
<212> TYPE: PRT
<213> ORGANISM: Artificial Sequence
<220> FEATURE:
<223> OTHER INFORMATION: Synthetic

<400> SEQUENCE: 881

```
Ile Ser Gly Ser Gly Val Asp Thr
1               5
```

<210> SEQ ID NO 882
<211> LENGTH: 39
<212> TYPE: DNA
<213> ORGANISM: Artificial Sequence
<220> FEATURE:
<223> OTHER INFORMATION: Synthetic

<400> SEQUENCE: 882

```
gctaaagatg gcgccttcta tagtggctac gaacactac                            39
```

<210> SEQ ID NO 883
<211> LENGTH: 13
<212> TYPE: PRT
<213> ORGANISM: Artificial Sequence
<220> FEATURE:
<223> OTHER INFORMATION: Synthetic

<400> SEQUENCE: 883

```
Ala Lys Asp Gly Ala Phe Tyr Ser Gly Tyr Glu His Tyr
1               5                   10
```

<210> SEQ ID NO 884
<211> LENGTH: 324
<212> TYPE: DNA
<213> ORGANISM: Artificial Sequence
<220> FEATURE:
<223> OTHER INFORMATION: Synthetic

<400> SEQUENCE: 884

```
gatgttgtga tgacccagtc tccaggcacc ctgtctttgt ctccagggga aagagccacc     60
ctctcctgca gggccagtca gagtgttagc agcagctact tagcctggta ccagcagaaa    120
```

-continued

| | |
|---|---|
| cctggccagg ctcccaggct cctcatctat ggtacatcca acagggcctc tggcatccca | 180 |
| gacaagttca ttggcagtgg gtctgggaca gacttcactc tcaccatcag cagactggag | 240 |
| tctgaagatt ttgcagtgta ttactgtcag cagtatggta gctcacctcg gacgttcggc | 300 |
| caagggacca aagtggatat caaa | 324 |

<210> SEQ ID NO 885
<211> LENGTH: 108
<212> TYPE: PRT
<213> ORGANISM: Artificial Sequence
<220> FEATURE:
<223> OTHER INFORMATION: Synthetic

<400> SEQUENCE: 885

Asp Val Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Asn Arg Ala Ser Gly Ile Pro Asp Lys Phe Ile
    50                  55                  60

Gly Ser Gly Ser Gly Thr Asp Phe Thr Leu Thr Ile Ser Arg Leu Glu
65                  70                  75                  80

Ser Glu Asp Phe Ala Val Tyr Tyr Cys Gln Gln Tyr Gly Ser Ser Pro
                85                  90                  95

Arg Thr Phe Gly Gln Gly Thr Lys Val Asp Ile Lys
            100                 105

<210> SEQ ID NO 886
<211> LENGTH: 21
<212> TYPE: DNA
<213> ORGANISM: Artificial Sequence
<220> FEATURE:
<223> OTHER INFORMATION: Synthetic

<400> SEQUENCE: 886
cagagtgtta gcagcagcta c                                            21

<210> SEQ ID NO 887
<211> LENGTH: 7
<212> TYPE: PRT
<213> ORGANISM: Artificial Sequence
<220> FEATURE:
<223> OTHER INFORMATION: Synthetic

<400> SEQUENCE: 887

Gln Ser Val Ser Ser Ser Tyr
1               5

<210> SEQ ID NO 888
<211> LENGTH: 9
<212> TYPE: DNA
<213> ORGANISM: Artificial Sequence
<220> FEATURE:
<223> OTHER INFORMATION: Synthetic

<400> SEQUENCE: 888 ggtacatcc                                                          9

<210> SEQ ID NO 889

<211> LENGTH: 3
<212> TYPE: PRT
<213> ORGANISM: Artificial Sequence
<220> FEATURE:
<223> OTHER INFORMATION: Synthetic

<400> SEQUENCE: 889

Gly Thr Ser
 1

<210> SEQ ID NO 890
<211> LENGTH: 27
<212> TYPE: DNA
<213> ORGANISM: Artificial Sequence
<220> FEATURE:
<223> OTHER INFORMATION: Synthetic

<400> SEQUENCE: 890
cagcagtatg gtagctcacc tcggacg                                          27

<210> SEQ ID NO 891
<211> LENGTH: 9
<212> TYPE: PRT
<213> ORGANISM: Artificial Sequence
<220> FEATURE:
<223> OTHER INFORMATION: Synthetic

<400> SEQUENCE: 891

Gln Gln Tyr Gly Ser Ser Pro Arg Thr
 1               5

<210> SEQ ID NO 892
<211> LENGTH: 360
<212> TYPE: DNA
<213> ORGANISM: Artificial Sequence
<220> FEATURE:
<223> OTHER INFORMATION: Synthetic

<400> SEQUENCE: 892
caggtgcagc tgcaggagtc cggccccggc ctggtgaagc cctcccagac cctgtccctg      60
acctgcaccg tgtccggcgg ctccatcggc tccggcggct actactggtc ctggatccgg     120
cagcaccccg gcaagggcct ggagtggatc ggctacgtgc actactccgg caacacctac     180
tacaacccct ccctgaagtc ccgggtgacc atctccgtgg acacctccaa gaaccagttc     240
tccctgaagc tgtcctccgt gaccgccgcc gacaccgccg tgtactactg cgcccgggcc     300
cccgggggct accactactt cgcctactgg ggccagggca ccctggtgac cgtgtcctcc     360

<210> SEQ ID NO 893
<211> LENGTH: 120
<212> TYPE: PRT
<213> ORGANISM: Artificial Sequence
<220> FEATURE:
<223> OTHER INFORMATION: Synthetic

<400> SEQUENCE: 893

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Gly Ser Gly
             20                  25                  30

Gly Tyr Tyr Trp Ser Trp Ile Arg Gln His Pro Gly Lys Gly Leu Glu
         35                  40                  45

Trp Ile Gly Tyr Val His Tyr Ser Gly Asn Thr Tyr Tyr Asn Pro Ser
     50                  55                  60

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Pro Arg Gly Tyr His Tyr Phe Ala Tyr Trp Gly Gln
            100                 105                 110

Gly Thr Leu Val Thr Val Ser Ser
        115                 120

<210> SEQ ID NO 894
<211> LENGTH: 324
<212> TYPE: DNA
<213> ORGANISM: Artificial Sequence
<220> FEATURE:
<223> OTHER INFORMATION: Synthetic

<400> SEQUENCE: 894
gagatcgtgc tgacccagtc ccccggcacc ctgtccctgt ccccggcga gcgggccacc      60 ctgtcctgcc gggcctccca gtccgtgtcc tcctcctacc tggcctggta ccagcagaag     120
cccggccagg ccccccggct gctgatctac ggcgcctcct cccgggccac cggcatcccc     180
gaccggttct ccggctccgg ctccggcacc gacttcaccc tgaccatctc ccggctggag     240
cccgaggact tcgccgtgta ctactgccag cagtacggct cctccccct gaccttcggc      300 ggcggcacca aggtggagat caag                                            324

<210> SEQ ID NO 895
<211> LENGTH: 108
<212> TYPE: PRT
<213> ORGANISM: Artificial Sequence
<220> FEATURE:
<223> OTHER INFORMATION: Synthetic

<400> SEQUENCE: 895

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
            100                 105

<210> SEQ ID NO 896
<211> LENGTH: 369
<212> TYPE: DNA
<213> ORGANISM: Artificial Sequence
<220> FEATURE:
<223> OTHER INFORMATION: Synthetic

<400> SEQUENCE: 896
caggtgcagc tggtggagtc cggcggcggc gtggtgcagc ccggccggtc cctgcggctg      60
tcctgcgccg cctccggctt caccttctcc tcctacggca tgcactgggt gcggcaggcc     120
```

```
cccggcaagg gcctggagtg ggtggccgtg ctgtggtacg acggcaccaa caagtactac    180
gccgactccg tgaagggccg gttcaccatc tcccgggaca actccaagaa caccctgtac    240
ctgcagatga actccctgcg ggccgaggac accgccgtgt actactgcgc ccgggaccac    300
gacttccggt ccggctacga gggctggttc gaccccgtgg gccagggcac cctggtgacc    360
gtgtcctcc                                                            369
```

<210> SEQ ID NO 897
<211> LENGTH: 123
<212> TYPE: PRT
<213> ORGANISM: Artificial Sequence
<220> FEATURE:
<223> OTHER INFORMATION: Synthetic

<400> SEQUENCE: 897

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Leu Trp Tyr Asp Gly Thr Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120
```

<210> SEQ ID NO 898
<211> LENGTH: 321
<212> TYPE: DNA
<213> ORGANISM: Artificial Sequence
<220> FEATURE:
<223> OTHER INFORMATION: Synthetic

<400> SEQUENCE: 898

```
gagatcgtgc tgacccagtc ccccgccacc ctgtccctgt ccccggcga gcgggccacc     60
ctgtcctgcc gggcctccca gtccgtgtcc tcctacctgg cctggtacca gcagaagccc    120
ggccaggccc ccggctgct gatctacgac gcctccaacc gggccaccgg catccccgcc    180
cggttctccg gctccggctc cggcaccgac ttcaccctga ccatctcctc cctggagccc    240
gaggacttcg ccgtgtacta ctgccagcac cggtccaact ggccccccac cttcggcggc    300
ggcaccaagg tggagatcaa g                                              321
```

<210> SEQ ID NO 899
<211> LENGTH: 107
<212> TYPE: PRT
<213> ORGANISM: Artificial Sequence
<220> FEATURE:
<223> OTHER INFORMATION: Synthetic

<400> SEQUENCE: 899

```
Glu Ile Val Leu Thr Gln Ser Pro Ala Thr Leu Ser Leu Ser Pro Gly
 1               5                  10                  15
```

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His Arg Ser Asn Trp Pro Pro
                 85                  90                  95

Thr Phe Gly Gly Gly Thr Lys Val Glu Ile Lys
            100                 105

<210> SEQ ID NO 900
<211> LENGTH: 369
<212> TYPE: DNA
<213> ORGANISM: Artificial Sequence
<220> FEATURE:
<223> OTHER INFORMATION: Synthetic

<400> SEQUENCE: 900
caggtgcagc tggtggagtc tgggggaggc gtggtccagc ctggggaggtc cctgagactc      60 tcctgtgcag cgtctggatt caccttcagt agttatggca tgcactgggt ccgccaggct     120
ccaggcaagg ggctggagtg ggtgtcattt ttatggtatg atggaactaa taaaaactat     180
gtagagtccg tgaagggccg attcaccatc tcaagagaca attccaagaa tatgctgtat     240
ctggaaatga acagcctgag agccgaggac acggctgtgt attactgtgc gagagatcac     300
gatttaggaa gtggttatga ggggtggttc gaccccctggg gccagggaac cctggtcacc     360
gtctcctca                                                              369

<210> SEQ ID NO 901
<211> LENGTH: 123
<212> TYPE: PRT
<213> ORGANISM: Artificial Sequence
<220> FEATURE:
<223> OTHER INFORMATION: Synthetic

<400> SEQUENCE: 901

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Phe Leu Trp Tyr Asp Gly Thr Asn Lys Asn Tyr Val Glu Ser Val
 50                  55                  60

Lys Gly Arg Phe Thr Ile Ser Arg Asp Asn Ser Lys Asn Met Leu Tyr
 65                  70                  75                  80

Leu Glu Met Asn Ser Leu Arg Ala Glu Asp Thr Ala Val Tyr Tyr Cys
                 85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
            115                 120

<210> SEQ ID NO 902

<211> LENGTH: 321
<212> TYPE: DNA
<213> ORGANISM: Artificial Sequence
<220> FEATURE:
<223> OTHER INFORMATION: Synthetic

<400> SEQUENCE: 902

```
gaaatagtgt tgacacagtc tccagccacc ctgtctttgt ctccagggga aagagccacc      60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcaacac cgtagcaact ggcctccac tttcggcgga    300
gggaccaagg tggaaatcaa a                                              321
```

<210> SEQ ID NO 903
<211> LENGTH: 107
<212> TYPE: PRT
<213> ORGANISM: Artificial Sequence
<220> FEATURE:
<223> OTHER INFORMATION: Synthetic

<400> SEQUENCE: 903

```
Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Ser Ser Tyr
             20                  25                  30
Leu Ala Trp Tyr Gln Gln Lys Pro Gly Gln Ala Pro Arg Leu Leu Ile
         35                  40                  45
Tyr Asp Ala Ser Asn Arg Ala Thr Gly Ile Pro Ala Arg Phe Ser Gly
     50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln His Arg Ser Asn Trp Pro Pro
                 85                  90                  95
Thr Phe Gly Gly Gly Thr Lys Val Glu Ile Lys
            100                 105
```

<210> SEQ ID NO 904
<211> LENGTH: 363
<212> TYPE: DNA
<213> ORGANISM: Artificial Sequence
<220> FEATURE:
<223> OTHER INFORMATION: Synthetic

<400> SEQUENCE: 904

```
caggtgcagc tgcaggagtc gggcccagga ctggtgaagc cttcacagac cctgtccctc      60
acctgcactg tctctggtgg ctccatcagc agtggtggtt actactggag ttggatccgc    120
cagcacccag ggaagggcct ggagtggatt gggtacatcc attatagtgg gaacacccac    180
tacaatccga ccctcaagag tcgaattacc atatcagtag acacgtctaa gaaccagttc    240
tcccttgagg tgaactctgt gactgccgcg gacacggccg tatactactg tgcgaggaat    300
atggttcggg gagttcactg gttcgacccc tggggccagg gaaccacggt caccgtctcc    360
tca                                                                  363
```

<210> SEQ ID NO 905
<211> LENGTH: 121
<212> TYPE: PRT

<213> ORGANISM: Artificial Sequence
<220> FEATURE:
<223> OTHER INFORMATION: Synthetic

<400> SEQUENCE: 905

```
Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
            20                  25                  30
Gly Tyr Tyr Trp Ser Trp Ile Arg Gln His Pro Gly Lys Gly Leu Glu
        35                  40                  45
Trp Ile Gly Tyr Ile His Tyr Ser Gly Asn Thr His Tyr Asn Pro Thr
    50                  55                  60
Leu Lys Ser Arg Ile Thr Ile Ser Val Asp Thr Ser Lys Asn Gln Phe
65                  70                  75                  80
Ser Leu Glu Val Asn Ser Val Thr Ala Ala Asp Thr Ala Val Tyr Tyr
                85                  90                  95
Cys Ala Arg Asn Met Val Arg Gly Val His Trp Phe Asp Pro Trp Gly
            100                 105                 110
Gln Gly Thr Thr Val Thr Val Ser Ser
        115                 120
```

<210> SEQ ID NO 906
<211> LENGTH: 324
<212> TYPE: DNA
<213> ORGANISM: Artificial Sequence
<220> FEATURE:
<223> OTHER INFORMATION: Synthetic

<400> SEQUENCE: 906

```
gaaatagtgt tgacacagtc tccaggcacc ctgtctttgt ctccagggga gagagccacc    60
ctcttctgtt gggccagtcg gagtgttagc agcagctact tagcctggta ccagcagaaa   120
cctggccagg ctcccaggct cctcatctct ggtgcatcca gcagggccac tggcatccca   180
gacaggttca gtggcagtgg gtctgggaca gacttcactc tcaccatcag cagactggag   240
cctgaagatt ttgcagtata tttctgtcaa cagtatagta gttcaccgct cactttcggc   300
ggagggacca agctggagat caaa                                          324
```

<210> SEQ ID NO 907
<211> LENGTH: 108
<212> TYPE: PRT
<213> ORGANISM: Artificial Sequence
<220> FEATURE:
<223> OTHER INFORMATION: Synthetic

<400> SEQUENCE: 907

```
Glu Ile Val Leu Thr Gln Ser Pro Gly Thr Leu Ser Leu Ser Pro Gly
 1               5                  10                  15
Glu Arg Ala Thr Leu Phe Cys Trp Ala Ser Arg Ser Val Ser Ser Ser
            20                  25                  30
Tyr Leu Ala Trp Tyr Gln Gln Lys Pro Gly Gln Ala Pro Arg Leu Leu
        35                  40                  45
Ile Ser Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Phe Cys Gln Gln Tyr Ser Ser Ser Pro
                85                  90                  95
```

Leu Thr Phe Gly Gly Gly Thr Lys Leu Glu Ile Lys
            100                 105

<210> SEQ ID NO 908
<211> LENGTH: 363
<212> TYPE: DNA
<213> ORGANISM: Artificial Sequence
<220> FEATURE:
<223> OTHER INFORMATION: Synthetic

<400> SEQUENCE: 908
caggtgcagc tgcaggagtc cggccccggc ctggtgaagc cctcccagac cctgtccctg    60
acctgcaccg tgtccggcgg ctccatctcc tccggcggct actactggtc ctggatccgg   120
cagcaccccg gcaagggcct ggagtggatc ggctacatcc actactccgg caacacctac   180
tacaacccct ccctgaagtc ccgggtgacc atctccgtgg acacctccaa gaaccagttc   240
tccctgaagc tgtcctccgt gaccgccgcc gacaccgccg tgtactactg cgcccggaac   300
atggtgcggg gcgtgcactg gttcgacccc tggggccagg gcaccctggt gaccgtgtcc   360
tcc                                                                 363

<210> SEQ ID NO 909
<211> LENGTH: 121
<212> TYPE: PRT
<213> ORGANISM: Artificial Sequence
<220> FEATURE:
<223> OTHER INFORMATION: Synthetic

<400> SEQUENCE: 909

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile His Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asn Met Val Arg Gly Val His Trp Phe Asp Pro Trp Gly
            100                 105                 110

Gln Gly Thr Leu Val Thr Val Ser Ser
        115                 120

<210> SEQ ID NO 910
<211> LENGTH: 324
<212> TYPE: DNA
<213> ORGANISM: Artificial Sequence
<220> FEATURE:
<223> OTHER INFORMATION: Synthetic

<400> SEQUENCE: 910
gagatcgtgc tgacccagtc ccccggcacc ctgtccctgt ccccggcga gcgggccacc    60 ctgtcctgcc gggcctcccg gtccgtgtcc tcctcctacc tggcctggta ccagcagaag   120
cccggcaggc cccccggct gctgatctac ggcgcctcct cccgggccac cggcatcccc   180
gaccggttct ccggctccgg ctccggcacc gacttcaccc tgaccatctc ccggctggag   240
cccgaggact tcgccgtgta ctactgccag cagtactcct cctcccccct gaccttcggc  300
ggcggcacca aggtggagat caag  324

<210> SEQ ID NO 911
<211> LENGTH: 108
<212> TYPE: PRT
<213> ORGANISM: Artificial Sequence
<220> FEATURE:
<223> OTHER INFORMATION: Synthetic

<400> SEQUENCE: 911

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Arg Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Leu Thr Phe Gly Gly Gly Thr Lys Val Glu Ile Lys
            100                 105
```

<210> SEQ ID NO 912
<211> LENGTH: 363
<212> TYPE: DNA
<213> ORGANISM: Artificial Sequence
<220> FEATURE:
<223> OTHER INFORMATION: Synthetic

<400> SEQUENCE: 912
caggtgcagc tgcaggagtc gggcctagga ctggtgaagc cttcacagac cctgtccctc  60
acctgcactg tctctggtgg ctccatcagc agtggtggtt actactggag ttggatccgc  120
cagcacccag ggaagggcct ggagtggatt gggtacatcc attatagtgg aacaccccac  180
tacaatccga ccctcaagag tcgaattacc atatcagtag acacgtctaa gaaccagttc  240
tcccttgagg tgaactctgt gactgccgcg gacacggccg tatactactg tgcgaggaat  300
atggttcggg gagttcactg gttcgacccc tggggccagg gaaccctggt caccgtctcc  360
tca  363

<210> SEQ ID NO 913
<211> LENGTH: 121
<212> TYPE: PRT
<213> ORGANISM: Artificial Sequence
<220> FEATURE:
<223> OTHER INFORMATION: Synthetic

<400> SEQUENCE: 913

```
Gln Val Gln Leu Gln Glu Ser Gly Leu Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45
```

```
Trp Ile Gly Tyr Ile His Tyr Ser Gly Asn Thr His Tyr Asn Pro Thr
 50                  55                  60

Leu Lys Ser Arg Ile Thr Ile Ser Val Asp Thr Ser Lys Asn Gln Phe
 65                  70                  75                  80

Ser Leu Glu Val Asn Ser Val Thr Ala Ala Asp Thr Ala Val Tyr Tyr
                 85                  90                  95

Cys Ala Arg Asn Met Val Arg Gly Val His Trp Phe Asp Pro Trp Gly
            100                 105                 110

Gln Gly Thr Leu Val Thr Val Ser Ser
        115                 120
```

<210> SEQ ID NO 914
<211> LENGTH: 324
<212> TYPE: DNA
<213> ORGANISM: Artificial Sequence
<220> FEATURE:
<223> OTHER INFORMATION: Synthetic

<400> SEQUENCE: 914

```
gaaatagtgt tgacacagtc tccaggcacc ctgtctttgt ctccagggga gagagccacc     60
ctcttctgtt gggccagtcg gagtgttagc agcagctact tagcctggta ccagcagaaa    120
cctggccagg ctcccaggct cctcatctct ggtgcatcca gcagggccac tggcatccca    180
gacaggttca gtggcagtgg gtctgggaca gacttcactc tcaccatcag cagactggag    240
cctgaagatt ttgcagtata tttctgtcaa cagtatagta gttcaccgct cactttcggc    300
ggagggacca aggtggaaat caaa                                           324
```

<210> SEQ ID NO 915
<211> LENGTH: 108
<212> TYPE: PRT
<213> ORGANISM: Artificial Sequence
<220> FEATURE:
<223> OTHER INFORMATION: Synthetic

<400> SEQUENCE: 915

```
Glu Ile Val Leu Thr Gln Ser Pro Gly Thr Leu Ser Leu Ser Pro Gly
 1               5                  10                  15

Glu Arg Ala Thr Leu Phe Cys Trp Ala Ser Arg Ser Val Ser Ser Ser
             20                  25                  30

Tyr Leu Ala Trp Tyr Gln Gln Lys Pro Gly Gln Ala Pro Arg Leu Leu
         35                  40                  45

Ile Ser Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln Tyr Ser Ser Ser Pro
             85                  90                  95

Leu Thr Phe Gly Gly Gly Thr Lys Val Glu Ile Lys
            100                 105
```

<210> SEQ ID NO 916
<211> LENGTH: 357
<212> TYPE: DNA
<213> ORGANISM: Artificial Sequence
<220> FEATURE:
<223> OTHER INFORMATION: Synthetic

<400> SEQUENCE: 916

```
caggtgcagc tgcaggagtc cggccccggc ctggtgaagc cctcccagac cctgtccctg     60
```

```
acctgcaccg tgtccggcgg ctccatcacc tccggcggct actactggtc ctggatccgg      120
cagcaccccg gcaagggcct ggagtggatc ggctacatca agttctccgg caacacctac      180
tacaacccct ccctgaagtc ccgggtgacc atctccgtgg acacctccaa gaaccagttc      240
tccctgaagc tgtcctccgt gaccgccgcc gacaccgccg tgtactactg cgcccgggcc      300
cccggctccc acaacttcga catctggggc cagggcacca tggtgaccgt gtcctcc        357
```

```
<210> SEQ ID NO 917
<211> LENGTH: 119
<212> TYPE: PRT
<213> ORGANISM: Artificial Sequence
<220> FEATURE:
<223> OTHER INFORMATION: Synthetic

<400> SEQUENCE: 917
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Lys Phe Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Pro Gly Ser His Asn Phe Asp Ile Trp Gly Gln Gly
            100                 105                 110

Thr Met Val Thr Val Ser Ser
        115

```
<210> SEQ ID NO 918
<211> LENGTH: 324
<212> TYPE: DNA
<213> ORGANISM: Artificial Sequence
<220> FEATURE:
<223> OTHER INFORMATION: Synthetic

<400> SEQUENCE: 918
gagatcgtgc tgacccagtc ccccggcacc ctgtccctgt cccccggcga gcgggccacc       60
ctgtcctgcc gggcctccgt gtccatctcc aacaactacc tggcctggta ccagcagaag      120
cccggccagg cccccggct gctgatctac ggcgcctcct cccgggccac cggcatcccc       180
gaccggttct ccggctccgg ctccggcacc gacttcaccc tgaccatccg cggctggag       240 cccgaggact tcgccccta ctactgccag cagtactccc ggtcccccat caccttcggc       300
cagggcaccc ggctggagat caag                                             324
```

```
<210> SEQ ID NO 919
<211> LENGTH: 108
<212> TYPE: PRT
<213> ORGANISM: Artificial Sequence
<220> FEATURE:
<223> OTHER INFORMATION: Synthetic

<400> SEQUENCE: 919
```

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Val Ser Ile Ser Asn Asn
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Arg Arg Leu Glu
 65                  70                  75                  80

Pro Glu Asp Phe Ala Pro Tyr Tyr Cys Gln Gln Tyr Ser Arg Ser Pro
                 85                  90                  95

Ile Thr Phe Gly Gln Gly Thr Arg Leu Glu Ile Lys
             100                 105
```

<210> SEQ ID NO 920
<211> LENGTH: 360
<212> TYPE: DNA
<213> ORGANISM: Artificial Sequence
<220> FEATURE:
<223> OTHER INFORMATION: Synthetic

<400> SEQUENCE: 920

```
gaggtgcagc tggtggagtc cggcggcggc ctggtgcagc ccggcggctc cctgcggctg    60
tcctgcgccg cctccggctt caccttcaac aacttcgcca tgtcctgggt gcggcaggcc   120
cccggcaagg gcctggagtg gtgtccgcc atctccggct ccggcgtgga cacctactac   180
gccgactccg tgaagggccg gttcaccatc tcccggaca actccaagaa caccctgtac   240
ctgcagatga actccctgcg ggccgaggac accgccgtgt actactgctc caaggacggc   300
gccttctact ccggctacga gcactactgg ggccagggca ccctggtgac cgtgtcctcc   360
```

<210> SEQ ID NO 921
<211> LENGTH: 120
<212> TYPE: PRT
<213> ORGANISM: Artificial Sequence
<220> FEATURE:
<223> OTHER INFORMATION: Synthetic

<400> SEQUENCE: 921

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Phe
             20                  25                  30

Ala Met Ser Trp Val Arg Gln Ala Pro Gly Lys Gly Leu Glu Trp Val
         35                  40                  45

Ser Ala Ile Ser Gly Ser Gly Val Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ser Lys Asp Gly Ala Phe Tyr Ser Gly Tyr Glu His Tyr Trp Gly Gln
             100                 105                 110

Gly Thr Leu Val Thr Val Ser Ser
         115                 120
```

<210> SEQ ID NO 922
<211> LENGTH: 324
<212> TYPE: DNA

<213> ORGANISM: Artificial Sequence
<220> FEATURE:
<223> OTHER INFORMATION: Synthetic

<400> SEQUENCE: 922

```
gagatcgtgc tgacccagtc ccccggcacc ctgtccctgt ccccggcga gcgggccacc      60
ctgtcctgcc gggcctccca gtccgtgtcc tcctcctacc tggcctggta ccagcagaag    120
cccggccagg ccccccggct gctgatctac ggcacctcct cccgggccac cggcatcccc    180
gaccggttct ccggctccgg ctccggcacc gacttcaccc tgaccatctc ccggctggag    240
cccgaggact cgccgtgta ctactgccag cagtacggct cctcccccg gaccttcggc      300
cagggcacca aggtggagat caag                                           324
```

<210> SEQ ID NO 923
<211> LENGTH: 108
<212> TYPE: PRT
<213> ORGANISM: Artificial Sequence
<220> FEATURE:
<223> OTHER INFORMATION: Synthetic

<400> SEQUENCE: 923

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
         35                  40                  45
Ile Tyr Gly Thr Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Arg Thr Phe Gly Gln Gly Thr Lys Val Glu Ile Lys
            100                 105
```

<210> SEQ ID NO 924
<211> LENGTH: 357
<212> TYPE: DNA
<213> ORGANISM: Artificial Sequence
<220> FEATURE:
<223> OTHER INFORMATION: Synthetic

<400> SEQUENCE: 924

```
caggtgcagc tggtgcagtc cggcgccgag gtgaagaagc ccggcgcctc cgtgaaggtg      60
tcctgcaagg cctccggcta caccttcacc tactacggca tctcctgggt gcggcaggcc    120
cccggccagg cctggagtg gatgggctgg atctccgcct acgacggcaa caccaactac    180
gcccagaagc tgcagggccg ggtgaccatg accaccgaca cctccacctc caccgcctac    240
atggagctgc ggtccctgcg gtccgacgac accgccgtgt actactgcgc ccggtactcc    300
tggaacaagc actggttcga ccctggggc cagggcaccc tggtgaccgt gtcctcc        357
```

<210> SEQ ID NO 925
<211> LENGTH: 119
<212> TYPE: PRT
<213> ORGANISM: Artificial Sequence
<220> FEATURE:
<223> OTHER INFORMATION: Synthetic

```
<400> SEQUENCE: 925

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ser Trp Asn Lys His Trp Phe Asp Pro Trp Gly Gln Gly
            100                 105                 110

Thr Leu Val Thr Val Ser Ser
            115
```

```
<210> SEQ ID NO 926
<211> LENGTH: 324
<212> TYPE: DNA
<213> ORGANISM: Artificial Sequence
<220> FEATURE:
<223> OTHER INFORMATION: Synthetic

<400> SEQUENCE: 926
gagatcgtgc tgacccagtc ccccggcacc ctgtccctgt cccccggcga gcgggccacc      60
ctgtcctgcc gggcctccca gtccgtgacc ggctcctacc tggcctggta ccagcagaag     120
cccggccagg cccccggct gctgatctac ggcgcctcct cccgggccac cggcatcccc     180
gaccggttct ccggctccgg ctccggcacc gacttcaccc tgaccatctc ccggctggag     240
cccgaggact cgccgtgta ctactgccag cagtccgcct ctcccccctg gaccttcggc     300
cagggcacca aggtggagat caag                                           324
```

```
<210> SEQ ID NO 927
<211> LENGTH: 108
<212> TYPE: PRT
<213> ORGANISM: Artificial Sequence
<220> FEATURE:
<223> OTHER INFORMATION: Synthetic

<400> SEQUENCE: 927

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ala Phe Ser Pro
                85                  90                  95

Trp Thr Phe Gly Gln Gly Thr Lys Val Glu Ile Lys
            100                 105
```

```
<210> SEQ ID NO 928
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid or absent

<400> SEQUENCE: 928

Xaa Xaa Xaa Xaa Xaa Xaa Xaa Xaa
 1               5

<210> SEQ ID NO 929
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid or absent

<400> SEQUENCE: 929

Xaa Xaa Xaa Xaa Xaa Xaa Xaa Xaa
 1               5

<210> SEQ ID NO 930
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(16)
<223> OTHER INFORMATION: Xaa = Any amino acid or absent

<400> SEQUENCE: 930

Xaa Xaa Xaa Xaa Xaa Xaa Xaa Xaa Xaa Xaa Xaa Xaa Xaa Xaa Xaa Xaa
 1               5                  10                  15

<210> SEQ ID NO 931
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(7)
<223> OTHER INFORMATION: Xaa = Any amino acid or absent

<400> SEQUENCE: 931

Xaa Xaa Xaa Xaa Xaa Xaa Xaa
 1               5

<210> SEQ ID NO 932
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any amino acid or absent
```

<400> SEQUENCE: 932

Xaa Xaa Xaa
 1

<210> SEQ ID NO 933
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any amino acid or absent

<400> SEQUENCE: 933

Xaa Xaa Xaa Xaa Xaa Xaa Xaa Xaa Xaa
 1               5

<210> SEQ ID NO 934
<211> LENGTH: 357
<212> TYPE: DNA
<213> ORGANISM: Artificial Sequence
<220> FEATURE:
<223> OTHER INFORMATION: Synthetic

<400> SEQUENCE: 934
caggtgcagc tgcaggagtc gggcccagga ctggtgaagc cttcacagac cctgtccctc      60
acctgcactg tctctggtgg ctccattacc agtggtggtt actactggac ctggatccgc     120
cagcacccag ggaagggcct ggaatggatt ggatacatca aatttagtgg aacacctac     180 tacaacccgt ccctcaggag tcgagtcacc atatcacttg acacgtctaa gaatcagttc     240
tccctgaata tgacctctgt gactgccgcg gacacggccg tgtattattg cgagagca      300 cctggaagtc ataactttga catctggggc caagggacaa tggtcaccgt ctcttca       357

<210> SEQ ID NO 935
<211> LENGTH: 119
<212> TYPE: PRT
<213> ORGANISM: Artificial Sequence
<220> FEATURE:
<223> OTHER INFORMATION: Synthetic

<400> SEQUENCE: 935

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Gly
             20                  25                  30

Gly Tyr Tyr Trp Thr Trp Ile Arg Gln His Pro Gly Lys Gly Leu Glu
         35                  40                  45

Trp Ile Gly Tyr Ile Lys Phe Ser Gly Asn Thr Tyr Tyr Asn Pro Ser
     50                  55                  60

Leu Arg Ser Arg Val Thr Ile Ser Leu Asp Thr Ser Lys Asn Gln Phe
 65                  70                  75                  80

Ser Leu Asn Met Thr Ser Val Thr Ala Ala Asp Thr Ala Val Tyr Tyr
                 85                  90                  95

Cys Ala Arg Ala Pro Gly Ser His Asn Phe Asp Ile Trp Gly Gln Gly
            100                 105                 110

Thr Met Val Thr Val Ser Ser
        115

<210> SEQ ID NO 936
<211> LENGTH: 324
<212> TYPE: DNA
<213> ORGANISM: Artificial Sequence
<220> FEATURE:
<223> OTHER INFORMATION: Synthetic

<400> SEQUENCE: 936

```
gaaatcgtgt tgacccagtc tccagacacc ctgtctttgt ctccagggga aagagccacc      60
ctctcctgca gggccagtgt gagtattagt aataactatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag aagactggag     240
tctgcagatt ttgcaccgta ttactgtcag caatatagta ggtcaccgat caccttcggc     300
caagggacac gactggagat taaa                                            324
```

<210> SEQ ID NO 937
<211> LENGTH: 108
<212> TYPE: PRT
<213> ORGANISM: Artificial Sequence
<220> FEATURE:
<223> OTHER INFORMATION: Synthetic

<400> SEQUENCE: 937

```
Glu Ile Val Leu Thr Gln Ser Pro Asp Thr Leu Ser Leu Ser Pro Gly
 1               5                  10                  15

Glu Arg Ala Thr Leu Ser Cys Arg Ala Ser Val Ser Ile Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Ser Ala Asp Phe Ala Pro Tyr Tyr Cys Gln Gln Tyr Ser Arg Ser Pro
                85                  90                  95

Ile Thr Phe Gly Gln Gly Thr Arg Leu Glu Ile Lys
            100                 105
```

<210> SEQ ID NO 938
<211> LENGTH: 360
<212> TYPE: DNA
<213> ORGANISM: Artificial Sequence
<220> FEATURE:
<223> OTHER INFORMATION: Synthetic

<400> SEQUENCE: 938

```
gaagtgcagc tggtggagtc tgggggagcc ttggtacaac tgggggggtc cctgagactc      60
tcctgtgcag cctctggatt cacctttaac aactttgcca tgacctgggt ccgccaggct     120
ccagggaagg gctggagtg gtctcaact attagtggta gtggcgttga cacatactgc     180
gcagactccg tgaagggccg gttcaccatc tccagagaca attccaagaa cacactgtat     240
ctgcaaatga acagcctgag agccgaggac acggccgtat attactgttc gaaagatggc     300
gccttctata gtggctacga aactactggg gccagggaa ccctggtcac cgtctcctca     360
```

<210> SEQ ID NO 939
<211> LENGTH: 120
<212> TYPE: PRT

<213> ORGANISM: Artificial Sequence
<220> FEATURE:
<223> OTHER INFORMATION: Synthetic

<400> SEQUENCE: 939

| Glu | Val | Gln | Leu | Val | Glu | Ser | Gly | Gly | Ala | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Asn | Asn | Phe |
| | | | 20 | | | | | 25 | | | | | 30 | | |

| Ala | Met | Thr | Trp | Val | Arg | Gln | Ala | Pro | Gly | Lys | Gly | Leu | Glu | Trp | Val |
| | | 35 | | | | | 40 | | | | | 45 | | | |

| Ser | Thr | Ile | Ser | Gly | Ser | Gly | Val | Asp | Thr | Tyr | Cys | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ser | Lys | Asp | Gly | Ala | Phe | Tyr | Ser | Gly | Tyr | Glu | His | Tyr | Trp | Gly | Gln |
| | | | 100 | | | | | 105 | | | | | 110 | | |

| Gly | Thr | Leu | Val | Thr | Val | Ser | Ser |
|---|---|---|---|---|---|---|---|
| | | 115 | | | | 120 | |

<210> SEQ ID NO 940
<211> LENGTH: 324
<212> TYPE: DNA
<213> ORGANISM: Artificial Sequence
<220> FEATURE:
<223> OTHER INFORMATION: Synthetic

<400> SEQUENCE: 940

```
gaaattgtgc tcacgcagtc tccaggcacc ctgtctttgt ctccagggga agagccacc      60
ctctcctgca gggccagtca gagtgttagc agcagctact tagcctgta ccagcagaaa     120
cctggccagg ctcccaggct cctcatctat ggtacatcca acagggccac tggcatccca    180
gacaggttca gtggcagtgg gtctgggaca gacttcactc tcaccatcag cagactggag    240
tctgaagatt ttgcagtgta ttactgtcag cagtatggta gctcacctcg acgttcggc     300
caagggacca aggtggagat caaa                                           324
```

<210> SEQ ID NO 941
<211> LENGTH: 108
<212> TYPE: PRT
<213> ORGANISM: Artificial Sequence
<220> FEATURE:
<223> OTHER INFORMATION: Synthetic

<400> SEQUENCE: 941

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Ser | Val | Ser | Ser | Ser |
| | | | 20 | | | | | 25 | | | | | 30 | | |

| Tyr | Leu | Ala | Trp | Tyr | Gln | Gln | Lys | Pro | Gly | Gln | Ala | Pro | Arg | Leu | Leu |
| | | 35 | | | | | 40 | | | | | 45 | | | |

| Ile | Tyr | Gly | Thr | Ser | Asn | Arg | Ala | Thr | Gly | Ile | Pro | Asp | Arg | Phe | Ser |
| | 50 | | | | | 55 | | | | | 60 | | | | |

| Gly | Ser | Gly | Ser | Gly | Thr | Asp | Phe | Thr | Leu | Thr | Ile | Ser | Arg | Leu | Glu |
| 65 | | | | | 70 | | | | | 75 | | | | | 80 |

| Ser | Glu | Asp | Phe | Ala | Val | Tyr | Tyr | Cys | Gln | Gln | Tyr | Gly | Ser | Ser | Pro |
| | | | | 85 | | | | | 90 | | | | | 95 | |

Arg Thr Phe Gly Gln Gly Thr Lys Val Glu Ile Lys
         100                 105

<210> SEQ ID NO 942
<211> LENGTH: 357
<212> TYPE: DNA
<213> ORGANISM: Artificial Sequence
<220> FEATURE:
<223> OTHER INFORMATION: Synthetic

<400> SEQUENCE: 942
caggtgcagc tggtgcagtc tggacctgag gtgaagaagc ctggggcctc agtgaaggtc      60
tcctgcaagg cttctggtta ccctttacc tactatggta tcagttggat acgacagacc     120
cctggacaag gcttgagtg gatgggatgg atcagcgctt acgatggtaa cacagactat     180
gcacagaagt tccaagacag aatcaccatg accacagaca tcctcgac acagcctac       240 atggaactga ggagcctgag atctgacgac acggccgtct attactgtgc gaggtatagt     300
tggaacaagc actggttcga ccctgggggc cagggaaccc tggtcaccgt ctcttca        357

<210> SEQ ID NO 943
<211> LENGTH: 119
<212> TYPE: PRT
<213> ORGANISM: Artificial Sequence
<220> FEATURE:
<223> OTHER INFORMATION: Synthetic

<400> SEQUENCE: 943

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Gly Ile Ser Trp Ile Arg Gln Thr Pro Gly Gln Gly Leu Glu Trp Met
        35                  40                  45

Gly Trp Ile Ser Ala Tyr Asp Gly Asn Thr Asp Tyr Ala Gln Lys Phe
    50                  55                  60

Gln Asp Arg Ile Thr Met Thr Thr Asp Thr Ser Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ser Trp Asn Lys His Trp Phe Asp Pro Trp Gly Gln Gly
            100                 105                 110

Thr Leu Val Thr Val Ser Ser
        115

<210> SEQ ID NO 944
<211> LENGTH: 324
<212> TYPE: DNA
<213> ORGANISM: Artificial Sequence
<220> FEATURE:
<223> OTHER INFORMATION: Synthetic

<400> SEQUENCE: 944
gaaattgtgt tgacacagtc tccaggcacc ctgtctttgt ctccagggga cagagccacc      60
ctctcctgca gggccagtca gagtgttacc ggcagctact tagcctggta ccagcagaaa     120
cctggccagg ctcccagact cctcatctat ggtgcatcca acagggccac tggcatccca    180
gacaggttca ctggcagtgg gtctgggaca gacttcactc tcaccatcag cagactggag    240
cctgaagatt ttgcagtgta tttctgtcaa cagtctgctt tctcaccgtg acgttcggc     300 cagggggacca aggtggaaat caaa 324

<210> SEQ ID NO 945
<211> LENGTH: 108
<212> TYPE: PRT
<213> ORGANISM: Artificial Sequence
<220> FEATURE:
<223> OTHER INFORMATION: Synthetic

<400> SEQUENCE: 945

Glu Ile Val Leu Thr Gln Ser Pro Gly Thr Leu Ser Leu Ser Pro Gly
1               5                   10                  15

Asp Arg Ala Thr Leu Ser Cys Arg Ala Ser Gln Ser Val Thr Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Ser Ala Phe Ser Pro
                85                  90                  95

Trp Thr Phe Gly Gln Gly Thr Lys Val Glu Ile Lys
            100                 105

<210> SEQ ID NO 946
<211> LENGTH: 361
<212> TYPE: DNA
<213> ORGANISM: Artificial Sequence
<220> FEATURE:
<223> OTHER INFORMATION: Synthetic

<400> SEQUENCE: 946
caggtgcagt tgcaggagtc gggcccagga ctggtgaagc cttcacagac cctgtccctc      60
acctgcactg tctctggtgg ctccatcggc agtggtggtt actactggag ctggatccgc     120
cagcacccag ggaagggcct ggagtggatt gggtacgtcc attacagtgg aacacccac     180 tacaacccgt ccctcaagag tcgactttcc atatcaatag acacgtctaa gatccagttc     240
tccctgaagc tgagctctgt gactgccgcg gacacggccg tgtattactg tgcgagagcc     300
ccccgtggat accattactt tgcctactgg ggccagggaa ccctggtcac cgtctcctca     360
g                                                                     361

<210> SEQ ID NO 947
<211> LENGTH: 120
<212> TYPE: PRT
<213> ORGANISM: Artificial Sequence
<220> FEATURE:
<223> OTHER INFORMATION: Synthetic

<400> SEQUENCE: 947

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Gly Ser Gly
            20                  25                  30

Gly Tyr Tyr Trp Ser Trp Ile Arg Gln His Pro Gly Lys Gly Leu Glu
        35                  40                  45

Trp Ile Gly Tyr Val His Tyr Ser Gly Asn Thr His Tyr Asn Pro Ser
    50                  55                  60

Leu Lys Ser Arg Leu Ser Ile Ser Ile Asp Thr Ser Lys Ile Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Pro Arg Gly Tyr His Tyr Phe Ala Tyr Trp Gly Gln
            100                 105                 110

Gly Thr Leu Val Thr Val Ser Ser
        115                 120

<210> SEQ ID NO 948
<211> LENGTH: 325
<212> TYPE: DNA
<213> ORGANISM: Artificial Sequence
<220> FEATURE:
<223> OTHER INFORMATION: Synthetic

<400> SEQUENCE: 948
gaaattgtgt tgacacaatc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatcttt ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgct cactttcggc     300
ggagggacca aggtggagat caaac                                           325

<210> SEQ ID NO 949
<211> LENGTH: 108
<212> TYPE: PRT
<213> ORGANISM: Artificial Sequence
<220> FEATURE:
<223> OTHER INFORMATION: Synthetic

<400> SEQUENCE: 949

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Phe Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
             85                  90                  95

Leu Thr Phe Gly Gly Gly Thr Lys Val Glu Ile Lys
         100                 105

<210> SEQ ID NO 950
<211> LENGTH: 330
<212> TYPE: PRT
<213> ORGANISM: Artificial Sequence
<220> FEATURE:
<223> OTHER INFORMATION: Synthetic

<400> SEQUENCE: 950

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 951
<211> LENGTH: 327
<212> TYPE: PRT
<213> ORGANISM: Artificial Sequence
<220> FEATURE:
<223> OTHER INFORMATION: Synthetic

<400> SEQUENCE: 951

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

-continued

```
Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 952
<211> LENGTH: 327
<212> TYPE: PRT
<213> ORGANISM: Artificial Sequence
<220> FEATURE:
<223> OTHER INFORMATION: Synthetic

<400> SEQUENCE: 952

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80
```

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 953
<211> LENGTH: 544
<212> TYPE: PRT
<213> ORGANISM: Homo sapiens

<400> SEQUENCE: 953

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125
```

-continued

```
Thr Asp Ser Pro Asp Leu Ala Thr Glu Asn Pro Glu Arg Leu Ile
130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
530                 535                 540
```

<210> SEQ ID NO 954
<211> LENGTH: 490
<212> TYPE: PRT
<213> ORGANISM: Homo sapiens

<400> SEQUENCE: 954

```
Met Val Ser Pro Arg Met Ser Gly Leu Leu Ser Gln Thr Val Ile Leu
 1               5                  10                  15

Ala Leu Ile Phe Leu Pro Gln Thr Arg Pro Ala Gly Val Phe Glu Leu
             20                  25                  30

Gln Ile His Ser Phe Gly Pro Gly Pro Gly Ala Pro Arg Ser
         35                  40                  45

Pro Cys Ser Ala Arg Leu Pro Cys Arg Leu Phe Phe Arg Val Cys Leu
 50                  55                  60

Lys Pro Gly Leu Ser Glu Glu Ala Ala Glu Ser Pro Cys Ala Leu Gly
 65                  70                  75                  80

Ala Ala Leu Ser Ala Arg Gly Pro Val Tyr Thr Glu Gln Pro Gly Ala
                 85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Pro Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365

Leu Asp Leu Gly His Ala Leu Arg Cys Arg Cys Arg Ala Gly Phe Ala
    370                 375                 380
```

```
Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
            405                 410                 415

Cys Ala Leu Gly Phe Gly Arg Asp Cys Arg Glu Arg Ala Asp Pro
            420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg
                485                 490

<210> SEQ ID NO 955
<211> LENGTH: 527
<212> TYPE: PRT
<213> ORGANISM: Mus musculus

<400> SEQUENCE: 955

Met Thr Pro Ala Ser Arg Ser Ala Cys Arg Trp Ala Leu Leu Leu Leu
1               5                   10                  15

Ala Val Leu Trp Pro Gln Gln Arg Ala Ala Gly Ser Gly Ile Phe Gln
            20                  25                  30

Leu Arg Leu Gln Glu Phe Val Asn Gln Arg Gly Met Leu Ala Asn Gly
        35                  40                  45

Gln Ser Cys Glu Pro Gly Cys Arg Thr Phe Phe Arg Ile Cys Leu Lys
    50                  55                  60

His Phe Gln Ala Thr Phe Ser Glu Gly Pro Cys Thr Phe Gly Asn Val
65                  70                  75                  80

Ser Thr Pro Val Leu Gly Thr Asn Ser Phe Val Val Arg Asp Lys Asn
                85                  90                  95

Ser Gly Ser Gly Arg Asn Pro Leu Gln Leu Pro Phe Asn Phe Thr Trp
            100                 105                 110

Pro Gly Thr Phe Ser Leu Asn Ile Gln Ala Trp His Thr Pro Gly Asp
        115                 120                 125

Asp Leu Arg Pro Glu Thr Ser Pro Gly Asn Ser Leu Ile Ser Gln Ile
130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                165                 170                 175

Ser Asp Asn Tyr Tyr Gly Glu Ser Cys Ser Arg Leu Cys Lys Lys Arg
            180                 185                 190

Asp Asp His Phe Gly His Tyr Glu Cys Gln Pro Asp Gly Ser Leu Ser
        195                 200                 205

Cys Leu Pro Gly Trp Thr Gly Lys Tyr Cys Asp Gln Pro Ile Cys Leu
    210                 215                 220

Ser Gly Cys His Glu Gln Asn Gly Tyr Cys Ser Lys Pro Asp Glu Cys
225                 230                 235                 240

Ile Cys Arg Pro Gly Trp Gln Gly Arg Leu Cys Asn Glu Cys Ile Pro
                245                 250                 255

His Asn Gly Cys Arg His Gly Thr Cys Ser Ile Pro Trp Gln Cys Ala
```

-continued

```
                260                 265                 270
Cys Asp Glu Gly Trp Gly Gly Leu Phe Cys Asp Gln Asp Leu Asn Tyr
            275                 280                 285
Cys Thr His His Ser Pro Cys Lys Asn Gly Ser Thr Cys Ser Asn Ser
        290                 295                 300
Gly Pro Lys Gly Tyr Thr Cys Thr Cys Leu Pro Gly Tyr Thr Gly Glu
305                 310                 315                 320
His Cys Glu Leu Gly Leu Ser Lys Cys Ala Ser Asn Pro Cys Arg Asn
                325                 330                 335
Gly Gly Ser Cys Lys Asp Gln Glu Asn Ser Tyr His Cys Leu Cys Pro
            340                 345                 350
Pro Gly Tyr Tyr Gly Gln His Cys Glu His Ser Thr Leu Thr Cys Ala
        355                 360                 365
Asp Ser Pro Cys Phe Asn Gly Ser Cys Arg Glu Arg Asn Gln Gly
    370                 375                 380
Ser Ser Tyr Ala Cys Glu Cys Pro Pro Asn Phe Thr Gly Ser Asn Cys
385                 390                 395                 400
Glu Lys Lys Val Asp Arg Cys Thr Ser Asn Pro Cys Ala Asn Gly Gly
                405                 410                 415
Gln Cys Gln Asn Arg Gly Pro Ser Arg Thr Cys Arg Cys Arg Pro Gly
            420                 425                 430
Phe Thr Gly Thr His Cys Glu Leu His Ile Ser Asp Cys Ala Arg Ser
        435                 440                 445
Pro Cys Ala His Gly Gly Thr Cys His Asp Leu Glu Asn Gly Pro Val
    450                 455                 460
Cys Thr Cys Pro Ala Gly Phe Ser Gly Arg Arg Cys Glu Val Arg Ile
465                 470                 475                 480
Thr His Asp Ala Cys Ala Ser Gly Pro Cys Phe Asn Gly Ala Thr Cys
                485                 490                 495
Tyr Thr Gly Leu Ser Pro Asn Asn Phe Val Cys Asn Cys Pro Tyr Gly
            500                 505                 510
Phe Val Gly Ser Arg Cys Glu Phe Pro Val Gly Leu Pro Pro Ser
        515                 520                 525

<210> SEQ ID NO 956
<211> LENGTH: 498
<212> TYPE: PRT
<213> ORGANISM: Macaca fascicularis

<400> SEQUENCE: 956

Ser Gly Val Phe Gln Leu Gln Leu Gln Glu Phe Val Asn Glu Arg Gly
1               5                   10                  15
Val Leu Ala Ser Gly Arg Pro Cys Glu Pro Gly Cys Arg Thr Phe Phe
            20                  25                  30
Arg Val Cys Leu Lys His Phe Gln Ala Val Val Ser Pro Gly Pro Cys
        35                  40                  45
Thr Phe Gly Ser Val Ser Thr Pro Val Leu Gly Thr Asn Ser Phe Ala
    50                  55                  60
Val Arg Asp Asp Ser Ser Gly Gly Gly Arg Asn Pro Leu Gln Leu Pro
65                  70                  75                  80
Phe Asn Phe Thr Trp Pro Gly Thr Phe Ser Leu Ile Ile Glu Ala Trp
                85                  90                  95
His Ala Pro Gly Asp Asp Leu Arg Pro Glu Ala Leu Pro Pro Asp Ala
            100                 105                 110
```

```
Leu Ile Ser Lys Ile Ala Ile Gln Gly Ser Leu Ala Val Gly Gln Asn
            115                 120                 125

Trp Leu Leu Asp Glu Gln Thr Ser Thr Leu Thr Arg Leu Arg Tyr Ser
        130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
            180                 185                 190

Gln Pro Ile Cys Leu Ser Gly Cys His Glu Gln Asn Gly Tyr Cys Ser
        195                 200                 205

Lys Pro Ala Glu Cys Leu Cys Arg Pro Gly Trp Gln Gly Arg Leu Cys
210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
            260                 265                 270

Thr Cys Ser Asn Ser Gly Gln Arg Ser Tyr Thr Cys Thr Cys Arg Pro
        275                 280                 285

Gly Tyr Thr Gly Val Asp Cys Glu Leu Glu Leu Ser Glu Cys Asp Ser
290                 295                 300

Asn Pro Cys Arg Asn Gly Gly Ser Cys Lys Asp Gln Glu Asp Gly Tyr
305                 310                 315                 320

His Cys Leu Cys Pro Pro Gly Tyr Tyr Gly Leu His Cys Glu His Ser
                325                 330                 335

Thr Leu Ser Cys Ala Asp Ser Pro Cys Phe Asn Gly Gly Ser Cys Arg
            340                 345                 350

Glu Arg Asn Gln Gly Ala Ser Tyr Ala Cys Glu Cys Pro Pro Asn Phe
        355                 360                 365

Thr Gly Ser Asn Cys Glu Lys Lys Val Asp Arg Cys Thr Ser Asn Pro
370                 375                 380

Cys Ala Asn Gly Gly Gln Cys Leu Asn Arg Gly Pro Ser Arg Met Cys
385                 390                 395                 400

Arg Cys Arg Pro Gly Phe Thr Gly Thr Tyr Cys Glu Arg His Val Ser
                405                 410                 415

Asp Cys Ala Arg Asn Pro Cys Ala His Gly Gly Thr Cys His Asp Leu
            420                 425                 430

Glu Ser Gly Leu Met Cys Thr Cys Pro Ala Gly Phe Ser Gly Arg Arg
        435                 440                 445

Cys Glu Val Arg Thr Ser Ile Asp Ala Cys Ala Ser Ser Pro Cys Phe
450                 455                 460

Asn Arg Ala Thr Cys Tyr Thr Asp Leu Ser Thr Asp Thr Phe Val Cys
465                 470                 475                 480

Asn Cys Pro Tyr Gly Phe Val Gly Ser Arg Cys Glu Phe Pro Met Gly
                485                 490                 495

Leu Pro

<210> SEQ ID NO 957
<211> LENGTH: 498
<212> TYPE: PRT
<213> ORGANISM: Macaca mulatta
```

<400> SEQUENCE: 957

```
Ser Gly Val Phe Gln Leu Gln Leu Gln Glu Phe Val Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Ser Val Ser Thr Pro Val Leu Gly Thr Asn Ser Phe Ala
    50                  55                  60

Val Arg Asp Asp Ser Ser Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
            180                 185                 190

Gln Pro Ile Cys Leu Ser Gly Cys His Glu Gln Asn Gly Tyr Cys Ser
        195                 200                 205

Lys Pro Ala Glu Cys Leu Cys Arg Pro Gly Trp Gln Gly Arg Leu Cys
    210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
            260                 265                 270

Thr Cys Ser Asn Ser Gly Gln Arg Ser Tyr Thr Cys Thr Cys Arg Pro
        275                 280                 285

Gly Tyr Thr Gly Val Asp Cys Glu Leu Glu Leu Ser Glu Cys Asp Ser
    290                 295                 300

Asn Pro Cys Arg Asn Gly Gly Ser Cys Lys Asp Gln Glu Asp Gly Tyr
305                 310                 315                 320

His Cys Leu Cys Pro Pro Gly Tyr Tyr Gly Leu His Cys Glu His Ser
                325                 330                 335

Thr Leu Ser Cys Ala Asp Ser Pro Cys Phe Asn Gly Gly Ser Cys Arg
            340                 345                 350

Glu Arg Asn Gln Gly Ala Ser Tyr Ala Cys Glu Cys Pro Pro Asn Phe
        355                 360                 365

Thr Gly Ser Asn Cys Glu Lys Lys Val Asp Arg Cys Thr Ser Asn Pro
    370                 375                 380

Cys Ala Asn Gly Gly Gln Cys Leu Asn Arg Gly Pro Ser Arg Met Cys
385                 390                 395                 400

Arg Cys Arg Pro Gly Phe Thr Gly Thr Tyr Cys Glu Arg His Val Ser
```

-continued

```
            405                 410                  415
Asp Cys Ala Arg Asn Pro Cys Ala His Gly Gly Thr Cys His Asp Leu
            420             425                 430

Glu Ser Gly Leu Met Cys Thr Cys Pro Ala Gly Phe Ser Gly Arg Arg
        435             440                 445

Cys Glu Val Arg Thr Ser Ile Asp Ala Cys Ala Ser Ser Pro Cys Phe
    450             455                 460

Asn Arg Ala Thr Cys Tyr Thr Asp Leu Ser Thr Asp Thr Phe Val Cys
465             470             475                         480

Asn Cys Pro Tyr Gly Phe Val Gly Ser Arg Cys Glu Phe Pro Val Gly
            485             490                 495

Leu Pro
```

HUMAN ANTIBODIES TO HUMAN DELTA LIKE LIGAND 4

CROSS-REFERENCE TO RELATED APPLICATIONS

This application is a continuation of U.S. non-provisional application Ser. No. 12/002,245 filed Dec. 14, 2007, which claims the benefit under 35 U.S.C § 119(e) of U.S. provisional application Nos. 60/874,922 filed Dec. 14, 2006, 60/916,415 filed May 7, 2007, and 60/985,323 filed Nov. 5, 2007, all of which are herein specifically incorporated by reference in their entirety.

BACKGROUND

The Notch-signaling pathway is a system for cell-to-cell communication used by a wide range of eukaryotes for many biological processes, such as differentiation, proliferation, and homeostasis. Delta like 4 (DI4) or delta-like ligand 4 (DII4) (hereinafter "DII4") is a member of the Delta family of Notch ligands which exhibits highly selective expression by vascular endothelium (Shutter et al. (2000) Genes Develop. 14:1313-1318). DII4 is a ligand for Notch receptors, including Notch1 and Notch 4. The nucleic acid and amino acid sequences for human DII4 are shown in SEQ ID NO:1-2, respectively.

Methods to produce antibodies useful as human therapeutics include generation of chimeric antibodies and humanized antibodies (see, for example, U.S. Pat. No. 6,949,245). See, for example, WO 94/02602 (Abgenix) and U.S. Pat. No. 6,596,541 (Regeneron Pharmaceuticals), which publications are herein specifically incorporated by reference, describing methods of generating nonhuman transgenic mice capable of producing human antibodies.

Japanese patent application 2003/047470A2 (Asahi Kasei Kogyo) describes antibodies to the extracellular portion of human Notch ligand protein.

BRIEF SUMMARY OF THE INVENTION

In a first aspect, the invention provides human antibodies, preferably recombinant human antibodies, that specifically bind human delta-like ligand 4 (hDII4). These antibodies are characterized by binding to hDII4 with high affinity and by the ability to neutralize DII4 activity. The antibodies of the invention are capable of blocking DII4 binding to its Notch receptor(s), and thus inhibit signaling by DII4. The antibodies can be full-length (for example, an IgG1 or IgG4 antibody) or may comprise only an antigen-binding portion (for example, a Fab, F(ab')$_2$ or scFv fragment), and may be modified to effect functionality, e.g., to eliminate residual effector functions (Glu which eliminates residual effector functions (Reddy et al. (2000) J. Immunol. 164:1925-1933).

In one embodiment, the antibody of the invention comprises a heavy chain variable region (HCVR) selected from the group consisting of SEQ ID NO:4, 20, 36, 52, 68, 84, 100, 116, 132, 148, 164, 180, 196, 212, 228, 244, 260, 276, 292, 308, 324, 340, 356, 372, 397, 413, 429, 445, 461, 477, 493, 509, 525, 541, 557, 573, 589, 605, 621, 637, 653, 669, 685, 701, 717, 733, 749, 765, 781, 797, 813, 893, 897, 901, 905, 909, 913, 917, 921, 925, 935, 939, 943, and 947 or a substantially identical sequence thereof. In a preferred embodiment, the HCVR is the amino acid sequence of SEQ ID NO:429 or 901.

In one embodiment, the antibody of the invention comprises a light chain variable region (LCVR) selected from the group consisting of SEQ ID NO:12, 28, 44, 60, 76, 92, 108, 124, 140, 156, 172, 188, 204, 220, 236, 252, 268, 284, 300, 316, 332, 348, 364, 380, 405, 421, 437, 453, 469, 485, 501, 517, 533, 549, 565, 581, 597, 613, 629, 645, 661, 677, 693, 709, 725, 741, 757, 773, 789, 805, 821, 895, 899, 903, 907, 911, 915, 919, 923, 927, 937, 941, 945, and 949 or a substantially identical sequence thereof. In a preferred embodiment, the LCVR is the amino acid sequence of SEQ ID NO:437 or 903.

In one embodiment, the antibody of the invention comprises a HCVR selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 397, 413, 429, 445, 461, 477, 493, 509, 525, 541, 557, 573, 589, 605, 621, 637, 653, 669, 685, 701, 717, 733, 749, 765, 781, 797, 813, 893, 897, 901, 905, 909, 913, 917, 921, 925, 935, 939, 943, and 947 or a substantially identical sequence thereof, and a LCVR selected from the group consisting of SEQ ID NO:12, 28, 44, 60, 76, 92, 108, 124, 140, 156, 172, 188, 204, 220, 236, 252, 268, 284, 300, 316, 332, 348, 364, 380, 405, 421, 437, 453, 469, 485, 501, 517, 533, 549, 565, 581, 597, 613, 629, 645, 661, 677, 693, 709, 725, 741, 757, 773, 789, 805, 821, 895, 899, 903, 907, 911, 915, 919, 923, 927, 937, 941, 945, and 949 or a substantially identical sequence thereof. In a preferred embodiment, the HCVR/LCVR are the amino acid sequence pairs SEQ ID NO:429/437 or 901/903.

In one embodiment, the invention features a human antibody or antibody fragment comprising a heavy chain complementary determining region 1 (CDR1) selected from the group consisting of SEQ ID NO:6, 22, 38, 54, 70, 86, 102, 118, 134, 150, 166, 182, 198, 214, 230, 246, 262, 278 294, 310, 326, 342, 358, 374, 399, 415, 431, 447, 463, 479, 495, 511, 527, 543, 559, 575, 591, 607, 623, 639, 655, 671, 687, 703, 719, 735, 751, 767, 783, 799, 815, 831, 847, 863 and 879, or a substantially identical sequence thereof.

In one embodiment, the invention features a human antibody or antibody fragment comprising a heavy chain CDR2 selected from the group consisting of SEQ ID NO:8, 24, 40, 56, 72, 88, 104, 120, 136, 152, 168, 184, 200, 216, 232, 248, 264, 280, 296, 312, 328, 344, 360, 376, 401, 417, 433, 449, 465, 481, 497, 513, 529, 545, 561, 577, 593, 609, 625, 641, 657, 673, 689, 705, 721, 737, 753, 769, 785, 801, 817, 833, 849, 865 and 881, or a substantially identical sequence thereof.

In one embodiment, the invention features a human antibody or antibody fragment comprising a heavy chain CDR3 selected from the group consisting of SEQ ID NO:10, 26, 42, 58, 74, 90, 106, 122, 138, 154, 170, 186, 202, 218, 234, 250, 266, 282, 298, 314, 330, 346, 362, 378, 403, 419, 435, 451, 467, 483, 499, 515, 531, 547, 563, 579, 595, 611, 627, 643, 659, 675, 691, 707, 723, 739, 755, 771, 787, 803, 819, 835, 851, 867 and 883, or a substantially identical sequence thereof.

In one embodiment, the invention features a human antibody or antibody fragment comprising a heavy chain CDR1 selected from the group consisting of SEQ ID NO: 6, 22, 38, 54, 70, 86, 102, 118, 134, 150, 166, 182, 198, 214, 230, 246, 262, 278 294, 310, 326, 342, 358, 374, 399, 415, 431, 447, 463, 479, 495, 511, 527, 543, 559, 575, 591, 607, 623, 639, 655, 671, 687, 703, 711119, 735, 751, 767, 783, 799, 815, 831, 847, 863 and 879, or a substantially identical sequence thereof; a heavy chain CDR2 selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 401, 417, 433, 449, 465, 481, 497, 513, 529, 545, 561, 577, 593, 609, 625, 641, 657, 673, 689, 705, 721, 737, 753, 769, 785, 801, 817, 833, 849, 865 and 881, or a substantially identical sequence thereof; and a heavy chain CDR3 selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 403, 419, 435, 451, 467, 483, 499, 515, 531, 547, 563, 579, 595, 611, 627, 643, 659, 675, 691, 707, 723, 739, 755, 771, 787, 803, 819, 835, 851, 867 and 883, or a substantially identical sequence thereof. In a preferred embodiment, the antibody or antibody fragment comprises heavy chain CDR1, CDR2 and CDR3 selected from the group consisting of SEQ ID NO:431/433/435; 374/376/378; 783/785/787; and 799/801/803.

In one embodiment, the invention features a human antibody or antibody fragment comprising a light chain CDR1 selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 407, 423, 439, 455, 471, 487, 503, 519, 535, 551, 567, 583, 599, 615, 631, 647, 663, 679, 695, 711, 727, 743, 759, 775, 791, 807, 823, 839, 855, 871 and 887, or a substantially identical sequence thereof.

In one embodiment, the invention features a human antibody or antibody fragment comprising a light chain CDR2 selected from the group consisting of SEQ ID NO:16, 32, 48, 64, 80, 96, 112, 128, 144, 160, 176, 192, 208, 224, 240, 256, 272, 288, 304, 320, 336, 352, 368, 384, 409. 425, 441, 457, 473, 489, 505, 521, 537, 553, 569, 585, 601, 617, 633, 649, 665, 681, 697, 713, 729, 745, 761, 777, 793, 809, 825, 841, 857, 873 and 889, or a substantially identical sequence thereof.

In one embodiment, the invention features a human antibody or antibody fragment comprising a light chain CDR3 selected from the group consisting of SEQ ID NO:18, 34, 50, 66, 82, 98, 11, 130, 146, 162, 178, 194, 210, 226, 242, 258, 274, 290, 306, 322, 338, 354, 370, 386, 411, 427, 443, 459, 475, 491, 507, 523, 539, 555, 571, 587, 603, 619, 635, 651, 667, 683, 699, 715, 731, 747, 763, 779, 795, 811, 827, 843, 859, 875 and 891, or a substantially identical sequence thereof.

In one embodiment, the invention features a human antibody or antibody fragment comprising a light chain CDR1 selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 407, 423, 439, 455, 471, 487, 503, 519, 535, 551, 567, 583, 599, 615, 631, 647, 663, 679, 695, 711, 727, 743, 759, 775, 791, 807, 823, 839, 855, 871 and 887, or a substantially identical sequence thereof; a light chain CDR2 selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 409. 425, 441, 457, 473, 489, 505, 521, 537, 553, 569, 585, 601, 617, 633, 649, 665, 681, 697, 713, 729, 745, 761, 777, 793, 809, 825, 841, 857, 873 and 889, or a substantially identical sequence thereof; and a light chain CDR3 selected from the group consisting of SEQ ID NO: 18, 34, 50, 66, 82, 98, 11, 130, 146, 162, 178, 194, 210, 226, 242, 258, 274, 290, 306, 322, 338, 354, 370, 386, 411, 427, 443, 459, 475, 491, 507, 523, 539, 555, 571, 587, 603, 619, 635, 651, 667, 683, 699, 715, 731, 747, 763, 779, 795, 811, 827, 843, 859, 875 and 891, or a substantially identical sequence thereof. In a preferred embodiment, the antibody or antibody fragment comprises the light chain CDR1, CDR2 and CDR3 selected from the group consisting of SEQ ID NO:439/441/443; 382/384/386; 791/793/795; and 807/809/811.

In a second aspect, the invention provides nucleic acid molecules encoding the antibodies, or antigen-binding portions, of the invention. Recombinant expression vectors carrying the antibody-encoding nucleic acids of the invention, and host cells into which such vectors have been introduced, are also encompassed by the invention, as are methods of making the antibodies of the invention by culturing the host cells of the invention.

In one embodiment, the antibody of the invention comprises a HCVR encoded by a nucleotide sequence selected from the group consisting of SEQ ID NO:3, 19, 35, 51, 67, 83, 99, 115, 131, 147, 163, 179, 195, 211, 227, 243, 259, 275, 291, 307, 323, 339, 355, 371, 396, 412, 428, 444, 460, 476, 492, 508, 524, 540, 556, 572, 588, 604, 620, 636, 652, 668, 684, 700, 716, 732, 748, 764, 780, 796, 812, 892, 896, 900, 904, 908, 912, 916, 920, 924, 934, 938, 942, and 946 or a substantially similar sequence having at least 95% homology thereof.

In one embodiment, the antibody of the invention comprises a LCVR encoded by a nucleotide sequence selected from the group consisting of SEQ ID NO:11, 27, 43, 59, 75, 91, 107, 123, 139, 155, 171, 187, 203, 219, 235, 251, 267, 283, 299, 315, 331, 347, 363, 379, 404, 420, 436, 452, 468, 484, 500, 516, 532, 548, 564, 580, 596, 612, 628, 644, 660, 676, 692, 708, 724, 740, 756, 772, 788, 804, 820, 894, 898, 902, 906, 910, 914, 918, 922, 926, 936, 940, 944, and 948 or a substantially similar sequence having at least 95% homology thereof.

In one embodiment, the antibody of the invention comprises a HCVR encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, 371, 396, 412, 428, 444, 460, 476, 492, 508, 524, 540, 556, 572, 588, 604, 620, 636, 652, 668, 684, 700, 716, 732, 748, 764, 780, 796, 812, 892, 896, 900, 904, 908, 912, 916, 920, 924, 934, 938, 942, and 946 or a substantially similar sequence having at least 95% homology thereof, and a LCVR encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, 379, 404, 420, 436, 452, 468, 484, 500, 516, 532, 548, 564, 580, 596, 612, 628, 644, 660, 676, 692, 708, 724, 740, 756, 772, 788, 804, 820, 894, 898, 902, 906, 910, 914, 918, 922, 926, 936, 940, 944, and 948 or a substantially similar sequence having at least 95% homology thereof.

In one embodiment, the invention features a human antibody or antibody fragment comprising a heavy chain CDR1 encoded by a nucleotide sequence selected from the group consisting of SEQ ID NO:5, 21, 37, 53, 69, 85, 101, 117, 133, 149, 165, 181, 197, 213, 229, 245, 261, 277, 293, 309, 325, 341, 357, 373, 398, 414, 430, 446, 462, 478, 494, 510, 526, 542, 558, 574, 590, 606, 622, 638, 654, 670, 686, 702, 718, 734, 750, 766, 782, 798, 814, 830, 846, 862 and 878, or a substantially similar sequence having at least 95% homology thereof.

In one embodiment, the invention features a human antibody or antibody fragment comprising a heavy chain CDR2 encoded by a nucleotide sequence selected from the group consisting of SEQ ID NO:7, 23, 39, 55, 71, 87, 103, 119, 135, 151, 167, 183, 100, 215, 231, 247, 263, 279, 295, 311, 327, 343, 359, 375, 400, 416, 432, 448, 464, 480, 496, 512, 528, 544, 560, 576, 592, 608, 624, 640, 656, 672, 688, 704, 720, 736, 752, 768, 784, 800, 816, 832, 848, 864 and 880, or a substantially similar sequence having at least 95% homology thereof.

In one embodiment, the invention features a human antibody or antibody fragment comprising a heavy chain CDR3 encoded by a nucleotide sequence selected from the group consisting of SEQ ID NO:9, 25, 41, 57, 73, 89, 105, 121, 137, 153, 169, 185, 201, 217, 233, 249, 265, 281, 297, 313, 329, 345, 361, 377, 402, 418, 434, 450, 466, 482, 498, 514, 530, 546, 562, 578, 594, 610, 626, 642, 658, 674, 690, 706, 722, 738, 754, 770, 786, 802, 818, 834, 850, 866 and 882, or a substantially similar sequence having at least 95% homology thereof.

In one embodiment, the invention features a human antibody or antibody fragment comprising a heavy chain CDR1 encoded by a nucleotide sequence selected from the group consisting of SEQ ID NO:5, 21, 37, 53, 69, 85, 101, 117, 133, 149, 165, 181, 197, 213, 229, 245, 261, 277, 293, 309, 325, 341, 357, 373, 398, 414, 430, 446, 462, 478, 494, 510, 526, 542, 558, 574, 590, 606, 622, 638, 654, 670, 686, 702, 718, 734, 750, 766, 782, 798, 814, 830, 846, 862 and 878, or a substantially similar sequence having at least 95% homology thereof; a heavy chain CDR2 encoded by a nucleotide sequence selected from the group consisting of SEQ ID NO:7, 23, 39, 55, 71, 87, 103, 119, 135, 151, 167, 183, 100, 215, 231, 247, 263, 279, 295, 311, 327, 343, 359, 375, 400, 416, 432, 448, 464, 480, 496, 512, 528, 544, 560, 576, 592, 608, 624, 640, 656, 672, 688, 704, 720, 736, 752, 768, 784, 800, 816, 832, 848, 864 and 880, or a substantially similar sequence having at least 95% homology thereof; and a heavy chain CDR3 encoded by a nucleotide sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, 377, 402, 418, 434, 450, 466, 482, 498, 514, 530, 546, 562, 578, 594, 610, 626, 642, 658, 674, 690, 706, 722, 738, 754, 770, 786, 802, 818, 834, 850, 866 and 882, or a substantially similar sequence having at least 95% homology thereof. In a preferred embodiment, the antibody or antibody fragment comprises heavy chain CDR1, CDR2 and CDR3 encoded b a nucleic acid sequence selected from the group consisting of SEQ ID NO:430/432/434; 373/375/377; 782/784/786; and 798/800/802.

In one embodiment, the invention features a human antibody or antibody fragment comprising a light chain CDR1 encoded by a nucleotide sequence selected from the group consisting of SEQ ID NO:13, 29, 45, 61, 77, 93, 109, 125, 141, 157, 173, 189, 205, 221, 237, 253, 269, 285, 301, 317, 333, 349, 365, 381, 406, 422, 438, 454, 470, 486, 502, 518, 534, 550, 566, 582, 598, 614, 630, 646, 662, 678, 694, 710, 726, 742, 758, 774, 790, 806, 822, 838, 854, 870 and 886, or a substantially similar sequence having at least 95% homology thereof.

In one embodiment, the invention features a human antibody or antibody fragment comprising a light chain CDR2 encoded by a nucleotide sequence selected from the group consisting of SEQ ID NO:15, 31, 47, 63, 79, 95, 111, 127, 143, 159, 175, 191, 207, 223, 239, 255, 271, 287, 303, 319, 335, 351, 367, 383, 408, 424, 440, 456, 472, 488, 504, 520, 536, 552, 568, 584, 600, 616, 632, 648, 664, 680, 696, 712, 728, 744, 760, 776, 792, 808, 824, 840, 856, 872, and 888, or a substantially similar sequence having at least 95% homology thereof.

In one embodiment, the invention features a human antibody or antibody fragment comprising a light chain CDR3 encoded by a nucleotide sequence selected from the group consisting of SEQ ID NO:17, 33, 49, 65, 81, 97, 113, 129, 145, 161, 177, 193, 209, 225, 241, 257, 273, 289, 305, 321, 337, 353, 369, 385, 410, 426, 442, 458, 474, 490, 506, 522, 538, 554, 570, 586, 602, 618, 634, 650, 666, 682, 698, 714, 730, 746, 762, 778, 794, 810, 826, 842, 858, 874 and 890, or a substantially similar sequence having at least 95% homology thereof.

In one embodiment, the invention features a human antibody or antibody fragment comprising a light chain CDR1 encoded by a nucleotide sequence selected from the group consisting of SEQ ID NO:13, 29, 45, 61, 77, 93, 109, 125, 141, 157, 173, 189, 205, 221, 237, 253, 269, 285, 301, 317, 333, 349, 365, 381, 406, 422, 438, 454, 470, 486, 502, 518, 534, 550, 566, 582, 598, 614, 630, 646, 662, 678, 694, 710, 726, 742, 758, 774, 790, 806, 822, 835, 851, 867 and 883, or a substantially similar sequence having at least 95% homology thereof; a light chain CDR2 encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, 383, 408, 424, 440, 456, 472, 488, 504, 520, 536, 552, 568, 584, 600, 616, 632, 648, 664, 680, 696, 712, 728, 744, 760, 776, 792, 808, 824, 840, 856, 872, and 888, or a substantially similar sequence having at least 95% homology thereof; and a light chain CDR3 encoded by a nucleotide sequence selected from the group consisting of SEQ ID NO: 17, 33, 49, 65, 81, 97, 113, 129, 145, 161, 177, 193, 209, 225, 241, 257, 273, 289, 305, 321, 337, 353, 369, 385, 410, 426, 442, 458, 474, 490, 506, 522, 538, 554, 570, 586, 602, 618, 634, 650, 666, 682, 698, 714, 730, 746, 762, 778, 794, 810, 826, 842, 858, 874 and 890, or a substantially similar sequence having at least 95% homology thereof. In a preferred embodiment, the antibody or antibody fragment comprises the light chain CDR1, CDR2 and CDR3 encoded by a nucleic acid sequence selected from the group consisting of SEQ ID NO:438/440/442; 381/383/385; 790/792/794; and 806/808/810.

In a third aspect, the invention features an isolated antibody or antibody fragment that specifically binds hDII4, comprising a CDR 1, 2 and 3 selected from the group consisting of (a) a heavy chain CDR1 region comprising an amino acid sequence of the formula $X^1$-$X^2$-$X^3$-$X^4$-$X^5$-$X^6$-$X^7$-$X^8$ (SEQ ID NO:928), wherein $X^1$ is Gly; $X^2$ is Phe or Tyr; $X^3$ is Thr; $X^4$ is Phe; $X^5$ is Ser, Thr or Asn; $X^6$ is Ser, Asn or Tyr; $X^7$ is Tyr or Phe; and $X^8$ is Gly or Ala; (b) a heavy chain CDR2 region comprising an amino acid sequence of the formula $X^1$-$X^2$-$X^3$-$X^4$-$X^5$-$X^6$-$X^7$-$X^8$ (SEQ ID NO:929), wherein $X^1$ is Ile or Leu; $X^2$ is Trp or Ser; $X^3$ is Tyr, Ala or Gly; $X^4$ is Asp, Ser or Tyr; $X^5$ is Gly or Asp; $X^6$ is Ser, Gly, Thr or Val; $X^7$ is Asn or Asp; and $X^8$ is Lys or Arg; (c) a heavy chain CDR3 region comprising an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$ (SEQ ID NO:930), wherein $X^1$ is Ala or Ser; $X^2$ is Arg or Lys; $X^3$ is Asp or Tyr; $X^4$ is Ser, Gly or His; $X^5$ is Asp, Ala or Thr; $X^6$ is Asn, or Phe; $X^7$ is Tyr, Arg or Lys; $X^8$ is His or Ser; $X^9$ is Gly or Trp; $X^{10}$ is Tyr or Phe; $X^{11}$ is Glu or Asp; $X^{12}$ is Gly, His or Pro; $X^{13}$ is Tyr, Trp or absent; $X^{14}$ is Phe or absent; $X^{15}$ is Asp or absent; and $X^{16}$ is Pro or absent.

In a preferred embodiment, the antibody or antibody fragment comprises heavy chain CDR 1, 2 and 3 selected from the group consisting of (a) a heavy chain CDR1 region comprising an amino acid sequence of the formula $X^1$-$X^2$-$X^3$-$X^4$-$X^5$-$X^6$-$X^7$-$X^8$ (SEQ ID NO:928), wherein $X^1$ is Gly; $X^2$ is Phe; $X^3$ is Thr; $X^4$ is Phe; $X^5$ is Ser or Asn; $X^6$ is Ser or Asn; $X^7$ is Tyr or Phe; and $X^8$ is Gly or Ala; (b) a heavy chain CDR2 region comprising an amino acid sequence of the formula $X^1$-$X^2$-$X^3$-$X^4$-$X^5$-$X^6$-$X^7$-$X^8$ (SEQ ID NO:929), wherein $X^1$ is Ile or Leu; $X^2$ is Trp or Ser; $X^3$ is Tyr or Gly; $X^4$ is Asp or Ser; $X^5$ is Gly; $X^6$ is Ser, Thr or Val; $X^7$ is Asn or Asp; and $X^8$ is Lys or Arg; (c) a heavy chain CDR3 region comprising an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$$X^{16}$ (SEQ ID NO:930), wherein $X^1$ is Ala or Ser; $X^2$ is Arg or Lys; $X^3$ is Asp; $X^4$ is Gly or His; $X^5$ is Asp or Ala; $X^6$ is Phe; $X^7$ is Tyr or Arg; $X^8$ is Ser; $X^9$ is Gly; $X^{10}$ is Tyr; $X^{11}$ is Glu; $X^{12}$ is Gly or His; $X^{13}$ is Tyr or Trp; $X^{14}$ is Phe or absent; $X^{15}$ is Asp or absent; and $X^{16}$ is Pro or absent.

In a further embodiment, the isolated antibody or antibody fragment further comprises (d) a light chain CDR1 region comprising an amino acid sequence of the formula $X^1$-$X^2$-$X^3$-$X^4$-$X^5$-$X^6$-$X^7$ (SEQ ID NO:931), wherein $X^1$ is Gln; $X^2$ is Ser; $X^3$ is Val; $X^4$ is Arg, Ser or Thr; $X^5$ is Ser or Gly; $X^6$ is Ser or Tyr; and $X^7$ is Tyr or absent; (e) a light chain CDR2 region comprising an amino acid sequence of the formula $X^1$-$X^2$-$X^3$ (SEQ ID NO:932), wherein $X^1$ is Gly or Asp; $X^2$ is Ala or Thr; and $X^3$ is Ser; and (f) a light chain CDR3 region comprising an amino acid sequence of the formula $X^1$-$X^2$-$X^3$-$X^4$-$X^5$-$X^6$-$X^7$-$X^8$-$X^9$ (SEQ ID NO:933), wherein $X^1$ is Gln; $X^2$ is Gln or His; $X^3$ is Tyr, Arg or Ser; $X^4$ is Gly, Ser or Ala; $X^5$ is Ser, Asn or Phe; $X^6$ is Trp or Ser; $X^7$ is Pro; $X^8$ is Trp, Pro or Arg; and $X^9$ is Thr.

In a preferred embodiment, the isolated antibody or antibody fragment further comprises (d) a light chain CDR1 region comprising an amino acid sequence of the formula $X^1$-$X^2$-$X^3$-$X^4$-$X^5$-$X^6$-$X^7$ (SEQ ID NO:931), wherein $X^1$ is Gln; $X^2$ is Ser; $X^3$ is Val; $X^4$ is Arg or Ser; $X^5$ is Ser; $X^6$ is Ser or Tyr; and $X^7$ is Tyr or absent; (e) a light chain CDR2 region comprising an amino acid sequence of the formula $X^1$-$X^2$-$X^3$ (SEQ ID NO:932), wherein $X^1$ is Gly or Asp; $X^2$ is Ala or Thr; and $X^3$ is Ser; and (f) a light chain CDR3 region comprising an amino acid sequence of the formula $X^1$-$X^2$-$X^3$-$X^4$-$X^5$-$X^6$-$X^7$-$X^8$-$X^9$ (SEQ ID NO:933), wherein $X^1$ is Gln; $X^2$ is Gln or His; $X^3$ is Tyr or Arg; $X^4$ is Gly or Ser; $X^5$ is Ser or Asn; $X^6$ is Trp or Ser; $X^7$ is Pro; $X^8$ is Pro or Arg; and $X^9$ is Thr.

In a fourth aspect, the invention features a fully human antibody or antibody fragment which binds hDll4 with an $IC_{50}$ of less than about 10 nM, as measured in in vitro assay or ELISA-based Dll4 blocking assay (described below). In a preferred embodiment, the antibody of the invention exhibits an $IC_{50}$ of about 500 pM or less. In an even more preferred embodiment, the antibody of the invention exhibits an $IC_{50}$ of about 100 pM or less.

In one embodiment, the invention provides a fully human monoclonal antibody which specifically binds and inhibits human Dll4 and exhibits an $IC_{50}$ of less than or equal to about 150 pM, 100 pM, 75 pM, or 50 pM, as measured by Notch-inducible luciferase bioassay with hDll4-Fc. As shown in the experimental section below, the anti-hDll4 antibodies of the invention do not cross-react with closely related delta proteins, such as hDll1 and hDll3.

In one embodiment, the invention provides an isolated human antibody, or an antigen-binding portion thereof, that binds hDll4 with a $K_D$ of less than about 500 pM, preferably less than about 300 pM, even more preferably less than about 100 pM, less than about 50 pM, less than about 10 pM, as determined by surface plasmon resonance (BIACORE™), for example, using dimeric hDll4 (Table 2).

The invention encompasses anti-hDll4 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of a galactosylation can be made in order to modify complement dependent cytotoxicity (CDC).

The invention includes anti-hDll4 antibodies which bind specific epitopes of hDll4 and are capable of blocking the biological activity of hDll4. The extracellular domain of Dll4 is composed of an N-terminal domain, a Delta/Serrate/Lag-2 (DSL) domain, and a tandem of eight epidermal growth factor (EGF)-like repeats. Generally, the EGF domains are recognized as occurring at about amino acid residues 218-251 (domain 1), 252-282 (domain 2), 284-322 (domain 3), 324-360 (domain 4), and 362-400 (domain 5), with the DSL domain at about amino acid residues 173-217 and the N-terminal domain at about amino acid residues 27-172 of hDll4 (SEQ ID NO:2).

In one embodiment, a blocking antibody of the invention binds within amino acids residues 27 to 524 of SEQ ID NO:2. In a more specific embodiment, a blocking antibody of the invention binds an epitope within the N-terminus-DSL domains 27-217 of SEQ ID NO:2; in an even more specific embodiment, the blocking antibody binds an epitope within about amino acid residues 27-172 (N-terminal domain) or 173-217 (DSL domain). In another embodiment, a blocking antibody of the invention binds the EGF-2 epitope within about amino acids residues 252-282 of SEQ ID NO:2.

In a fifth aspect, the invention features a composition comprising a recombinant human anti-human Dll4 antibody and an acceptable carrier. Further included in the invention are vectors and host cells comprising vectors which contain nucleic acid molecules encoding the human anti-hDll4 antibody of the invention, as well as methods of producing these novel antibodies, comprising growing a host cell comprising nucleic acid encoding the anti-hDll4 antibody of the invention or an antibody fragment, under conditions permitting production of the protein and recovering the protein so produced.

In a sixth aspect, the invention features methods for inhibiting hDll4 activity using an antibody, or antigen-binding portion thereof, of the invention. In one embodiment, the method comprises contacting hDll4 with the instant antibody or antigen-binding portion thereof, such that hDll4 is inhibited from binding to Notch receptor, for example Notch-1. In another embodiment, the method comprises administering an antibody or antibody fragment of the invention, to a human subject suffering from a disorder which is ameliorated by inhibition of Dll4 activity. The disorder treated is a disease or condition which is improved, ameliorated, inhibited or prevented by removal, inhibition or reduction of Dll4 activity, for example, pathological vascularization associated with tumor angiogenesis and cancer, immunodeficiency diseases, transplant rejection, or inflammation; and neurodegenerative conditions, e.g., associated with prion disease.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods

DEFINITIONS

"Delta-like ligand 4", "Dll4", "hDll4" are used interchangeably to refer to the protein encoded by the nucleic acid sequence of SEQ ID NO:1 and the protein having the amino acid sequence of SEQ ID NO:2.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "high affinity" antibody refers to those antibodies having a binding affinity to hDll4 of at least $10^{-8}$ M; preferably $10^{-9}$ M; even more preferably $10^{-10}$ M, as measured by surface plasmon resonance, e.g., BIACORE™ or solution-affinity ELISA.

By the term "slow off rate" or "Koff" is meant an antibody that dissociates from hDll4 with a rate constant of $1 \times 10^{-3}$ $s^{-1}$ or less, preferably $1 \times 10^{-4}$ $s^{-1}$ or less, as determined by surface plasmon resonance, e.g., BIACORE™.

A "neutralizing" or "blocking" antibody, is intended to refer to an antibody whose binding to Dll4 results in inhibition of the biological activity of Dll4. This inhibition of the biological activity of Dll4 can be assessed by measuring one or more indicators of Dll4 biological activity. These indicators of Dll4 biological activity can be assessed by one or more of several standard in vitro or in vivo assays known in the art (see examples below). Preferably, the ability of an antibody to neutralize Dll4 activity is assessed by inhibition of Dll4 binding to a Notch receptor.

The term "antigen-binding portion" of an antibody (or simply "antibody portion" or "antibody fragment"), as used herein, refers to one or more fragments of an antibody that retain the ability to specifically bind to an antigen (e.g., hDll4). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain; and (vi) an isolated CDR. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc. Natl. Acad Sci. USA 90:6444-6448; Poljak et al. (1994) Structure 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "human antibody", as used herein, is intended to include antibodies having variable and constant regions derived from human germlne immunoglobulin sequences. The human antibodies of the invention may include amino acid residues not encoded by human germlne immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germlne of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germlne immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germlne VH and VL sequences, may not naturally exist within the human antibody germlne repertoire in vivo.

An "isolated antibody", as used herein, is intended to refer to an antibody that is substantially free of other antibodies having different antigenic specificities (e.g., an isolated antibody that specifically binds hDII4 is substantially free of antibodies that specifically bind antigens other than hDII4). An isolated antibody that specifically binds hDII4 may, however, have cross-reactivity to other antigens, such as hDII4 molecules from other species. Moreover, an isolated antibody may be substantially free of other cellular material and/or chemicals.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the dissociation constant of a particular antibody-antigen interaction.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In preferred embodiments, an antibody is said to specifically bind an antigen when the equilibrium dissociation constant is less than or equal to $10^{-8}$ M, more preferably when the equilibrium dissociation constant is less than or equal to $10^{-9}$ M, and most preferably when the dissociation constant is less than or equal to $10^{-10}$ M.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide analog or variant" as used herein refers to a polypeptide that is comprised of a segment of at least 25 amino acids that has substantial identity to a portion of an amino acid sequence and that has at least one of the following properties: (1) specific binding to hDII4 under suitable binding conditions, or (2) ability to block DII4 binding to a Notch receptor. Typically, polypeptide analogs or variants comprise a conservative amino acid substitution (or insertion or deletion) with respect to the naturally-occurring sequence. Analogs typically are at least 20 amino acids long, preferably at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton 1984 W. H. Freeman and Company, New York; Introduction to Protein Structure (Branden & Tooze, eds., 1991, Garland Publishing, NY); and Thornton et at. 1991 Nature 354:105, which are each incorporated herein by reference.

Non-peptide analogs are commonly used in the pharmaceutical industry as drugs with properties analogous to those of the template peptide. These types of non-peptide compound are termed "peptide mimetics" or "peptidomimetics" (see, for example, Fauchere (1986) J. Adv. Drug Res. 15:29; and Evans et al. (1987) J. Med. Chem. 30:1229, which are incorporated herein by reference. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al. (1992) Ann. Rev. Biochem. 61:387, incorporated herein by reference), for example, by adding internal cysteine residues capable of forming intramolecular disulfide bridges which cyclize the peptide.

The term "percent sequence identity" in the context of nucleic acid sequences refers to the residues in two sequences which are the same when aligned for maximum correspondence. The length of sequence identity comparison may be over a stretch of at least about nine nucleotides or more, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson (1990) Methods Enzymol. 183: 63-98 and (2000) Methods Mol. Biol. 132:185-219, each herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence. Generally, the art uses the terms "percent sequence identity", "percent sequence similarity" and "percent sequence homology" interchangeably. In this application, these terms shall have the same meaning with respect to nucleic acid sequences.

The term "substantial similarity", or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 90%, preferably at least about 95%, and more preferably at least about 96%, 97%, 98% or 99% of the nucleotide bases, as measured by any well-known algorithm of sequence identity, such as FASTA, BLAST or Gap, as discussed above.

As applied to polypeptides, the term "substantial identity" or "substantially identical" means that two peptide sequences, when optimally aligned, such as by the programs GAP or BESTFIT using default gap weights, share at least 80% sequence identity, preferably at least 90% or 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215:403 410 and Altschul et al. (1997) Nucleic Acids Res. 25:3389 402, each of which is herein incorporated by reference.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

Preparation of Human Antibodies

Methods for generating human antibodies include, for example, VELOCIMMUNE® (Regeneron Pharmaceuticals), XENOMOUSE™ technology (Abgenix), the "minilocus" approach, and phage display. The VELOCIMMUNE® technology (U.S. Pat. No. 6,596,541) encompasses a method of generating a high specificity fully human antibody to a select antigen. This technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

The XENOMOUSE™ technology (Green et al. (1994) Nature Genetics 7:13-21) generates a mouse having both human variable and constant regions from both the heavy chain and kappa light chain loci. In an alternative approach, others have utilized a "minilocus" approach in which an exogenous Ig locus is mimicked through inclusion of individual genes from the Ig locus (see, for example, U.S. Pat. No. 5,545,807). The DNA encoding the variable regions can be isolated with or without being operably linked to the DNA encoding the human heavy and light chain constant region.

Other methods of generating human antibodies, including isolation from a human donor, are known. See, for example, U.S. Pat. No. 6,787,637, herein specifically incorporated by reference in its entirety.

Antibodies may be therapeutically useful in blocking a ligand-receptor interaction or inhibiting receptor component interaction, rather than by killing cells through fixation of complement and participation in CDC. The constant region of an antibody is important in the ability of an antibody to fix complement and participate in CDC or direct cell killing through antibody-dependent cellular cytoxicity (ADCC). Thus, the isotype of an antibody may be selected on the basis of the desirability for the antibody to fix complement.

Human immunoglobulins can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-heavy chain disulfide bonds and a molecule of about 75-80 kDa is formed composed of a single light and heavy chain. These forms have been difficult to separate, even after affinity purification.

The frequency of appearance of the second form in various intact IgG isotypes is due to, but not limited to, structural differences associated with the hinge region isotype of the antibody. In fact, a single amino acid substitution in the hinge region of the human IgG4 hinge can significantly reduce the appearance of the second form (Angal et al. 1993 Molecular Immunology 30:105) to levels typically observed using a human IgG1 hinge. The instant invention encompasses antibodies having one or more mutations in the hinge, CH2 or CH3 region which may be desirable, for example, in production to improve the yield, or modulate effector functions.

Antibodies of the invention are preferably prepared with the use of VELOCIMMUNE® technology. A transgenic mouse in which the endogenous immunoglobulin heavy and light chain variable regions are replaced with the corresponding human variable regions is challenged with the antigen of interest, and lymphatic cells (such as B-cells) recovered from the mice that express antibodies. The lymphatic cells may be fused with a myeloid-type cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies may be isolated directly from antigen-specific lymphocytes. In various embodiments, the transgenic mouse comprises 12 functional human variable heavy chain genes and 11 functional human variable kappa light chain genes; 25 to 30 human variable heavy chain genes and from 18 to 20 human variable kappa light chain genes; 43 to 48 human variable heavy chain genes and 20 to 22 human variable kappa light chain genes; or about 80 human variable heavy chain genes and about 40 human variable kappa light chain genes.

In general, the antibodies of the instant invention possess very high affinities, typically possessing $K_D$ of from about $10^{-9}$ through about $10^{-11}$ M, when measured by binding to antigen either immobilized on solid phase or in solution phase. The mouse constant regions are replaced with desired human constant regions to generate the fully human antibodies of the invention, for example wild-type or modified IgG1 or IgG4 (for example, SEQ ID NO:950, 951, or 952). While the constant region selected may vary according to specific use, high affinity antigen-binding and target specificity characteristics reside in the variable region.

Cancer, infectious diseases, autoimmunity, immunodeficiency, transplants, inflammation, injury and degenerative conditions can be treated by modulation of the immune system. In cases of disease due to inappropriate function or hyperactivity of the immune system, such as autoimmunity or inflammation, can be ameliorated through inhibition of immune cell function or reduction of immune cell numbers. This can be accomplished by blockade of positive signals or stimulation of negative signals on immune cell populations critical to the disease process, such as T, B or NK cells, neutrophils, macrophages, antigen presenting cells, mast cells or other cell types. Overactivity can also be inhibited through elimination of various immune cell populations by stimulation of apoptosis, targeting of specific surface receptors with depleting antibodies or antibody-drug conjugates, or the blockade or alteration of the differentiation of immune cell lineages or specific cell types. Inefficient or reduced immune function can cause or exacerbate disorders such as cancer, infectious disease, and other immunodeficiencies. Hypoactivity of the immune system can be improved through activation of immune cells by stimulation of positive signals by crosslinking or agonistic antibodies or blockade of negative signals. Immune cell populations can be increased by stimulation of development of some or all immune cell lineages, prevention of apoptosis, or elimination of inhibitory signals. In a specific application, the antibodies of the invention are useful for treatment, inhibition or amelioration of a condition or disease such as, for example, cancer, immunodeficiency, transplant rejection, or inflammation.

Epitope Mapping and Related Technologies

To screen for antibodies which bind to a particular epitope (e.g., those which block binding of IgE to its high affinity receptor), a routine cross-blocking assay such as that described in Harlow and Lane (1990) supra can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (U.S. patent Publication No. 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the hDll4 antibodies of the invention into groups of antibodies binding different epitopes.

Agents useful for altering the structure of the immobilized antigen are enzymes, such as, for example proteolytic enzymes, for example, trypsin, endoproteinase Glu-C, endoproteinase Asp-N, chymotrypsin, etc. Agents useful for altering the structure of the immobilized antigen may also be chemical agents, such as, succinimidyl esters and their derivatives, primary amine-containing compounds, hydrazines and carbohydrazines, free amino acids, etc.

The antigen protein may be immobilized on either biosensor chip surfaces or polystyrene beads. The latter can be processed with, for example, an assay such as multiplex LUMINEX™ detection assay (Luminex Corp., Austin, Tex.). Because of the capacity of LUMINEX™ to handle multiplex analysis with up to 100 different types of beads, LUMINEX™ provides almost unlimited antigen surfaces with various modifications, resulting in improved resolution in antibody epitope profiling over a biosensor assay.

Therapeutic Administration and Formulations

The administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa.). These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Powell et al. "Compendium of excipients for parenteral formulations" PDA (1998) J Pharm Sci Technol. 52:238-311 and the citations therein for additional information related to excipients and carriers well known to pharmaceutical chemists.

EXAMPLES

Example 1

Generation of Human Antibodies to Human DII4

Mice may be immunized by any method known in the art (see, for example, Harlow and Lane supra). In one embodiment, hDII4 antigen is administered directly to VELOCIMMUNE® mice comprising DNA loci encoding human Ig heavy chain variable regions and kappa light chain variable regions, with an adjuvant to stimulate the immune response. Such an adjuvant includes complete and incomplete Freund's adjuvant, MPL+TDM adjuvant system (Sigma), or RIBI (muramyl dipeptides) (see O'Hagan 2000 Vaccine Adjuvant, by Human Press, Totawa, N.J.). The antibody immune response is monitored by standard antigen specific immunoassay. When a desired immune response is achieved, antibody-expressing B cells were harvested and fused with mouse myeloma cells to preserve their viability, forming hybridoma cell lines. Such hybridoma cell lines are screened and selected to identify cell lines that produce antigen-specific antibodies using assays as described below.

Alternatively, antigen-specific hybridoma cells may be isolated by flow cytometry. Briefly, after fusion to myeloma cells, pooled hybridoma cells were grown for 10 days in HAT medium. The cells were then harvested and stained with biotin-labeled DII4 at 2 mg/ml for one hour, followed by addition of phycoerythrin-streptavidin. The fluorescence-labeled cells were sorted by flow cytometry (single cell per well into 96 well plates containing hybridoma growth medium), cultured for 8-10 days, and conditioned media screened for the presence of functionally desirable monoclonal antibodies, as described below.

Anti-hDII4 antibodies generated via direct isolation of splenocytes. Antigen-specific antibodies may also be isolated directly from antigen-immunized B cells without fusion to myeloma cells, as described in U.S. Patent Publication 2007/0280945A1, herein specifically incorporated by reference in its entirety. Stable recombinant antibody-expressing CHO cell lines were established from the isolated proper recombinants.

Example 2

Antigen Binding Affinity Determination

Equilibrium dissociation constants ($K_D$ values) for antigen binding to the selected antibodies described above were determined by surface kinetics on a real-time biosensor surface plasmon resonance assay (BIACORE™ 2000). The antibody was captured on a goat anti-mouse IgG polyclonal antibody surface created through direct chemical coupling to a BIACORE™ chip to form a captured antibody surface. Varying concentrations of monomeric hDII4 or dimeric hDII4-hFc were injected over the captured antibody surfaces, and antigen-antibody binding and dissociation monitored in real time. Kinetic analysis was performed to calculate $K_D$, dissociation rate constants, and half-life of antigen/antibody complex dissociation (Table 1). A similar method was applied to measure single B cell-derived monoclonal antibodies modified to contain a human IgG constant domain. Antibodies were presented by goat anti-hFc polyclonal antibody reagent (Jackson Immuno Research Lab) immobilized on BIACORE™ chip, and exposed to either dimeric DII4-mFc or monomeric DII4 protein (Table 2).

Antibody-antigen binding affinity may also be assessed using an ELISA based solution competition assay. Briefly, on a 96-well microtiter plate, antibodies (purified proteins or in conditioned medium) were premixed with serial dilutions of antigen protein (monomeric or dimeric) ranging from 0 to 10 µg/ml with a constant concentration of antibody. After a 2 hr incubation of antigen with antibody, the solutions were transferred to a microtiter plate precoated with antigen for measurement of free antibody (MAXISORB™, VWR, West Chester, Pa.). The plate was coated with 1 µg/ml hDII4-hFc protein in PBS solution overnight at 4° C. and nonspecific binding sites blocked with BSA for 2 hrs. After a 1 hr incubation following transfer, the plate was washed and the plate-bound antibodies were detected with an HRP-conjugated goat anti-mouse IgG polyclonal antibody reagent (Jackson Immuno Laboratory) and developed using colorimetric substrates (OPTEIA™; BD Biosciences Pharmingen, San Diego, Calif.). The enzymatic reaction was stopped with 1 M phosphoric acid, optical absorptions at 450 nm were recorded and the data were analyzed using a sigmoidal dose-response model and an $IC_{50}$ values were reported (Table 1).

TABLE 1

| Antibody | $K_D$ DII4 (nM) | $K_D$ DII4-Fc (nM) | $IC_{50}$ DII4-Fc (nM) |
|---|---|---|---|
| 13B6 | 2.79 | 0.188 | 0.06 |
| 15E10 | 0.55 | 0.023 | 0.58 |
| 22G12 | 1.29 | 0.076 | 0.03 |
| 24C8 | 0.52 | 0.047 | 0.01 |
| VAV 2H4-19 | 1.51 | 0.611 | 0.10 |
| VAV 4H10-9 | 13.70 | 0.662 | 0.30 |
| VAV 7B9-9 | 0.88 | 0.021 | 0.27 |

TABLE 1-continued

| Antibody | $K_D$ DII4 (nM) | $K_D$ DII4-Fc (nM) | $IC_{50}$ DII4-Fc (nM) |
|---|---|---|---|
| VAW 10E4-9 | 89.00 | 0.468 | 0.06 |
| VAW 10G11-2 | 31.30 | 1.430 | 1.66 |
| VAW 1C6-1 | 45.80 | 0.092 | 0.25 |
| VAW 1G2-4 | 83.80 | 0.035 | 0.40 |
| VAW 1H2-2 | 67.00 | 0.148 | 0.30 |
| VAW 2H3-2 | 0.30 | 0.150 | 0.26 |
| VAW 3A7-2 | 1.64 | 0.162 | 0.02 |
| VAW 3A9-5 | NA | 2.510 | 16.00 |
| VAW 3F12-8 | 8.12 | 0.648 | 0.07 |
| VAW 6B8-12 | 0.89 | 0.060 | 0.43 |
| VAW 6C6-2 | 91.70 | 0.092 | 0.50 |
| VAW 6G12-10 | 3.74 | 0.527 | 0.19 |
| VAW 7C10-11 | 17.10 | 0.853 | 0.28 |
| VAW 8A10-14 | 1.41 | 0.648 | 0.08 |
| VAW 8G1-12 | 6.09 | 8.300 | 8.60 |
| VAW 9B11-2 | 62.20 | 0.048 | 0.00 |
| VAW 9F12-6 | 16.00 | 1.350 | 0.02 |
| VAW 9G10-1 | 56.10 | 0.555 | 0.10 |

TABLE 2

| Antibody | $K_D$ DII4 (nM) | $K_D$ DII4-Fc (nM) |
|---|---|---|
| 314266-06F12-B7 | 2.17 | 0.075 |
| 318518-01A04-D5 | 0.237 | 0.244 |
| 318518-01A10-D8 | 0.399 | 0.018 |
| 318518-01B09-C3 | 0.833 | 0.180 |
| 318518-01B11-D4 | 0.382 | 0.088 |
| 318518-01E07-H2 | 0.165 | 0.238 |
| 318518-01G04-F3 | 0.501 | 0.107 |
| 318518-01G05-B5 | 1.06 | 0.196 |
| 318518-02A07-B3 | 0.208 | 0.148 |
| 318518-02B06-E2 | 2.15 | 0.193 |
| 318518-02B08-F7 | N/A | N/A |
| 318518-02C04-D1 | 0.478 | 0.331 |
| 318518-02F05-D10 | 1.28 | 0.035 |
| 318518-02G03-F2 | 1.31 | 0.042 |
| 318518-02G04-B11 | 0.813 | 0.048 |
| 318518-02G08-F11 | N/A | N/A |
| 318518-03A03-B2 | 0.136 | 0.124 |
| 318518-03C10-F2 | 1.18 | 0.131 |
| 318518-03D04-B5 | 0.904 | 0.136 |
| 318518-03D07-G11 | 3.74 | 0.163 |
| 318518-03F04-A6 | 0.501 | 0.088 |
| 318518-03F06-A3 | 0.556 | 0.037 |
| 318518-03H03-F3 | 8.89 | 0.084 |
| 318518-14A06-E7 | 4.54 | 0.282 |
| 318518-14A07-C4 | 0.235 | 0.035 |
| 318518-14D08-G1 | 0.541 | 0.046 |
| 318518-14H08-A2 | 6.67 | 0.128 |
| 318518-1H08-E9 | 0.225 | 0.050 |

Example 3

Inhibition of DII4 and Notch Interaction

The ability of the antibodies to block DII4 binding to Notch was evaluated with an ELISA-based immunoassay. Briefly, Notch-hFc recombinant protein was coated on a 96-well plate in PBS buffer overnight at 4° C. at 1 mg/ml, and the nonspecific binding sites were blocked with BSA. This plate was used to measure free biotin-DII4-hFc from antibody titration sample solutions. To make the antibody titration samples, a constant amount of biotin-DII4-hFc at 25 pM was pre-mixed with varied amounts of antibody, either in crude hybridoma condition medium or as purified antibody protein, ranging from 0 to 50 nM in serial dilutions, followed by 2 hr incubation at room temperature to allow antibody-antigen binding to reach equilibrium. The equilibrated sample solutions were then transferred to the Notch-hFc coated plates for the measurement of free biotin-DII4-hFc. After 1 hour binding, the plate was washed and bound biotin-DII4-hFc was detected using HRP conjugated streptavidin (Poly HRP streptavidin, Pierce Endogen), and developed using TMB substrate (BD Pharmigen). Data was analyzed using GraphPad Prism software and $IC_{50}$ values were determined as the amount of antibody required to achieve 50% reduction of biotin-DII4-hFc bound to the plate-coated Notch-Fc (Table 3) (*conditioned media).

TABLE 3

| Antibody | $IC_{50}$ (nM) |
|---|---|
| VAV 2H4-19 | 0.01 |
| VAW 3A7-2 | 0.017 |
| VAW 9G10-1 | 0.019 |
| VAW 10E4-9 | 0.032 |
| VAW 8A10-11 | 0.04 |
| VAW 9F12-6 | 0.059 |
| VAW 3F12-8 | 0.066 |
| VAW 1C6-1 | 0.086 |
| VAW 1G2-4 | 0.11 |
| VAW 6C6-2 | 0.119 |
| VAV 7B9-4 | 0.123 |
| VAW 1H2-2 | 0.154 |
| VAW 2H3-2 | 0.168 |
| VAW 6B8-12 | 0.255 |
| VAW 6G12-10 | 0.257 |
| VAW 7C10-11 | 0.273 |
| VAV 4H10-9 | 0.599 |
| VAW 10G11-2 | 0.931 |
| VAW 3A9-5 | 3.8 |
| VAW 8G1-12 | 10.7 |
| VAW 9B11-2 | 0.069 |
| 15E10* | 0.04 |
| 22G12 | 0.10 |
| 13B6 | 0.11 |
| 24C8 | 0.031 |
| 314266-06F12-B7 | 0.07 |
| 318518-01A04-D5 | 0.11 |
| 318518-01A10-D8 | 0.05 |
| 318518-01B09-C3 | 0.03 |
| 318518-01B11-D4 | 0.03 |
| 318518-01E07-H2 | 1.17 |
| 318518-01G04-F3 | 0.02 |
| 318518-01G05-B5 | 1.08 |
| 318518-02A07-B3 | 0.03 |
| 318518-02B06-E2 | 0.09 |
| 318518-02B08-F7 | N/A |
| 318518-02C04-D1 | 0.60 |
| 318518-02F05-D10 | 0.16 |
| 318518-02G03-F2 | 0.07 |
| 318518-02G04-B11 | 1.09 |
| 318518-02G08-F11 | N/A |
| 318518-03A03-B2 | 0.57 |
| 318518-03C10-F2 | 0.12 |
| 318518-03D04-B5 | 0.04 |
| 318518-03D07-G11 | 0.45 |
| 318518-03F04-A6 | 0.01 |
| 318518-03F06-A3 | 0.02 |
| 318518-03H03-F3 | 0.17 |
| 318518-14A06-E7 | 0.04 |
| 318518-14A07-C4 | 0.02 |
| 318518-14D08-G1 | 0.14 |
| 318518-14H08-A2 | 0.25 |
| 318518-1H08-E9 | 0.03 |

The ability of selected purified anti-hDII4 antibodies to block DII4 binding to Notch was also evaluated with the ELISA-based immunoassay described above, modified by replacing 25 pM of biotin-DII4-hFc with 30 pM of biotin-DII4-hFc, and reducing antibody-antigen incubation duration from 2 hrs to 1 hr. For convenience, antibody 318518-01A10-D8 was renamed "REGN281" (HCVR/LCVR SEQ ID NOs: 429/437 and hIgG1 SEQ ID NO:950). Derived antibodies tested included REGN421 (HCVR/LCVR SEQ ID NO:901/

903, hIgG1 SEQ ID NO:950); and REGN422 (HCVR/LCVR SEQ ID NO:901/903, with modified hIgG4 SEQ ID NO:952). Results are shown in Table 4.

TABLE 4

| Antibody | IC$_{50}$ (nM) |
|---|---|
| REGN281 | 0.042 |
| REGN421 | 0.045 |
| REGN422 | 0.039 |

Ability of antibody to neutralize Dll4 mediated cellular function was also tested in vitro using Dll4 expressing human umbilical vein endothelial cells (HUVEC). Inhibition of Notch mediated hHes1 and EphB2 gene expression in HUVEC with the derived antibodies was monitored as follows: low passage HUVEC were cultured in MCDB-131 media (Vec Technologies). One day prior to analysis, HUVEC cells were seeded at a density of $2 \times 10^5$ cells/well in 24-well plates in 1 ml total media volume. The test antibody or other inhibitor was added directly to the individual sample wells in triplicate followed by 5-hour culture at 37° C. At the end of the culture period, media was removed and total RNA was isolated using QIAZOL™ and the RNEASY™ lipid tissue kit (Qiagen). mRNA level quantification was performed by the use of PCR and the fluorogenic 5' nuclease assay (TAQMAN® assay, Appied Biosystems). For each sample, cDNA was synthesized from 1-2 mg of total RNA. cDNA generated from an equivalent amount of starting RNA (typically 25 ng) was loaded in triplicate on ABI PRISM™ optical reaction plates. For each RNA sample a "no RT" control was also run in which no reverse transcriptase was added to allow for subtraction of any potential genomic DNA contributions to the signal. 2x Mastermix (TAQMAN® 2xPCR Mastermix; ABI) was added to each reaction to a final concentration of 1x. Additionally, TAQMAN® probe and primers for the gene of interest were added to each reaction. Each primer was used at a final concentration of 900 nM and the probe was added at a final concentration of 200 nM. Human genomic DNA was used as a standard. The assays were performed under standard TAQMAN® conditions on a ABI 7900HT instrument. Levels of Hes1 and EphrinB2 were measured and normalized to an endogenous control gene (cyclophilin) (Table 5). Probes and primers: human Hes1 probe (SEQ ID NO:387); Oligos: hHes1-869F (SEQ ID NO:388); hHes1-940R (SEQ ID NO:389), human ephrinB2 probe: hEphB2-773T (SEQ ID NO:390); Oligos: hEphB2-752F (SEQ ID NO:391) hEphB2-812R (SEQ ID NO:392); human cyclophilin: probe: hCyclophilin-343T (SEQ ID NO:393); Oligos: hCyclophilin-323F (SEQ ID NO:394); hCyclophilin-389R (SEQ ID NO:395).

TABLE 5

| Antibody | EphrinB2 Expression IC$_{50}$ (nM) | Hes1 Expression IC$_{50}$ (nM) |
|---|---|---|
| 22G12 | 0.379 | 0.381 |
| 15E10 | 2.56 | 4.49 |
| VAW 3A7-2 | 0.409 | 0.533 |
| 314266-06F12-B7 | 0.239 | 0.405 |
| 318518-01A10-D8 | 0.305 | 0.329 |
| 318518-01G04-F3 | 0.088 | 0.172 |
| 318518-01H08-E9 | 0.413 | 0.548 |
| 318518-02A07-B3 | 0.398 | 0.128 |
| 318518-03F04-A6 | 0.158 | 0.115 |
| 318518-03F06-A3 | 0.304 | 0.692 |
| 318518-014A07-C4 | 0.175 | 0.312 |

TABLE 5-continued

| Antibody | EphrinB2 Expression IC$_{50}$ (nM) | Hes1 Expression IC$_{50}$ (nM) |
|---|---|---|
| 318518-014D08-G1 | 0.510 | 0.568 |
| hDll4-hFc | 0.843 | 0.974 |

HUVEC Proliferation Assay. The ability of antibody to block Dll4 mediated growth inhibition of Human umbilical vein endothelial cells (HUVEC) cells was tested in an in vitro cell proliferation assay. Low passage HUVEC cells were obtained and cultured in MCDB-131 media (Vec Technologies). One day prior to analysis 12-well tissue culture plates were coated with hDll4-hFc in PBS at 4° C. overnight (0.2 µg/ml; 0.5 ml PBS/well). Plates were washed 1x with PBS and HUVEC cells were seeded at a density of $4 \times 10^3$ cells/well in 1.0 ml total media volume. Immediately following addition of cells anti-hDll4 antibodies were added in 0.5 ml total volume over a range of concentrations to generate an inhibition curve. Cells were grown for 96-hours at 37° C. Cell number was quantitated using the CCK-8 reagent (Dojindo). All assays were run in triplicate. (Table 6, NB, not blocking).

TABLE 6

| Antibody | IC$_{50}$ (nM) |
|---|---|
| 15E10 | 0.284 |
| VAW9B11-2 | 1.868 |
| VAW8D8-12 | NB |
| 13B6 | 5.01 |
| VAW2H4-19 | NB |
| VAW3A7-2 | 0.198 |
| VAW8A10-14 | 0.214 |
| 22G12 | 0.888 |
| 318518-06F12-B7 | 2.067 |
| 318518-01A10-D8 | 0.096 |
| 318518-01G04-F3 | 0.106 |
| 318518-01H08-E9 | 0.188 |
| 318518-02A07-B3 | 0.200 |
| 318518-03F04-A6 | 0.184 |
| 318518-03F06-A3 | 0.188 |
| 318518-014A07-C4 | 0.159 |
| 318518-014D08-G1 | 0.165 |

Notch-Inducible Luciferase Assay. A bioassay was developed to determine the ability of selected purified antibodies to neutralize Dll4-mediated cellular function in vitro using an engineered HEK293 cell line (ATCC) that constitutively expresses human Notch 1 and contains a Notch-responsive promoter driving luciferase. Inhibition of Notch-inducible luciferase activity was determined as follows: 1 day prior to assay, each well of an opaque 96 well tissue culture plate was coated with 100 µl of either 1 nM or 1.5 nM hDll4-hFc in PBS overnight at 4° C. Cells were seeded onto the coated plates at $2 \times 10^4$ cells/well in media. Purified antibody protein, in serial dilutions starting from 2 nM in cell media, was incubated with the cells at 37° C. for 24 hrs. Luciferase activity was determined by adding an equal well volume of STEADY-GLO® Substrate (Promega) (Table 7).

TABLE 7

| | IC$_{50}$ (pM) | |
|---|---|---|
| Antibody | 1 nM hDll4-hFc | 1.5 nM hDll4-hFc |
| REGN281 | 50.5 | 78.7 |
| REGN421 | 54.4 | 87.3 |
| REGN422 | 88.2 | 131.1 |

Example 4

Inhibition of Notch1 Cleavage

The ability of selected anti-hDll4 antibodies to inhibit Notch1 cleavage was tested by examination of total cleaved Notch1 protein by SDS-Page/Western blotting. Low passage HUVEC cells were cultured as described above. One day prior to analysis 6-well plates were coated with hDll4-hFc in PBS at 4° C. overnight (0.2 µg/ml; 1.0 ml PBS/well). Plates were washed 1× with PBS and HUVEC cells were seeded at 7.5×10⁵ cells/well in 2.0 ml total media volume. Immediately following cell seeding, anti-hDll4 antibody was added to each well at 10 nM final concentration. Cells were grown for 24 hours at 37° C. following which whole cell extracts were prepared and analyzed by SDS-PAGE. Levels of cleaved Notch1 were determined using an anti-cleaved Notch1 (Val1744) antibody (Cell Signaling) and standard western blotting techniques. The anti-hDll4 antibodies were able to entirely block the Notch1 cleavage induced by plate coated hDll4-hFc (data not shown).

Example 5

ADCC and CDC Assays

Antibody-dependent cell-mediated cytotoxicity (ADCC) induced by two test antibodies (REGN421, REGN422) was assessed using a panel of eight target cell lines with varying hDll4 expression levels. The eight target cell lines were (1) HUVECs; (2) HUVECs stimulated with 10 nM VEGF for 24 hours; (3) Colo205; (4) engineered C6 rat glioma cells expressing eGFP; (5) engineered C6 rat glioma cells expressing hDll4; (6) engineered HT1080 cells expressing eGFP; (7) engineered HT1080 cells expressing hDll4; and (8) HT29. Human Dll4 or eGFP was integrated into the C6 cell or HT1080 genome through retroviral transfection. Briefly, cells from each target cell line (10,000 cells/well in 50 µl) were first mixed with an equal volume of serially diluted REGN421 or REGN422, resulting in a final antibody concentration ranging from 0.169 pM to 10 nM, and incubated for 10 min at room temperature in a 96-well plate format (control=wells without antibody). Separately, human peripheral blood mononuclear cells (PBMCs, effector cells) were prepared following a conventional Ficoll-Hypaque gradient centrifugation enrichment procedure. Approximately 300,000 PBMCs were added to each mixture of antibody and target cells to give a final ratio of effector to target cells of approximately 30:1. The 96-well plates were then incubated for 4 h at 37° C., 5% $CO_2$ followed by centrifugation at 250×g. Supernatants were harvested and assayed for lactate dehydrogenase (LDH) activity using the CYTOTOX 96® Non-Radioactive Cytotoxicity Assay system (Promega). Results are shown in Table 8. REGN421-induced dose dependent cell lysis was only observed in C6 cells expressing hDll4 (col. 5), which exhibited the highest hDll4 expression among all cell lines (as determined by immunoprecipitation/Western blot and flow cytometry). The maximum cell cytotoxicity in the C6-hDll4 cell line ranged from 20% to 60%. No REGN421-induced cell lysis was observed in the remaining seven target cell lines. REGN422 did not induce cell lysis in any of the target cell lines.

TABLE 8

| | % Maximum Cytotoxicity | | | | | | | |
|---|---|---|---|---|---|---|---|---|
| Ab | 1 | 2 | 3 | 4 | 5 | 6 | 7 | 8 |
| REGN421 | 0 | 0 | 0 | 0 | 20-60 | 0 | 0 | 0 |
| REGN422 | 0 | 0 | 0 | 0 | 0 | 0 | 0 | 0 |

Complement-dependent cytotoxicity (CDC) induced by REGN421 was assessed using the same panel of cells lines described above. Briefly, cells from each of the target cell lines (50,000 cells/well in 50 µl) were first mixed with an equal volume of serially diluted REGN421, resulting in a final antibody concentration ranging from 0.169 pM to 10 nM, and incubated for 10 min at room temperature in a 96-well plate format. Normal human serum, with complement components (Quidel Corp., San Diego, Calif.) was added to each well to give a final serum concentration of 5%. The plates were then incubated at 37° C., 5% $CO_2$ for 2 hours followed by addition of CELLTITER-BLUE® reagent (Promega) (controls=wells without antibody and wells with antibody but no serum). The plates were incubated overnight and cell survival (CDC levels) assayed. As a positive control, Daudi cells were treated with rituximab. REGN421 exhibited no CDC toward any of the target cell lines tested (data not shown).

Example 6

Epitope Mapping and Specificity

In order to determine epitope binding specificity, a series of seven chimeric Dll4 proteins were generated in which specific human Dll4 domains were substituted into a mouse Dll4 protein as follows: #1 contained the human N-terminal and DSL domains (S27-Q218); #2 contained human N-terminal, DSL and EGF-1 domains (S27-N252); #3 contained human N-terminal, DSL, EGF-1 and EGF-2 domains (S27-Q283); #4 contained human N-terminal, DSL, EGF-1, EGF-2, EGF-3, EGF-4 and EGF-5; #5 contained human N-terminal domain (S27-R172); #6 contained human DSL domain (V173-Q218); and #7 contained human EGF-2 domain (E252-D282). The chimeric proteins were fused to a mouse IgG2a-Fc fragment and expressed in CHO-$K_i$ cell. The conditioned media were harvested and protein expression confirmed by western blot.

Binding specificity of test antibodies to hDll4, mDll4, and chimeric proteins #1, #2, #3, and #4 were tested as follows: purified antibodies 22G12, VAW3A7-2, and 15E10 were amine coupled between 5000-6000 RU on CM5 chip. Conditioned media from CHO K1 cells containing the chimeric Dll4 proteins, hDll4-mFc, and mDll4-mFc were injected sequentially followed by surface regeneration over antibody-coupled surfaces. A blank amine coupled flowcell surface was used as a control for nonspecific binding of the conditioned media. Results are summarized in Table 9. 22G12 bound an epitope between S27-Q218 of hDll4; VAW3A7-2 bound an epitope between Q283-E400 hDll4; and 15E10 bound an epitope between E252-D282 of hDll4.

TABLE 9

| Antibody | hDII4-mFc | mDII4-mFc | Chimeric Proteins #1 | #2 | #3 | #4 |
|---|---|---|---|---|---|---|
| 22G12 | + | − | + | + | + | + |
| VAW3A7-2 | + | − | − | − | − | + |
| 15E10 | + | − | − | − | + | + |

Binding specificity of purified test mAb to hDII4, mDII4 and the chimeric proteins (described above) was determined (REGN279=314266-6F12-B7; REGN287=318518-1G04-F3; REGN289=318518-1H08-E9; REGN290=318518-2A07-B3; REGN306=318518-3F06-A3). Briefly, each DII4 protein was captured (70-130 RU) on goat anti-mouse IgG antibody surfaces, followed by injection of test mAb at a concentration of 100 μg/ml. An antibody that bound mDII4-mFc was used as a positive control (positive control=6C10). The results (Table 10) show that REGN279 bound an epitope between S27-Q218 of hDII4; REGN287 bound between Q283-E400 of hDII4; REGN289, REGN290 and REGN306 bound between S27-E400 of hDII4.

TABLE 10

| Antibody | hDII4-mFc | mDII4-mFc | Chimeric human-mouse DII4 Fusion Proteins #1 | #2 | #3 | #4 | #5 | #6 | #7 |
|---|---|---|---|---|---|---|---|---|---|
| REGN279 | + | − | + | + | + | + | + | − | − |
| REGN287 | + | − | − | − | − | + | + | − | − |
| REGN289 | + | − | + | + | + | + | − | + | − |
| REGN290 | + | − | + | + | + | + | − | + | − |
| REGN306 | + | − | + | + | + | + | − | + | − |
| Control | + | + | + | + | + | + | + | + | + |

Further epitope binding specificity determinations were conducted as described above with the following purified test antibodies: REGN281=318518-1A10-D8; REGN305=318518-3F04-A6; REGN309=318518-14A07-C4; REGN310=318518-14D08-G1; REGN421, and REGN422. Briefly, each of the DII4 proteins was captured (240-470 RU) on goat anti-mouse IgG antibody surfaces, followed by injection of test antibody at a concentration of 100 μg/ml (Table 11).

TABLE 11

| Antibody | hDII4-mFc | mDII4-mFc | Chimeric human-mouse DII4 Fusion Proteins #1 | #2 | #3 | #4 | #5 | #6 | #7 |
|---|---|---|---|---|---|---|---|---|---|
| REGN281 | + | − | + | + | + | + | + | + | − |
| REGN305 | + | − | − | − | − | + | − | − | − |
| REGN309 | + | − | + | + | + | − | + | + | − |
| REGN310 | + | − | − | − | + | − | + | + | + |
| REGN421 | + | − | + | + | + | + | + | + | − |
| REGN422 | + | − | + | + | + | + | + | + | − |

Western blot analysis. Binding specificity of selected antibodies to chimeric, mouse and human DII4 was determined by Western blot. Briefly, hDII4-mFc (200 ng per lane), mDII4-mFc (200 ng per lane), and chimeric proteins #1-#7 (approximate 150 ng per lane) were subjected to electrophoresis on duplicate SDS-PAGE gels using non-reducing sample buffer. Each gel was then transferred to a PVDF membrane. Blots were first exposed to REGN421 at 0.2 μg/ml and then to HRP-conjugated anti-hIgG antibody (Pierce). Control blots were exposed to HRP-conjugated anti-mFc antibody (Pierce). Results: REGN421 recognized hDII4-mFc and chimeric proteins containing the human N-terminal domain (#5), a human DSL domain (#6), or both (#1, #2, #3, and #4). REGN421 did not recognize a chimeric protein containing a human EGF-2 domain (#7).

Protease digestion analysis. Binding between REGN281 and hDII4 was further assessed by protective protease digestion and liquid chromatography/mass spectrometry (LC/MS) using an HPLC1100 (Agilent) and LCQ Classical Ion Trap Mass Spectrometer (Thermo). Briefly, a mixture of hDII4 and REGN281, in a molar ratio of 1:5, or hDII4 alone, was incubated with protease overnight at either 25° C. (for GluC protease) or 37° C. (for trypsin). Each of the resulting proteolytic digest mixtures was then subjected to LC/MS. Unique peptide peaks present in proteolytic digests performed in the absence of REGN281, which either diminished or disappeared in proteolytic digests performed in the presence of REGN281, indicate potential REGN281 binding sites on hDII4 that were protected from protease digestion by the binding of REGN281 to hDII4. These unique peptide peaks were analyzed by mass spectrometry. The observed mass, predicted mass, and the N-terminal sequences of the peptides are shown in Table 12.

TABLE 12

| Peak | Observed Mass | Predicted Mass | hDII4 Peptide (SEQ ID NO:2) | Protease | Domain |
|---|---|---|---|---|---|
| G1 | 521 | 521.5 | Phe37-Glu40 | GluC | N-terminal |
| G2 | 1362.8 | 1363.4 | Ala121-Glu132 | GluC | N-terminal |
| T1 | 758 | 760.8 | Pro49-Arg55 | Trypsin | N-terminal |
| T2 | 587.1 | 587.2 | Tyr169-Arg172 | Trypsin | N-terminal |
| T3 | 1607.4 | 1607.6 | Val173-Arg186 | Trypsin | DSL |
| T4 | 1399 | 1400.7 | Gly42-Arg55 | Trypsin | N-terminal |
| T5 | 569.2 | 569.3 | Thr56-Arg59 | Trypsin | N-terminal |
| T7 | 2615 | 2613.4 | Ile143-Arg166 | Trypsin | N-terminal |
| T8 | 1807.2 | 1806.9 | Ser27-Arg41 | Trypsin | N-terminal |

Example 7

Binding Affinity of Purified Antibodies to Human and Monkey DII4

The binding affinities of selected purified antibodies to hDII4, M. facscicularis DII4 (mfDII4, SEQ 1N NO:956), and M. mulatta DII4 (mmDII4, SEQ ID NO:957) monomers were determined using a BIACORE™ 2000 & 3000. Goat anti-hFc polyclonal antibody reagent immobilized on a BIACORE™ chip was used to present REGN281, REGN421, and REGN422. Varying concentrations of each proteins, hDII4 (from 12.5 nM to 100 nM), mfDII4 (from 3.13. nM to 100 nM), or mmDII4 (from 12.5 nM to 100 nM) were used as analyte, and injected over the antibody surfaces. Antigen-antibody binding and dissociation of bound complex were monitored in real time (Table 13).

TABLE 13

| | ka (M-1s-1) | | | kd (s-1) | | | $K_D$ (nM) | | |
|---|---|---|---|---|---|---|---|---|---|
| | hDll4 | mfDll4 | mmDll4 | hDll4 | mfDll4 | mmDll4 | hDll4 | mfDll4 | mmDll4 |
| REGN281 | $1.56 \times 10^5$ | $6.64 \times 10^4$ | $9.27 \times 10^4$ | $2.30 \times 10^{-5}$ | $2.04 \times 10^{-5}$ | $3.05 \times 10^{-5}$ | 0.148 | 0.307 | 0.329 |
| REGN421 | $1.63 \times 10^5$ | $7.28 \times 10^4$ | $9.70 \times 10^4$ | $2.17 \times 10^{-5}$ | $2.02 \times 10^{-5}$ | $3.23 \times 10^{-5}$ | 0.133 | 0.278 | 0.333 |
| REGN422 | $1.64 \times 10^5$ | $8.01 \times 10^4$ | $9.27 \times 10^4$ | $2.36 \times 10^{-5}$ | $2.88 \times 10^{-5}$ | $3.41 \times 10^{-5}$ | 0.144 | 0.360 | 0.375 |

The binding affinities of anti-hDll4 antibodies toward hDll4 and mmDll4 dimers were also determined using a BIACORE™ 2000 and the method describe above, except that hDll4 was replaced with hDll4-mFc (from 3.13 nM to 100 nM), or mmDll4 with mmDll4-mFc (from 0.78 nM to 25 nM) as analyte (Table 14).

TABLE 14

| | ka (M-1s-1) | | kd (s-1) | | $K_D$ (nM) | |
|---|---|---|---|---|---|---|
| | hDll4-mFc | mmDll4-mFc | hDll4-mFc | mmDll4-mFc | hDll4-mFc | mmDll4-mFc |
| REGN281 | $3.02 \times 10^5$ | $3.16 \times 10^5$ | $4.96 \times 10^{-6}$ | $4.64 \times 10^{-6}$ | 0.0163 | 0.0147 |
| REGN421 | $3.43 \times 10^5$ | $3.35 \times 10^5$ | $4.70 \times 10^{-6}$ | $3.80 \times 10^{-6}$ | 0.0137 | 0.013 |
| REGN422 | $3.46 \times 10^5$ | $4.23 \times 10^5$ | $4.60 \times 10^{-6}$ | $4.15 \times 10^{-6}$ | 0.0133 | 0.0098 |

Example 8

Cross-Reactivity of Antibodies with hDll1, hDll3, mDll4, or mfDll4

Cross-reactivity of the antibodies to human delta-like ligand1 (SEQ ID NO:953) and human delta-like ligand 3 (SEQ ID NO:954) proteins was determined. REGN281, REGN421 and REGN422 were presented by a goat anti-human kappa (hK) polyclonal antibody reagent (Southern Biotech) immobilized on a BIACORE™ chip, and either hDll4-hFc or hDll1-hFc protein at 100 µg/ml were used as analyte injected over the antibody surfaces. All three anti-hDll4 antibodies only bound to hDll4-hFc, and did not bind hDll1-hFc.

An alternative BIACORE™ format was used to assess cross-reactivity between anti-hDll4 antibody and either hDll1-hFc or hDll3-hFc. Briefly, ligands hDll4-hFc, hDll1-hFc, and hDll3-hFc were each covalently linked to a CM-5 chip, through amine coupling, to an RU range of about 8,000 to 10,000. REGN421, at 300 µg/ml, was injected over the surface of each chip. REGN421 bound only to hDll4-hFc; no binding was observed to either hDll1-hFc or hDll3-hFc. The same result was observed for REGN422 instead of REGN421.

OCTET™-based binding assays were employed to determine the binding between selected purified anti-hDll4 antibodies and hDll4-hFc, hDll3-hFc, hDll1-hFc, mfDll4-mmh, or mDll4-mFc. Briefly, strepavidin high binding FA biosensors (ForteBio, Inc., Menlo Park, Calif.) were first incubated with biotin-anti-hK at 5 µg/ml for 10 min at 30° C., to achieve saturation. Biotin-anti-hK-bound biosensors were then incubated with antibodies REGN281, REGN421 or REGN422, at 20 µg/ml for 10 min at 30° C., to achieve saturation. The antibody-bound biosensors were then incubated with either hDll4-hFc or hDll3-hFc, hDll1-hFc, or mDll4-mFc, at 200 nM, or mfDll4-mmh at 100 nM, for 10 min at 30° C. Changes in the thickness of the biological layer after each incubation were measured. Human Dll4-hFc and mfDll4-mmh bound to anti-hDll4 antibody-bound biosensors, whereas hDll3-hFc, hDll1-hFc, and mDll4-mFc did not bind to anti-hDll4 antibody-bound biosensors.

Example 9

Effect of Anti-hDll4 Antibody on Tumor Growth

The effect of REGN421 on tumor growth was evaluated on tumors implanted in Severe Combined Immunodeficiency (SCID) mice expressing a humanized Dll4 protein (SCID× hDll4). Briefly, the humanized Dll4 mouse was made by replacing the entire extracellular domain of the mouse Dll4 gene with the corresponding extracellular region of the human Dll4 gene (7 kb) in embryonic stem (ES) cells. Homozygous hDll4 mice were generated and bred into SCID background. Each mouse was then implanted subcutaneously (SC) with $2.5 \times 10^6$ human HT1080 tumor cells. After the tumors were established in the mice (~100-150 mm³ 18 days after implantation), mice were measured and treated with hFc, hDll4-Fc or REGN421. A total of 7 mice were divided into three groups. The first group (n=3) was treated subcutaneously with hFc at 25 mg/kg; the second group (n=1) was treated with hDll4-Fc at 25 mg/kg; and the third group (n=3) was treated with REGN421 at 10 mg/kg. The treatments were repeated every 48 hours starting at day 18. In vivo tumor measurements were obtained three days before the initial treatment (day 15), on the same day of each treatment (days 18, 20, and 22), and on day 25. Tumor size was calculated using the formula l×w²/2. Results are shown in Table 15. On day 25, mice were euthanized and each tumor was removed and measured ex vivo and calculated (length×width×depth) (Table 16).

In addition, a group of SCID mice expressing endogenous mDll4 (n=2) was implanted with tumor cells and treated with hDll4-Fc (25 mg/kg) following the same dosing schedule.

TABLE 15

| Mouse | Treatment | Tumor Size (mm³) | | | | |
|---|---|---|---|---|---|---|
| | | Day 15 | Day 18 | Day 20 | Day 22 | Day 25 |
| SCID | hDll4-hFc | 162.0 | 232.8 | 320.0 | 336.0 | 253.1 |
| SCID | hDll4-hFc | 22.5 | 117.0 | 117.0 | 108.0 | 68.8 |
| SCIDxhDll4 | hDll4-hFc | 288.0 | 320.0 | 352.0 | 446.0 | 320.0 |
| SCIDxhDll4 | hFc | 162.0 | 288.0 | 320.0 | 500.0 | 550.0 |
| SCIDxhDll4 | hFc | 162.0 | 220.5 | 352.0 | 662.0 | 661.5 |
| SCIDxhDll4 | hFc | 93.8 | 135.0 | 179.6 | 352.0 | 726.0 |
| SCIDxhDll4 | REGN421 | 144.0 | 245.0 | 320.0 | 162.0 | 144.0 |
| SCIDxhDll4 | REGN421 | 87.5 | 162.0 | 153.0 | 225.0 | 135.0 |
| SCIDxhDll4 | REGN421 | 144.0 | 196.0 | 272.0 | 162.0 | 152.5 |

TABLE 16

| Mouse | Treatment | Tumor Size (mm³) |
|---|---|---|
| SCID | hDll4-hFc | 308.0 |
| SCID | hDll4-hFc | 105.0 |
| SCIDxhDll4 | hDll4-hFc | 480.0 |
| SCIDxhDll4 | hFc | 924.0 |
| SCIDxhDll4 | hFc | 1020.0 |
| SCIDxhDll4 | hFc | 792.0 |
| SCIDxhDll4 | REGN421 | 168.0 |
| SCIDxhDll4 | REGN421 | 84.0 |
| SCIDxhDll4 | REGN421 | 189.0 |

We claim:

1. An isolated human antibody or antibody fragment which specifically binds human delta-like 4 (hDII4), comprising heavy-chain CDR1, CDR2 and CDR3, which comprise the amino acid sequences of SEQ ID NOS:399, 401 and 403, respectively, and light-chain CDR1, CDR2 and CDR3, which comprise the amino acid sequences of SEQ ID NOS:407, 409 and 411, respectively, wherein said antibody or antibody fragment binds an epitope within the N-terminal domain of hDII4.

2. The human antibody or antibody fragment of claim 1 being capable of binding dimeric hDII4 with an affinity constant ($K_D$) of about 75 pM or less, as measured by surface plasmon resonance.

3. An isolated human antibody fragment which specifically binds hDII4, comprising a heavy-chain variable region comprising the amino acid sequence of SEQ ID NO:397, and a light-chain variable region comprising the amino acid sequence of SEQ ID NO:405, wherein said antibody or antibody fragment binds an epitope within the N-terminal domain of hDII4.

4. The human antibody or antibody fragment of claim 3 being capable of binding dimeric hDII4 with a $K_D$ of about 75 pM or less, as measured by surface plasmon resonance.

5. A pharmaceutical composition comprising the antibody or antibody fragment of claim 1 and a pharmaceutically acceptable carrier.

6. A pharmaceutical composition comprising the antibody or antibody fragment of claim 3 and a pharmaceutically acceptable carrier.

* * * * *